United States Patent
Kass et al.

(10) Patent No.: US 11,639,508 B2
(45) Date of Patent: May 2, 2023

(54) ENGINEERED TSC2

(71) Applicant: The Johns Hopkins University, Baltimore, MD (US)

(72) Inventors: David A. Kass, Baltimore, MD (US); Mark J. Ranek, Baltimore, MD (US); Kristen Kokkonen, Baltimore, MD (US); Jonathan D. Powell, Baltimore, MD (US); Chirag Patel, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 608 days.

(21) Appl. No.: 16/631,069

(22) PCT Filed: Jul. 13, 2018

(86) PCT No.: PCT/US2018/042142
§ 371 (c)(1),
(2) Date: Jan. 14, 2020

(87) PCT Pub. No.: WO2019/014624
PCT Pub. Date: Jan. 17, 2019

(65) Prior Publication Data
US 2020/0149062 A1   May 14, 2020

Related U.S. Application Data

(60) Provisional application No. 62/532,909, filed on Jul. 14, 2017.

(51) Int. Cl.
*C12N 15/85* (2006.01)
*A61K 35/17* (2015.01)

(52) U.S. Cl.
CPC .............. *C12N 15/85* (2013.01); *A61K 35/17* (2013.01)

(58) Field of Classification Search
None
See application file for complete search history.

(56) References Cited

U.S. PATENT DOCUMENTS

| | | | |
|---|---|---|---|
| 6,232,452 | B1 | 5/2001 | Sampson et al. |
| 9,149,506 | B2 | 10/2015 | Chakraborty et al. |
| 2007/0281326 | A1 | 12/2007 | Wechsler et al. |
| 2010/0144538 | A1 | 6/2010 | Belouchi et al. |
| 2014/0113959 | A1 | 4/2014 | Bancel et al. |
| 2014/0227237 | A1 | 8/2014 | June et al. |
| 2016/0075784 | A1 | 3/2016 | Yu et al. |
| 2016/0251410 | A1 | 9/2016 | Tirosh et al. |
| 2022/0118017 | A1 | 4/2022 | Kass et al. |

FOREIGN PATENT DOCUMENTS

| | | |
|---|---|---|
| WO | WO 2011031786 | 3/2011 |
| WO | WO 2016049280 | 3/2016 |
| WO | WO 2020/146625 | 7/2020 |

OTHER PUBLICATIONS

PCT International Preliminary Report on Patentability in International Application No. PCT/US2020/012924, dated Jun. 16, 2021, 8 pages.
Alzabin et al., "Effector T cells in rheumatoid arthritis: Lessons from animal models," FEBS letters, 2011, 5853649-3659.
Andras, "mTOR activation is a biomarker and a cental pathway to autoimmune disorders, cancer, obesity, and aging," Annals of the New York Academy of Sci., 2015, 1346:1:33-44.
Balif et al., Quantitative phosphorylation profiling of the ERK p90 ribosomal S6 kinase-signaling cassette and its targets, the tuberous sclerosis tumor suppressors, PNAS, 2005, 102(3)667-667.
Bhuiyda et al. "Enhanced autophagy ameliorates cardiac proteinopathy," The Journal of Clinical Investigation, 123(12):5284-5297.
Burgoyne et al., "cGMP-Dependent Activation of Protein Kinase G Precludes Disulfide Activation Implications for Blood Pressure Control," Hypertension, Nov. 2012, 60(5):1301-1308.
Burgoyne et al., "Enhanced autophagy ameliorates cardiac proteinopathy," The Journal of Clinical Investigation, 123(12):5284-5297Cysteine Redox Sensor in PKGIa Enables Oxidant-Induced Activation, Science, 2007, 317(7): 1939-1397.
Burgoyne et al., Cysteine redox sensor in PKGIa enables oxidant-induced activation, Science, (2007), 317 (5843), pp. 1393-1397.
Burgoyne et al., Redox Signaling in Cardiac Physiology and Pathology, Circulation Research, 2012, 1091-1106.
Burnett et al., "RAFT1 phosphorylation of the translational regulators p70 S6 kinase and 4E-BP1," Proc Natl Acad Sci USA, Feb. 1998, 95(4):1432-1437.
Cacciauoti et el., "Role of ubiquitin-proteasome system (UPS) in left ventricular hypertrophy (LVH)," 2014, Am J Cardiovasc Dis., 4(1):1-5.
Carbone et al., "Regulatory T cell proliferative potential is impaired in human autoimmune disease," Nat. Med., 2013, 20:1:69-74.
Chau et al., Mitigation of the progression of heart failure with sildenafil involves inhibition of RhoA/Rho-kinase pathway, Am J Physiol Heart Circ Physiol, (2011), 300 (6), pp. H2272-2279.

(Continued)

*Primary Examiner* — James D Schultz
(74) *Attorney, Agent, or Firm* — Fish & Richardson P.C.

(57) ABSTRACT

Provided herein are engineered TSC2 polypeptides, and nucleic acid sequences encoding them, in which the ability of a serine residue to be phosphorylated is altered. In some aspects, the TSC2 serine residue cannot be phosphorylated (e.g., by substituting the serine residue with an alanine residue). In some aspects, the TSC2 serine acts as if it is constitutively phosphorylated (e.g., by substituting the serine residue with a glutamic acid residue). Also provided herein are engineered immune cells comprising altered TSC2 polypeptides or nucleic acid sequences encoding them, and methods of making and using such engineered immune cells.

10 Claims, 90 Drawing Sheets
Specification includes a Sequence Listing.

(56) References Cited

OTHER PUBLICATIONS

Depre et al., Activation of the cardiac proteasome during pressure overload promotes ventricular hypertrophy, Circulation, (2006), 114 (17), pp. 1821-1828.
Depre et al., The role of the ubiquitin-proteasome pathway in cardiovascular disease, Cardiovasc Res, (2010), 85 (2), pp. 251-252.
Dibble et al., "Signal integration by mTORC1 coordinates nutrient input with biosynthetic output," Nature Cell Biology, Jun. 2013, 15:555-564.
European Search Report in Appl. No. 18831991.7, dated Apr. 16, 2021, 8 pages.
Fiedler et al., "Inhibition of calcineurin-NFAT hypertrophy signaling by cGMP-dependent protein kinase type I in cardiac myocytes," Proceedings of the National Academy of Sciences of the United States of America, (2002), 99 (17), pp. 11363-11368.
Filomeni et al., "Oxidative stress and autophagy: the clash between damage and metabolic needs," Cell Death and Differentitation, 2015, 22:377-388.
Filomeni et al., "Under the ROS: Thiol network is the principal suspect for autophagy commitment," Autophagy, 2010, 6(7):999-1005.
Gerner et al., "Targeting T and B lymphocytes in inflammatory bowel diseases: Lessons from clinical trials," Digestive Diseases, 2013, 31:3-4.
Guo et al., "Curcumin activates autophagy and attenuates oxidative damage in EA.hy926 cells via the Akt/mTOR pathway," Molecular Medicine Reports, 2016, 13:2187-2193.
Hamacher-Brady et al., "Enhancing Macroautophagy Protects against Ischemia/Reperfusion Injury in Cardiac Myocytes*," Journal of Biological Chemistry, 2006, 281(40): 29776-29788.
Hariharan et al., "Oxidative Stress Stimulates Autophagic Flux During Ischemia/Reperfusion," Antioxidants & Redox Signal, Jun. 2011, 14(11):2179-2190.
Heitman et al., "Targets for Cell Cycle Arrest by the Immunosuppressant Rapamycin in Yeast," American Association for the Advancement of Science, 1991, 905-909.
Hou et al., "Activation of cGMP-dependent Protein Kinase by Protein Kinase C*," The Journal of Biological Chemistry, 2003, 278(19):9:16706-16712.
Huang et al., "The TSC1-TSC2 complex: a molecular switchboard controlling cell growth," Biochem J., 2008, 412(2):179-190.
Inoki et al., "Rheb GTPase is a direct target of TSC2 GAP activity and regulates mTOR signaling," Genes & Development, 2003, 17:1829-1834.
Inoki et al., "TSC2 Integrates Wnt and Energy Signals via a Coordinated Phosphorylation by AMPK and GSK3 to Regulate Cell Growth," Cell, Sep. 2006, 126(5):955-968.
Inoki et al., "TSC2 Mediates Cellular Energy Response to Control Cell Growth and Survival," Cell, Nov. 2003, 115:577-590.
Islam et al., "Tuberous sclerosis complex," Handbook of Clinical Neurology, 2015, 97-109.
Jacinto et al., Mammalian TOR complex 2 controls the actin cytoskeleton and is rapamycin insensitive, Nature cell biology, (2004), 6 (11), pp. 1122-1128.
Jacobs, et al., "Identification of mechanically regulated phosphorylation sites on tuberin (TSC2) that control mechanistci target ff Rapamycin (Mtor) signaling," J. Biol. Chem., 2017, 292(17):6987-6997 DOI: 10.1074/jbc.M117.777805.
Jeffery et al., "Clinical potential of regulatory T cell therapy in liver diseases: An overview and current perspectives," 2016, Front. In Immuno., 7.
Johnson et al., "Driving gene-engineered T cell immunotherapy of cancer," Cell Res., 2016, 27:1:38-58.
Kass et al., "Heart Failure A PKGarious Balancing Act" Circulation, 2012, 797-799.
Kiffin et al., Forum Review Oxidative Stress and Autophagy, Antioxidants & Redox Signaling, 2006, 8(1&2)152-179.
Kim et al., "AMPK and mTOR regulate autophagy through direct phosphorylation of Ulk1," Nature Cell Biology, FeB. 2011, 13(2):132-141.

Kinoshita et al., "Inhibition of TRPC6 Channel Activity Contributes to the Antihypertrophic Effects of Natriuretic Peptides-Guanylyl Cyclase-A Signaling in the Heart," Circulation Research, 2010, 160:1849-1860.
Klaeger et al., "The target landscape of clinical kinase drugs," Science, 2017, 358(6367), 44 pages.
Koitabashi et al., "Cyclic GMP/PKG-Dependent Inhibition of TRPC6 Channel Activity and Expression Negatively Regulates Cardiomyocyte NFAT Activation: Novel Mechanism of Cardiac Stress Modulation by PDE5 Inhibition" J Mol Cell Cardiol, 2010, 48(4): 713-724.
Kokkonen et al., "Nanodomain Regulation of Cardiac Cyclic Nucleotide Signaling by Phosphodiesterases," Annu. Rev. Pharmacol. Toxicol., 2017, 57:455-79.
Laplante et al., "mTOR signaling in growth control and disease," Cell., 2012, 149(2):274-293.
Lavandero et al., "Cardiovascular autophagy," Autophagy, 2013, 9:10, 1455-1466.
Lee et al., "mTOR Pathway as a Target in Tissue Hypertrophy," The Annual Review of Pharmacology and Toxicology, 2007, 47:443-67.
Lee et al., "Phosphodiesterase 9A Controls Nitric-oxide Independent cGMP and Hypertrophic Heart Disease," nature, 2015, 519(7544):472-476.
Li et al., "The Role of the Proteasome in Heart Disease," Biochim Biophys Acta., 2011, 1809(2):141-149.
Liang et al., "Role of autophagy in the pathogenesis of mutiple sclerosis," Neurosci Bull., Aug. 2015, 31:4:435-444.
Linke et al., "The Giant Protein Titin as an Integrator of Myocyte Signaling Pathways," Physiology, 2010, 25:186-198.
Ma et al., "Impaired Autophagosome Clearance Contributes to Cardiomyocyte Death in Ischemia-Reperfusion Injury," Circulation, 2012, 125(25):3170-3181.
Mahne et al., "Therapeutic regulatory T cells subvert effector T cell function in inflamed islets to halt autoimmune diabetes," 2015, 194:7:3147-3155.
Manning et al., "Rheb fdls a GAP between TSC and TOR," Trends in Biochemical Sciences, 2003, 573-576.
Matsui et al., "Distinct Roles of Autophagy in the Heart During Ischemia and Reperfusion Roles of AMP-Activated Protein Kinase and Beclin 1 in Mediating Autophagy," Circulation Research, 2007, 100:914-922.
McMullen et al., "Inhibition of mTOR Signaling With Rapamycin Regresses Established Cardiac Hypertrophy Induced by Pressure Overload," Circulation, 2004, 109:3050-3055.
Mei et al., "Autophagy and oxidative stress in cardiovascular diseases," Biochim Biophys Acta., 2015, 1852(2):243-251.
Menon et al., "Spatial Control of the TSC Complex Integrates Insulin and Nutrient Regulation of mTORC1 at the Lysosome," Cell., 2014, 156(4):771-785.
Mertins et al., "Proteogenomics connects somatic mutations to signaling in breast cancer," Nature, 2016, 534(7605): 55-62.
Moore et al., "Protein kinase C and P2Y12 take center stage in thrombinmediated activation of mammalian target of rapamycin complex 1 in human platelets," Journal of Thrombosis and Haemostasis, 2014, 748-760.
Morales et al., "Inhibition of class I histone deacetylases blunts cardiac hypertrophy through TSC2-dependent mTOR repression," Sci Signal., 2016, 22 pages.
Morgan et al., "Genetic Modification of T Cells," Biomedicines Apr. 2016, 4(9):1-14.
Nagayama et al., "Sildenafil Stops Progressive Chamber, Cellular, and Molecular Remodeling and Improves Calcium Handling and Function in Hearts With Pre-existing Advanced Hypertrophy due to Pressure-Overload," J Am Coll Cardiol., 2009, 53(2):207-215.
Nakai et al., "The role of autophagy in cardiomyocytes in the basal state and in response to hemodynamic stress," Nature Medicine, 2007, 619-624.
Nakamura et al., "Prevention of PKGIα oxidation augments cardioprotection in the stressed heart," The Journal of Clinical Investigation, 2015, 125(6):2468-2472.
Nishida et al., "The role of autophagy in the heart," Cell Death and Differentiation, 2009, 31-38.

(56) References Cited

OTHER PUBLICATIONS

Onda et al., "Tsc2+/− mice develop tumors in multiple sites that express gelsolin and are influenced by genetic background," The Journal of Clinical Investigation, 1999, 687-695.

Parry et al., "Functional amyloid signaling via the inflammasome, necrosome, and signalosome: new therapeutic targets in heart failure," Frontiers of Cardiovascular Medicine, 2015, 14 pages.

Pattison et al., "Atg7 Induces Basal Autophagy and Rescues Autophagic Deficiency in CryABR120G Cardiomyocytes," Circ Res., 2011, 109(2):151-160.

PCT International Preliminary Report on Patentability in PCT Appln. No. PCT/US2018/042142, dated Jan. 14, 2020, 10 pages.

PCT International Search Report and Written Opinion in PCT Appln. No. PCT/US2018/042142, dated Nov. 8, 2018, 19 pages.

Prysyazhna et al., "Single atom substitution in mouse protein kinase G eliminates oxidant sensing to cause hypertension," Nature Medicine, 2012, 18(2):286-290.

Rainer et al., "Cardiomyocyte-Specific TGFβ Suppression Blocks Neutrophil Infiltration, Augments Multiple Cytoprotective Cascades, and Reduces Early Mortality after Myocardial Infarction," Circ Res., 2014, 114(8):1246-1257.

Ran et al., "Genome engineering using the CRISPR-Cas9 system," Nat Protoc., 2013, 8(11):2281-2308.

Ranek et al., "Genetically induced moderate inhibition of 20S proteasomes in cardiomyocytes facilitates heart failure in mice during systolic overload," Journal of Molecular and Cellular Cardiology, 2015, 85:273-281.

Ranek et al., "Muscarinic 2 receptors modulate cardiac proteasome function in a protein kinase G-dependent manner," Journal of Molecular and Cellular Cardiology, 2014, 69:43-51.

Ranek et al., "Protein Kinase G Positively Regulates Proteasome-Mediated Degradation of Misfolded Proteins," Circulation, 2013, 128(4):365-376.

Roth et al., "Reprogramming human T cell function and specificity with non-viral genome targeting," Nature, 2018, 559(7714):405-409.

Sarbassov et al., "Prolonged Rapamycin Treatment Inhibits mTORC2 Assembly and Akt/PKB," Molecular Cell, 2006, 159-168.

Sarbassov et al., "Rictor, a Novel Binding Partner of mTOR, Defines a Rapamycin-Insensitive and Raptor-Independent Pathway that Regulates the Cytoskeleton," Current Biology, 2004, 1296-1302.

Scherz-Shouval et al., "Oxidation as a Post-Translational Modification that Regulates Autophagy," Autophagy, 2007, 3:4, 371-373.

Schisler et al., "CHIP protects against cardiac pressure overload through regulation of AMPK," The journal of Clinical Investtigation, Aug. 2013, 123:3588-3599.

Sciarretta et al., "Mammalian Target of Rapamycin Signaling in Cardiac Physiology and Disease," Circulation Research, Jan. 2014, 114(3): 549-546.

Sciarretta et al., "mTOR Signaling in Cardiac Physiology and Disease," Circ Res., 2014, 114(3):549-564.

Sciarretta et al., "Rheb is a critical regulator of autophagy during myocardial ischemia: pathophysiological implications in obesity and metabolic syndrome," Circulation, 2012, 125(9):1134-1146.

Sharma et al., "Ultradeep Human Phosphoproteome Reveals a Distinct Regulatory Nature of Tyr and Ser/Thr-Based Signaling," Cell Reports Resource, 2014, 1583-1594.

Shende et al., "Cardiac Raptor Ablation Impairs Adaptive Hypertrophy, Alters Metabolic Gene Expression, and Causes Heart Failure in Mice," Circulation, 2011, 123:1073-1082.

Shioi et al., "Rapamycin Attenuates Load-Induced Cardiac Hypertrophy in Mice," Circulation, 2003,107:1664-1670.

Shirakabe et al., "Aging and Autophagy in the Heart," Circ Res., 2016, 118(10):1563-1576.

Shirakabe et al., "Drp1-Dependent Mitochondrial Autophagy Plays a Protective Role Against Pressure-Overload-Induced Mitochondrial Dysfunction and Heart Failure," Circulation, 133(13):1249-1263.

Takimoto et al., "Chronic inhibition of cyclic GMP phosphodiesterase 5A prevents and reverses cardiac hypertrophy," nature medicine, 2005, 11(2):214-222.

Takimoto et al., "Regulator of G protein signaling 2 mediates cardiac compensation to pressure overload and antihypertrophic effects of PDE5 inhibition in mice," The Journal of Clinical Investigation, 2009, 119(2):408-420.

Taneike et al., "mTOR Hyperactivation by Ablation of Tuberous Sclerosis Complex 2 in the Mouse Heart Induces Cardiac Dysfunction with the Increased Number of Small Mitochondria Mediated through the Down-Regulation of Autophagy," PLOS One, 2016, 1-18.

Tannous et al., "Autophagy is an adaptive response in desmin-related cardiomyopathy," PNAS, 2008, 15(28):9745-9750.

Teng et al., "From mice to humans: developments in cancer immunoediting," The Journal of Clinical Investigation, Aug. 2015, 125(9):3338-3346.

Tokudome et al., "Regulator of G-Protein Signaling Subtype 4 Mediates Antihypertrophic Effect of Locally Secreted Natriuretic Peptides in the Heart," Molecular Cardiology, 2008, 2329-2339.

Tripathi et al., "Reactive nitrogen species regulate autophagy through ATM-AMPK-TSC2-mediated suppression of mTORC1," Proceedings of the National Academy of Sciences, 2013, 110(32): E2950-E2957.

Völkers et al., "Mechamstic Target of Rapamycin Complex 2 Protects the Heart From Ischemic Damage," Circulation, 2013, 128(19): 2132-2144.

Wang et al., "Heart Failure and Protein Quality Control," Circulation Research, 2006, 99:1315-1328.

Wang et al., "Proteasome functional insufficiency in cardiac pathogenesis," American Journal Physiological Society, 2011, 301:H2207-H2219.

Wang et al., "Protein Quality Control and Degradation in Cardiomyocytes," Journal of Molecular and Cellular Cardiology, 2008, 45(1):11-27.

Willis et al., "Proteotoxicity and Cardiac Dysfunction—Alzheimer's Disease of the Heart?," The New England Journal of Medicine, 2013, 368:455-64.

Wolff et al., "Differential Scales of Protein Quality Control," Cell, 2014, 52-64.

Wolfson et al., "Sestrin2 is a leucine sensor for the mTORC1 pathway," Science, Jan. 2016, 351:43-48.

Yamada et al., "Role of regulatory T cell in the pathogenesis of inflammatory bowel disease," World J. of Gastro., 2016, 22:7:2195-2205.

Zanetti, "Tapping CD4 T Cells for Cancer Immunotherapy: The Choice of Personalized Genomics," The Journal of Immunology, Mar. 2015, 194(5):2049-2056.

Zhai et al., "Glycogen synthase kinase-3b controls autophagy during myocardial ischemia and reperfusion," Autophagy, 2012, 8:1,138-139.

Zhang et al., "Calyxin Y induces hydrogen peroxide-dependent autophagy and apoptosis via JNK activation in human non-small cell lung cancer NCI-H460 cells," Cancer Letters, 2013, 340:51-62.

Zhang et al., "Coordinated regulation of protein synthesis and degradation by mTORC1," Nature, 2014, 513(7518):440-443.

Zhang et al., "Expression, Activity, and Pro-Hypertrophic Effects of PDE5A in Cardiac Myocytes," Cell Signal., 2008, 20(12): 2231-2236.

Zhang et al., "Insulin Stimulates Adipogenesis through the Akt-TSC2-mTORC1 Pathway," PLoS One 4, Jul. 2009, 4(7):1-14.

Zheng et al., "Autophagy and p62 in Cardiac Proteinopathy," Circulation Research, Jul. 2011, 109(3):296-308.

Zhou et al., "GSK-3α is a central regulator of age-related pathologies in mice," The Journal of Clinical Investigation, 20013, 1239(4):1821-1832.

Zhu et al., "Cardiac autophagy is a maladaptive response to hemodynamic stress," The Journal of Clinical Investigation, 2007, 117(7):1782-1793.

International Search Report and Written Opinion in Appln. No. PCT/US2020/012924, dated Apr. 23, 2020, 11 pages.

(56) References Cited

OTHER PUBLICATIONS

York et al., "Tuberin nuclear localization can be regulated by phosphorylation of it carboxyl terminus," Mol. Cancer Res., 2006, 4:11:885-897.
Ballif et al., "Quantitative phosphorylation profiling of the ERK/p90 ribosomal S6 kinase-signaling cassette and its targets, the tuberous sclerosis tumor suppressors," PNAS, Jan. 12, 2005, 102(3):667-672.
Benhamron et al., "Direct activation of mTOR in B lymphocytes confers impairment in B-cell maturation and loss of marginal zone B cells," European Journal of Immunology, Jun. 24, 2011, 41(8):2390-2396.
Extended European Search Report in European Application No. 20738372.0, dated Sep. 19, 2022, 12 pages.
Fowler, "Rapamycin-resistant effector T-cell therapy," Immunological Reviews, Dec. 13, 2013, 257(1):210-225.
Linke et al., "mTORC1 and mTORC2 as regulators of cell metabolism in immunity," FEBS Letters, Jun. 2017, 591(19):3089-3103.
Manning et al., "Identification of the tuberous sclerosis complex-2 tumor suppressor gene product tuberin as a target of the phosphoinositide 3-kinase/akt pathway," Molecular Cell, Jul. 1, 2002, 10(1):151-162.
Ranek et al., "PKG1-modified TSC2 regulates mTORC1 activity to counter adverse cardiac stress," Nature, Feb. 2019, 566(7743):264-269.

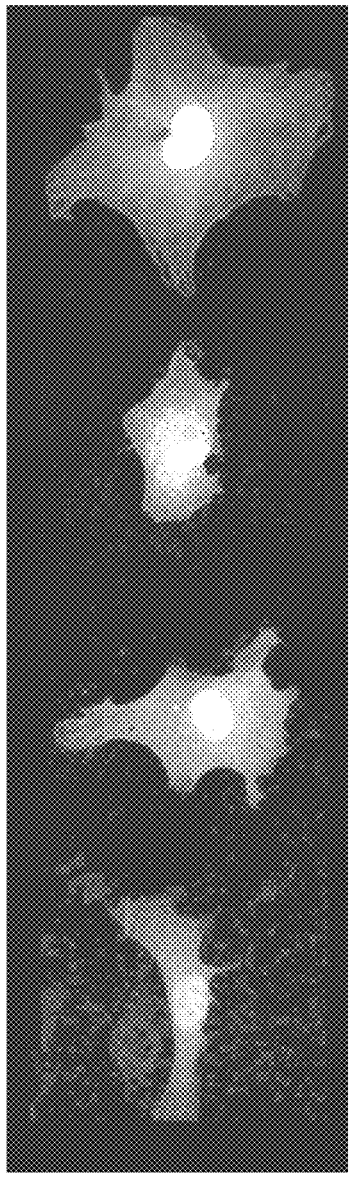
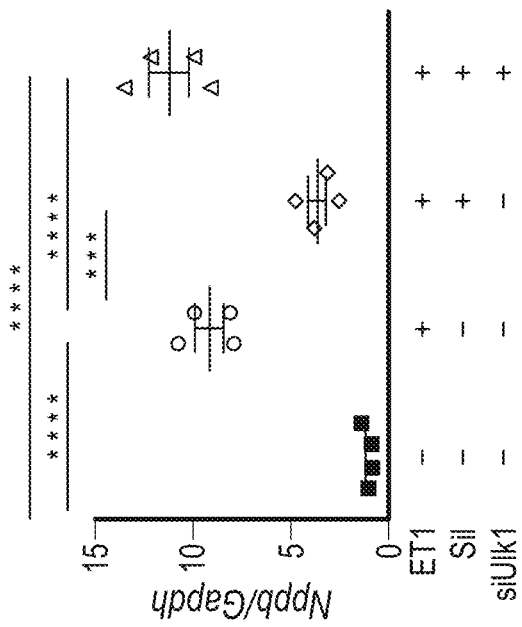
Figure 1D
Figure 1E

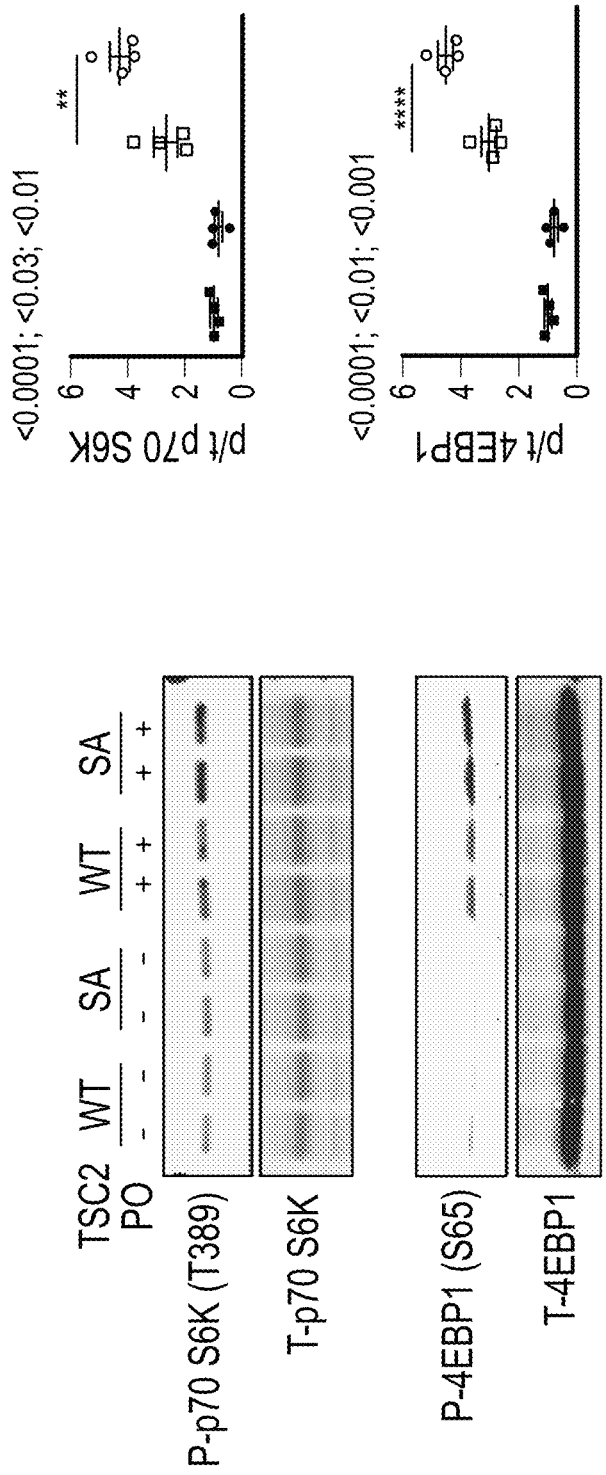
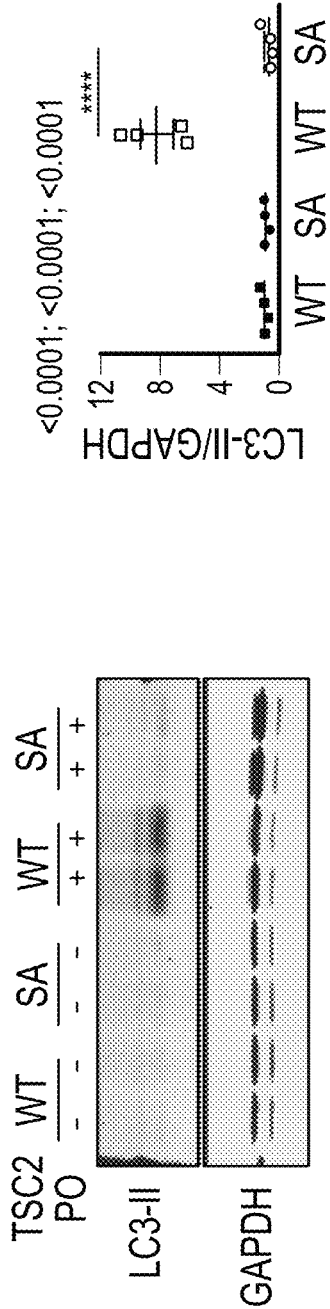
Figure 3E
Figure 3F

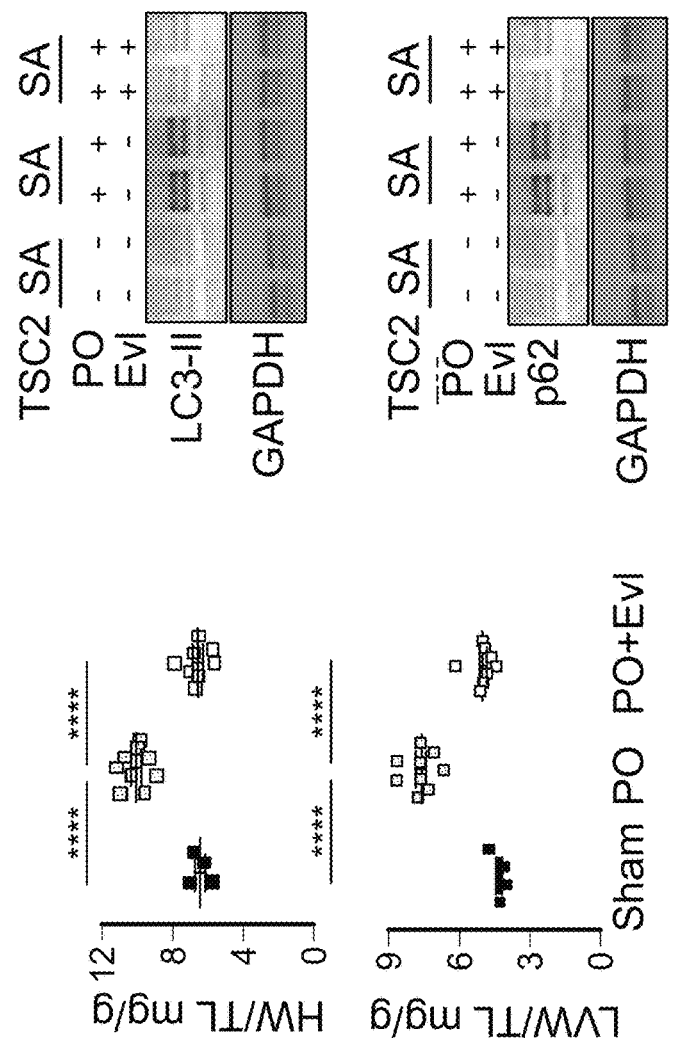
Figure 4D
Figure 4C
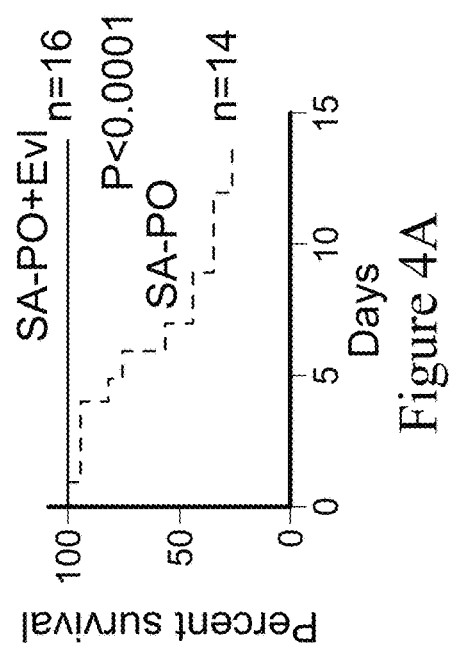
Figure 4A
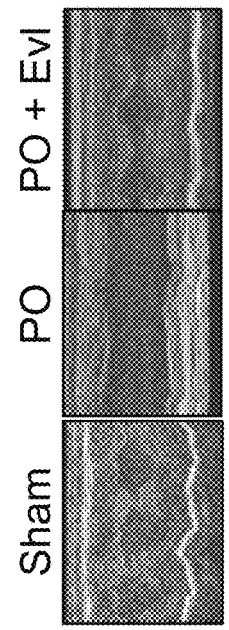
Figure 4B

| SEQ ID NO | Description | Figure Number |
|---|---|---|
| 1 | Mutant human TSC2 S1364A polypeptide sequence | Figure 15 |
| 2 | Mutant human TSC2 S1364E polypeptide sequence | Figure 16 |
| 3 | Mutant human TSC2 S1364A nucleic acid sequence | Figure 17 |
| 4 | Mutant human TSC2 S1364E nucleic acid sequence | Figure 18 |
| 5 | Wild-type human TSC2 polypeptide sequence | Figure 19 |
| 6 | Wild-type mouse TSC2 polypeptide sequence | Figure 20 |
| 7 | Wild-type rat TSC2 polypeptide sequence | Figure 21 |
| 8 | Mutant mouse TSC2 S1365A polypeptide sequence | Figure 22 |
| 9 | Mutant rat TSC2 S1366A polypeptide sequence | Figure 23 |
| 10 | Mutant mouse TSC2 S1364E polypeptide sequence | Figure 24 |
| 11 | Mutant rat TSC2 S1364E polypeptide sequence | Figure 25 |

Figure 14

SEQ ID NO: 1

```
        10         20         30         40         50
MAKPTSKDSG LKEKFKILLG LGTPRPNPRS AEGKQTEFII TAEILRELSM
        60         70         80         90        100
ECGLNNRIRM IGQICEVAKT KKFEEHAVEA LWKAVADLLQ PERPLEARHA
       110        120        130        140        150
VLALLKAIVQ GQGERLGVLR ALFFKVIKDY PSNEDLHERL EVFKALTDNG
       160        170        180        190        200
RHITYLEEEL ADFVLQWMDV GLSSEFLLVL VNLVKFNSCY LDEYIARMVQ
       210        220        230        240        250
MICLLCVRTA SSVDIEVSLQ VLDAVVCYNC LPAESLPLFI VTLCRTINVK
       260        270        280        290        300
ELCEPCWKLM RNLLGTHLGH SAIYNMCHLM EDRAYMEDAP LLRGAVFFVG
       310        320        330        340        350
MALWGAHRLY SLRNSPTSVL PSFYQAMACP NEVVSYEIVL SITRLIKKYR
       360        370        380        390        400
KELQVVAWDI LLNIIERLLQ QLQTLDSPEL RTIVHDLLTT VEELCDQNEF
       410        420        430        440        450
HGSQERYFEL VERCADQRPE SSLLNLISYR AQSIHPAKDG WIQNLQALME
       460        470        480        490        500
RFFRSESRGA VRIKVLDVLS FVLLINRQFY EEELINSVVI SQLSHIPEDK
       510        520        530        540        550
DHQVRKLATQ LLVDLAEGCH THHFNSLLDI IEKVMARSLS PPPELEERDV
       560        570        580        590        600
AAYSASLEDV KTAVLGLLVI LQTKLYTLPA SHATRVYEML VSHIQLHYKH
       610        620        630        640        650
SYTLPIASSI RLQAFDFLLL LRADSLHRLG LPNKDGVVRF SPYCVCDYME
       660        670        680        690        700
PERGSEKKTS GPLSPPTGPP GPAPAGPAVR LGSVPYSLLF RVLLQCLKQE
       710        720        730        740        750
SDWKVLKLVL GRLPESLRYK VLIFTSPCSV DQLCSALCSM LSGPKTLERL
       760        770        780        790        800
RGAPEGFSRT DLHLAVVPVL TALISYHNYL DKTKQREMVY CLEQGLIHRC
       810        820        830        840        850
ASQCVVALSI CSVEMPDIII KALPVLVVKL THISATASMA VPLLEFLSTL
       860        870        880        890        900
ARLPHLYRNF AAEQYASVFA ISLPYTNPSK FNQYIVCLAH HVIAMWFIRC
       910        920        930        940        950
RLPFRKDFVP FITKGLRSNV LLSFDDTPEK DSFRARSTSL NERPKSLRIA
       960        970        980        990       1000
RPPKQGLNNS PPVKEFKESS AAEAFRCRSI SVSEHVVRSR IQTSLTSASL
      1010       1020       1030       1040       1050
GSADENSVAQ ADDSLKNLHL ELTETCLDMM ARYVFSNFTA VPKRSPVGEF
      1060       1070       1080       1090       1100
LLAGGRTKTW LVGNKLVTVT TSVGTGTRSL LGLDSGELQS GPESSSSPGV
      1110       1120       1130       1140       1150
HVRQTKEAPA KLESQAGQQV SRGARDRVRS MSGGHGLRVG ALDVPASQFL
      1160       1170       1180       1190       1200
GSATSPGPRT APAAKPEKAS AGTRVPVQEK TNLAAYVPLL TQGWAEILVR
      1210       1220       1230       1240       1250
RPTGNTSWLM SLENPLSPFS SDINNMPLQE LSNALMAAER FKEHRDTALY
      1260       1270       1280       1290       1300
KSLSVPAAST AKPPPLPRSN TVASFSSLYQ SSCQGQLHRS VSWADSAVVM
      1310       1320       1330       1340       1350
```

Figure 15

```
EEGSPGEVPV LVEPPGLEDV EAALGMDRRT DAYSRSSSVS SQEEKSLHAE
       1360       1370       1380       1390       1400
ELVGRGIPIE RVVASEGGRP SVDLSFQPSQ PLSKSSSSPE LQTLQDILGD
       1410       1420       1430       1440       1450
PGDKADVGRL SPEVKARSQS GTLDGESAAW SASGEDSRGQ PEGPLPSSSP
       1460       1470       1480       1490       1500
RSPSGLRPRG YTISDSAPSR RGKRVERDAL KSRATASNAE KVPGINPSFV
       1510       1520       1530       1540       1550
FLQLYHSPFF GDESNKPILL PNESQSFERS VQLLDQIPSY DTHKIAVLYV
       1560       1570       1580       1590       1600
GEGQSNSELA ILSNEHGSYR YTEFLTGLGR LIELKDCQPD KVYLGGLDVC
       1610       1620       1630       1640       1650
GEDGQFTYCW HDDIMQAVFH IATLMPTKDV DKHRCDKKRH LGNDFVSIVY
       1660       1670       1680       1690       1700
NDSGEDFKLG TIKGQFNFVH VIVTPLDYEC NLVSLQCRKD MEGLVDTSVA
       1710       1720       1730       1740       1750
KIVSDRNLPF VARQMALHAN MASQVHHSRS NPTDIYPSKW IARLRHIKRL
       1760       1770       1780       1790       1800
RQRICEEAAY SNPSLPLVHP PSHSKAPAQT PAEPTPGYEV GQRKRLISSV

EDFTEFV
```

Figure 15 - Continued

SEQ ID NO: 2

```
           10         20         30         40         50
    MAKPTSKDSG LKEKFKILLG LGTPRPNPRS AEGKQTEFII TAEILRELSM
           60         70         80         90        100
    ECGLNNRIRM IGQICEVAKT KKFEEHAVEA LWKAVADLLQ PERPLEARHA
          110        120        130        140        150
    VLALLKAIVQ GQGERLGVLR ALFFKVIKDY PSNEDLHERL EVFKALTDNG
          160        170        180        190        200
    RHITYLEEEL ADFVLQWMDV GLSSEFLLVL VNLVKFNSCY LDEYIARMVQ
          210        220        230        240        250
    MICLLCVRTA SSVDIEVSLQ VLDAVVCYNC LPAESLPLFI VTLCRTINVK
          260        270        280        290        300
    ELCEPCWKLM RNLLGTHLGH SAIYNMCHLM EDRAYMEDAP LLRGAVFFVG
          310        320        330        340        350
    MALWGAHRLY SLRNSPTSVL PSFYQAMACP NEVVSYEIVL SITRLIKKYR
          360        370        380        390        400
    KELQVVAWDI LLNIIERLLQ QLQTLDSPEL RTIVHDLLTT VEELCDQNEF
          410        420        430        440        450
    HGSQERYFEL VERCADQRPE SSLLNLISYR AQSIHPAKDG WIQNLQALME
          460        470        480        490        500
    RFFRSESRGA VRIKVLDVLS FVLLINRQFY EEELINSVVI SQLSHIPEDK
          510        520        530        540        550
    DHQVRKLATQ LLVDLAEGCH THHFNSLLDI IEKVMARSLS PPPELEERDV
          560        570        580        590        600
    AAYSASLEDV KTAVLGLLVI LQTKLYTLPA SHATRVYEML VSHIQLHYKH
          610        620        630        640        650
    SYTLPIASSI RLQAFDFLLL LRADSLHRLG LPNKDGVVRF SPYCVCDYME
          660        670        680        690        700
    PERGSEKKTS GPLSPPTGPP GPAPAGPAVR LGSVPYSLLF RVLLQCLKQE
          710        720        730        740        750
    SDWKVLKLVL GRLPESLRYK VLIFTSPCSV DQLCSALCSM LSGPKTLERL
          760        770        780        790        800
    RGAPEGFSRT DLHLAVVPVL TALISYHNYL DKTKQREMVY CLEQGLIHRC
          810        820        830        840        850
    ASQCVVALSI CSVEMPDIII KALPVLVVKL THISATASMA VPLLEFLSTL
          860        870        880        890        900
    ARLPHLYRNF AAEQYASVFA ISLPYTNPSK FNQYIVCLAH HVIAMWFIRC
          910        920        930        940        950
    RLPFRKDFVP FITKGLRSNV LLSFDDTPEK DSFRARSTSL NERPKSLRIA
          960        970        980        990       1000
    RPPKQGLNNS PPVKEFKESS AAEAFRCRSI SVSEHVVRSR IQTSLTSASL
         1010       1020       1030       1040       1050
    GSADENSVAQ ADDSLKNLHL ELTETCLDMM ARYVFSNFTA VPKRSPVGEF
         1060       1070       1080       1090       1100
    LLAGGRTKTW LVGNKLVTVT TSVGTGTRSL LGLDSGELQS GPESSSSPGV
         1110       1120       1130       1140       1150
    HVRQTKEAPA KLESQAGQQV SRGARDRVRS MSGGHGLRVG ALDVPASQFL
         1160       1170       1180       1190       1200
    GSATSPGFRT APAAKPEKAS AGTRVPVQEK TNLAAYVPLL TQGWAEILVR
         1210       1220       1230       1240       1250
    RPTGNTSWLM SLENPLSPFS SDINNMPLQE LSNALMAAER FKEHRDTALY
         1260       1270       1280       1290       1300
    KSLSVPAAST AKPPPLPRSN TVASFSSLYQ SSCQGQLHRS VSWADSAVVM
         1310       1320       1330       1340       1350
```

Figure 16

```
EEGSPGEVPV LVEPPGLEDV EAALGMDRRT DAYSRSSSVS SQEEKSLHAE
      1360       1370       1380       1390       1400
ELVGRGIPIE RVVESEGGRP SVDLSFQPSQ PLSKSSSSPE LQTLQDILGD
      1410       1420       1430       1440       1450
PGDKADVGRL SPEVKARSQS GTLDGESAAW SASGEDSRGQ PEGPLPSSSP
      1460       1470       1480       1490       1500
RSPSGLRPRG YTISDSAPSR RGKRVERDAL KSRATASNAE KVPGINPSFV
      1510       1520       1530       1540       1550
FLQLYHSPFF GDESNKPILL PNESQSFERS VQLLDQIPSY DTHKIAVLYV
      1560       1570       1580       1590       1600
GEGQSNSELA ILSNEHGSYR YTEFLTGLGR LIELKDCQPD KVYLGGLDVC
      1610       1620       1630       1640       1650
GEDGQFTYCW HDDIMQAVFH IATLMPTKDV DKHRCDKKRH LGNDFVSIVY
      1660       1670       1680       1690       1700
NDSGEDFKLG TIKGQFNFVH VIVTPLDYEC NLVSLQCRKD MEGLVDTSVA
      1710       1720       1730       1740       1750
KIVSDRNLPF VARQMALHAN MASQVHHSRS NPTDIYPSKW IARLRHIKRL
      1760       1770       1780       1790       1800
RQRICEEAAY SNPSLPLVHP PSHSKAPAQT PAEPTPGYEV GQRKRLISSV

EDFTEFV
```

Figure 16 - Continued

SEQ ID NO: 3 atggccaaaccaacaagcaaagattcaggcttgaaggagaagtttaagattctgttgggactgggaacaccgaggccaaatcccaggtctg
cagagggtaaacagacggagtttatcatcaccgcggaaatactgagagaactgagcatggaatgtggcctcaacaatcgcatccggatgat
agggcagatttgtgaagtcgcaaaaaccaagaaatttgaagagcacgcagtggaagcactctggaaggcggtcgcggatctgttgcagcc
ggagcggccgctggaggcccggcacgcggtgctggctctgctgaaggccatcgtgcaggggcagggcgagcgtttgggggtcctcag
agccctcttcttaaggtcatcaaggattacccttccaacgaagaccttcacgaaaggctggaggttttcaaggccctcacagacaatgggag
acacatcacctacttggaggaagagctggctgactttgtcctgcagtggatggatgttggcttgtcctcggaattccttctggtgctggtgaact
tggtcaaattcaatagctgttacctcgacgagtacatcgcaaggatggttcagatgatctgtctgctgtgcgtccggaccgcgtcctctgtgga
catagaggtctccctgcaggtgctggacgccgtggtctgctacaactgcctgccggctgagagcctcccgctgttcatcgttaccctctgtcg
caccatcaacgtcaaggagctctgcgagccttgctggaagctgatgcggaacctccttggcacccacctgggccacagcgccatctacaa
catgtgccacctcatggaggacagagcctacatggaggacgcgcccctgctgagaggagccgtgttttttgtgggcatggctctctgggga
gcccaccggctctattctctcaggaactcgccgacatctgtgttgccatcattttaccaggccatggcatgtccgaacgaggtggtgtcctatg
agatcgtcctgtccatcaccaggctcatcaagaagtataggaaggagctccaggtggtggcgtgggacattctgctgaacatcatcgaacg
gctccttcagcagctccagaccttggacagcccggagctcaggaccatcgtccatgacctgttgaccacggtggaggagctgtgtgacca
gaacgagttccacgggtctcaggagagatactttgaactggtggagagatgtgcggaccagaggcctgagtcctccctcctgaacctgatc
tcctatagagcgcagtccatccacccggccaaggacggctggattcagaacctgcaggcgctgatggagagattcttcaggagcgagtcc
cgaggcgccgtgcgcatcaaggtgctggacgtgctgtcctttgtgctgctcatcaacaggcagttctatgaggaggagctgattaactcagt
ggtcatctcgcagctctcccacatccccgaggataaagaccaccaggtccgaaagctggccacccagttgctggtggacctggcagagg
gctgccacacacaccacttcaacagcctgctggacatcatcgagaaggtgatggcccgctccctctccccacccccggagctggaagaaa
gggatgtggccgcatactcggcctccttggaggatgtgaagacagccgtcctggggcttctggtcatccttcagaccaagctgtacaccctg
cctgcaagccacgccacgcgtgtgtatgagatgctggtcagccacattcagctccactacaagcacagctacaccctgccaatcgcgagc
agcatccggctgcaggcctttgacttcctgttgctgctgcgggccgactcactgcaccgcctgggcctgcccaacaaggatggagtcgtgc
ggttcagcccctactgcgtctgcgactacatggagccagagagaggctctgagaagaagaccagcggccccctttctcctcccacagggc
ctcctggccccggcgcctgcaggccccgccgtgcggctggggtccgtgccctactccctgctcttccgcgtcctgctgcagtgcttgaagca
ggagtctgactggaaggtgctgaagctggttctgggcaggctgcctgagtcccgcgctataaagtgctcatctttacttccccttgcagtgtg
gaccagctgtgctctgctctctgctccatgctttcaggcccaaagacactggagcggctccgaggcgccccagaaggcttctccagaactg
acttgcacctggccgtggttccagtgctgacagcattaatctcttaccataactacctggacaaaaccaaacagcgcgagatggtctactgcc
tggagcagggcctcatccaccgctgtgccagccagtgcgtcgtggccttgtccatctgcagcgtggagatgcctgacatcatcatcaaggc
gctgcctgttctggtggtgaagctcacgcacatctcagccacagccagcatggccgtcccactgctggagttcctgtccactctggccaggc
tgccgcacctctacaggaactttgccgcggagcagtatgccagtgtgttcgccatctcccctgccgtacaccaaccctccaagtttaatcagt
acatcgtgtgtctggcccatcacgtcatagccatgtggttcatcaggtgccgcctgcccttccggaaggattttgtccctttcatcactaagggc
ctgcggtccaatgtcctcttgtcttttgatgacacccccgagaaggacagcttcagggcccggagtactagtctcaacgagagacccaaga
gtctgaggatagccagaccccccaaacaaggcttgaataactctccaccgtgaaagaattcaaggagagctctgcagccgaggccttcc
ggtgccgcagcatcagtgtgtctgaacatgtggtccgcagcaggatacagacgtccctcaccagtgccagcttggggtctgcagatgaga
actccgtggcccaggctgacgatagcctgaaaaacctccacctggagctcacggaaacctgtctggacatgatggctcgatacgtcttctcc
aacttcacggctgtcccgaagaggtctcctgtgggcgagttcctcctagcgggtggcaggaccaaaacctggctggttgggaacaagcttg
tcactgtgacgacaagcgtgggaaccgggacccggtcgttactaggcctggactcggggggagctgcagtccggcccggagtcgagctc
cagccccggggtgcatgtgagacagaccaaggaggcgccggccaagctggagtcccaggctgggcagcaggtgcccgtgggggccc
gggatcgggtccgttccatgtcgggggggccatggtcttcgagttggcgccctggacgtgccggcctcccagttcctgggcagtgccacttc
tccaggaccacggactgcaccagccgcgaaacctgagaaggcctcagctggcacccgggttcctgtgcaggagaagacgaacctggcg
gcctatgtgcccctgctgacccagggctgggcggagatcctggtccggaggcccacagggaacaccagctggctgatgagcctggaga
acccgctcagcccttctcctcggacatcaacaacatgcccctgcaggagctgtctaacgccctcatggcggctgagcgcttcaaggagca
ccgggacacagccctgtacaagtcactgtcggtgccggcagccagcacggccaaaccccctcctctgcctcgctccaacacagtggcctc
tttctcctccctgtaccagtccagctgccaaggacagctgcacaggagcgtttcctgggcagactccgccgtggtcatggaggagggaagt
ccgggcgaggttcctgtgctggtggagccccagggttggaggacgttgaggcagcgctaggcatggacaggcgcacggatgcctaca
gcaggtcgtcctcagtctccagccaggaggagaagtcgctccacgcggagagctggttgcaggggcatccccatcgagcgagtcgtc

Figure 17

GCCtcggagggtggccggccctctgtggacctctccttccagccctcgcagccctgagcaagtccagctcctctcccgagctgcagac
tctgcaggacatcctcggggaccctggggacaaggccgacgtgggccggctgagccctgaggttaaggcccggtcacagtcagggacc
ctggacggggaaagtgctgcctggtcggcctcgggcgaagacagtcggggccagcccgagggtcccttgccttccagctcccccgctc
gcccagtggcctccggccccgaggttacaccatctccgactcggccccatcacgcaggggcaagagagtagagagggacgccttaaag
agcagagccacagcctccaatgcagagaaagtgccaggcatcaacccagtttcgtgttcctgcagctctaccattccccttctttggcga
cgagtcaaacaagccaatcctgctgcccaatgagtcacagtcctttgagcggtcggtgcagctcctcgaccagatcccatcatacgacacc
cacaagatcgccgtcctgtatgttggagaaggccagagcaacagcgagctcgccatcctgtccaatgagcatggctcctacaggtacacg
gagttcctgacgggcctgggccggctcatcgagctgaaggactgccagccggacaaggtgtacctgggaggcctggacgtgtgtggtga
ggacggccagttcacctactgctggcacgatgacatcatgcaagccgtcttccacatcgccaccctgatgcccaccaaggacgtggacaa
gcaccgctgcgacaagaagcgccacctgggcaacgactttgtgtccattgtctacaatgactccggtgaggacttcaagcttggcaccatca
agggccagttcaactttgtccacgtgatcgtcacccccgctggactacgagtgcaacctggtgtccctgcagtgcaggaaagacatggaggg
ccttgtggacaccagcgtggccaagatcgtgtctgaccgcaacctgcccttcgtggcccgccagatggccctgcacgcaaatatggcctca
caggtgcatcatagccgctccaaccccaccgatatctaccccctccaagtggattgcccggctccgccacatcaagcggctccgccagcgg
atctgcgaggaagccgcctactccaaccccagcctacctctggtgcacctccgtcccatagcaaagccctgcacagactccagccgag
cccacacctggctatgaggtgggccagcggaagcgcctcatctcctcggtggaggacttcaccgagtttgtgtga Figure 17 - Continued

SEQ ID NO: 4 atggccaaaccaacaagcaaagattcaggcttgaaggagaagtttaagattctgttgggactgggaacaccgaggccaaatcc
caggtctgcagagggtaaacagacggagtttatcatcaccgcggaaatactgagagaactgagcatggaatgtggcctcaaca
atcgcatccggatgatagggcagatttgtgaagtcgcaaaaaccaagaaatttgaagagcacgcagtggaagcactctggaag
gcggtcgcggatctgttgcagccggagcggccgctggaggcccggcacgcggtgctggctctgctgaaggccatcgtgcag
gggcagggcgagcgtttgggggtcctcagagccctcttctttaaggtcatcaaggattaccttccaacgaagaccttcacgaaa
ggctggaggttttcaaggccctcacagacaatgggagacacatcacctacttggaggaagagctggctgactttgtcctgcagt
ggatggatgttggcttgtcctcggaattccttctggtgctggtgaacttggtcaaattcaatagctgttacctcgacgagtacatcgc
aaggatggttcagatgatctgtctgctgtgcgtccggaccgcgtcctctgtggacatagaggtctccctgcaggtgctggacgcc
gtggtctgctacaactgcctgccggctgagagcctcccgctgttcatcgttaccctctgtcgcaccatcaacgtcaaggagctctg
cgagccttgctggaagctgatgcggaacctccttggcacccacctgggccacagcgccatctacaacatgtgccacctcatgga
ggacagagcctacatggaggacgcgcccctgctgagaggagccgtgttttttgtgggcatggctctctggggagcccaccggc
tctattctctcaggaactcgccgacatctgtgttgccatcattttaccaggccatggcatgtccgaacgaggtggtgtcctatgagat
cgtcctgtccatcaccaggctcatcaagaagtataggaaggagctccaggtggtggcgtgggacattctgctgaacatcatcga
acggctccttcagcagctccagaccttggacagcccggagctcaggaccatcgtccatgacctgttgaccacggtggaggagc
tgtgtgaccagaacgagttccacgggtctcaggagagatactttgaactggtggagagatgtgcggaccagaggcctgagtcct
ccctcctgaacctgatctcctatagagcgcagtccatccacccggccaaggacggctggattcagaacctgcaggcgctgatg
gagagattcttcaggagcgagtcccgaggcgccgtgcgcatcaaggtgctggacgtgctgtcctttgtgctgctcatcaacagg
cagttctatgaggaggagctgattaactcagtggtcatctcgcagctctcccacatccccgaggataaagaccaccaggtccga
aagctggccacccagttgctggtggacctggcagagggctgccacacacaccacttcaacagcctgctggacatcatcgagaa
ggtgatggcccgctccctctccccaccccggagctggaagaaagggatgtggccgcatactcggcctccttggaggatgtga
agacagccgtcctggggcttctggtcatccttcagaccaagctgtacaccctgcctgcaagccacgccacgcgtgtgtatgagat
gctggtcagccacattcagctccactacaagcacagctacaccctgccaatcgcgagcagcatccggctgcaggcctttgactt
cctgttgctgctgcgggccgactcactgcaccgcctgggcctgcccaacaaggatggagtcgtgcggttcagcccctactgcgt
ctgcgactacatggagccagagagaggctctgagaagaagaccagcggccccctttctcctcccacagggcctcctggcccg
gcgcctgcaggccccgccgtgcggctggggtccgtgccctactccctgctcttccgcgtcctgctgcagtgcttgaagcagga
gtctgactggaaggtgctgaagctggttctgggcaggctgcctgagtccctgcgctataaagtgctcatctttacttcccccttgcag
tgtggaccagctgtgctctgctctctgctccatgctttcaggcccaaagacactggagcggctccgaggcgccccagaaggctt
ctccagaactgacttgcacctggccgtggttccagtgctgacagcattaatctcttaccataactacctggacaaaaccaaacagc
gcgagatggtctactgcctggagcagggcctcatccaccgctgtgccagccagtgcgtcgtggccttgtccatctgcagcgtgg
agatgcctgacatcatcatcaaggcgctgcctgttctggtggtgaagctcacgcacatctcagccacagccagcatggccgtcc
cactgctggagttcctgtccactctggccaggctgccgcacctctacaggaactttgccgcggagcagtatgccagtgtgttcgc
catctccctgccgtacaccaaccccctccaagtttaatcagtacatcgtgtgtctggcccatcacgtcatagccatgtggttcatcag
gtgccgcctgcccttccggaaggattttgtccctttcatcactaagggcctgcggtccaatgtcctcttgtcttttgatgacaccccc
gagaaggacagcttcagggcccggagtactagtctcaacgagagacccaagagtctgaggatagccagacccccaaacaa
ggcttgaataactctccacccgtgaaagaattcaaggagagctctgcagccgaggccttccggtgccgcagcatcagtgtgtct
gaacatgtggtccgcagcaggatacagacgtccctcaccagtgccagcttggggtctgcagatgagaactccgtggcccaggc
tgacgatagcctgaaaaacctccacctggagctcacggaaacctgtctggacatgatggctcgatacgtcttctccaacttcacg
gctgtcccgaagaggtctcctgtgggcgagttcctcctagcgggtggcaggaccaaaacctggctggttgggaacaagcttgtc
actgtgacgacaagcgtgggaaccgggacccggtcgttactaggcctggactcgggggagctgcagtccggcccggagtcg
agctccagccccggggtgcatgtgagacagaccaaggaggcgccggccaagctggagtcccaggctgggcagcaggtgtc
ccgtggggcccgggatcgggtccgttccatgtcgggggccatggtcttcgagttggcgccctggacgtgccggcctcccagt
tcctgggcagtgccacttctccaggaccacggactgcaccagccgcgaaacctgagaaggcctcagctggcacccgggttcct
gtgcaggagaagacgaacctggcggcctatgtgcccctgctgacccagggctggggcgagatcctggtccggaggcccaca
gggaacaccagctggctgatgagcctggagaacccgctcagcccttctcctcggacatcaacaacatgccctgcaggagct
gtctaacgccctcatggcggctgagcgcttcaaggagcaccgggacacagccctgtacaagtcactgtcggtgccggcagcc

Figure 18 agcacggccaaaccccctcctctgcctcgctccaacacagtggcctctttctcctccctgtaccagtccagctgccaaggacagc
tgcacaggagcgtttcctgggcagactccgccgtggtcatggaggagggaagtccgggcgaggttcctgtgctggtggagcc
cccagggttggaggacgttgaggcagcgctaggcatggacaggcgcacggatgcctacagcaggtcgtcctcagtctccagc
caggaggagaagtcgctccacgcggaggagctggttggcaggggcatccccatcgagcgagtcgtcGAGtcggagggtg
gccggccctctgtggacctctccttccagccctcgcagcccctgagcaagtccagctcctctcccgagctgcagactctgcagg
acatcctcggggaccctggggacaaggccgacgtgggccggctgagccctgaggttaaggcccggtcacagtcagggaccc
tggacggggaaagtgctgcctggtcggcctcgggcgaagacagtcggggccagcccgagggtcccttgccttccagctcccc
ccgctcgcccagtggcctccggccccgaggttacaccatctccgactcggccccatcacgcaggggcaagagagtagagag
ggacgccttaaagagcagagccacagcctccaatgcagagaaagtgccaggcatcaaccccagtttcgtgttcctgcagctcta
ccattcccccttctttggcgacgagtcaaacaagccaatcctgctgcccaatgagtcacagtcctttgagcggtcggtgcagctcc
tcgaccagatcccatcatacgacacccacaagatcgccgtcctgtatgttggagaaggccagagcaacagcgagctcgccatc
ctgtccaatgagcatggctcctacaggtacacggagttcctgacgggcctgggccggctcatcgagctgaaggactgccagcc
ggacaaggtgtacctgggaggcctggacgtgtgtggtgaggacggccagttcacctactgctggcacgatgacatcatgcaag
ccgtcttccacatcgccaccctgatgcccaccaaggacgtggacaagcaccgctgcgacaagaagcgccacctgggcaacg
actttgtgtccattgtctacaatgactccggtgaggacttcaagcttggcaccatcaagggccagttcaactttgtccacgtgatcgt
cacccgctggactacgagtgcaacctggtgtccctgcagtgcaggaaagacatggagggccttgtggacaccagcgtggcc
aagatcgtgtctgaccgcaacctgcccttcgtggcccgccagatggccctgcacgcaaatatggcctcacaggtgcatcatagc
cgctccaaccccaccgatatctaccccctccaagtggattgcccggctccgccacatcaagcggctccgccagcggatctgcga
ggaagccgcctactccaaccccagcctacctctggtgcaccctccgtcccatagcaaagcccctgcacagactccagccgagc
ccacacctggctatgaggtgggccagcggaagcgcctcatctcctcggtggaggacttcaccgagtttgtgtga Figure 18 - Continued

SEQ ID NO: 5

```
         10         20         30         40         50
 MAKPTSKDSG LKEKFKILLG LGTPRPNPRS AEGKQTEFII TAEILRELSM
         60         70         80         90        100
 ECGLNNRIPM IGQICEVAKT KKFEEHAVEA LWKAVADLLQ PERPLEARHA
        110        120        130        140        150
 VLALLKAIVQ GQGERLGVLR ALFFKVIKDY PSNEDLHERL EVFKALTDNG
        160        170        180        190        200
 RHITYLEEEL ADFVLQWMDV GLSSEFLLVL VNLVKFNSCY LDEYIARMVQ
        210        220        230        240        250
 MICLLCVRTA SSVDIEVSLQ VLDAVVCYNC LPAESLPLFI VTLCRTINVK
        260        270        280        290        300
 ELCEPCWKLM RNLLGTHLGH SAIYNMCHLM EDRAYMEDAP LLRGAVFFVG
        310        320        330        340        350
 MALWGAHRLY SLRNSPTSVL PSFYQAMACP NEVVSYEIVL SITRLIKKYR
        360        370        380        390        400
 KELQVVAWDI LLNIIERLLQ QLQTLDSPEL RTIVHDLLTT VEELCDQNEF
        410        420        430        440        450
 HGSQERYFEL VERCADQRPE SSLLNLISYR AQSIHPAKDG WIQNLQALME
        460        470        480        490        500
 RFFRSESRGA VRIKVLDVLS FVLLINRQFY EEELINSVVI SQLSHIPEDK
        510        520        530        540        550
 DHQVRKLATQ LLVDLAEGCH THHFNSLLDI IEKVMARSLS PPPELEERDV
        560        570        580        590        600
 AAYSASLEDV KTAVLGLLVI LQTKLYTLPA SHATRVYEML VSHIQLHYKH
        610        620        630        640        650
 SYTLPIASSI RLQAFDFLLL LRADSLHRLG LPNKDGVVRF SPYCVCDYME
        660        670        680        690        700
 PERGSEKKTS GPLSPPTGPP GPAPAGPAVR LGSVPYSLLF RVLLQCLKQE
        710        720        730        740        750
 SDWKVLKLVL GRLPESLRYK VLIFTSPCSV DQLCSALCSM LSGPKTLERL
        760        770        780        790        800
 RGAPEGFSRT DLHLAVVPVL TALISYHNYL DKTKQREMVY CLEQGLIHRC
        810        820        830        840        850
 ASQCVVALSI CSVEMPDIII KALPVLVVKL THISATASMA VPLLEFLSTL
        860        870        880        890        900
 ARLPHLYRNF AAEQYASVFA ISLPYTNPSK FNQYIVCLAH HVIAMWFIRC
        910        920        930        940        950
 RLPFRKDFVP FITKGLRSNV LLSFDDTPEK DSFRARSTSL NERPKSLRIA
        960        970        980        990       1000
 RPPKQGLNNS PPVKEFKESS AAEAFRCRSI SVSEHVVRSR IQTSLTSASL
       1010       1020       1030       1040       1050
 GSADENSVAQ ADDSLKNLHL ELTETCLDMM ARYVFSNFTA VPKRSPVGEF
       1060       1070       1080       1090       1100
 LLAGGRTKTW LVGNKLVTVT TSVGTGTRSL LGLDSGELQS GPESSSSPGV
       1110       1120       1130       1140       1150
 HVRQTKEAPA KLESQAGQQV SRGARDRVRS MSGGHGLRVG ALDVPASQFL
       1160       1170       1180       1190       1200
 GSATSPGPRT APAAKPEKAS AGTRVPVQEK TNLAAYVPLL TQGWAEILVR
       1210       1220       1230       1240       1250
 RPTGNTSWLM SLENPLSPFS SDINNMPLQE LSNALMAAER FKEHRDTALY
       1260       1270       1280       1290       1300
 KSLSVPAAST AKPPPLPRSN TVASFSSLYQ SSCQGQLHRS VSWADSAVVM
       1310       1320       1330       1340       1350
```

Figure 19

```
EEGSPGEVPV LVEPPGLEDV EAALGMDRRT DAYSRSSSVS SQEEKSLHAE
    1360       1370       1380       1390       1400
ELVGRGIPIE RVVSSEGGRP SVDLSFQPSQ PLSKSSSSPE LQTLQDILGD
    1410       1420       1430       1440       1450
PGDKADVGRL SPEVKARSQS GTLDGESAAW SASGEDSRGQ PEGPLPSSSP
    1460       1470       1480       1490       1500
RSPSGLRPRG YTISDSAPSR RGKRVERDAL KSRATASNAE KVPGINPSFV
    1510       1520       1530       1540       1550
FLQLYHSPFF GDESNKPILL PNESQSFERS VQLLDQIPSY DTHKIAVLYV
    1560       1570       1580       1590       1600
GEGQSNSELA ILSNEHGSYR YTEFLTGLGR LIELKDCQPD KVYLGGLDVC
    1610       1620       1630       1640       1650
GEDGQFTYCW HDDIMQAVFH IATLMPTKDV DKHRCDKKRH LGNDFVSIVY
    1660       1670       1680       1690       1700
NDSGEDFKLG TIKGQFNFVH VIVTPLDYEC NLVSLQCRKD MEGLVDTSVA
    1710       1720       1730       1740       1750
KIVSDRNLPF VARQMALHAN MASQVHHSRS NPTDIYPSKW IARLRHIKRL
    1760       1770       1780       1790       1800
RQRICEEAAY SNPSLPLVHP PSHSKAPAQT PAEPTPGYEV GQRKRLISSV

EDFTEFV
```

Figure 19 - Continued

```
                         SEQ ID NO: 6
       10         20         30         40         50
MAKPTSKDSG LKEKFKILLG LGTSRPNPRC AEGKQTEFII TSEILRELSG
       60         70         80         90        100
ECGLNNRIRM IGQICDVAKT KKLEEHAVEA LWKAVSDLLQ PERPPEARHA
      110        120        130        140        150
VLTLLKAIVQ GQGDRLGVLR ALFFKVIKDY PSNEDLHERL EVFKALTDNG
      160        170        180        190        200
RHITYLEEEL AEFVLQWMDV GLSSEFLLVL VNLVKFNSCY LDEYIASMVH
      210        220        230        240        250
MICLLCIRTV SSVDIEVSLQ VLDAVVCYNC LPAESLPLFI ITLCRTINVK
      260        270        280        290        300
ELCEPCWKLM RNLLGTHLGH SAIYNMCRIM EDRSYMEDAP LLRGAVFFVG
      310        320        330        340        350
MALWGAHRLY SLKNSPTSVL PSFYEAMTCP NEVVSYEIVL SITRLIKKYR
      360        370        380        390        400
KELQAVTWDI LLDIIERLLQ QLQNLDSPEL KTIVHDLLTT VEELCDQNEF
      410        420        430        440        450
HGSQERYYEL VESYADQRPE SSLLNLISYR AQSIHPAKDG WIQNLQLLME
      460        470        480        490        500
RFFRNECRSA VAIKVLDVLS FVLLIIRQFY EEELINSVVI SQLSHIPEDK
      510        520        530        540        550
DHQVRKLATQ LLVDLAEGCH THHFNSLLDI IEKVMARSLS PPPELEERDL
      560        570        580        590        600
AVHSASLEDV KTAVLGLLVI LQTKLYTLPA SHATRVYESL ISHIQLHYKH
      610        620        630        640        650
GYSLPIASSI RLQAFDFLLL LRADSLHRLG LPNKDGVVRF SPYCLCDCME
      660        670        680        690        700
LDRASEKKAS GPLSPPTGPP SPVPMGPAVR LGYLPYSLLF RVLLQCLKQE
      710        720        730        740        750
SDWKVLKLVL SRLPESLRYK VLIFTSPCSV DQLSSALCSM LSAPKTLERL
      760        770        780        790        800
RGTPEGFSRT DLHLAVVPVL TALISYHNYL DKTRQREMVY CLEQGLIYRC
      810        820        830        840        850
ASQCVVALAI CSVEMPDIII KALPVLVVKL THISATASMA IPLLEFLSTL
      860        870        880        890        900
ARLPHLYRNF VPEQYASVFA ISLPYTNPSK FNQYIVCLAH HVIAMWFIRC
      910        920        930        940        950
RLPFRKDFVP YITKGLRSNV LLSFDDTPEK DSFRARSTSL NERPKSLRIA
      960        970        980        990       1000
RAPKQGLNNS PPVKEFKESC AAEAFRCRSI SVSEHVVRSR IQTSLTSASL
     1010       1020       1030       1040       1050
GSADENSMAQ ADDNLKNLHL ELTETCLDMM ARYVFSNFTA VPKRSPVGEF
     1060       1070       1080       1090       1100
LLAGGRTKTW LVGNKLVTVT TSVGTGTRSL LGLDSGDLQG GSDSSSDPST
     1110       1120       1130       1140       1150
HVRQTKEAPA KLESQAGQQV SRGARDRVRS MSGGHGLRVG VLDTSAPYSP
     1160       1170       1180       1190       1200
GGSASLGPQT AVAAKPEKPP AGAQLPTAEK TNLAAYVPLL TQGWAEILVR
     1210       1220       1230       1240       1250
RPTGNTSWLM SLENPLSPFS SDINNMPLQE LSNALMAAER FKEHGHAPVQ
     1260       1270       1280       1290       1300
```

Figure 20

```
VIVSATGCTA KPPTLPRSNT VASFSSLYQP SCQGQLHRSV SWADSAMVLE
    1310       1320       1330       1340       1350
EGSPGETQVP VEPPELEDFE AALGTDRHCQ RPDTYSRSSS ASSQEEKSHL
    1360       1370       1380       1390       1400
EELAAGGIPI ERAISSEGAR PAVDLSFQPS QPLSKSSSSP ELQTLQDILG
    1410       1420       1430       1440       1450
DLGDKIDIGR LSPEAKVRSQ SGILDGEAAT WSATGEESRI TVPPEGPLPS
    1460       1470       1480       1490       1500
SSPRSPSGLR PRGYTISDSA PSRRGKRVER DNFKSRAAAS SAEKVPGINP
    1510       1520       1530       1540       1550
SFVFLQLYHS PFFGDESNKP ILLPNESFER SVQLLDQIPS YDTHKIAVLY
    1560       1570       1580       1590       1600
VGEGQSSSEL AILSNEHGSY RYTEFLTGLG RLIELKDCQP DKVYLGGLDV
    1610       1620       1630       1640       1650
CGEDGQFTYC WHDDIMQAVF HIATLMPTKD VDKHRCDKKR HLGNDFVSII
    1660       1670       1680       1690       1700
YNDSGEDFKL GTIKQGQFNF VHVIITPLDY KCNLLTLQCR KDGPACKCEW
    1710       1720       1730       1740       1750
WRQPGEIVVW ALPVVMELTV TILLCHLQMA SQVHHSRSNP TDIYPSKWIA
    1760       1770       1780       1790       1800
RLRHIKRLRQ RIREEVHYSN PSLPLMHPPA HTKAPAQAPE ATPTYETGQR
    1810
KRLISSVDDF TEFV
```

Figure 20 - Continued

SEQ ID NO: 7

```
         10         20         30         40         50
MAKPTSKDSG LKEKFKILLG LGTSRPNPRC AEGKQTEFII TAEILRELSG
         60         70         80         90        100
ECGLNNRIRM IGQICDVAKT KKLEEHAVEA LWKAVSDLLQ PERPPEARHA
        110        120        130        140        150
VLALLKAIVQ GQGDRLGVLR ALFFKVIKDY PSNEDLHERL EVFKALTDNG
        160        170        180        190        200
RHITYLEEEL AEFVLQWMDV GLSSEFLLVL VNLVKFNSCY LDEYIAPMVH
        210        220        230        240        250
MICLLCIRTV SSVDIEVSLQ VLDAVVCYNC LPAESLPLFI ITLCRTVNVK
        260        270        280        290        300
ELCEPCWKLM RNLLGTHLGH SAIYNMCRIM ENRSYMEDAP LLRGAVFFVG
        310        320        330        340        350
MALWGAHRLY SLKNSPTSVL PSFYEAMTCP NEVVSYEIVL SITRLIKKYR
        360        370        380        390        400
KELQAVTWDI LLDIIERLLQ QLQNLDSPEL RTIVHDLLTT VEELCDQNEF
        410        420        430        440        450
HGSQERYYEL VESYADQRPE SSLLNLITYR AQSIHPAKDG WIQNLQLLME
        460        470        480        490        500
RFFRNECRSA VRIKVLDVLS FVLLINRQFY EEELINSVVI SQLSHIPEDK
        510        520        530        540        550
DHQVRKLATQ LLVDLAEGCH THHFNSLLDI IEKVMARSLS PPLELEERDL
        560        570        580        590        600
AVYSASLEDV KTAVLGLLVI LQTKLYTLPA SHATRVYETL ISHIQLHYKH
        610        620        630        640        650
GYSLPIASSI RLQAFDFLLL LRADSLHRLG LPNKDGVVRF SPYCLCDCAE
        660        670        680        690        700
LDRASEKKAS GPLSPPTGPP SPVPTGPAVR LGHLPYSLLF RVLLQCLKQE
        710        720        730        740        750
TDWKVLKLVL SKLPESLRYK VLIFTSPCSV DQLSSALCSM LSAPKTLERL
        760        770        780        790        800
RGTPEGFSRT DLHLAVVPVL TALISYHNYL DKTRQREMVY CLEQGLIYRC
        810        820        830        840        850
ASQCVVALAI CSVEMPDIII KALPVLVVKL THISATASMA IPLLEFLSTL
        860        870        880        890        900
ARLPHLYRNF AAEQYASVFA ISLPYTNPSK FNQYIVCLAH HVIAMWFIRC
        910        920        930        940        950
RLPFRKDFVP YITKGLRSNV LLSFDDTPEK DKFRARSTSL NERPKSLRIA
        960        970        980        990       1000
RAPKQGLNNS PPVKEFKESC AAEAFRCRSI SVSEHVVRSR IQTSLTSASL
       1010       1020       1030       1040       1050
GSADENSMAQ ADDNLKNLHL ELTETCLDMM ARYVFSNFTA VPKRSPVGEF
       1060       1070       1080       1090       1100
LLAGGRTKTW LVGNKLVTVT TSVGTGTRSL LGLDSGDLQG GSASSSDPGT
       1110       1120       1130       1140       1150
HVRQTKEAPA KLESQAGQQV SRGARDRVRS MSGGHGLRVG VLDTSAPYTP
       1160       1170       1180       1190       1200
GGPASLGAQA APAARPEKPC AGAQLPAAEK ANLAAYVPLL TQGWAEILVR
       1210       1220       1230       1240       1250
RPTGNTSWLM SLENPLSPFS SDINNMPLQE LSNALMAAER FKEHRDTALY
       1260       1270       1280       1290       1300
```

Figure 21

```
KSLSVPAAGT AKPPTLPRSN TVASFSSLYQ PSCQGQLHRS VSWADSAVVL
    1310       1320       1330       1340       1350
EEGSPGEAHV PVEPPELEDF EAALGTDRHC QRPDAYSRSS SASSQEEKSH
    1360       1370       1380       1390       1400
LEELAAGGIP IERAISSEGA RPTVDLSFQP SQPLSKSSSS PELQTLQDIL
    1410       1420       1430       1440       1450
GDLGDKTDIG RLSPEAKVRS QSGILDGEAA TWSAPGEESR ITVPPEGPLP
    1460       1470       1480       1490       1500
SSSPRSPSGL RPRGYTISDS APSRRGKRVE RDNFKSRTAA SSAEKVPGIN
    1510       1520       1530       1540       1550
PSFVFLQLYH SPFCGDESNK PILLPNESFE RSVQLLDQIP SYDTHKIAVL
    1560       1570       1580       1590       1600
YVGEGQSSSE LAILSNEHGS YRYTEFLTGL GRLIELKDCQ PDKVYLGGLD
    1610       1620       1630       1640       1650
VCGEDGQFTY CWHDDIMQAV FHIATLMPTK DVDKHRCDKK RHLGNDFVSI
    1660       1670       1680       1690       1700
IYNDSGEDFK LGTIKGQFNF VHVIITPLDY KCNLLTLQCR KDMEGLVDTS
    1710       1720       1730       1740       1750
VAKIVSDRNL SFVARQMALH ANMASQVHHR RSNPTDIYPS KWIARLRHIK
    1760       1770       1780       1790       1800
RLRQRIREEV HYSNPSLPLM HPPAHTKVPA QAPTEATPTY ETGQRKRLIS

SVDDFTEFV
```

Figure 21 - Continued

SEQ ID NO: 8

```
        10         20         30         40         50
MAKPTSKDSG LKEKFKILLG LGTSRPNPRC AEGKQTEFII TSEILRELSG
        60         70         80         90        100
ECGLNNRIRM IGQICDVAKT KKLEEHAVEA LWKAVSDLLQ PERPPEARHA
       110        120        130        140        150
VLTLLKAIVQ GQGDRLGVLR ALFFKVIKDY PSNEDLHERL EVFKALTDNG
       160        170        180        190        200
RHITYLEEEL AEFVLQWMDV GLSSEFLLVL VNLVKFNSCY LDEYIASMVH
       210        220        230        240        250
MICLLCIRTV SSVDIEVSLQ VLDAVVCYNC LPAESLPLFI ITLCRTINVK
       260        270        280        290        300
ELCEPCWKLM RNLLGTHLGH SAIYNMCRIM EDRSYMEDAP LLRGAVFFVG
       310        320        330        340        350
MALWGAHRLY SLKNSPTSVL PSFYEAMTCP NEVVSYEIVL SITRLIKKYR
       360        370        380        390        400
KELQAVTWDI LLDIIERLLQ QLQNLDSPEL KTIVHDLLTT VEELCDQNEF
       410        420        430        440        450
HGSQERYYEL VESYADQRPE SSLLNLISYR AQSIHPAKDG WIQNLQLLME
       460        470        480        490        500
RFFRNECRSA VAIKVLDVLS FVLLIIRQFY EEELINSVVI SQLSHIPEDK
       510        520        530        540        550
DHQVRKLATQ LLVDLAEGCH THHFNSLLDI IEKVMARSLS PPPELEERDL
       560        570        580        590        600
AVHSASLEDV KTAVLGLLVI LQTKLYTLPA SHATRVYESL ISHIQLHYKH
       610        620        630        640        650
GYSLPIASSI RLQAFDFLLL LRADSLHRLG LPNKDGVVRF SPYCLCDCME
       660        670        680        690        700
LDRASEKKAS GPLSPPTGPP SPVPMGPAVR LGYLPYSLLF RVLLQCLKQE
       710        720        730        740        750
SDWKVLKLVL SRLPESLRYK VLIFTSPCSV DQLSSALCSM LSAPKTLERL
       760        770        780        790        800
RGTPEGFSRT DLHLAVVPVL TALISYHNYL DKTRQREMVY CLEQGLIYRC
       810        820        830        840        850
ASQCVVALAI CSVEMPDIII KALPVLVVKL THISATASMA IPLLEFLSTL
       860        870        880        890        900
ARLPHLYRNF VPEQYASVFA ISLPYTNPSK FNQYIVCLAH HVIAMWFIRC
       910        920        930        940        950
RLPFRKDFVP YITKGLRSNV LLSFDDTPEK DSFRARSTSL NERPKSLRIA
       960        970        980        990       1000
RAPKQGLNNS PPVKEFKESC AAEAFRCRSI SVSEHVVRSR IQTSLTSASL
      1010       1020       1030       1040       1050
GSADENSMAQ ADDNLKNLHL ELTETCLDMM ARYVFSNFTA VPKRSPVGEF
      1060       1070       1080       1090       1100
LLAGGRTKTW LVGNKLVTVT TSVGTGTRSL LGLDSGDLQG GSDSSDPST
      1110       1120       1130       1140       1150
HVRQTKEAPA KLESQAGQQV SRGARDRVRS MSGGHGLRVG VLDTSAPYSP
      1160       1170       1180       1190       1200
GGSASLGPQT AVAAKPEKPP AGAQLPTAEK TNLAAYVPLL TQGWAEILVR
      1210       1220       1230       1240       1250
RPTGNTSWLM SLENPLSPFS SDINNMPLQE LSNALMAAER FKEHGHAPVQ
      1260       1270       1280       1290       1300
```

Figure 22

```
VIVSATGCTA KPPTLPRSNT VASFSSLYQP SCQGQLHRSV SWADSAMVLE
       1310       1320       1330       1340       1350
EGSPGETQVP VEPPELEDFE AALGTDRHCQ RPDTYSRSSS ASSQEEKSHL
       1360       1370       1380       1390       1400
EELAAGGIPI ERAISEGAR  PAVDLSFQPS QPLSKSSSSP ELQTLQDILG
       1410       1420       1430       1440       1450
DLGDKIDIGR LSPEAKVRSQ SGILDGEAAT WSATGEESRI TVPPEGPLPS
       1460       1470       1480       1490       1500
SSPRSPSGLR PRGYTISDSA PSRRGKRVER DNFKSRAAAS SAEKVPGINP
       1510       1520       1530       1540       1550
SFVFLQLYHS PFFGDESNKP ILLPNESFER SVQLLDQIPS YDTHKIAVLY
       1560       1570       1580       1590       1600
VGEGQSSSEL AILSNEHGSY RYTEFLTGLG RLIELKDCQP DKVYLGGLDV
       1610       1620       1630       1640       1650
CGEDGQFTYC WHDDIMQAVF HIATLMPTKD VDKHRCDKKR HLGNDFVSII
       1660       1670       1680       1690       1700
YNDSGEDFKL GTIKQGQFNF VHVIITPLDY KCNLLTLQCR KDGPACKCEW
       1710       1720       1730       1740       1750
WRQPGEIVVW ALPVVMELTV TILLCHLQMA SQVHHSRSNP TDIYPSKWIA
       1760       1770       1780       1790       1800
RLRHIKRLRQ RIREEVHYSN PSLPLMHPPA HTKAPAQAPE ATPTYETGQR
       1810
KRLISSVDDF TEFV
```

Figure 22 - Continued

SEQ ID NO: 9

```
         10         20         30         40         50
  MAKPTSKDSG LKEKFKILLG LGTSRPNPRC AEGKQTEFII TAEILRELSG
         60         70         80         90        100
  ECGLNNRIRM IGQICDVAKT KKLEEHAVEA LWKAVSDLLQ PERPPEARHA
        110        120        130        140        150
  VLALLKAIVQ GQGDRLGVLR ALFFKVIKDY PSNEDLHERL EVFKALTDNG
        160        170        180        190        200
  RHITYLEEEL AEFVLQWMDV GLSSEFLLVL VNLVKFNSCY LDEYIAPMVH
        210        220        230        240        250
  MICLLCIRTV SSVDIEVSLQ VLDAVVCYNC LPAESLPLFI ITLCRTVNVK
        260        270        280        290        300
  ELCEPCWKLM RNLLGTHLGH SAIYNMCRIM ENRSYMEDAP LLRGAVFFVG
        310        320        330        340        350
  MALWGAHRLY SLKNSPTSVL PSFYEAMTCP NEVVSYEIVL SITRLIKKYR
        360        370        380        390        400
  KELQAVTWDI LLDIIERLLQ QLQNLDSPEL RTIVHDLLTT VEELCDQNEF
        410        420        430        440        450
  HGSQERYYEL VESYADQRPE SSLLNLITYR AQSIHPAKDG WIQNLQLLME
        460        470        480        490        500
  RFFRNECRSA VRIKVLDVLS FVLLINRQFY EEELINSVVI SQLSHIPEDK
        510        520        530        540        550
  DHQVRKLATQ LLVDLAEGCH THHFNSLLDI IEKVMARSLS PPLELEERDL
        560        570        580        590        600
  AVYSASLEDV KTAVLGLLVI LQTKLYTLPA SHATRVYETL ISHIQLHYKH
        610        620        630        640        650
  GYSLPIASSI RLQAFDFLLL LRADSLHRLG LPNKDGVVRF SPYCLCDCAE
        660        670        680        690        700
  LDRASEKKAS GPLSPPTGPP SPVPTGPAVR LGHLPYSLLF RVLLQCLKQE
        710        720        730        740        750
  TDWKVLKLVL SKLPESLRYK VLIFTSPCSV DQLSSALCSM LSAPKTLERL
        760        770        780        790        800
  RGTPEGFSRT DLHLAVVPVL TALISYHNYL DKTRQREMVY CLEQGLIYRC
        810        820        830        840        850
  ASQCVVALAI CSVEMPDIII KALPVLVVKL THISATASMA IPLLEFLSTL
        860        870        880        890        900
  ARLPHLYRNF AAEQYASVFA ISLPYTNPSK FNQYIVCLAH HVIAMWFIRC
        910        920        930        940        950
  RLPFRKDFVP YITKGLRSNV LLSFDDTPEK DKFRARSTSL NERPKSLRIA
        960        970        980        990       1000
  RAPKQGLNNS PPVKEFKESC AAEAFRCRSI SVSEHVVRSR IQTSLTSASL
       1010       1020       1030       1040       1050
  GSADENSMAQ ADDNLKNLHL ELTETCLDMM ARYVFSNFTA VPKRSPVGEF
       1060       1070       1080       1090       1100
  LLAGGRTKTW LVGNKLVTVT TSVGTGTRSL LGLDSGDLQG GSASSSDPGT
       1110       1120       1130       1140       1150
  HVRQTKEAPA KLESQAGQQV SRGARDRVRS MSGGHGLRVG VLDTSAPYTP
       1160       1170       1180       1190       1200
  GGPASLGAQA APAARPEKPC AGAQLPAAEK ANLAAYVPLL TQGWAEILVR
       1210       1220       1230       1240       1250
  RPTGNTSWLM SLENPLSPFS SDINNMPLQE LSNALMAAER FKEHRDTALY
       1260       1270       1280       1290       1300
```

Figure 23

```
KSLSVPAAGT AKPPTLPRSN TVASFSSLYQ PSCQGQLHRS VSWADSAVVL
    1310       1320       1330       1340       1350
EEGSPGEAHV PVEPPELEDF EAALGTDRHC QRPDAYSRSS SASSQEEKSH
    1360       1370       1380       1390       1400
LEELAAGGIP IERAIASEGA RPTVDLSFQP SQPLSKSSSS PELQTLQDIL
    1410       1420       1430       1440       1450
GDLGDKTDIG RLSPEAKVRS QSGILDGEAA TWSAPGEESR ITVPPEGPLP
    1460       1470       1480       1490       1500
SSSPRSPSGL RPRGYTISDS APSRRGKRVE RDNFKSRTAA SSAEKVPGIN
    1510       1520       1530       1540       1550
PSFVFLQLYH SPFCGDESNK PILLPNESFE RSVQLLDQIP SYDTHKIAVL
    1560       1570       1580       1590       1600
YVGEGQSSSE LAILSNEHGS YRYTEFLTGL GRLIELKDCQ PDKVYLGGLD
    1610       1620       1630       1640       1650
VCGEDGQFTY CWHDDIMQAV FHIATLMPTK DVDKHRCDKK RHLGNDFVSI
    1660       1670       1680       1690       1700
IYNDSGEDFK LGTIKGQFNF VHVIITPLDY KCNLLTLQCR KDMEGLVDTS
    1710       1720       1730       1740       1750
VAKIVSDRNL SFVARQMALH ANMASQVHHR RSNPTDIYPS KWIARLRHIK
    1760       1770       1780       1790       1800
RLRQRIREEV HYSNPSLPLM HPPAHTKVPA QAPTEATPTY ETGQRKRLIS

SVDDFTEFV
```

Figure 23 - Continued

SEQ ID NO: 10

```
         10         20         30         40         50
  MAKPTSKDSG LKEKFKILLG LGTSRPNPRC AEGKQTEFII TSEILRELSG
         60         70         80         90        100
  ECGLNNRIRM IGQICDVAKT KKLEEHAVEA LWKAVSDLLQ PERPPEARHA
        110        120        130        140        150
  VLTLLKAIVQ GQGDRLGVLR ALFFKVIKDY PSNEDLHERL EVFKALTDNG
        160        170        180        190        200
  RHITYLEEEL AEFVLQWMDV GLSSEFLLVL VNLVKFNSCY LDEYIASMVH
        210        220        230        240        250
  MICLLCIRTV SSVDIEVSLQ VLDAVVCYNC LPAESLPLFI ITLCRTINVK
        260        270        280        290        300
  ELCEPCWKLM RNLLGTHLGH SAIYNMCRIM EDRSYMEDAP LLRGAVFFVG
        310        320        330        340        350
  MALWGAHRLY SLKNSPTSVL PSFYEAMTCP NEVVSYEIVL SITRLIKKYR
        360        370        380        390        400
  KELQAVTWDI LLDIIERLLQ QLQNLDSPEL KTIVHDLLTT VEELCDQNEF
        410        420        430        440        450
  HGSQERYYEL VESYADQRPE SSLLNLISYR AQSIHPAKDG WIQNLQLLME
        460        470        480        490        500
  RFFRNECRSA VAIKVLDVLS FVLLIIRQFY EEELINSVVI SQLSHIPEDK
        510        520        530        540        550
  DHQVRKLATQ LLVDLAEGCH THHFNSLLDI IEKVMARSLS PPPELEERDL
        560        570        580        590        600
  AVHSASLEDV KTAVLGLLVI LQTKLYTLPA SHATRVYESL ISHIQLHYKH
        610        620        630        640        650
  GYSLPIASSI RLQAFDFLLL LRADSLHRLG LPNKDGVVRF SPYCLCDCME
        660        670        680        690        700
  LDRASEKKAS GPLSPPTGPP SPVPMGPAVR LGYLPYSLLF RVLLQCLKQE
        710        720        730        740        750
  SDWKVLKLVL SRLPESLRYK VLIFTSPCSV DQLSSALCSM LSAPKTLERL
        760        770        780        790        800
  RGTPEGFSRT DLHLAVVPVL TALISYHNYL DKTRQREMVY CLEQGLIYRC
        810        820        830        840        850
  ASQCVVALAI CSVEMPDIII KALPVLVVKL THISATASMA IPLLEFLSTL
        860        870        880        890        900
  ARLPHLYRNF VPEQYASVFA ISLPYTNPSK FNQYIVCLAH HVIAMWFIRC
        910        920        930        940        950
  RLPFRKDFVP YITKGLRSNV LLSFDDTPEK DSFRARSTSL NERPKSLRIA
        960        970        980        990       1000
  RAPKQGLNNS PPVKEFKESC AAEAFRCRSI SVSEHVVRSR IQTSLTSASL
       1010       1020       1030       1040       1050
  GSADENSMAQ ADDNLKNLHL ELTETCLDMM ARYVFSNFTA VPKRSPVGEF
       1060       1070       1080       1090       1100
  LLAGGRTKTW LVGNKLVTVT TSVGTGTRSL LGLDSGDLQG GSDSSSDPST
       1110       1120       1130       1140       1150
  HVRQTKEAPA KLESQAGQQV SRGARDRVRS MSGGHGLRVG VLDTSAPYSP
       1160       1170       1180       1190       1200
  GGSASLGPQT AVAAKPEKPP AGAQLPTAEK TNLAAYVPLL TQGWAEILVR
       1210       1220       1230       1240       1250
  RPTGNTSWLM SLENPLSPFS SDINNMPLQE LSNALMAAER FKEHGHAPVQ
       1260       1270       1280       1290       1300
```

Figure 24

```
VIVSATGCTA KPPTLPRSNT VASFSSLYQP SCQGQLHRSV SWADSAMVLE
    1310       1320       1330       1340       1350
EGSPGETQVP VEPPELEDFE AALGTDRHCQ RPDTYSRSSS ASSQEEKSHL
    1360       1370       1380       1390       1400
EELAAGGIPI ERAI SEGAR PAVDLSFQPS QPLSKSSSSP ELQTLQDILG
    1410       1420       1430       1440       1450
DLGDKIDIGR LSPEAKVRSQ SGILDGEAAT WSATGEESRI TVPPEGPLPS
    1460       1470       1480       1490       1500
SSPRSPSGLR PRGYTISDSA PSRRGKRVER DNFKSRAAAS SAEKVPGINP
    1510       1520       1530       1540       1550
SFVFLQLYHS PFFGDESNKP ILLPNESFER SVQLLDQIPS YDTHKIAVLY
    1560       1570       1580       1590       1600
VGEGQSSSEL AILSNEHGSY RYTEFLTGLG RLIELKDCQP DKVYLGGLDV
    1610       1620       1630       1640       1650
CGEDGQFTYC WHDDIMQAVF HIATLMPTKD VDKHRCDKKR HLGNDFVSII
    1660       1670       1680       1690       1700
YNDSGEDFKL GTIKQGQFNF VHVIITPLDY KCNLLTLQCR KDGPACKCEW
    1710       1720       1730       1740       1750
WRQPGEIVVW ALPVVMELTV TILLCHLQMA SQVHHSRSNP TDIYPSKWIA
    1760       1770       1780       1790       1800
RLRHIKRLRQ RIREEVHYSN PSLPLMHPPA HTKAPAQAPE ATPTYETGQR
    1810
KRLISSVDDF TEFV
```

Figure 24 - Continued

SEQ ID NO: 11

```
          10         20         30         40         50
   MAKPTSKDSG LKEKFKILLG LGTSRPNPRC AEGKQTEFII TAEILRELSG
          60         70         80         90        100
   ECGLNNRIRM IGQICDVAKT KKLEEHAVEA LWKAVSDLLQ PERPPEARHA
         110        120        130        140        150
   VLALLKAIVQ GQGDRLGVLR ALFFKVIKDY PSNEDLHERL EVFKALTDNG
         160        170        180        190        200
   RHITYLEEEL AEFVLQWMDV GLSSEFLLVL VNLVKFNSCY LDEYIAPMVH
         210        220        230        240        250
   MICLLCIRTV SSVDIEVSLQ VLDAVVCYNC LPAESLPLFI ITLCRTVNVK
         260        270        280        290        300
   ELCEPCWKLM RNLLGTHLGH SAIYNMCRIM ENRSYMEDAP LLRGAVFFVG
         310        320        330        340        350
   MALWGAHRLY SLKNSPTSVL PSFYEAMTCP NEVVSYEIVL SITRLIKKYR
         360        370        380        390        400
   KELQAVTWDI LLDIIERLLQ QLQNLDSPEL RTIVHDLLTT VEELCDQNEF
         410        420        430        440        450
   HGSQERYYEL VESYADQRPE SSLLNLITYR AQSIHPAKDG WIQNLQLLME
         460        470        480        490        500
   RFFRNECRSA VRIKVLDVLS FVLLINRQFY EEELINSVVI SQLSHIPEDK
         510        520        530        540        550
   DHQVRKLATQ LLVDLAEGCH THHFNSLLDI IEKVMARSLS PPLELEERDL
         560        570        580        590        600
   AVYSASLEDV KTAVLGLLVI LQTKLYTLPA SHATRVYETL ISHIQLHYKH
         610        620        630        640        650
   GYSLPIASSI RLQAFDFLLL LRADSLHRLG LPNKDGVVRF SPYCLCDCAE
         660        670        680        690        700
   LDRASEKKAS GPLSPPTGPP SPVPTGPAVR LGHLPYSLLF RVLLQCLKQE
         710        720        730        740        750
   TDWKVLKLVL SKLPESLRYK VLIFTSPCSV DQLSSALCSM LSAPKTLERL
         760        770        780        790        800
   RGTPEGFSRT DLHLAVVPVL TALISYHNYL DKTRQREMVY CLEQGLIYRC
         810        820        830        840        850
   ASQCVVALAI CSVEMPDIII KALPVLVVKL THISATASMA IPLLEFLSTL
         860        870        880        890        900
   ARLPHLYRNF AAEQYASVFA ISLPYTNPSK FNQYIVCLAH HVIAMWFIRC
         910        920        930        940        950
   RLPFRKDFVP YITKGLRSNV LLSFDDTPEK DKFRARSTSL NERPKSLRIA
         960        970        980        990       1000
   RAPKQGLNNS PPVKEFKESC AAEAFRCRSI SVSEHVVRSR IQTSLTSASL
        1010       1020       1030       1040       1050
   GSADENSMAQ ADDNLKNLHL ELTETCLDMM ARYVFSNFTA VPKRSPVGEF
        1060       1070       1080       1090       1100
   LLAGGRTKTW LVGNKLVTVT TSVGTGTRSL LGLDSGDLQG GSASSSDPGT
        1110       1120       1130       1140       1150
   HVRQTKEAPA KLESQAGQQV SRGARDRVRS MSGGHGLRVG VLDTSAPYTP
        1160       1170       1180       1190       1200
   GGPASLGAQA APAARPEKPC AGAQLPAAEK ANLAAYVPLL TQGWAEILVR
        1210       1220       1230       1240       1250
   RPTGNTSWLM SLENPLSPFS SDINNMPLQE LSNALMAAER FKEHRDTALY
        1260       1270       1280       1290       1300
```

Figure 25

```
KSLSVPAAGT AKPPTLPRSN TVASFSSLYQ PSCQGQLHRS VSWADSAVVL
    1310       1320       1330       1340       1350
EEGSPGEAHV PVEPPELEDF EAALGTDRHC QRPDAYSRSS SASSQEEKSH
    1360       1370       1380       1390       1400
LEELAAGGIP IERAIESEGA RPTVDLSFQP SQPLSKSSSS PELQTLQDIL
    1410       1420       1430       1440       1450
GDLGDKTDIG RLSPEAKVRS QSGILDGEAA TWSAPGEESR ITVPPEGPLP
    1460       1470       1480       1490       1500
SSSPRSPSGL RPRGYTISDS APSRRGKRVE RDNFKSRTAA SSAEKVPGIN
    1510       1520       1530       1540       1550
PSFVFLQLYH SPFCGDESNK PILLPNESFE RSVQLLDQIP SYDTHKIAVL
    1560       1570       1580       1590       1600
YVGEGQSSSE LAILSNEHGS YRYTEFLTGL GRLIELKDCQ PDKVYLGGLD
    1610       1620       1630       1640       1650
VCGEDGQFTY CWHDDIMQAV FHIATLMPTK DVDKHRCDKK RHLGNDFVSI
    1660       1670       1680       1690       1700
IYNDSGEDFK LGTIKGQFNF VHVIITPLDY KCNLLTLQCR KDMEGLVDTS
    1710       1720       1730       1740       1750
VAKIVSDRNL SFVARQMALH ANMASQVHHR RSNPTDIYPS KWIARLRHIK
    1760       1770       1780       1790       1800
RLRQRIREEV HYSNPSLPLM HPPAHTKVPA QAPTEATPTY ETGQRKRLIS

SVDDFTEFV
```

Figure 25 - Continued

|  | Mice Aged 2-3 Months | | | | | |
|---|---|---|---|---|---|---|
|  | TSC2 WT | TSC2 S1365A | p-value | TSC2 WT | TSC2 S1365E | p-value |
|  | n=5 | n=4 | | n=6 | n=7 | |
| Body Weight (g) | 22.5 ± 3.3 | 21.8 ± 3.4 | 0.80 | 23.8 ± 3.1 | 23.9 ± 2.9 | 0.80 |
| Heart Weight (mg) | 117.0 ± 24.7 | 114.9 ± 12.7 | 0.88 | 133.5 ± 25.0 | 113.6 ± 12.4 | 0.88 |
| Left Ventricular Weight (mg) | 81.2 ± 13.4 | 75.4 ± 4.8 | 0.44 | 125.3 ± 25.6 | 80.6 ± 9.6 | 0.44 |
| Lung Weight (mg) | 133.4 ± 15.0 | 130.2 ± 19.8 | 0.72 | 141.446 ± 24.5 | 128.3 ± 13.0 | 0.72 |
| Tibial Length (mm) | 18.2 ± 0.8 | 17.8 ± 0.3 | 0.30 | 5.4 ± 0.4 | 17.6 ± 0.5 | 0.30 |
| HW/TL | 6.4 ± 1.1 | 6.5 ± 0.6 | 0.92 | 4.2 ± 0.5 | 6.4 ± 0.6 | 0.92 |
| LVW/TL | 4.5 ± 0.6 | 4.3 ± 0.3 | 0.57 | 4.8 ± 0.4 | 4.6 ± 0.5 | 0.57 |
| LuW/TL | 7.3 ± 0.7 | 7.3 ± 0.5 | 1.00 | 3.1 ± 0.3 | 7.3 ± 0.7 | 1.00 |
| Heart Rate (bpm) | 675.8 ± 21.4 | 683.2 ± 42.9 | 0.80 | 1.4 ± 0.1 | 690.0 ± 67.9 | 0.80 |
| %Ejection Fraction | 82.1 ± 1.6 | 81.8 ± 2.6 | 0.74 | 1.0 ± 0.1 | 83.4 ± 3.7 | 0.74 |
| %Fractional Shortening | 57.7 ± 1.9 | 57.4 ± 2.9 | 0.76 | 671.3 ± 74.3 | 58.6 ± 4.4 | 0.76 |

Supplemental Table 1.

Baseline cardiac morphometry and function based on echocardiography and direct tissue measurements obtained in homozygous TSC2 S1365A (left side) or S1365E (right side) knock-in mice and corresponding littermate (TSC2-WT) controls. HW – heart weight; LVW – left ventricular weight; LuW – lung weight. There are no significant baseline differences.

|  | Mice Aged 9-12 Months | | | | | |
|---|---|---|---|---|---|---|
|  | TSC2 WT | TSC2 S1365A | p-value | TSC2 WT | TSC2 S1365E | p-value |
|  | n=8 | n=7 | | n=6 | n=7 | |
| Body Weight (g) | 29.6 ± 3.1 | 29.2 ± 4.2 | 0.37 | 30.2 ± 3.0 | 28.5 ± 3.5 | 0.37 |
| Heart Weight (mg) | 159.5 ± 25.0 | 167.3 ± 32.2 | 0.31 | 163.4 ± 25.6 | 147.9 ± 26.3 | 0.31 |
| Left Ventricular Weight (mg) | 125.3 ± 25.6 | 134.6 ± 33.9 | 0.50 | 119.2 ± 23.1 | 109.3 ± 27.1 | 0.50 |
| Lung Weight (mg) | 141.446 ± 24.5 | 161.5 ± 37.5 | 0.11 | 149.2 ± 26.9 | 130.3 ± 17.4 | 0.11 |
| HW/BW | 5.4 ± 0.4 | 5.8 ± 0.9 | 0.31 | 5.4 ± 0.4 | 5.2 ± 0.4 | 0.31 |
| LVW/BW | 4.2 ± 0.5 | 4.6 ± 1.0 | 0.65 | 3.9 ± 0.4 | 3.8 ± 0.5 | 0.65 |
| LuW/BW | 4.8 ± 0.4 | 5.5 ± 1.0 | 0.19 | 4.9 ± 0.3 | 4.6 ± 0.5 | 0.19 |
| LVID;d | 3.1 ± 0.3 | 3.6 ± 1.6 | 0.71 | 3.2 ± 0.3 | 3.2 ± 0.2 | 0.71 |
| LVID;s | 1.4 ± 0.1 | 2.3 ± 2.0 | 0.72 | 1.1 ± 0.2 | 1.5 ± 0.2 | 0.72 |
| LVPW;d | 1.0 ± 0.1 | 1.1 ± 0.1 | 0.41 | 1.1 ± 0.2 | 1.0 ± 0.1 | 0.41 |
| Heart Rate (bpm) | 671.3 ± 74.3 | 659.3 ± 86.4 | 0.56 | 704.2 ± 37.5 | 683.6 ± 25.3 | 0.56 |
| %Ejection Fraction | 80.8 ± 1.9 | 66.2 ± 24.6 | 0.90 | 77.2 ± 2.9 | 77.0 ± 2.7 | 0.90 |
| %Fractional Shortening | 52.3 ± 2.2 | 40.5 ± 19.4 | 0.89 | 52.3 ± 3.1 | 52.1 ± 2.8 | 0.89 |

Supplemental Table 2.

Cardiac morphometry and function based on echocardiography and direct tissue measurements obtained in 9-12 month aged homozygous S1365A (left side) or TSC2 S1365E (right side) knock-in mice and corresponding littermate controls (TSC2-WT). There are no significant differences. HW – heart weight; LVW – left ventricular weight; LuW – lung weight. There are no significant baseline differences.

Figure 26

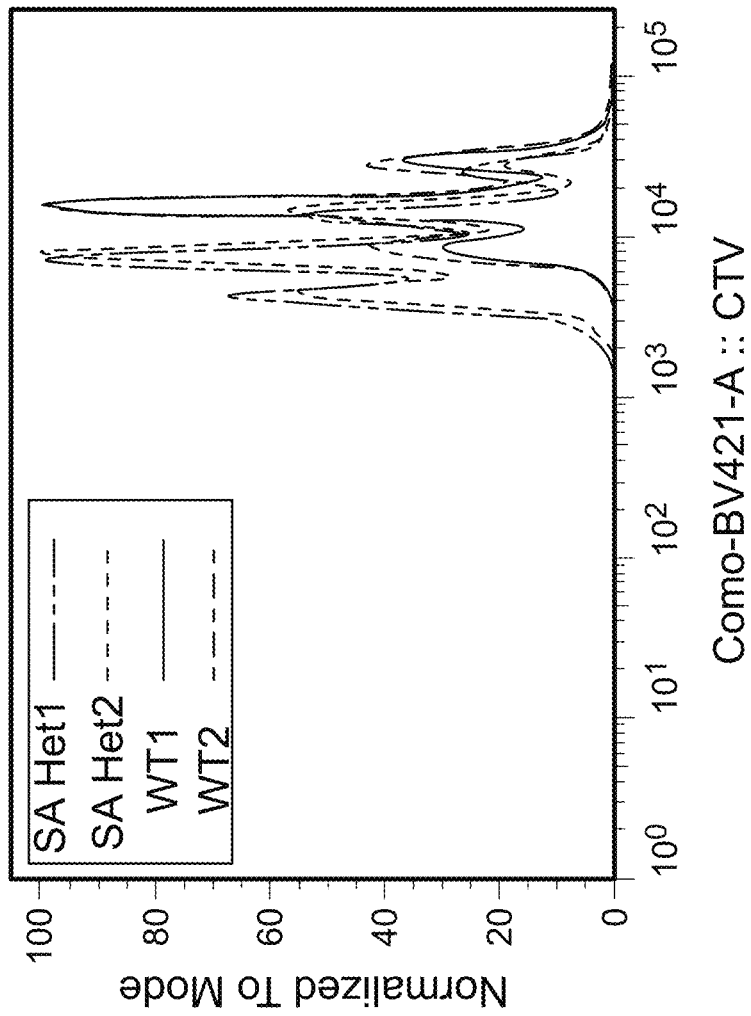
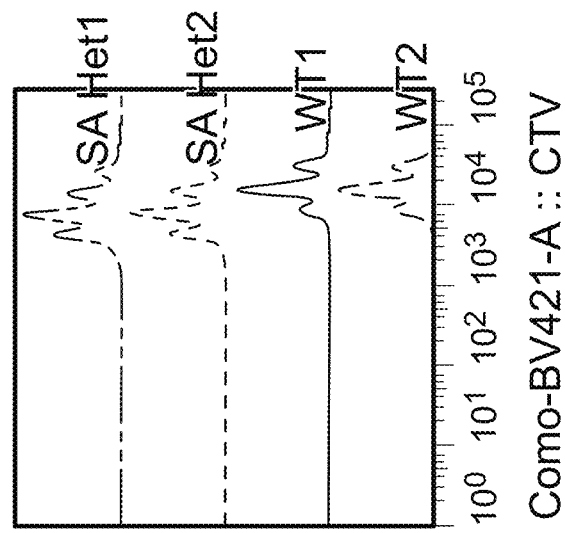
Figure 36A

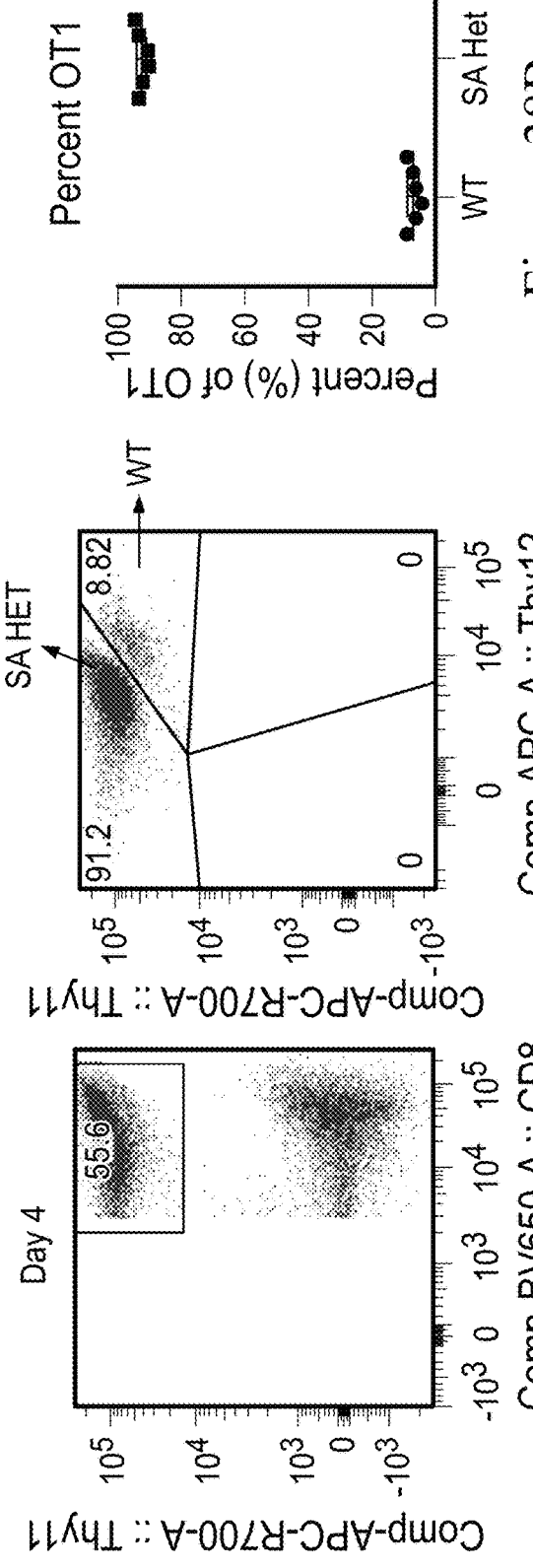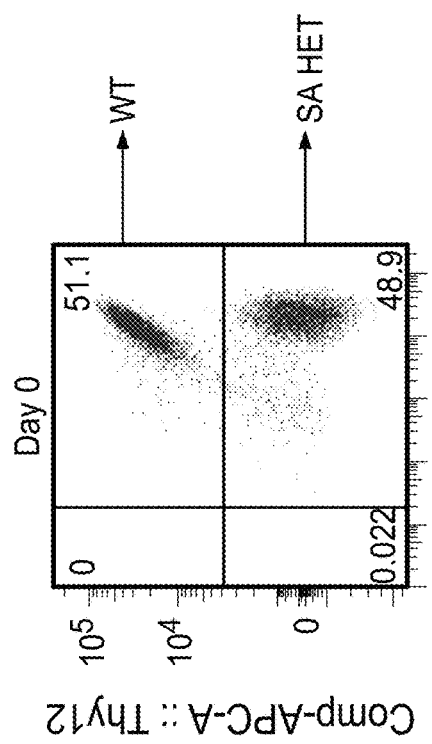
Figure 38A
Figure 38B

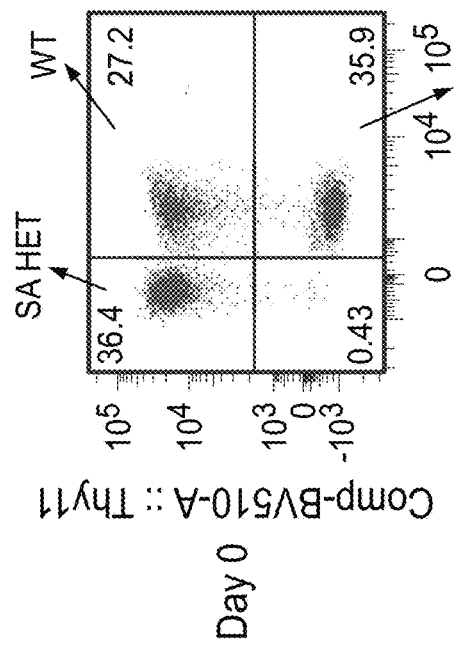
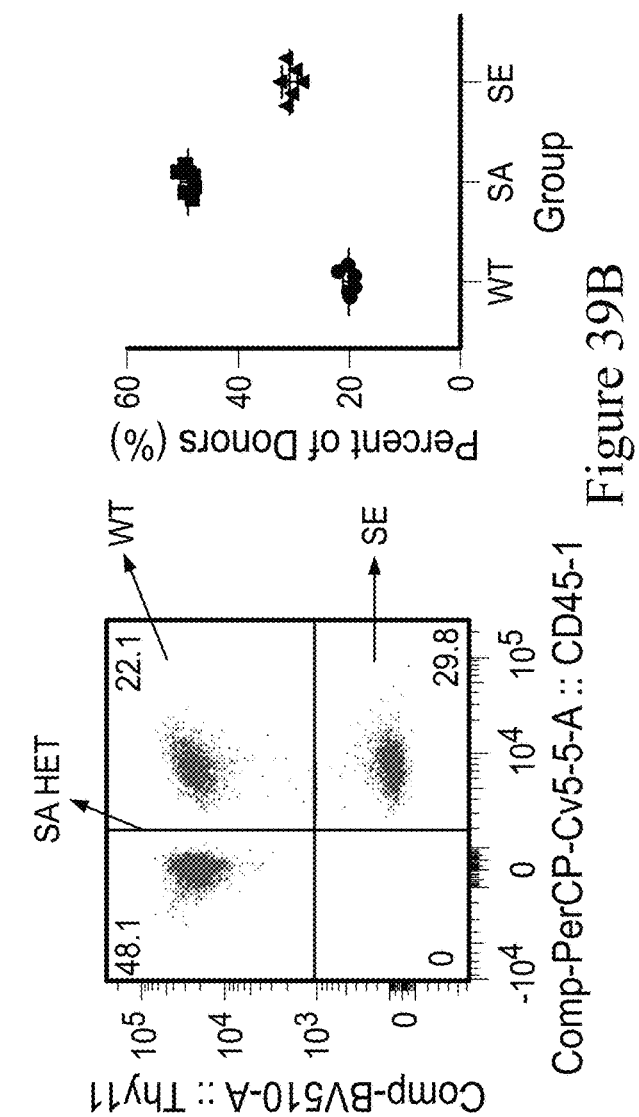
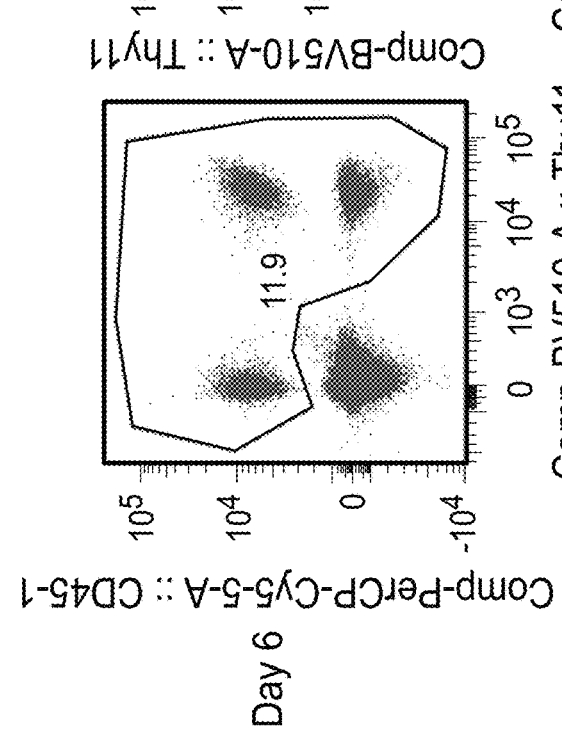
Figure 39A
Figure 39B

Figure 43A
Figure 43B
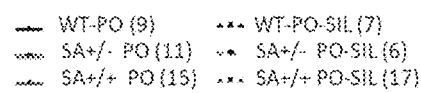
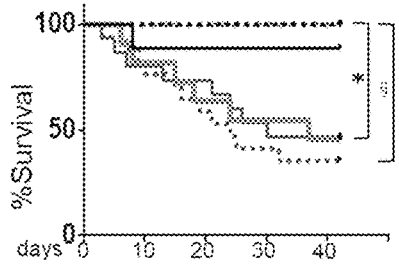
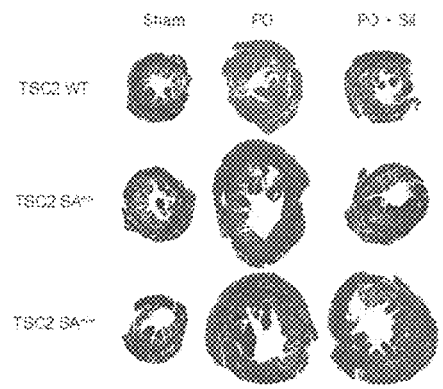
Figure 43C
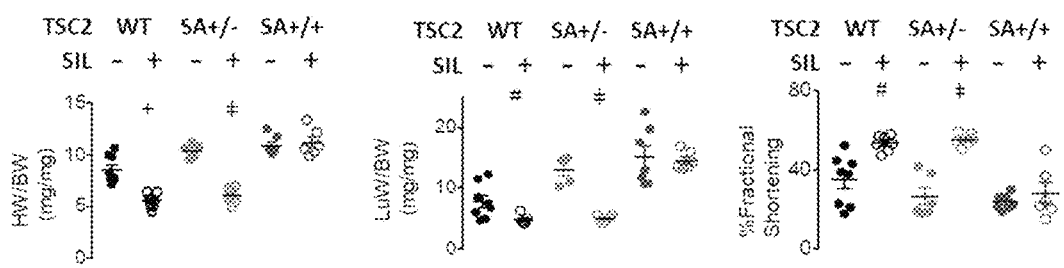
Figure 43D
Figure 43E
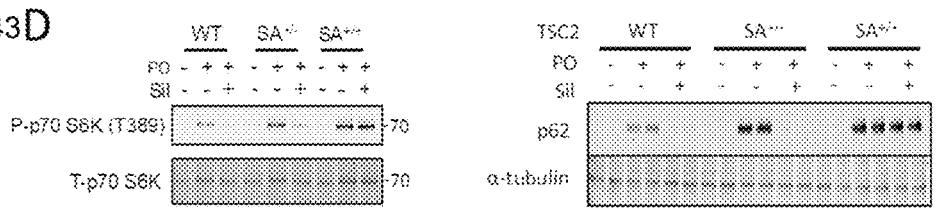
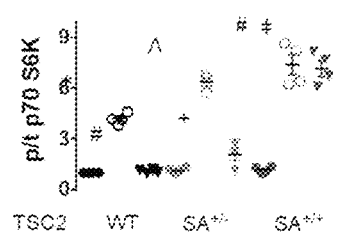

Figure 44 A 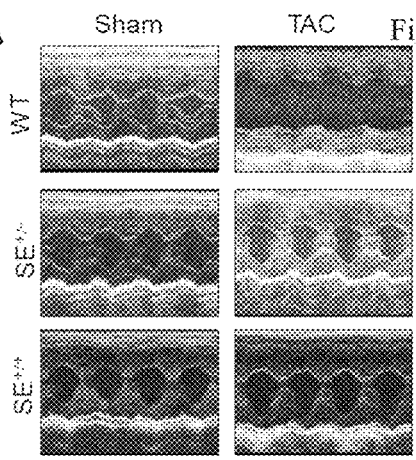 Figure 44 B 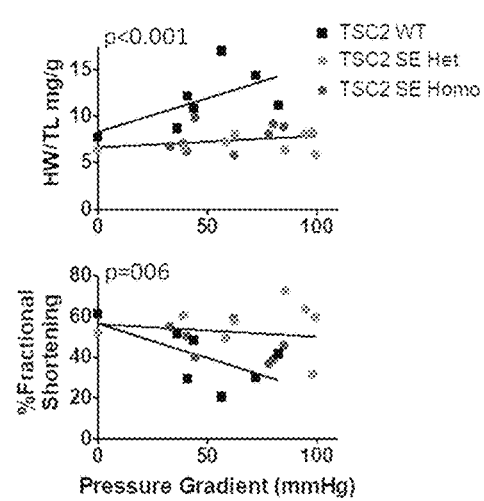
Figure 44 C 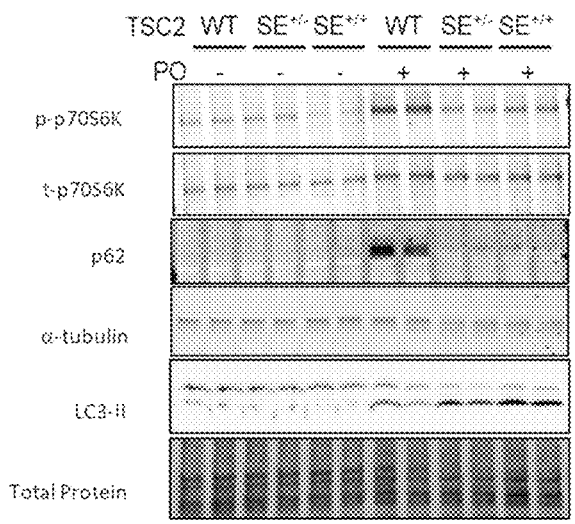 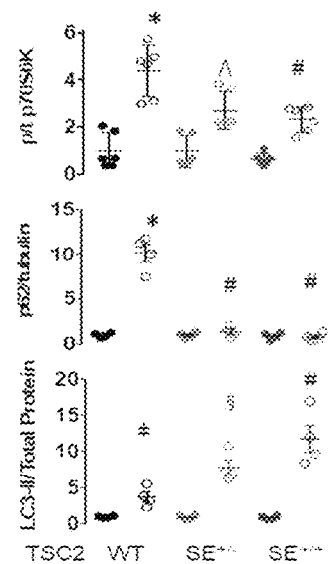

Figure 58 a
Figure 58 b
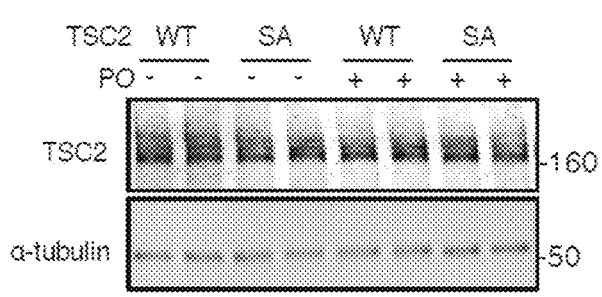
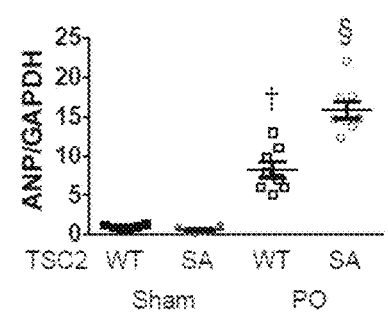

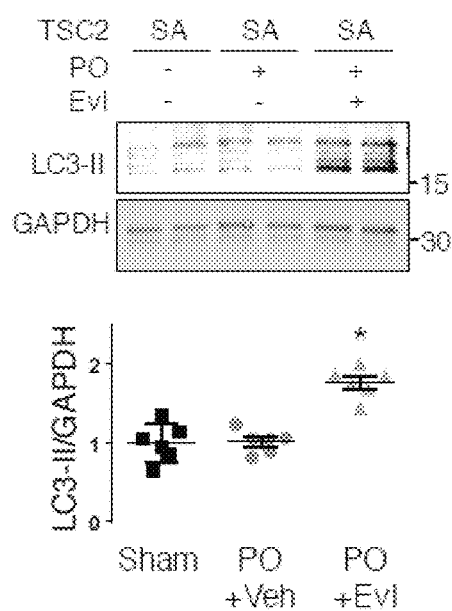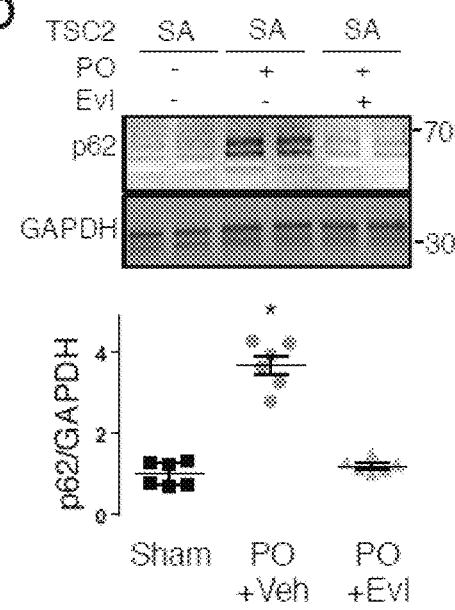
Figure 61 a  Figure 61 b

ENGINEERED TSC2

CROSS-REFERENCE TO RELATED APPLICATIONS

This application is a National Stage application under 35 U.S.C. § 371 of International Application No. PCT/US2018/042142 having an International Filing Date of Jul. 13, 2018, which claims the benefit of U.S. patent application Ser. No. 62/532,909, filed on Jul. 14, 2017. The disclosure of the prior applications are considered part of (and are incorporated by reference in) the disclosure of this application.

GOVERNMENT SUPPORT

This invention was made with government support under RO1HL119012-01, HHSN268201000032C, P01HL107153, HL135827-01, and T32-007227 awarded by the National Institutes of Health. The government has certain rights in the invention.

BACKGROUND

The mechanistic target of rapamycin complex 1 (mTORC1) coordinates biosynthetic and recycling pathways to control cell growth and metabolic homeostasis (1, 2). mTORC1 stimulates anabolic growth and suppresses protein recycling by autophagy. In addition to its role in normal physiology, mTORC1 contributes to disease such as autoimmune disorders, cancer, and heart failure (3), where its hyperactivation is a therapeutic target (4).

Broad suppression, however, risks compromising the normal role of mTORC1, whereas disease-dependent modulation could provide a more targeted approach. Many intrinsic regulators of mTORC1 do so by phosphorylating Tuberous Sclerosis Complex 2 ("TSC2," also referred to as "tuberin"), a GTPase activating protein that modifies Rheb-GTP binding to stimulate or suppress mTORC1 (5).

TSC2 is constitutively inhibitory, as gene deletion and loss-of-function mutations induce mTORC1 hyperactivity, causing tumors and neurological disease. Growth/metabolic stimulation of extra-cellular response kinase (ERK1/2), protein kinase B (Akt), and p90Rsk reduce TSC2 inhibition (6), whereas energy depletion-stimulated AMP-activated protein kinase (AMPK) or glycogen synthase kinase-3β (GSK-3β) enhances TSC2 inhibition of mTORC1 (7). Each kinase targets 2-5 different residues, and in order to block a particular enzyme effect, all the related sites must be silenced (7, 8). Perhaps as a consequence, no models altering such regulation in vivo have been reported.

In immune cells, upon the activation of the T-Cell Receptor (TCR), or corresponding surface receptor that triggers the immune cell to perform a designated task, the mTORC1 signaling pathway is engaged and ultimately determines the outcome of antigen recognition and cellular signaling response to the immune microenvironment. Through genetic gain or loss of function studies of components of the mTORC1 protein complex and its regulating proteins, a prominent role for mTORC1 in T-cell and other immune and inflammatory cell activity, differentiation, and function has been identified.

In T-cells, stimulation of mTORC1 results in enhancement of their effector function. This can involve clonal expansion so that the population size of a specific antigen-receptive cell is amplified to combat a foreign (or perceived to be foreign as in the case of autoimmune disease) body. It can also involve the enhanced synthesis and release of cytokines that coordinate an immune response. Stimulation of mTORC1 also enhances cytotoxic responses controlled by T cells to target foreign cells (e.g. tumor cells, virus, bacteria, other foreign bodies) with the goal of eliminating these cells from the host.

In T-cells, sustained mTORC1 stimulation results in a suppression of immunological effector (cytotoxic) function, termed anergy or exhaustion. It also compromises cell memory (or persistence) of the T-cell to a prior immunological antigen-recognition event and response.

In T-cells, the suppression of mTORC1 activity allows cells to remain in a more undifferentiated state, where they can replicate while still maintaining full differentiation potential. Reducing activity also enhances memory/persistence in effector T-cells and reduces the development of immunological anergy and exhaustion.

mTORC1 stimulation and inhibition play roles in cells that regulate immunological self-recognition, e.g. control over the immune system to recognize self from foreign cells and cell products. This is principally controlled by regulatory T-cells (Treg) that are central for suppressing immune reactions to self-antigens.

mTORC1 stimulation and inhibition also play roles in the modulation of inflammatory cells, such as neutrophils and macrophages. These cells are commonly engaged in autoimmune disease where identification of a self-antigen has resulted in the activation of an immunological response, and local release of cytokines and other factors stimulates inflammatory cells to attack the body and cause disease. The regulation of neutrophil and macrophage function to the corresponding inflammatory response also depends on their ability to control cell growth, metabolism, and protein homeostasis, and mTORC1 plays a central role to these factors and thus the functionality of these inflammatory cells.

SUMMARY

The present disclosure relates generally to engineered TSC2 polypeptides in which the ability of a residue corresponding to a serine residue in a wild-type TSC2 polypeptide to be phosphorylated is altered. In some embodiments, a TSC2 polypeptide is engineered at a serine residue corresponding to S1364 of the human TSC2 polypeptide sequence (SEQ ID NO: 5) such that the ability of the engineered TSC2 polypeptide to be phosphorylated at this position is decreased (e.g., an S1364A substitution). In some embodiments, a TSC2 polypeptide is engineered at a serine residue corresponding to S1364 of the human TSC2 polypeptide sequence (SEQ ID NO: 5) such that the engineered TSC2 acts as if it is constitutively phosphorylated at this position (e.g., an S1364E substitution). Other embodiments of the invention will be described in more detail herein.

In some aspects, provided herein are polypeptides comprising SEQ ID NO: 1 and nucleic acids encoding polypeptides comprising SEQ ID NO: 1. In some embodiments, the nucleic acid comprises the sequence of SEQ ID NO: 3. In some embodiments, a vector includes a nucleic acid sequence encoding a polypeptide comprising SEQ ID NO: 1. In some embodiments, a cell comprises the vector, wherein the nucleic acid encoding the polypeptide comprising SEQ ID NO: 1 is operably linked to a nucleic acid that drives expression of the polypeptide in the cell. In some embodiments, the cell is an immune cell. In some embodiments, the immune cell is a cytotoxic T cell or a chimeric antigen receptor T cell (CAR-T cell). In some embodiments, upon activation, the cytotoxic T cell or CAR-T cell exhibits a higher level of mTORC1 signaling than a reference cytotoxic T cell or a reference CAR-T cell that lacks the vector. In some embodiments, upon activation, the cytotoxic T cell or CAR-T cell expresses one or more cytokines at a higher level than a reference cytotoxic T cell or a reference CAR-T cell that lacks the vector, wherein the one or more cytokines are selected from the group consisting of: interferon gamma, tumor necrosis factor alpha, interleukin 2, and combinations thereof. In some embodiments, the immune cell is a helper T cell. In some embodiments, the helper T cell exhibits a higher level of mTORC1 signaling than a reference helper T cell that lacks the vector. In some embodiments, the immune cell is a regulatory T cell. In some embodiments, upon activation, the regulatory T cell exhibits a higher level of mTORC1 signaling than a reference regulatory T cell that lacks the vector. In some embodiments, the cell further comprises a genetic alteration in which a wild type nucleic acid sequence encoding TSC2 has been rendered inactive.

In some aspects, provided herein are cells comprising a vector, wherein the vector comprises a nucleic acid encoding a mutant TSC2 polypeptide, wherein the mutant TSC2 polypeptide includes an altered amino acid at a position corresponding to S1364 of SEQ ID NO: 5, S1365 of SEQ ID NO: 6, or S1366 of SEQ ID NO: 7. In some embodiments, the altered amino acid comprises a methionine, an alanine, a valine, a leucine, an isoleucine, or a phenylalanine residue. In some embodiments, the mutant TSC2 polypeptide comprises an amino acid sequence as set forth in one of SEQ ID NOs: 1, 8, or 9. In some embodiments, the nucleic acid encoding the mutant TSC2 polypeptide is operably linked to a nucleic acid that drives expression of the mutant TSC2 polypeptide in the cell.

In some aspects, provided herein are polypeptides comprising SEQ ID NO: 2 and nucleic acids encoding polypeptides comprising SEQ ID NO: 2. In some embodiments, the nucleic acid comprises the sequence of SEQ ID NO: 4. In some embodiments, a vector includes a nucleic acid sequence encoding a polypeptide comprising SEQ ID NO: 2. In some embodiments, a cell comprises the vector, wherein the nucleic acid encoding the polypeptide comprising SEQ ID NO: 2 is operably linked to a nucleic acid that drives expression of the polypeptide in the cell. In some embodiments, the cell is an immune cell. In some embodiments, the immune cell is a memory T cell. In some embodiments, upon activation, the memory T cell exhibits a lower level of mTORC1 signaling than a reference memory T cell that lacks the vector. In some embodiments, upon activation, the memory T cell expresses one or more cytokines at a lower level than a reference memory T cell that lacks the vector, wherein the one or more cytokines are selected from the group consisting of: interferon gamma, tumor necrosis factor alpha, interleukin 2, and combinations thereof. In some embodiments, the cell further comprises a genetic alteration in which a wild type nucleic acid sequence encoding TSC2 has been rendered inactive.

In some aspects, provided herein are cells comprising a vector, wherein the vector comprises a nucleic acid encoding a mutant TSC2 polypeptide, wherein the mutant TSC2 polypeptide includes an altered amino acid at a position corresponding to S1364 of SEQ ID NO: 5, S1365 of SEQ ID NO: 6, or S1366 of SEQ ID NO: 7. In some embodiments, the altered amino acid comprises an aspartic acid or a glutamic acid residue. In some embodiments, the mutant TSC2 polypeptide comprises an amino acid sequence as set forth in one of SEQ ID NOs: 2, 10, or 11. In some embodiments, the nucleic acid encoding the mutant TSC2 polypeptide is operably linked to a nucleic acid that drives expression of the mutant TSC2 polypeptide in the cell.

In some aspects, provided herein are methods of treating a disease in a subject in need thereof, comprising administering to a subject an engineered immune cell comprising a vector, wherein the vector comprises a nucleic acid encoding a polypeptide comprising SEQ ID NO: 1 operably linked to a nucleic acid that drives expression of the polypeptide in the T cell, and wherein upon recognizing an antigen associated with the disease, the immune cell exhibits increased activity as compared to a reference immune cell that lacks the vector. In some embodiments, the engineered immune cell is a cytotoxic T cell. In some embodiments, the increased activity of the cytotoxic T cell comprises increased mTORC1 signaling. In some embodiments, the increased activity of the cytotoxic T cell comprises increased expression of one or more cytokines selected from the group consisting of: interferon gamma, tumor necrosis factor alpha, interleukin 2, and combinations thereof. In some embodiments, the engineered immune cell is a helper T cell. In some embodiments, the increased activity of the helper T cell comprises increased mTORC1 signaling. In some embodiments, the disease is cancer, a viral disease, a bacterial disease, fungal disease, or a parasitic disease. In some embodiments, the engineered immune cell is a regulatory T cell. In some embodiments, the increased activity of the regulatory T cell comprises increased mTORC1 signaling. In some embodiments, the disease is asthma, an autoimmune disease, or graft vs. host disease. In some embodiments, the engineered immune cell comprises a genetic alteration in a wild type nucleic acid sequence encoding TSC2, wherein the genetic alteration renders the wild-type TSC2 inactive. In some embodiments, the engineered immune cell is derived from an endogenous immune cell obtained from the subject.

In some aspects, provided herein are methods of generating a persistent T cell in a subject, comprising administering to a subject an engineered immune cell comprising a vector, wherein the vector comprises a nucleic acid encoding a polypeptide comprising SEQ ID NO: 2 operably linked to a nucleic acid that drives expression of the polypeptide in the engineered immune cell, wherein the engineered immune cell recognizes an antigen, wherein upon recognizing the antigen, the engineered immune cell exhibits decreased activity as compared to a reference immune cell that lacks the vector, and wherein upon recognizing the antigen, the engineered immune cell becomes the persistent T cell. In some embodiments, the decreased activity of the engineered immune cell comprises decreased mTORC1 signaling. In some embodiments, the engineered immune cell is derived from an endogenous immune cell obtained from the subject. In some embodiments, the engineered immune cell is a CD8+ T cell, and the persistent T cell is a memory T cell. In some embodiments, the CD8+ T cell is further engineered to express a chimeric antigen receptor or a T cell receptor. In some embodiments, the engineered immune cell is a regulatory T cell, and the persistent T cell is a persistent T regulatory cell.

In some aspects, provided herein are methods of generating a persistent T cell in vitro comprising providing an immune cell, introducing into the immune cell a vector comprising a nucleic acid encoding a polypeptide comprising SEQ ID NO: 2 operably linked to a nucleic acid that drives expression of the polypeptide in the immune cell, thereby generating an engineered immune cell, wherein the engineered immune cell exhibits decreased mTORC1 signaling as compared to a reference immune cell that lacks the vector, contacting the engineered immune cell with an antigen that is recognized by the engineered immune cell, and culturing the engineered immune cell under conditions and for a time sufficient such that the engineered immune cell becomes the persistent T cell. In some embodiments, the immune cell is a CD8+ T cell, and the persistent T cell is a memory T cell. In some embodiments, the CD8+ T cell is further engineered to express a chimeric antigen receptor or a T cell receptor. In some embodiments, the memory T cell is administered to a subject. In some embodiments, the subject exhibits a disease, and administration of the memory T cell to the subject treats the disease. In some embodiments, the disease is cancer, a viral disease, a bacterial disease, fungal disease, or a parasitic disease. In some embodiments, the immune cell is obtained from the subject. In some embodiments, the immune cell is a regulatory T cell, and the persistent T cell is a persistent T regulatory cell. In some embodiments, the persistent T regulatory cell is administered to a subject. In some embodiments, the subject exhibits a disease, and administration of the persistent T regulatory cell to the subject treats the disease. In some embodiments, the disease is asthma, an autoimmune disease, or graft vs. host disease. In some embodiments, the immune cell is obtained from the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 14. Summary table of sequences in FIGS. 15-25.

FIG. 15. Mutant human TSC2 polypeptide sequence with the engineered alanine mutation.

FIG. 16. Mutant human TSC2 polypeptide sequence with the engineered glutamic acid mutation.

FIG. 17. Mutant human TSC2 nucleic acid sequence with the engineered alanine mutation.

FIG. 18. Mutant human TSC2 nucleic acid sequence with the engineered glutamic acid mutation.

FIG. 19. Wild-type human TSC2 polypeptide sequence.

FIG. 20. Wild-type mouse TSC2 polypeptide sequence.

FIG. 21. Wild-type rat TSC2 polypeptide sequence.

FIG. 22. Alanine mutant mouse TSC2polypeptide sequence.

FIG. 23. Alanine mutant rat TSC2 polypeptide sequence.

FIG. 24. Glutamic acid mutant mouse TSC2 polypeptide sequence.

FIG. 25. Glutamic acid mutant rat TSC2 polypeptide sequence.

FIG. 26. Table 1: Baseline heart morphology and function in TSC2 S1365A knock-in or S1365E knock-in mutants versus litter mate controls assessed in adult mice aged 9-12 weeks of age. HW—heart weight; LVW—left ventricular weight; LuW—lung weight. None of the parameters were significantly different between groups.

FIG. 38: Adoptive cell therapy using TSC2SA/OT1 CD8+ T cells better infiltrates B16-OVA melanoma than TSC2WT/ OV1 CD8+ T. A) Equal numbers (5E5 each) of WT and mutant CD8+ T cells were transferred into tumor bearing mice. B) On Day 4 post-ACT, mice were sacrificed to analyze the adoptive transferred T cells in the tumor (tumor infiltrating lymphocytes (TILs)).

FIG. 39: TSC2SA homozygous mutant transgenic (OTI) CD8+ T cells expand more robustly in vivo in response to infection as compared to WT and TSC2 SE homozygous mutant OTI CD8 T cells. A) Approximately equal numbers (2500) of CD8 OT1 cells from all three genotypes were combined into a one sample for IV transfer into WT (Thy1.2/ Thy1.2) hosts. Mice were subsequently infected (i.p.) with Vaccinia-OVA virus (1E6 pfu/mouse) to induce an acute viral infection. B) Cells with the SA TSC2 mutant expanded in vivo between 2-3 fold more as compared to WT and SE TSC2 expressing cells.

FIG. 43. Mice with S1365A knock-in mutation have normal resting cardiac phenotype but worse heart disease and mortality following pressure-overload stress. A) Kaplan-Meier curves for percent survival in mice harboring WT or heterozygote or homozygote knock-in SA mutation (SA+/−, SA+/+ respectively) subjected to pressure overload stress on the heart (PO). Mice are also co-treated with either vehicle control or sildenafil (SIL), the latter to stimulate myocardial protein kinase G activity. Mortality in SA+/− and SA+/+ mice after PO is marked and very different from WT controls. SIL cannot rescue mortality in SA+/+ mice, but does so in SA+/− mice, indicating that the presence of 50% WT allele in the heterozygote allows for phosphorylation of S1365 by PKG and reverses the mortality. B) Masson's trichrome stain of left ventricle cross sections from TSC2 WT, SA$^{+/-}$, SA$^{+/+}$ mice that were subjected to sham or PO and treated with vehicle or Sil. Data shows marked worse heart enlargement and hypertrophy following PO in SA+/− and SA+/+ mice. This is reversed by SIL in SA+/− mice. C) Heart (HW) and lung (LuW) weights, and fractional shortening for same experiments show near complete suppression of hypertrophy and lung congestion with SIL-treatment in WT and SA+/− but no effect in SA+/+− PO hearts. +<0.01 vs. WT vehicle, #<0.0001 vs. WT vehicle, ‡<0.0001 vs. SA$^{+/-}$ vehicle. D) p/t p70S6K increases after PO in SA+/+>SA+/−>WT, and is reduced by SIL only in WT and SA$^{+/-}$ mice. E) Disparities in p62 expression between models also show counteractive efficacy of SIL only in WT and SA$^{+/-}$ mice. *<0.0001 vs. WT Sham, ^<0.001 vs. WT PO, #<0.0001 vs. WT PO, +<0.0001 vs. SA$^{+/-}$ PO, ‡<0.0001 vs. SA$^{+/-}$ Sil.

FIG. 44. Mice with S1365E Knock-in mutation are protected against pressure-overload induced hypertrophy and cardiac dysfunction. A and B) Echocardiographs (A) of mice expressing SE$^{+/-}$ or SE$^{+/+}$ KI mutation subjected to 6-weeks of PO display reduced ventricular hypertrophy (B, top) and improved fractional shortening (B, bottom) despite similar corresponding increases in pressure load, each measured at time of terminal study. C) p/t70S6K, p62/tubulin, and LC3-II/total protein for same experiments. Expression of the SE TSC2 mutation reduced growth signaling (p-p70S6K) and enhanced autophagy signaling (↓p62 and ↑LC3-II). *<0.0001 vs. WT Sham, ‡<0.05 vs. WT Sham, ^<0.01 vs. WT PO, §<0.001 vs. WT PO, #<0.0001 vs. WT PO.

FIG. 58. A) Immunoblot of TSC2 protein from SA and WT (littermate controls) both in sham and PO treated groups. There is no difference in expression levels among these groups or conditions. B) Gene expression of A-type natriuretic peptide (ANP, nppa) and GAPDH from SA and WT mouse hearts measured at rest and after PO. N=8/group; p<0.0001 by 1-way ANOVA; †p<0.0001 vs. Sham, § p<0.0001 vs. PO by Tukey multiple comparisons test.

FIG. 61. TSC2 SA/SA mice were exposed to PO with vehicle or Everolimus (Evl) co-treatment. A) LC3-II expression increased in SA-TAC hearts treated with Evl. B) p62 expression increased with SA-TAC, consistent with reduced autophagy, but was returned to sham control levels by Evl-co-therapy. N=6/group. P<0.0001 by 1-way ANOVA, *p<0.0001 versus other two groups by post-hoc Tukey test.

DETAILED DESCRIPTION

Figure 1A:
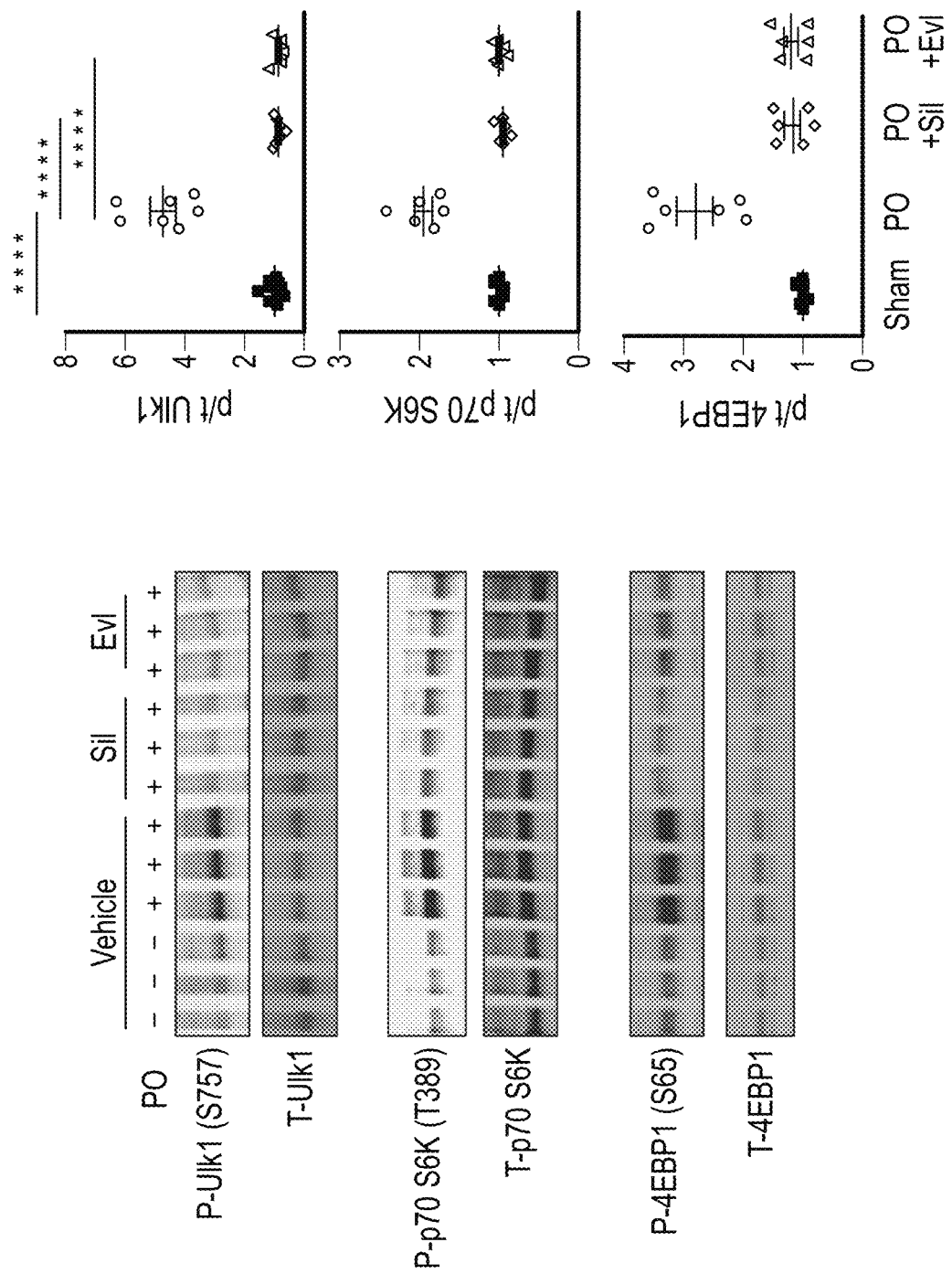
FIG. 1. A) Phosphorylated/total Ulk1, p70 S6K and 4EBP1 from mice +/− sustained pressure-overload stress (PO) treated with vehicle, sildenafil (Sil, 200 mg/kg/day) or everolimus (Evl, 10 mg/kg/day) starting 1 week post-PO (n=6/group). B) LC3-II and p62 protein changes show increased autophagy with both therapies. C) LC3-II increase with bafilomycin A (BFA) increases further with cGMP; the effect is blocked by DT3. D) Autophagic flux in myocytes stimulated with ET-1 +/− cGMP or DT3. Flux increase is indicated by red/yellow puncta. E) Myocyte stress (Nppb) stimulated by ET-1 is blocked by SIL but not if Ulk1 is genetically silenced. **: $p<0.0001$; *: $p<0.001$; **: $p<0.01$; *: $p<0.05$ by Tukey multiple comparisons test following significance ($p<0.001$ or lower) deduced by 1-way ANOVA.

As used herein, the word "a" before a noun represents one or more of the particular noun. For example, the phrase "a genetic alteration" encompasses "one or more genetic alterations."

As used herein, the term "about" means approximately, in the region of, roughly, or around. When used in conjunction with a numerical range, the term "about" modifies that range by extending the boundaries above and below the numerical values set forth. In general, the term "about" is used herein to modify a numerical value above and below the stated value by a variance of 10%.

As used herein, the term "subject" means a vertebrate, including any member of the class mammalia, including humans, domestic and farm animals, and zoo, sports or pet animals, such as mouse, rabbit, pig, sheep, goat, cattle, horse (e.g., race horse), and higher primates. In some embodiments, the subject is a human. In some embodiments, the subject has a disease. In some embodiments, the subject has cancer. In some embodiments, the subject has a viral disease. In some embodiments, the subject has a bacterial disease. In some embodiments, the subject has a fungal disease. In some embodiments, the subject has a parasitic disease. In some embodiments, the subject has asthma. In some embodiments, the subject has an autoimmune disease. In some embodiments, the subject has graft vs. host disease.

Engineered TSC2 Polypeptides that Exhibit Decreased Ability to be Phosphorylated Provided herein are engineered TSC2 polypeptides that cannot be phosphorylated at a residue that has been substituted for a serine residue, or that cannot be phosphorylated to the extent that a non-engineered TSC2 polypeptide having the serine residue can be phosphorylated. For example, provided herein are engineered TSC2 polypeptides having an amino acid at a residue corresponding to the serine residue at position S1364 of the human TSC2 polypeptide sequence (SEQ ID NO: 5). In some embodiments, the serine residue at position S1364 of SEQ ID NO: 5, or a serine residue in a TSC2 polypeptide that corresponds to the serine residue at position S1364 of SEQ ID NO: 5, is substituted with an amino acid with an aliphatic side chain. In some embodiments, the serine residue at position S1364 of SEQ ID NO: 5, or a serine residue in a polypeptide that corresponds to the serine residue at position S1364 of SEQ ID NO: 5, is substituted with a methionine residue, an alanine residue, a valine residue, a leucine residue, an isoleucine residue, or a phenylalanine residue. In some embodiments, an engineered TSC2 polypeptide having an alanine substitution at the serine residue at position S1364 of the human TSC2 polypeptide sequence is provided (e.g., SEQ ID NO: 1). In some embodiments, engineered TSC2 polypeptides disclosed herein cannot be phosphorylated to the extent that a non-engineered TSC2 polypeptide having the serine residue can be phosphorylated. In some embodiments, engineered TSC2 polypeptides disclosed herein are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less than a non-engineered TSC2 polypeptide having the serine residue. In some embodiments, engineered TSC2 polypeptides disclosed herein cannot be phosphorylated.

Provided herein are also engineered TSC2 polypeptides having an amino acid substitution at a residue corresponding to the serine residue at position S1365 of the mouse TSC2 polypeptide sequence (SEQ ID NO: 6) such that engineered TSC2 polypeptides cannot be phosphorylated at that residue, or cannot be phosphorylated to the extent that a non-engineered TSC2 polypeptide having the serine residue can be phosphorylated. In some embodiments, the serine residue at position S1365 of SEQ ID NO: 6, or a serine residue in a TSC2 polypeptide that corresponds to the serine residue at position S1365 of SEQ ID NO: 6, is substituted with an amino acid with an aliphatic side chain. In some embodiments, the serine residue at position S1365 of SEQ ID NO: 6, or a serine residue in a polypeptide that corresponds to the serine residue at position S1365 of SEQ ID NO: 6, is substituted with a methionine residue, an alanine residue, a valine residue, a leucine residue, an isoleucine residue, or a phenylalanine residue. In some embodiments, an engineered TSC2 polypeptide having an alanine substitution at the serine residue at position S1365 of the mouse TSC2 polypeptide sequence is provided (e.g., SEQ ID NO: 8). In some embodiments, engineered TSC2 polypeptides disclosed herein cannot be phosphorylated to the extent that a non-engineered TSC2 polypeptide having the serine residue can be phosphorylated. In some embodiments, engineered TSC2 polypeptides disclosed herein are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less than a non-engineered TSC2 polypeptide having the serine residue. In some embodiments, engineered TSC2 polypeptides disclosed herein cannot be phosphorylated.

Provided herein are also engineered TSC2 polypeptides having an amino acid substitution at a residue corresponding to the serine residue at position S1366 of the rat TSC2 polypeptide sequence (SEQ ID NO: 7) such that engineered TSC2 polypeptides cannot be phosphorylated at that residue, or cannot be phosphorylated to the extent that a non-engineered TSC2 polypeptide having the serine residue can be phosphorylated. In some embodiments, the serine residue at position S1366 of SEQ ID NO: 7, or a serine residue in a TSC2 polypeptide that corresponds to the serine residue at position S1366 of SEQ ID NO: 7, is substituted with an amino acid with an aliphatic side chain. In some embodiments, the serine residue at position S1366 of SEQ ID NO: 7, or a serine residue in a polypeptide that corresponds to the serine residue at position S1366 of SEQ ID NO: 7, is substituted with a methionine residue, an alanine residue, a valine residue, a leucine residue, an isoleucine residue, or a phenylalanine residue. In some embodiments, an engineered TSC2 polypeptide having an alanine substitution at the serine residue at position S1366 of the mouse TSC2 polypeptide sequence is provided (SEQ ID NO: 9). In some embodiments, engineered TSC2 polypeptides disclosed herein cannot be phosphorylated to the extent that a non-engineered TSC2 polypeptide having the serine residue can be phosphorylated. In some embodiments, engineered TSC2 polypeptides disclosed herein are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less than a non-engineered TSC2 polypeptide having the serine. In some embodiments, engineered TSC2 polypeptides disclosed herein cannot be phosphorylated.

Provided herein are also vectors that include nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated, and cells having such vectors. A vector that includes nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated can be any appropriate type of vector. Examples of vectors include, without limitation, plasmids (e.g., expression plasmids) and vectors (e.g., viral vectors such as lentiviral vectors, retroviral vectors, adenovirus vectors, and adeno-associated virus vectors). In some cases, a vector that includes nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated can be a lentiviral vector. A vector that includes nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated also can include one or more addition features (e.g., one or more additional features to modulate polypeptide expression). Examples of features that can modulate polypeptide expression include, without limitation, an origin of replication, a promoter, a polyA tail, a terminator, and a microRNA response element. In some cases, when a vector described herein also includes a promoter, the promoter can operably linked to a nucleic acid sequence that encodes polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated (e.g., such that the promoter can drive expression of the nucleic acid sequence). A promoter can be any appropriate promoter. In some cases, a promoter can be constitutive promoter. In some cases, a promoter can be a viral promoter. In some cases, a promoter can be an inducible promoter. In some cases, a promoter can be a cell-specific and/or tissue-specific promoter. Examples of promoters that can be used to drive expression of nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated include, without limitation, CMV. In some embodiments, a promoter can be as described elsewhere (see, e.g., Morgan et al., 2016 *Biomedicines*. 4:9).

In some embodiments, cells having vectors that include nucleic acid sequences that encode engineered TSC2 polypeptides that cannot be phosphorylated at a position that corresponds to a wild-type serine residue in any of the polypeptides described herein (or that cannot be phosphorylated to the extent that a TSC2 polypeptide having a serine residue at these positions can be phosphorylated) do not express endogenous, wild-type TSC2. For example, the nucleic acid sequence encoding wild-type TSC2 can be modified by any of a variety of genetic manipulation techniques known in the art including, but not limited to, CRISPR-based methods, TALEN-based methods, and other genetic targeting or recombination methods (see, e.g., Roth et al., 2018 *Nature* doi: 10.1038/s41586-018-0326-5).

TSC2 polypeptides disclosed herein can be engineered at S1364 of the human TSC2 polypeptide sequence (SEQ ID NO: 5), S1365 of the mouse TSC2 polypeptide sequence (SEQ ID NO: 6), or S1366 of the rat TSC2 polypeptide sequence (SEQ ID No: 7) with any mutation or modification that results in TSC2 being unable to be phosphorylated (or that results in a decreased ability of TSC2 to be phosphorylated) at the respective positions in human (S1364), mouse (S1365), or rat (S1366). In some cases, TSC2 polypeptides from other species (e.g., monkey) can be engineered with any mutation or modification (e.g., a residue corresponding to human S1364, mouse S1365, and/or rat S1366) that results in TSC2 being unable to be phosphorylated (or that results in a decreased ability of TSC2 to be phosphorylated).

Provided herein are also nucleic acids encoding engineered TSC2 polypeptides that cannot be phosphorylated at position corresponding to a serine residue in the wild-type TSC2 polypeptide sequence, or that cannot be phosphorylated to the extent that a non-engineered TSC2 polypeptide having the serine residue can be phosphorylated. For example, provided herein are nucleic acids encoding engineered TSC2 polypeptides having an amino acid substitution at a residue corresponding to the serine residue at position S1364 of the human TSC2 polypeptide sequence (SEQ ID NO: 5), position S1365 of the mouse TSC2 polypeptide sequence (SEQ ID NO: 6), or position S1366 of the rat TSC2 polypeptide sequence (SEQ ID NO: 7). In some embodiments, a nucleic acid sequence encoding an engineered TSC2 polypeptide having an amino acid substitution at the serine residue at position S1364 of the human TSC2 polypeptide sequence is provided (e.g., the nucleic acid sequence of SEQ ID NO: 3). In some embodiments, nucleic acids provided herein encode engineered TSC2 polypeptides in which the serine residue at position S1364 of SEQ ID NO: 5, or position S1365 of SEQ ID NO: 6, or position 1366 of SEQ ID NO: 7, or a serine residue in a TSC2 polypeptide that corresponds to the serine residues at these positions, are substituted with an amino acid with an aliphatic side chain. In some embodiments, nucleic acids provided herein encode engineered TSC2 polypeptides in which the serine residue at position S1364 of SEQ ID NO: 5, or position S1365 of SEQ ID NO: 6, or position 1366 of SEQ ID NO: 7, or a serine residue in a TSC2 polypeptide that corresponds to the serine residues at these positions, are substituted with a methionine residue, an alanine residue, a valine residue, a leucine residue, an isoleucine residue, or a phenylalanine residue. In some embodiments, nucleic acids provided herein include the genetic codons of GCT, GCC, GCA, or GCG at positions that are translated to the amino acid alanine at position S1364 of the human TSC2 polypeptide sequence (SEQ ID NO: 5), or position S1365 of the mouse TSC2 polypeptide sequence (SEQ ID NO: 6), or position S1366 of the rat TSC2 polypeptide sequence (SEQ ID NO: 7). In some embodiments, nucleic acids provided herein include the genetic codons of GTT, GTC, GTA, or GTG at positions that are translated to the amino acid valine at position S1364 of the human TSC2 polypeptide sequence (SEQ ID NO: 5), or position S1365 of the mouse TSC2 polypeptide sequence (SEQ ID NO: 6), or position S1366 of the rat TSC2 polypeptide sequence (SEQ ID NO: 7). In some embodiments, nucleic acids provided herein encode engineered TSC2 polypeptides that cannot be phosphorylated to the extent that a non-engineered TSC2 polypeptide having the serine residue can be phosphorylated. In some embodiments, nucleic acids disclosed herein encode engineered TSC2 polypeptides that are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less than a non-engineered TSC2 polypeptide having the serine residue can be phosphorylated. In some embodiments, nucleic acids disclosed herein encode engineered TSC2 polypeptides that cannot be phosphorylated.

Methods of Treating Disease Using Cells Having Engineered TSC2 Polypeptides that Exhibit Reduced Ability to be Phosphorylated Cells Having Engineered TSC2 Polypeptides that Exhibit Reduced Ability to be Phosphorylated Provided herein are cells expressing engineered TSC2 polypeptides that cannot be phosphorylated at position corresponding to a serine residue in the wild-type TSC2 polypeptide sequence, or that cannot be phosphorylated to the full extent as that of a wild-type TSC2 polypeptide having the serine residue. For example, provided herein are cells expressing engineered TSC2 polypeptides having an amino acid substitution at a position corresponding to the serine residue at position S1364 of the human TSC2 polypeptide sequence (SEQ ID NO: 5). In some embodiments, cells provided herein express engineered TSC2 polypeptides in which the serine residue at position S1364 of SEQ ID NO: 5, or a serine residue in a TSC2 polypeptide that corresponds to the serine residue at position S1364 of SEQ ID NO: 5, is substituted with an amino acid with an aliphatic side chain. In some embodiments, cells provided herein express engineered TSC2 polypeptides in which the serine residue at position S1364 of SEQ ID NO: 5, or a serine residue in a polypeptide that corresponds to the serine residue at position S1364 of SEQ ID NO: 5, is substituted with a methionine residue, an alanine residue, a valine residue, a leucine residue, an isoleucine residue, or a phenylalanine residue. In some embodiments, cells disclosed herein express an engineered TSC2 polypeptide (e.g., SEQ ID NO: 1) having an amino acid substitution at the serine residue at position S1364 of the human TSC2 polypeptide sequence. In some embodiments, cells provided herein express engineered TSC2 polypeptides that cannot be phosphorylated to the extent that a non-engineered TSC2 polypeptide having the serine residue can be phosphorylated. In some embodiments, cells provided herein express engineered TSC2 polypeptides that are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less that a non-engineered TSC2 polypeptide having the serine residue. In some embodiments, cells provided herein express engineered TSC2 polypeptides that cannot be phosphorylated.

Provided herein are also cells expressing engineered TSC2 polypeptides having an amino acid substitution at a residue corresponding to the serine residue at position S1365 of the mouse TSC2 polypeptide sequence (SEQ ID NO: 6) such that engineered TSC2 polypeptides cannot be phosphorylated at the engineered residue, or cannot be phosphorylated to the extent that a non-engineered TSC2 polypeptide having the serine residue can be phosphorylated. In some embodiments, cells provided herein express an engineered TSC2 polypeptide in which the serine residue at position S1365 of SEQ ID NO: 6, or a serine residue in a TSC2 polypeptide that corresponds to the serine residue at position S1365 of SEQ ID NO: 6, is substituted with an amino acid with an aliphatic side chain. In some embodiments, cells provided herein express an engineered TSC2 polypeptide in which the serine residue at position S1365 of SEQ ID NO: 6, or a serine residue in a polypeptide that corresponds to the serine residue at position S1365 of SEQ ID NO: 6, is substituted with a methionine residue, an alanine residue, a valine residue, a leucine residue, an isoleucine residue, or a phenylalanine residue. In some embodiments, cells provided herein express an engineered TSC2 polypeptide (e.g., SEQ ID NO: 8) having an amino acid substitution at the serine residue at position S1365 of the mouse TSC2 polypeptide sequence. In some embodiments, cells provided herein express engineered TSC2 polypeptides that cannot be phosphorylated to the extent that a non-engineered TSC2 polypeptide having the serine residue can be phosphorylated. In some embodiments, cells provided herein express engineered TSC2 polypeptides that are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less that a non-engineered TSC2 polypeptide having the serine residue. In some embodiments, cells provided herein express engineered TSC2 polypeptides that cannot be phosphorylated.

Provided herein are also cells expressing an engineered TSC2 polypeptide having an amino acid substitution at a residue corresponding to the serine residue at position S1366 of the rat TSC2 polypeptide sequence (SEQ ID NO: 7) such that engineered TSC2 polypeptides cannot be phosphorylated at the engineered residue, or cannot be phosphorylated to the extent that a non-engineered TSC2 polypeptide having the serine residue can be phosphorylated. In some embodiments, cells provided herein express an engineered TSC2 polypeptide in which the serine residue at position S1366 of SEQ ID NO: 7, or a serine residue in a TSC2 polypeptide that corresponds to the serine residue at position S1366 of SEQ ID NO: 7, is substituted with an amino acid with an aliphatic side chain. In some embodiments, cells provided herein express an engineered TSC2 polypeptide in which the serine residue at position S1366 of SEQ ID NO: 7, or a serine residue in a polypeptide that corresponds to the serine residue at position S1366 of SEQ ID NO: 7, is substituted with a methionine residue, an alanine residue, a valine residue, a leucine residue, an isoleucine residue, or a phenylalanine residue. In some embodiments, cells provided herein express an engineered TSC2 polypeptide (e.g., SEQ ID NO: 9) having an amino acid substitution at the serine residue at position S1366 of the rat TSC2 polypeptide sequence. In some embodiments, cells provided herein express engineered TSC2 polypeptides that cannot be phosphorylated to the extent that a non-engineered TSC2 polypeptide having the serine residue can be phosphorylated. In some embodiments, cells provided herein express engineered TSC2 polypeptides that are phosphorylated to an extent that is about 5%, 10%, 15%, 20%, 25%, 30%, 35%, 40%, 45%, 50%, 55%, 60%, 65%, 70%, 75%, 80%, 85%, 90%, 95% or less that a non-engineered TSC2 polypeptide having the serine residue. In some embodiments, cells provided herein express engineered TSC2 polypeptides that cannot be phosphorylated.

Provided herein are also cells harboring vectors that include nucleic acid sequences that encode polypeptides that cannot be phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be phosphorylated, and cells having such vectors. A vector that includes nucleic acid sequences that encode polypeptides that cannot be phosphorylated at position corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the extent that a TSC2 polypeptide having a serine residue at these positions can be introduced into a cell using any appropriate methods and/or techniques. A vector can be introduced into a cell in a transient manner (e.g., maintained as a vector) or in a stable manner (e.g., integrated into the genome). Examples of methods and/or techniques that can be used to introduce one or more vectors into a cell include, without limitation, transfection, transduction, electroporation, and infection. In some embodiments, nucleic acids encoding engineered TSC2 polypeptides are operably linked to nucleic acids that drive expression of the engineered TSC2 polypeptides in the vectors (e.g., promoter sequences).

In some embodiments, cells having engineered TSC2 polypeptides that cannot be phosphorylated, or that cannot be phosphorylated to the extent of a wild-type TSC2 polypeptide can have, or can express, endogenous TSC2 proteins. For example, a cell having an engineered TSC2 polypeptide also can have an endogenous wild-type nucleic acid sequence encoding a wild-type TSC2 polypeptide. In some embodiments of cells having (e.g., expressing) both: 1) engineered TSC2 polypeptides that cannot be phosphorylated, or that cannot be phosphorylated to the extent of a wild-type TSC2 polypeptide, and 2) an endogenous TSC2 protein, the cells exhibit the same or similar activity as a corresponding cell lacking (e.g., not expressing) the endogenous TSC2 protein.

In some embodiments, cells having engineered TSC2 polypeptides that cannot be phosphorylated, or that cannot be phosphorylated to the extent of a wild-type TSC2 polypeptide, do not have, or do not express, endogenous, wild-type TSC2 proteins. For example, a cell having an engineered TSC2 polypeptide can have a genetic alteration in which a wild-type nucleic acid sequence encoding the TSC2 polypeptide has been rendered inactive. In some embodiments, the nucleic acid sequence encoding wild-type TSC2 can be modified by any of a variety of genetic manipulation techniques known in the art including, but not limited to, CRISPR-based methods, TALEN-based methods, and other genetic targeting or recombination methods (see, e.g., Roth et al., 2018 Nature doi: 10.1038/s41586-018-0326-5). In some embodiments, a wild-type nucleic acid sequence encoding a TSC2 polypeptide can be rendered inactive by removing, replacing, or mutating a nucleic acid sequence that contributes to expression of the TSC2 polypeptide including, but not limited to, a promoter sequence, an enhancer sequence, a coding sequence of a transcription factor that regulates expression of TSC2, the coding sequence of the TSC2 polypeptide itself, or combinations thereof. In some embodiments, a wild-type nucleic acid sequence encoding a TSC2 polypeptide can be rendered inactive via a frameshift caused by one or more modifications or mutations in the nucleic acid sequence encoding the TSC2 polypeptide.

In some embodiments, cells that can be engineered to include an engineered TSC2 polypeptide that cannot be phosphorylated at a position that corresponds to a wild-type serine residue (or that cannot be phosphorylated to the extent that a TSC2 polypeptide having a serine residue at these positions can be phosphorylated) include immune cells. For example, the immune cells can be CD4+ T cells, CD8+ T cells, Natural Killer cells (NK cells), macrophages, neutrophils, regulatory T cells (Tregs), helper T cells, or any other immune cells and/or inflammatory cells known in the art.

CD8+ T cells have been investigated in T cell-based therapies for their role in cellular immune responses. Tumor-specific CD8+ T cells have been found in patients with hematologic malignancies and solid tumors and within the pool of tumor-infiltrating lymphocytes. (Zanetti M, Tapping CD4 T cells for cancer immunotherapy: the choice of personalized genomics, J Immunol. 2015 Mar. 1; 194(5): 2049-56). The role of CD8+ T cells has been demonstrated in mouse models of cancer. The presence of CD8+ T cells in tumors has also been shown in human. It has also been shown that the engagement of checkpoint receptors on activated CD8+ T cells represents a major mechanism of tumor-induced immunosuppression. In addition, a high density of CD8+ T cells has been found to be associated with longer patient survival when tumors display high densities of tertiary lymphoid structures in lung, colorectal, and renal cell cancers. (Michele W. L. Teng et al, From mice to humans: developments in cancer immunoediting, J Clin Invest. 2015 September; 125(9):3338-46.)

In some embodiments, CD8+ effector T cells can be generated by stimulating the splenocytes and expanding them in effector promoting conditions with IL-2. Strong IL-2 signaling preferentially skews CD8+ T cells to differentiate into effector T cells. After some time, CD8+ cultures can be processed to remove non-viable cells and assessed for effector function by re-stimulating viable cells with PMA and Ionomycin along with a Golgi blocker to capture cytokines within the cells for later flow cytometry analysis. Cells can then be processed and stained to assess cytokine function. High expression of Interferon gamma (IFNg), tumor necrosis factor alpha (TNFa), and Interleukin-2 (IL-2) are indicators of CD8+ effector T cells.

CD4+ T cells are also known to play a role in adaptive immune responses. Various types of CD4+ T cells contribute to anti-tumor immunity through their diverse functions. For example, CD4+ T cells facilitate B cells with isotype switching and affinity maturation. CD4+ T cells are also involved in facilitating the activation and expansion of CD8+ T cells, and the generation and maintenance of memory CD8+ T cells. CD4+ T cells are further involved in tumor protection. For example, activated CD4+ T cells have been found to induce delayed-type hypersensitivity—like reactions and attract inflammatory cells including macrophages, granulocytes, eosinophils, and NK cells in or around the tumor.

A T regulatory cell or "Treg cell" refers to a cell that can modulate a T cell response. Regulatory T cells are known for their ability to downregulate the function of other T cells. (Zanetti M, Tapping CD4 T cells for cancer immunotherapy: the choice of personalized genomics, J Immunol. 2015 Mar. 1; 194(5):2049-56). Treg cells express the transcription factor Foxp3, which is not unregulated upon T cell activation and discriminates Tregs from activated effector cells. Tregs are identified by the cell surface markers CD25, CTLA4, and GITR. Several Treg subsets have been identified that have the ability to inhibit autoimmune and chronic inflammatory responses and to maintain immune tolerance in tumor-bearing hosts. These subsets include interleukin 10- (IL-10-) secreting T regulatory type 1 (Tr1) cells, transforming growth factor-β- (TGF-(β-) secreting T helper type 3 (Th3) cells, and "natural" CD4+/CD25+ Tregs (Trn).

In some embodiments, an immune cell that is engineered to include an engineered TSC2 polypeptide can be a cytotoxic T cell. In some embodiments, a cytotoxic T cell can be engineered to express a chimeric antigen receptor ("CAR") or a T cell receptor ("TCR").

In some embodiments, an immune cell that is engineered to include an engineered TSC2 polypeptide can be a B cell. B cells are known to be involved in immunune responses and T cell activation. For example, B cells can act as antigen-specific antigen presenting cells. A signal through binding of an antigen to membrane Ig can enhance B cell antigen presentation and T-cell-dependent B cell activation. As a result of helper T cell recognition of antigen on the B cell surface, the T cell becomes activated and then activates the B cell.

In some embodiments, an immune cell that is engineered to include an engineered TSC2 polypeptide can be expanded (e.g., clonally expanded). For example, an immune cell that is engineered to include an engineered TSC2 polypeptide can be clonally expanded ex vivo (e.g., for use in an adoptive cell therapy). In cases where an immune cell that is engineered to include an engineered TSC2 polypeptide is used in an adoptive cell therapy, the adoptive cell therapy can be any appropriate adoptive cell therapy. Examples of adoptive cell therapies include, without limitation, dendritic cell therapy and synthetic dendritic cell therapy. In some cases, adoptive cell therapy can include the extraction of tumor infiltrating lymphocytes.

In some embodiments, increased mTORC1 signaling can be determined by any of a variety of techniques or methods known in the art. For example, mTORC1 signaling typically results in increased growth, decreased autophagy, and phosphorylation of Ulk1 (Unc-51-like kinase-1), p70S6K, and 4EBP1 (eIF4E binding protein-1).

Cancers

In some embodiments, compositions and methods provided herein can be used to treat cancer. For example, an immune cell that is engineered to include an engineered TSC2 polypeptide (e.g., expressed from a vector introduced into the cell, which vector includes a nucleic acid sequence that encodes the engineered TSC2 polypeptide) that cannot be phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), or that cannot be phosphorylated to the full extent as that of a wild-type TSC2 polypeptide, can be administered to a subject having cancer (e.g., in an adoptive cell therapy) such that the cancer is treated. In some embodiments, the engineered immune cell administered to the subject does not have or express an endogenous, wild type TSC polypeptide. In some embodiments, the engineered immune cell administered to the subject does have or express an endogenous, wild type TSC2 polypeptide. In some embodiments, a CD8+ T effector cell that recognizes a cancer cell (e.g., via a specific antigen on the cancer cell surface) can be engineered to include a TSC2 polypeptide that cannot be phosphorylated, or that cannot be phosphorylated to the full extent as that of a wild-type TSC2 polypeptide, which CD8+ T effector cell is then administered to a subject that has such a cancer cell. In some embodiments, a CD8+ T effector cell that is engineered to include a TSC2 polypeptide that cannot be phosphorylated, or that cannot be phosphorylated to the full extent as that of a wild-type TSC2 polypeptide, is also engineered to express a chimeric antigen receptor or a T cell receptor. In some embodiments, an immune cell that is engineered to include an engineered TSC2 polypeptide that cannot be phosphorylated, or that cannot be phosphorylated to the full extent as that of a wild-type TSC2 polypeptide, is more effective in treating cancer in a subject than an immune cell that lacks the engineered TSC2 polypeptide.

Cancer types that can be treated include, without limitation, lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer, acute lymphoblastic leukemia (ALL), acute myeloid leukemia (AML), cancer in adolescents, adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, Waldenstrom Macroglobulinemia, and Wilms' tumor.

Viral Diseases

In some embodiments, any of the compositions and methods or methods disclosed provided herein can be used to treat viral diseases. Viral diseases that can be treated include, without limitation, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenza virus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV). Viral diseases that can be treated also include viral skin diseases, such as Herpes or shingles, and systemic viral diseases such as influenza, the common cold, and encephalitis.

Bacterial Diseases

In some embodiments, any of the compositions and methods provided herein can be used to treat bacterial diseases. Bacterial diseases that can be treated include, without limitation, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococ-* cus, *Neisseria, Clostridium, Bacillus, Corynebacterium, Mycobacterium, Campylobacter, Vibrio, Serratia, Providencia, Chromobacterium, Brucella, Yersinia, Haemophilus, Bordetella*, or *Borrelia*.

Fungal Diseases

In some embodiments, any of the compositions and methods provided herein can be used to treat fungal diseases. Fungal diseases that can be treated include, without limitation, candidiasis, aspergillosis, histoplasmosis, and cryptococcal meningitis.

Parasitic Diseases

In some embodiments, any of the compositions and methods provided herein can be used to treat parasitic diseases. Parasitic diseases that can be treated include, without limitation, malaria, pneumocystis carnii pneumonia, leishmaniasis, cryptosporidiosis, toxoplasmosis, and trypanosome infection.

Methods of Treating a Disease with an Agent that Result in Reduced Phosphorylation of TSC2 Polypeptides in Immune Cells Provided herein are also methods of treating a disease (e.g., any of the variety of cancers, viral diseases, bacterial diseases, fungal diseases, or parasitic diseases disclosed herein) in a subject by administering one or more agents that result in reduced phosphorylation of TSC2 polypeptides in an immune cells. In some embodiments, administration of an agent that results in reduced phosphorylation of TSC2 polypeptides in immune cells results in reduced phosphorylation of a TSC2 polypeptide at a serine residue at position S1364 of the human TSC2 polypeptide sequence (SEQ ID NO: 5). In some embodiments, administration of an agent that results in reduced phosphorylation of TSC2 polypeptides in immune cells results in reduced phosphorylation of a TSC2 polypeptide at a serine residue at position S1365 of the human TSC2 polypeptide sequence (SEQ ID NO: 6). In some embodiments, administration of an agent that results in reduced phosphorylation of TSC2 polypeptides in immune cells results in reduced phosphorylation of a TSC2 polypeptide at a serine residue at position S1366 of the human TSC2 polypeptide sequence (SEQ ID NO: 7). In some embodiments, administration of an agent to a subject that results in reduced phosphorylation of TSC2 polypeptides in immune cells results in a population of TSC2 polypeptides in the immune cell that exhibit decreased phosphorylation as compared to a population of TSC2 polypeptides in an immune cell in a reference subject that has not been administered the agent. For example, administration of an agent to a subject that results in reduced phosphorylation of TSC2 polypeptides in immune cells can result in a population of TSC2 polypeptides in the immune cell wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% or more of the TSC2 polypeptides in the cell are not phosphorylated (e.g., a serine residue at position S1364 of the human TSC2 polypeptide sequence (SEQ ID NO: 5), at a serine residue at position S1365 of the human TSC2 polypeptide sequence (SEQ ID NO: 6), or at a serine residue at position S1366 of the human TSC2 polypeptide sequence (SEQ ID NO: 7) as compared to a population of TSC2 polypeptides in an immune cell in a reference subject, wherein the reference subject has not been administered the agent. Method of determining whether a TSC2 polypeptide or population of TSC2 polypeptides are phosphorylated are known in the art. For example, TSC2 polypeptides from an immune cell(s) from a subject that has been administered the agent or from an immune cell(s) that has been contacted with the agent in vitro can be isolated (e.g., with a TSC2-specific antibody) and the phosphorylation state of the TSC2 polypeptides can be assayed with a phospho-specific antibody. Those of ordinary skill in the art will be aware of other suitable methods for determining whether a TSC2 polypeptide or population of TSC2 polypeptides are phosphorylated.

In some embodiments, an agent that results in reduced phosphorylation of TSC2 polypeptides in immune cells is a kinase inhibitor. A variety of kinases are known that can be inhibited, including without limitation: AKT1, AKT2, AKT3, CRIK, DMPK1, DMPK2, MRCKa, MRCKb, ROCK1, ROCK2, BARK1, BARK2, GPRK4, GPRK5, GPRK6, GPRK7, RHOK, MAST1, MAST2, MAST3, MAST4, MASTL, LATS1, LATS2, NDR1, NDR2, PDK1, PKACa, PKACb, PKACg, PRKX, PRKY, PKC (e.g., PKCa, PKCb, PKCg, PKCd, PKCt, PKCe, PKCh, PKCi, or PKCz), PKN1, PKN2, PKN3, MSK1, MSK2, p70S6K, p70S6Kb, RSK1, RSK2, RSK3, RSK4, RSKL1, RSKL2, SgK494, SGK1, SGK2, SGK3, YANK1, YANK2, YANK3, ADCK3, ADCK4, ADCK1, ADCK2, ADCK5, AlphaK1, AlphaK2, AlphaK3, ChaK1, ChaK2, eEF2K, BAZ1A, BAZ1B, ABR, BCR, BLVRA, BRD2, BRD3, BRD4, BRDT, Col4A3BP, FASTK, G11, GTF2F1, BCKDK, PDHK1, PDHK2, PDHK3, PDHK4, ATM, ATR, DNAPK, FRAP, SMG1, TRRAP, RIOK1, RIOK2, RIOK3, TAF1, TAF1L, TIF1D, TIF1a, TIF1b, TIF1g, VACAMKL, CaMK1a, CaMK1b, CaMK1d, CaMK1g, CaMK4, CaMK2a, CaMK2b, CaMK2d, CaMK2g, AMPKa1, AMPKa2, BRSK1, BRSK2, CHK1, HUNK, LKB1, MARK1, MARK2, MARK3, MARK4, MELK, NIM1, NuaK1, NuaK2, PASK, QIK, QSK, SIK, SNRK, CASK, DAPK1, DAPK2, DAPK3, DRAK1, DRAK2, DCLK1, DCLK2, DCLK3, MAPKAPK2, MAPKAPK3, MAPKAPK5, MNK1, MNK2, SgK085, TTN, caMLCK, skMLCK, smMLCK, PHKg1, PHKg2, PIM1, PIM2, PIM3, PKD1, PKD2, PKD3, PSKH1, PSKH2, CHK2, STK33, SgK495, SSTK, TSSK1, TSSK2, TSSK3, TSSK4, Trb1, Trb2, Trb3, Obscn, SPEG, Trad, Trio, CK1a, CK1a2, CK1d, CK1e, CK1g1, CK1g2, CK1g3, TTBK1, TTBK2, VRK1, VRK2, VRK3, CCRK, CDC2, CDK10, CDK11a, CDK11b, CDK2, CDK3, CDK4, CDK6, CDK5, CDK7, CDK19, CDK8, CDK9, CHED, CRK7, PCTAIRE1, PCTAIRE2, PCTAIRE3, PFTAIRE1, PFTAIRE2, CDKL1, CDKL2, CDKL3, CDKL4, CDKL5, CK2al, CK2a2, CLK1, CLK2, CLK3, CLK4, DYRK1A, DYRK1B, DYRK2, DYRK3, DYRK4, HIPK1, HIPK2, HIPK3, HIPK4, PRP4, GSK3A, GSK3B, Erk1, Erk2, Erk3, Erk4, Erk5, Erk7, JNK1, JNK2, JNK3, NLK, p38 (e.g., p38a, p38b, p38d, or p38g), ICK, MAK, MOK, MSSK1, SRPK1, SRPK2, NME1A, NME1B, NME3, NME4, NME5, NME6, NME7a, TXNDC3, TXNDC6, AurA, AurB, AurC, BUB1, BUBR1, PRPK, CaMKK1, CaMKK2, CDC7, Dusty, Haspin, IKKa, IKKb, IKKe, TBK1, IRE1, IRE2, MS, MOS, AAK1, BIKE, GAK, MPSK1, NEK1, NEK3, NEK5, NEK10, NEK11, NEK2, NEK4, NEK6, NEK7, NEK8, NEK9, SBK, SgK069, SgK110, PINK1, SgK223, SgK269, CLIK1, CLIK1L, SgK307, NRBP1, NRBP2, RNAseL, SgK196, SgK396, PAN3, GCN2, HRI, PEK, PKR, PLK1, PLK2, PLK3, PLK4, SCYL1, SCYL2, SCYL3, SgK071, SgK493, Slob, TBCK, TLK1, TLK2, PBK, TTK, Fused, ULK1, ULK2, ULK3, ULK4, PIK3R4, MYT1, Wee1, Wee1B, Wnk1, Wnk2, Wnk3, Wnk4, FAM198A, FAM198B, FAM20A, FAM20B, FAM20C, FJB1, ANPa, ANPb, CYGD, CYGF, HSER, COT, NIK, MAP3K5, MAP3K6, MAP3K7, MAP3K1, MEKK15, MAP3K2, MAP3K3, MAP3K4, OSR1, STLK3, GCK, HPK1, KHS1, KHS2, HGK, MINK, NRK, TNIK, MST1, MST2, MYO3A, MYO3B, PAK1, PAK2, PAK3, PAK4, PAK5, PAK6, LOK, SLK, STLK5, STLK6, TAO1, TAO2, TAO3, MST3, MST4, YSK1, MAP2K1, MAP2K2, MAP2K3, MAP2K6, MAP2K4, MAP2K5, MAP2K7, ALK, LTK, ABL1, ABL2, ACK, TNK1, AXL, MER, TYRO3, CCK4, CSK, CTK, DDR1, DDR2, EGFR, ErbB2, ErbB3, ErbB4, EphA1, EphA10, EphA2, EphA3, EphA4, EphA5, EphA6, EphA7, EphA8, EphB1, EphB2, EphB3, EphB4, EphB6, FAK, PYK2, FGFR1, FGFR2, FGFR3, FGFR4, FER, FES, IGF1R, INSR, IRR, JAK1, JAK2, JAK3, TYK2, LMR1, LMR2, LMR3, MET, RON, MUSK, FLT3, FMS, KIT, PDGFRa, PDGFRb, RET, ROR1, ROR2, RYK, ROS, FRK, BRK, SRM, FGR, FYN, SRC, YES, BLK, HCK, LCK, LYN, SYK, ZAP70, SuRTK106, BMX, BTK, ITK, TEC, TXK, TIE1, TIE2, TRKA, TRKB, TRKC, FLT1, FLT4, KDR, IRAK1, IRAK2, IRAK3, IRAK4, LIMK1, LIMK2, TESK1, TESK2, LRRK1, LRRK2, HH498, ILK, DLK, LZK, MLK1, MLK2, MLK3, MLK4, TAK1, ZAK, KSR1, KSR2, ARAF, BRAF, RAF1, ANKRD3, RIPK1, RIPK2, RIPK3, SgK288, ALK1, ALK2, ALK4, ALK7, BMPR1A, BMPR1B, TGFbR1, ACTR2, ACTR2B, BMPR2, MISR2, TGFbR2, MLKL. In some embodiments, a kinase to be inhibited can be one or more of: PKC, p38, MK2 or MK3.

In some embodiments, the agent is a kinase inhibitor (e.g., a kinase inhibitor that inhibits one or more of the kinases disclosed herein). In some embodiments, the agent includes two or more kinase inhibitor. In some embodiments, the agent includes a kinase inhibitor in combination with at least one other second agent (e.g., a second agent that increases the immune response of an immune cell). A variety of kinase inhibitors are known in the art. Non-limiting examples of kinase inhibitors include: MK-5108, palbociclib, capmatinib, rabusertib, SCH-900776, PF-477736, PF-477736, volitinib, crenolanib, pacritinib, adavosertib, afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, and vemurafenib. In some embodiments, a kinase inhibitor to be administered to a subject to treat a disease inhibits one or more of PKC, p38, MK2 or MK3. Non-limiting examples of kinase inhibitors that inhibit one or more of PKC, p38, MK2 and/or MK3 include: ruboxistaurin, chelerythrine, miyabenol C, myricitrin, gossypol, verbascoside, bryostatin 1, pamapimod, PH-797804, BIRB 796, VX-702, SB239063, SB202190, SB203580, SCIO 469, and BMS 582949. In some embodiments, a kinase inhibitor can be as described elsewhere (see, e.g., Klaeger et al., 2017 *Science* 358:1148).

In some embodiments, administration to a subject of an agent that results in reduced phosphorylation of TSC2 polypeptides in immune cells is effective in the treatment of a disease (e.g., any of the variety of cancers, viral diseases, bacterial diseases, fungal diseases, or parasitic diseases disclosed herein). In some embodiments, administration to a subject of an agent that results in reduced phosphorylation of TSC2 polypeptides in immune cells results in increased mTORC1 signaling in the immune cells such that the immune cells exhibit increased immune activity as compared to a reference immune cell from a reference subject that has not been administered the agent. In some embodiments, administration of an agent to a subject that results in reduced phosphorylation of TSC2 polypeptides in immune cells results in reduced phosphorylation of TSC2 polypeptides (e.g., a population of TSC2 polypeptides in the cell in which the number of TSC2 polypeptides in the population that are phosphorylate is reduced as compared to a population of TSC2 polypeptides in a reference immune cell from a reference subject that has not been administered the agent) in one or more of CD4+ T cells, CD8+ T cells, Natural Killer cells (NK cells), macrophages, neutrophils, regulatory T cells (Tregs), helper T cells, or any other immune and inflammatory cells known in the art. In some embodiments, administration of an agent to a subject that results in reduced phosphorylation of TSC2 polypeptides in immune cells results in clonal expansion, enhanced synthesis and release of cytokines (e.g., cytokines known in the art to be associated with an increased immune response, including but not limited to TNFα, IFN-γ, IFN-α, IFN-β, TGF-β, IL-2, IL-3, IL-4, IL-5, IL-6, IL-10, IL-12, IL-13, and GM-CSF), and other downstream effects known to be associated with an increased immune response. A person of ordinary skill in the art will be aware of such downstream effects known to be associated with an increased immune response and will be able to determine whether such downstream effects are occurring or have occurred. In some embodiments, an clinical outcome can be determined in a subject that has been administered an agent that results in reduced phosphorylation of TSC2 polypeptides. Non-limiting examples of clinical outcomes include, increased survival (e.g., number of days, months, or years), increased progression-free survival (e.g., number of days, months, or years), increased overall response rate, decreased numbers of cancer cells, decreased tumor burden, and/or decreased numbers of pathogens (e.g., bacteria, viruses, fungi) as compared to a reference subject that has not been administered the agent.

An agent (e.g., a kinase inhibitor, one or more kinase inhibitors, or a kinase inhibitor in combination with a second) can be administered to a subject once or multiple times over a period of time ranging from days to weeks. In some cases, one or more agents can be formulated into a pharmaceutically acceptable composition for administration to a subject having a disease (e.g., cancer). For example, a therapeutically effective amount of an agent can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more agents can be designed for oral or parenteral (including subcutaneous, intramuscular, intravenous, and intradermal)

administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more agents can be administered locally or systemically. For example, a composition provided herein can be administered locally by injection into tumors. In some cases, a composition provided herein can be administered systemically, orally, or by injection to a subject (e.g., a human).

Effective doses can vary depending on the severity of the disease, the route of administration, the age and general health condition of the subject, excipient usage, the possibility of co-usage with other therapeutic treatments such as use of other agents, and the judgment of the treating physician.

When referring to cancer, an effective amount of a composition containing one or more agents can be any amount that reduces the number of cancer cells present within the subject without producing significant toxicity to the subject. For example, an effective amount of dosage of an agent can be in the range of from about 0.1 mg/kg to about 100 mg/kg of body weight/day, for example, from about 1.0 mg/kg to about 50 mg/kg of body weight/day. In some embodiments, the dosage of an agent is in the range of from about 0.1 mg/kg to about 1.0 mg/kg of body weight/day; from about 0.1 mg/kg to about 5 mg/kg of body weight/day; from about 0.1 mg/kg to about 10 mg/kg of body weight/day; from about 0.1 mg/kg to about 25 mg/kg of body weight/day; from about 0.1 mg/kg to about 50 mg/kg of body weight/day; from about 1.0 mg/kg to about 5.0 mg/kg of body weight/day; from about 1.0 mg/kg to about 10 mg/kg of body weight/day; from about 1.0 mg/kg to about 20 mg/kg of body weight/day; from about 1.0 mg/kg to about 25 mg/kg of body weight/day; from about 1.0 mg/kg to about 40 mg/kg of body weight/day; from about 1.0 mg/kg to about 100 mg/kg of body weight/day; from about 10 mg/kg to about 100 mg/kg of body weight/day; from about 25 mg/kg to about 100 mg/kg of body weight/day; from about 50 mg/kg to about 100 mg/kg of body weight/day; from about 5.0 mg/kg to about 50 mg/kg of body weight/day; from about 10 mg/kg to about 50 mg/kg of body weight/day; or from about 25 mg/kg to about 50 mg/kg of body weight/day.

If a particular subject fails to respond to a particular amount, then the amount of an agent can be increased by, for example, two fold. After receiving this higher amount, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an agent can be any amount that reduces the number of cancer cells present within the subject without producing significant toxicity to the subject. For example, the frequency of administration of an agent can be from about two to about three times a week to about two to about three times a month. The frequency of administration of an agent can remain constant or can be variable during the duration of treatment. A course of treatment with a composition containing an agent can include rest periods. For example, a composition containing one or more agents can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more agents can be any duration that reduces the severity of the condition (e.g., the number of cancer cells present within the subject) without producing significant toxicity to the subject. In some cases, the effective duration can vary from several days to several weeks. In general, the effective duration can range in duration from about one week to about four weeks. Multiple factors can influence the actual effective duration used for a particular treatment. For example, an effective duration can vary with the frequency of administration, effective amount, use of multiple treatment agents, route of administration, and severity of the condition being treated.

In some embodiments, an agent can be contacted with an immune cell in vitro for any of a variety of purposes including, without limitation, testing specific cell types, testing the effective, maximum, and/or minimum dosage of the agent, and/or testing duration of contact of the agent. In some embodiments, a test agent can be contacted with an immune cell in vitro to determine whether it is effective. Any suitable immune cell can be contacted in vitro with the agent including, without limitation, CD4+ T cells, CD8+ T cells, Natural Killer cells (NK cells), macrophages, neutrophils, regulatory T cells (Tregs), helper T cells, or any other immune and inflammatory cells known in the art. In some embodiments, the in vitro agent is a kinase inhibitor. In some embodiments, the in vitro agent includes two or more kinase inhibitors. In some embodiments, the in vitro agent includes a kinase inhibitor in combination with at least one other second agent (e.g., a second agent that increases the immune response of an immune cell). Effectiveness of the in vitro agent(s) on stimulating the immune cell can be assessed by any of a variety of techniques known in the art. In some embodiments, clonal expansion is assessed. In some embodiments, enhanced synthesis and release of cytokines (e.g., cytokines known in the art to be associated with an increased immune response, including but not limited to TNFα, IFN-γ, TGF-β, IL-4, IL-10, IL-13) is assessed. Those of ordinary skill in the art will be aware of and will be able to employ other suitable assessment methods for determining the effectiveness of an agent(s) on an immune cell in vitro.

Engineered TSC2 Polypeptides that are Pseudo-phosphorylated

Provided herein are also engineered TSC2 polypeptides that act as if they are constitutively phosphorylated. Such engineered TSC2 polypeptides can be considered to be "pseudo-phosphorylated". In some embodiments, provided herein are pseudo-phosphorylated TSC2 polypeptides having an amino acid substitution at a residue corresponding to the serine residue at position S1364 of the human TSC2 polypeptide sequence (SEQ ID NO: 5). In some embodiments, the serine residue at position S1364 of SEQ ID NO: 5, or a serine residue in a polypeptide that corresponds to the serine residue at position S1364 of SEQ ID NO: 5, is substituted with an aspartic acid or a glutamic acid residue. In some embodiments, a pseudo-phosphorylated TSC2 polypeptide having a glutamic acid substitution at the serine residue at position S1364 of the human TSC2 polypeptide sequence is provided (e.g., SEQ ID NO: 2).

Provided herein are also pseudo-phosphorylated TSC2 polypeptides having an amino acid substitution at a residue corresponding to the serine residue at position S1365 of the mouse TSC2 polypeptide sequence (SEQ ID NO: 6) such that engineered TSC2 polypeptides act as if they are constitutively phosphorylated. In some embodiments, the serine residue at position S1365 of SEQ ID NO: 6, or a serine residue in a polypeptide that corresponds to the serine residue at position S1365 of SEQ ID NO: 6, is substituted with an aspartic acid or a glutamic acid residue. In some embodiments, a pseudo-phosphorylated TSC2 polypeptide having an amino acid substitution at the serine residue at position S1365 of the mouse TSC2 polypeptide sequence is provided (e.g., SEQ ID NO: 10).

Provided herein are also pseudo-phosphorylated TSC2 polypeptides having an amino acid substitution at a residue corresponding to the serine residue at position S1366 of the rat TSC2 polypeptide sequence (SEQ ID NO: 7) such that engineered TSC2 polypeptides act as if they are constitutively phosphorylated. In some embodiments, the serine residue at position S1366 of SEQ ID NO: 7, or a serine residue in a polypeptide that corresponds to the serine residue at position S1366 of SEQ ID NO: 7, is substituted with an aspartic acid or a glutamic acid residue. In some embodiments, a pseudo-phosphorylated TSC2 polypeptide having an amino acid substitution at the serine residue at position S1366 of the rat TSC2 polypeptide sequence is provided (e.g., SEQ ID NO: 11).

In some embodiments, pseudo-phosphorylated TSC2 polypeptides exhibit increased activity in their ability to down-regulate the mTORC1 pathway as compared to wild-type TSC2 polypeptides that are not phosphorylated at the engineered amino acid position.

Provided herein are also vectors that include nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7), and cells having such vectors. A vector that includes nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) can be any appropriate type of vector. Examples of vectors include, without limitation, plasmids (e.g., expression plasmids) and vectors (e.g., viral vectors such as lentiviral vectors, retroviral vectors, adenovirus vectors, and adeno-associated virus vectors). In some cases, a vector that includes nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) can be a lentiviral vector. A vector that includes nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) also can include one or more addition features (e.g., one or more additional features to modulate polypeptide expression). Examples of features that can modulate polypeptide expression include, without limitation, an origin of replication, a promoter, a polyA tail, a terminator, and a microRNA response element. In some cases, when a vector described herein also includes a promoter, the promoter can operably linked to a nucleic acid sequence that encodes polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) (e.g., such that the promoter can drive expression of the nucleic acid sequence). A promoter can be any appropriate promoter. In some cases, a promoter can be constitutive promoter. In some cases, a promoter can be a viral promoter. In some cases, a promoter can be an inducible promoter. In some cases, a promoter can be a cell-specific and/or tissue-specific promoter. Examples of promoters that can be used to drive expression of nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) include, without limitation, CMV. In some embodiments, a promoter can be as described elsewhere (see, e.g., Morgan et al., 2016 *Biomedicines*. 4:9).

In some embodiments, cells having vectors that include nucleic acid sequences that encode polypeptides that act as if they are constitutively phosphorylated at a serine residue in any of the polypeptides described herein do not express endogenous, wild-type TSC2. For example, the nucleic acid sequence encoding wild-type TSC2 can be modified by any of a variety of genetic manipulation techniques known in the art including, but not limited to, CRISPR-based methods, TALEN-based methods, and other genetic targeting or recombination methods (see, e.g., Roth et al., 2018 *Nature* doi: 10.1038/s41586-018-0326-5). In some embodiments, cells having vectors that include nucleic acid sequences that encode engineered pseudo-phosphorylated TSC2 polypeptides that act as if they are constitutively phosphorylated at a position that corresponds to a wild-type serine residue in any of the polypeptides described herein do express endogenous, wild-type TSC2. In some embodiments of cells having both: 1) vectors that include nucleic acid sequences that encode engineered TSC2 polypeptides that act as if they are constitutively phosphorylated, and 2) a nucleic acid sequence encoding an endogenous TSC2 protein, the cells exhibit the same or similar activity as a corresponding cell lacking the nucleic acid sequence encoding the endogenous TSC2 protein.

TSC2 polypeptides disclosed herein can be engineered at S1364 of the human TSC2 polypeptide sequence (SEQ ID NO: 5), S1365 of the mouse TSC2 polypeptide sequence (SEQ ID NO: 6), or S1366 of the rat TSC2 polypeptide sequence (SEQ ID No: 7) with any mutation or modification that results in TSC2 mimicking constitutive phosphorylated at the respective positions in human (S1364), mouse (S1365), or rat (S1366). In some cases, TSC2 polypeptides from other species (e.g., monkey) can be engineered with any mutation or modification (e.g., a residue corresponding to human S1364, mouse S1365, and/or rat S1366) that results in TSC2 mimicking constitutive phosphorylated.

Provided herein are also nucleic acids encoding engineered TSC2 polypeptides that act as if they are constitutively phosphorylated at a position corresponding to a serine residue in a wild-type TSC2 polypeptide sequence. In some embodiments, nucleic acids provided herein encode pseudo-phosphorylated TSC2 polypeptides that exhibit increased activity in their ability to down-regulate the mTORC1 pathway as compared to wild-type TSC2 polypeptides that are not phosphorylated at the engineered position. In some embodiments, provided herein are nucleic acids encoding pseudo-phosphorylated TSC2 polypeptides having an amino acid substitution at a residue corresponding to the serine residue at position S1364 of the human TSC2 polypeptide sequence (SEQ ID NO: 5), or position S1365 of the mouse TSC2 polypeptide sequence (SEQ ID NO: 6), or position S1366 of the rat TSC2 polypeptide sequence (SEQ ID NO: 7). In some embodiments, nucleic acids provided herein encode pseudo-phosphorylated TSC2 polypeptides in which the serine residue at position S1364 of SEQ ID NO: 5, position S1365 of SEQ ID NO: 6, or position 1366 of SEQ ID NO: 7, or a serine residue in a TSC2 polypeptide that corresponds to the serine residues at those positions, is substituted with an aspartic acid or a glutamic acid residue. In some embodiments, nucleic acids provided herein include the genetic codons GAA or GAG at positions that are translated to a glutamic acid residue at position S1364 of the human TSC2 polypeptide sequence (SEQ ID NO: 5), position S1365 of the mouse TSC2 polypeptide sequence (SEQ ID NO: 6), or position S1366 of the rat TSC2 polypeptide sequence (SEQ ID NO: 7). In some embodiments, nucleic acids provided herein include the genetic codons GAT or GAC at positions that are translated to an aspartic acid residue at position S1364 of the human TSC2 polypeptide sequence (SEQ ID NO: 5), position S1365 of the mouse TSC2 polypeptide sequence (SEQ ID NO: 6), or position S1366 of the rat TSC2 polypeptide sequence (SEQ ID NO: 7). In some embodiments, a nucleic acid sequence encoding an engineered TSC2 polypeptide having a glutamic acid substitution at the serine residue at position S1364 of the human TSC2 polypeptide sequence is provided (e.g., a nucleic acid sequence of SEQ ID NO: 4).

Methods of Treating Disease Using Cells Having Engineered TSC2 Polypeptides that are Pseudo-phosphorylated Cells Having Engineered TSC2 Polypeptides that are Pseudo-phosphorylated Provided herein are cells expressing engineered TSC2 polypeptides that act as if they are constitutively phosphorylated at a position corresponding to a serine residue in the wild-type TSC2 polypeptide sequence. In some embodiments, cells provided herein include pseudo-phosphorylated TSC2 polypeptides that exhibit increased activity in their ability to down-regulate the mTORC1 pathway as compared to wild-type TSC2 polypeptides that are not phosphorylated at the engineered position. In some embodiments, cells provided herein express pseudo-phosphorylated TSC2 polypeptides in which the serine residue at position S1364 of SEQ ID NO: 5, or a serine residue in a polypeptide that corresponds to the serine residue at position S1364 of SEQ ID NO: 5, is substituted with an aspartic acid or a glutamic acid residue. For example, provided herein are cells expressing pseudo-phosphorylated TSC2 polypeptides having a glutamic acid substitution at a residue corresponding to the serine residue at position S1364 of the human TSC2 polypeptide sequence (e.g., SEQ ID NO: 2).

Provided herein are also cells expressing pseudo-phosphorylated TSC2 polypeptides having an amino acid substitution at a residue corresponding to the serine residue at position S1365 of the mouse TSC2 polypeptide sequence (SEQ ID NO: 6) such that engineered TSC2 polypeptides act as if they are constitutively phosphorylated at the serine residue. In some embodiments, the cells provided herein express a pseudo-phosphorylated TSC2 polypeptide in which the serine residue at position S1365 of SEQ ID NO: 6, or a serine residue in a polypeptide that corresponds to the serine residue at position S1365 of SEQ ID NO: 6, is substituted with an aspartic acid or a glutamic acid residue. In some embodiments, cells provided herein express a pseudo-phosphorylated TSC2 polypeptide having a glutamic acid substitution at the serine residue at position S1365 of the mouse TSC2 polypeptide sequence (e.g., SEQ ID NO: 10).

Provided herein are also cells expressing a pseudo-phosphorylated TSC2 polypeptide having an amino acid substitution at a residue corresponding to the serine residue at position S1366 of the rat TSC2 polypeptide sequence (SEQ ID NO: 7) such that engineered TSC2 polypeptides act as if they are constitutively phosphorylated at the serine residue. In some embodiments, cells provided herein express a pseudo-phosphorylated TSC2 polypeptide in which the serine residue at position S1366 of SEQ ID NO: 7, or a serine residue in a polypeptide that corresponds to the serine residue at position S1366 of SEQ ID NO: 7, is substituted with a aspartic acid or a glutamic acid residue. In some embodiments, cells provided herein express an engineered TSC2 polypeptide having a glutamic acid substitution at the serine residue at position S1366 of the mouse TSC2 polypeptide sequence (e.g., SEQ ID NO: 11).

Provided herein are also cells harboring vectors that include nucleic acids that encode polypeptides that act as if they are constitutively phosphorylated at a serine residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7). A vector that includes nucleic acid sequences that encode polypeptides that act as if they are constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) can be introduced into a cell using any appropriate methods and/or techniques. A vector can be introduced into a cell in a transient manner (e.g., maintained as a vector) or in a stable manner (e.g., integrated into the genome). Examples of methods and/or techniques that can be used to introduce one or more vectors into a cell include, without limitation, transfection, transduction, electroporation, and infection. In some embodiments, nucleic acids encoding pseudo-phosphorylated TSC2 polypeptides are operably linked to nucleic acids that drive expression of pseudo-phosphorylated TSC2 polypeptides in the vectors (e.g., promoter sequences).

In some embodiments, cells having pseudo-phosphorylated TSC2 polypeptides that act as if they are constitutively phosphorylated can have, or can express, endogenous, TSC2 proteins. For example, a cell having a pseudo-phosphorylated TSC2 polypeptide also can have an endogenous wild-type nucleic acid sequence encoding a wild-type TSC2 polypeptide. In some embodiments of cells having (e.g., expressing) both: 1) engineered pseudo-phosphorylated TSC2 polypeptides that act as if they are constitutively phosphorylated, and 2) an endogenous TSC2 protein, the cells exhibit the same or similar activity as a corresponding cell lacking (e.g., not expressing) the endogenous TSC2 protein.

In some embodiments, cells having pseudo-phosphorylated TSC2 polypeptides that act as if they are constitutively phosphorylated do not have, or do not express, endogenous, wild-type TSC2 proteins. For example, a cell having a pseudo-phosphorylated TSC2 polypeptide can have a genetic alteration in which a wild-type nucleic acid sequence encoding the TSC2 polypeptide has been rendered inactive. In some embodiments, the nucleic acid sequence encoding wild-type TSC2 can be modified by any of a variety of genetic manipulation techniques known in the art including, but not limited to, CRISPR-based methods, TALEN-based methods, and other genetic targeting or recombination methods (see, e.g., Roth et al., 2018 *Nature* doi: 10.1038/s41586-018-0326-5). In some embodiments, a wild-type nucleic acid sequence encoding a TSC2 polypeptide can be rendered inactive by removing, replacing, or mutating a nucleic acid sequence that contributes to expression of the TSC2 polypeptide including, but not limited to, a promoter sequence, an enhancer sequence, a coding sequence of a transcription factor that regulates expression of TSC2, the coding sequence of the TSC2 polypeptide itself, or combinations thereof. In some embodiments, a wild-type nucleic acid sequence encoding a TSC2 polypeptide can be rendered inactive via a frameshift caused by one or more modifications or mutations in the nucleic acid sequence encoding the TSC2 polypeptide.

In some embodiments, cells that can be engineered to include a pseudo-phosphorylated TSC2 polypeptide include immune cells. For example, the immune cells can be CD4+ T cells, CD8+ T cells, Natural Killer cells (NK cells), macrophages, neutrophils, regulatory T cells (Tregs), helper T cells, B cells, or any other immune cells and/or inflammatory cells known in the art. Relevant aspects of certain of these cells are disclosed elsewhere herein.

In some embodiments, an immune cell that is engineered to include an engineered TSC2 polypeptide can be a cytotoxic T cell. In some embodiments, a cytotoxic T cell can be engineered to express a CAR or a TCR.

In some embodiments, an immune cell that is engineered to include an engineered TSC2 polypeptide can be expanded (e.g., clonally expanded). For example, an immune cell that is engineered to include an engineered TSC2 polypeptide can be clonally expanded ex vivo (e.g., for use in an adoptive cell therapy). In cases where an immune cell that is engineered to include an engineered TSC2 polypeptide is used in an adoptive cell therapy, the adoptive cell therapy can be any appropriate adoptive cell therapy. Examples of adoptive cell therapies include, without limitation, dendritic cell therapy and synthetic dendritic cell therapy. In some cases, adoptive cell therapy can include the extraction of tumor infiltrating lymphocytes.

In some embodiments, decreased mTORC1 signaling can be determined by any of a variety of techniques or methods known in the art. For example, inhibited mTORC1 signaling typically results in decreased growth, increased autophagy, and less phosphorylation of Ulk1 (Unc-51-like kinase-1), p70S6K (ribosomal protein S6 kinase), and 4EBP1 (eIF4E binding protein-1).

Cancers

In some embodiments, the compositions and methods provided herein can be used to treat cancer. For example, an immune cell that is engineered to include an engineered TSC2 polypeptide (e.g., expressed from a vector introduced into the cell, which vector includes a nucleic acid sequence that encodes the engineered TSC2 polypeptide) that acts as if it is constitutively phosphorylated at a residue corresponding to S1364 of the human TSC2 polypeptide sequence (SEQ ID NO: 5), S1365 of the mouse TSC2 polypeptide sequence (SEQ ID NO: 6), or S1366 of the rat TSC2 polypeptides sequence (SEQ ID No: 7) can be administered to a subject having cancer (e.g., in an adoptive cell therapy) such that the cancer is treated. In some embodiments, the engineered immune cell administered to the subject does not have or express an endogenous, wild type TSC polypeptide. In some embodiments, the engineered immune cell administered to the subject does have or express an endogenous, wild type TSC2 polypeptide. In some embodiments, a CD8+ T effector cell that recognizes a cancer cell (e.g., via a specific antigen on the cancer cell surface) can be engineered to include a TSC2 polypeptide that acts as if it is constitutively phosphorylated, which CD8+ T effector cell is then administered to a subject that has such a cancer cell. In some embodiments, a CD8+ T effector cell that is engineered to include a TSC2 polypeptide acts as if it is constitutively phosphorylated is also engineered to express a chimeric antigen receptor or a T cell receptor. In some embodiments, an immune cell that is engineered to include an engineered TSC2 polypeptide that acts as if it is constitutively phosphorylated is more effective in treating cancer in a subject than an immune cell that lacks the engineered TSC2 polypeptide.

Cancer types that can be treated include, without limitation, lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer, acute lymphoblastic leukemia (ALL), acute myeloid leukemia (AML), cancer in adolescents, adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, Waldenstrom Macroglobulinemia, and Wilms' tumor.

Other Diseases

In some embodiments, the compositions and methods provided herein can be are useful for other situations and/or can be used to treat other diseases. Examples of other situations where the compositions and methods provided herein can be useful include, without limitation, situations of tissue, skin, and organ transplantation. Examples of other diseases that the compositions and methods can be used to treat include, without limitation, graft-versus-host disease (GVHD), allergies, asthma, autoimmune diseases (such as systemic lupus erythematosus and rheumatoid arthritis), multiple sclerosis, and inflammatory bowel disease. In some embodiments, cells comprising a pseudo-phosphorylated TSC2 polypeptide can be administered to patients in need (e.g., in an adoptive cell therapy) resulting in decreased mTORC1 activities and thus treating diseases including situations of tissue, skin and organ transplantation, in graft-versus-host disease (GVHD), or allergies, or in autoimmune diseases such as systemic lupus erythematosus and multiple sclerosis.

Methods of Generating a Persistent T Cell in a Subject

Also provided herein are methods of generating a persistent T cell a subject. In some embodiments, methods of generating a persistent T cell in a subject include administering to a subject (e.g., in an adoptive cell therapy) an engineered immune cell comprising a vector. In some embodiments, the vector comprises a nucleic acid encoding a polypeptide comprising SEQ ID NO: 2 that is operably linked to a nucleic acid that drives expression of the polypeptide in the engineered immune cell. In some embodiments, the engineered immune cell recognizes an antigen. In some embodiments, upon recognizing the antigen, the engineered immune cell exhibits decreased activity as compared to a reference T cell that lacks the vector. In some embodiments, upon recognizing the antigen, the engineered immune cell becomes a persistent T cell.

In some embodiments, the decreased activity of the engineered immune cell comprises decreased mTORC1 signaling.

In some embodiments, the engineered immune cell is derived from an endogenous immune cell obtained from the subject. As used herein, the phrase "derived from" means that the endogenous immune cell is obtained from the subject, after which it is modified (e.g., via introduction of a vector having an nucleic acid sequence encoding a modified TSC2 polypeptide as described herein) to generate the engineered immune cell.

In some embodiments, the engineered immune cell is a CD8+ T cell. In some embodiments, the persistent T cell is a memory T cell. In some embodiments, the CD8+ T cell is further engineered to express a CAR or a TCR. In some embodiments, the engineered immune cell is a regulatory T cell. In some embodiments, the persistent T cell is a persistent T regulatory cell.

Methods of Generating a Persistent T Cell In Vitro

Also provided herein are methods of generating a persistent T cell in vitro. In some embodiments, methods of generating a persistent T cell in vitro include providing an immune cell, introducing into the immune cell a vector thereby generating an engineered immune cell, contacting the engineered immune cell with an antigen that is recognized by the engineered immune cell, and culturing the engineered immune cell under conditions and for a time sufficient such that the engineered immune cell becomes the persistent T cell. In some embodiments, the vector comprises a nucleic acid encoding a polypeptide comprising SEQ ID NO: 2 that is operably linked to a nucleic acid that drives expression of the polypeptide in the immune cell. In some embodiments, the engineered immune cell exhibits decreased mTORC1 signaling as compared to a reference immune cell that does not comprise the vector.

In some embodiments, the immune cell is a CD8+ T cell, and the generated persistent T cell is a memory T cell. In some embodiments, the CD8+ T cell is further engineered to express a chimeric antigen receptor or a T cell receptor.

In some embodiments, a persistent T cell generated in vitro is administered to a subject (e.g., in an adoptive cell therapy). In some embodiments, the subject exhibits a disease. In some embodiments, administration of the persistent T cell to the subject treats the disease. In some embodiments, the disease is cancer, a viral disease, a bacterial disease, fungal disease, or a parasitic disease (e.g., any of the cancers, viral diseases, bacterial diseases, fungal diseases, or parasitic diseases disclosed herein).

In some embodiments, the immune cell is obtained from the subject to be treated (e.g., an autologous cell). In some embodiments, the immune cell is obtained from a subject other than the subject to be treated (e.g., an allogenic cell). In some embodiments, the immune cell is a regulatory T cell, and the persistent T cell is a persistent T regulatory cell. In some embodiments, the persistent T regulatory cell is administered to a subject (e.g., in an adoptive cell therapy). In some embodiments, the subject exhibits a disease. In some embodiments, administration of the persistent T regulatory cell to the subject treats the disease. In some embodiments, the disease is asthma, an autoimmune disease, or graft vs. host disease. In some embodiments, the immune cell is obtained from the subject (e.g., any of the cancers, viral diseases, bacterial diseases, fungal diseases, or parasitic diseases disclosed herein).

REFERENCES (Identified By Numbers Within Parentheses Throughout the Specification)

1. C. C. Dibble et al., Signal integration by mTORC1 coordinates nutrient input with biosynthetic output. *Nat Cell Biol* 15, 555 (June 2013).
2. R. L. Wolfson et al., Sestrin2 is a leucine sensor for the mTORC1 pathway. *Science* 351, 43 (Jan. 1, 2016).
3. S. Sciarretta et al., Mammalian target of rapamycin signaling in cardiac physiology and disease. *Circ Res* 114, 549 (Jan. 31, 2014).
4. M. Laplante et al., mTOR signaling in growth control and disease. *Cell* 149, 274 (Apr. 13, 2012).
5. K. Inoki et al., Rheb GTPase is a direct target of TSC2 GAP activity and regulates mTOR signaling. *Genes Dev* 17, 1829 (Aug. 1, 2003).
6. S. Menon et al., Spatial control of the TSC complex integrates insulin and nutrient regulation of mTORC1 at the lysosome. *Cell* 156, 771 (Feb. 13, 2014).
7. K. Inoki et al., TSC2 integrates Wnt and energy signals via a coordinated phosphorylation by AMPK and GSK3 to regulate cell growth. *Cell* 126, 955 (Sep. 8, 2006).
8. H. H. Zhang et al., Insulin stimulates adipogenesis through the Akt-TSC2-mTORC1 pathway. *PLoS One* 4, e6189 (Jul. 10, 2009).
9. D. I. Lee et al., Phosphodiesterase 9A controls nitric-oxide-independent cGMP and hypertrophic heart disease. *Nature* 519, 472 (Mar. 26, 2015).
10. K. Kokkonen et al., Nanodomain Regulation of Cardiac Cyclic Nucleotide Signaling by Phosphodiesterases. *Annu Rev Pharmacol Toxicol* 57, 455 (Jan. 6, 2017).
11. J. Kim et al., AMPK and mTOR regulate autophagy through direct phosphorylation of Ulk1. *Nat Cell Biol* 13, 132 (February 2011).
12. P. E. Burnett et al., RAFT1 phosphorylation of the translational regulators p70 S6 kinase and 4E-BP1. *Proc Natl Acad Sci USA* 95, 1432 (Feb. 17, 1998).
13. Q. Zheng et al., Autophagy and p62 in cardiac proteinopathy. *Circ Res* 109, 296 (Jul. 22, 2011).
14. N. Hariharan et al., Oxidative stress stimulates autophagic flux during ischemia/reperfusion. *Antioxid Redox Signal* 14, 2179 (June 2011).
15. P. Mertins et al., Proteogenomics connects somatic mutations to signalling in breast cancer. *Nature* 534, 55 (Jun. 2, 2016).
16. J. R. Burgoyne et al., cGMP-dependent activation of protein kinase G precludes disulfide activation: implications for blood pressure control. *Hypertension* 60, 1301 (November 2012).
17. T. Nakamura et al., Prevention of PKG1α oxidation augments cardioprotection in the stressed heart. *J Clin Invest* 125, 2468 (June 2015).

The invention will be further described in the following examples, which do not limit the scope of the invention described in the claims.

EXAMPLES

Example 1

PKG1α Suppression of Hypertrophy Requires mTORC1-Ulk1 Regulated Autophagy

Cyclic GMP-stimulated protein kinase 1α (PKG1α), the primary downstream kinase of nitric oxide and natriuretic peptide signaling, confers anti-proliferative and anti-fibrotic effects in multiple tissues subjected to mechanical and neurohumoral stress (9, 10). In studies examining downstream effectors of PKG1α, it was discovered that it suppresses mTORC1 activation. Intact mice were subjected to 6 weeks of pressure-overload (PO) with or without co-treatment with a phosphodiesterase type-5 inhibitor (sildenafil, SIL), which stimulates PKG1α by blocking cGMP hydrolysis (9).

Figure 1B:
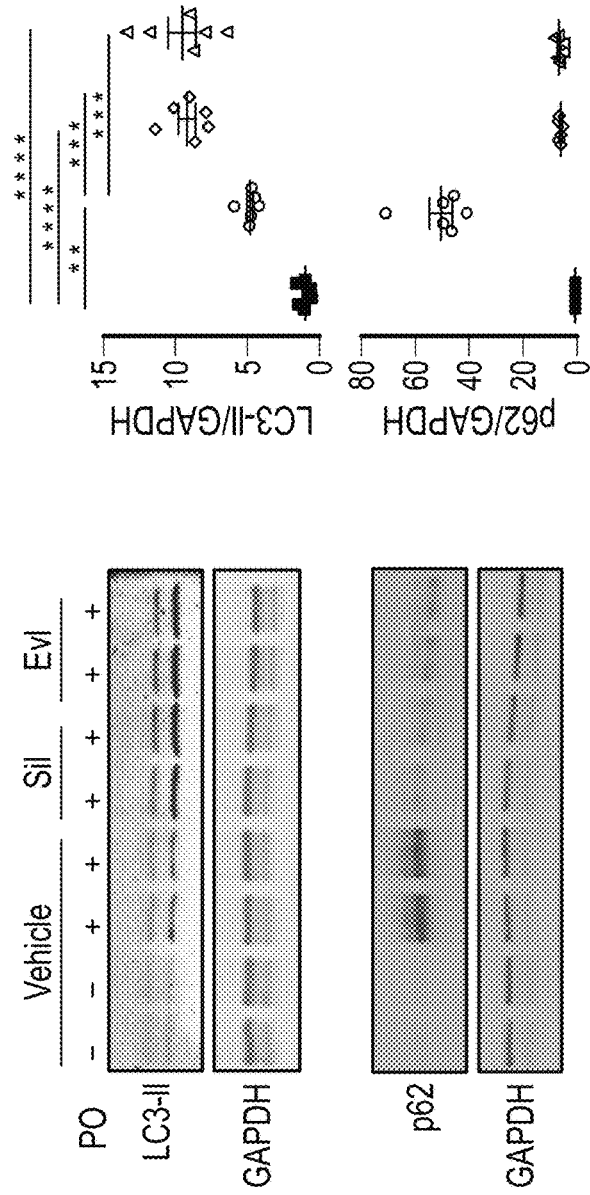
Figure 1C:
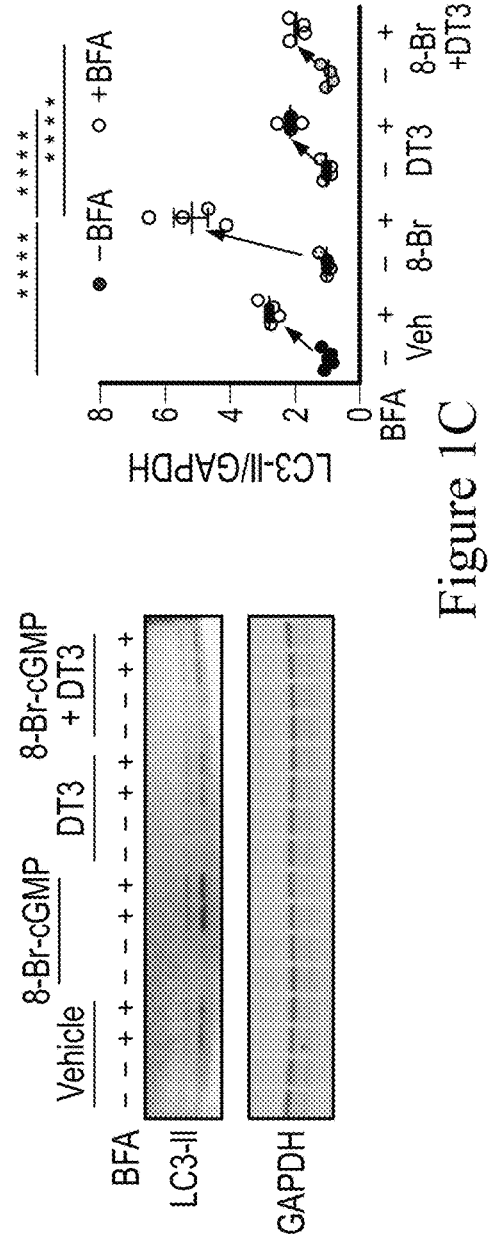
Figure 27:
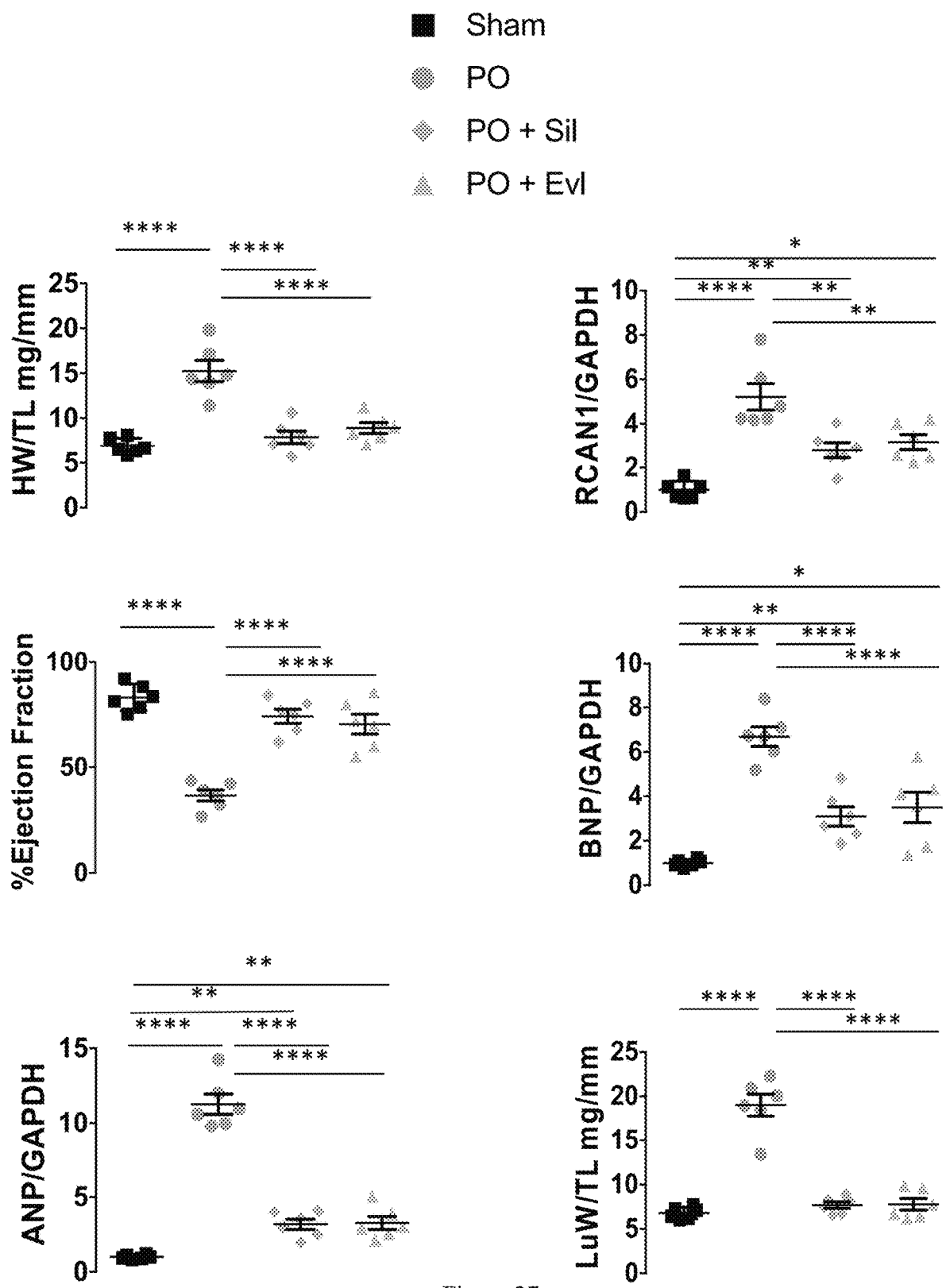
FIG. 27. Suppression of pathological muscle growth and heart dysfunction.

PO enhanced mTORC1 activation as reflected by phosphorylation of three primary targets—Ulk1 (Unc-51-like kinase-1) to inhibit autophagy (11), and p70S6K, and 4EPB1 (elF4E binding protein-1) to stimulate growth (12). SIL blocked these changes, mimicking effects from an mTORC1 inhibitor (everolimus, Evl) (FIG. 1A). Both therapies equally suppressed pathological muscle growth and heart dysfunction (FIG. 27). Both SIL and Evl also stimulated autophagy, as reflected by higher LC3-II (microtubule-associated protein light-chain 3-II) and reduced p62 (FIG. 1B). Autophagic flux (AuF) was directly measured in myocytes by the rise in LC3-II after exposure to Bafilomycin A1 (13) that blocks lysosomal proteolysis. This rise was greater with PKG1α activation and blocked by DT3, a PKG1α antagonist (FIG. 1C). Myocytes expressing a tandem GFP-RFP-LC3 AuF reporter (14) (shifts from diffuse green to red/yellow punctae with greater AuF) and stimulated to hypertrophy with endothelin-1 (ET-1) showed AuF rise with PKG1α was coupled to smaller cell size (FIG. 1D). Reduced hypertrophy was reflected by lower Nppb gene expression with SIL, but this was prevented when Ulk1 was genetically silenced (FIG. 1E). This shows PKGα suppression of hypertrophy requires mTORC1-Ulk1 regulated autophagy.

Example 2

PKG1α Targets TSC2

Figure 2A:
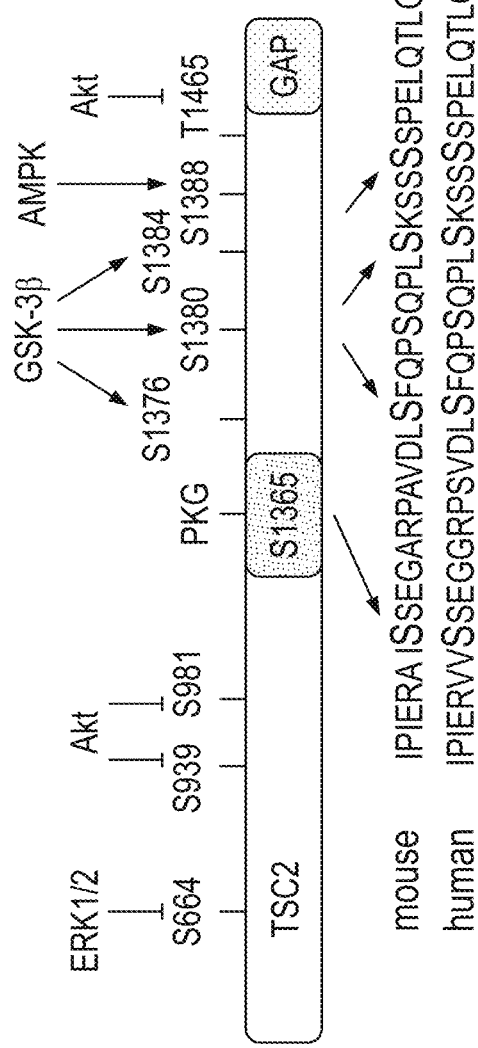
FIG. 2. A) TSC2 phospho-target map showing S1365 relative to other known sites in mouse and human. B) Effect of expression of WT, S1365E (SE), or S1365A (SA) TSC2 mutants with and without sildenafil (SIL) treatment in myocytes stimulated by ET1 or vehicle (n=6). C) Effect of each TSC2 mutant on mTORC1 activation. Vehicle>ET1 response ($p<0.0001$) for WT and SA TSC2, but p=NS with SE expression. D) mTORC1 activation from PO in vivo in WT is suppressed in C42S-PKG1α mice. E) Autophagic flux (AuF) is enhanced in cells expressing C42S by LC3-II/BFA assay. F) Nppb stimulated by ET1 in myocytes expressing WT and C42S PKG1α and S1365 TSC2 mutants. G) Fluorescent microscopy of these myocytes in presence or absence of concomitant Ulk1 gene silencing. Upper: LC3-GFP-RFP (AuF) fluorescence; lower: Alexa-568 phalloidin actin staining for hypertrophy. **: $p<0.0001$; *: $p<0.001$; **: $p<0.01$; *: $p<0.05$ by Tukey multiple comparisons test following significance ($p<0.001$ or lower) deduced by 1-way ANOVA.
Figure 2B:
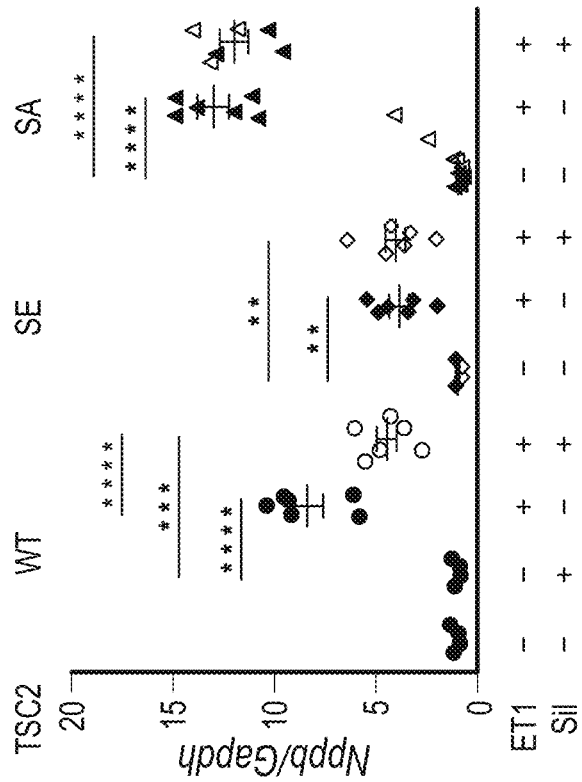
Figures 2C, 2D:
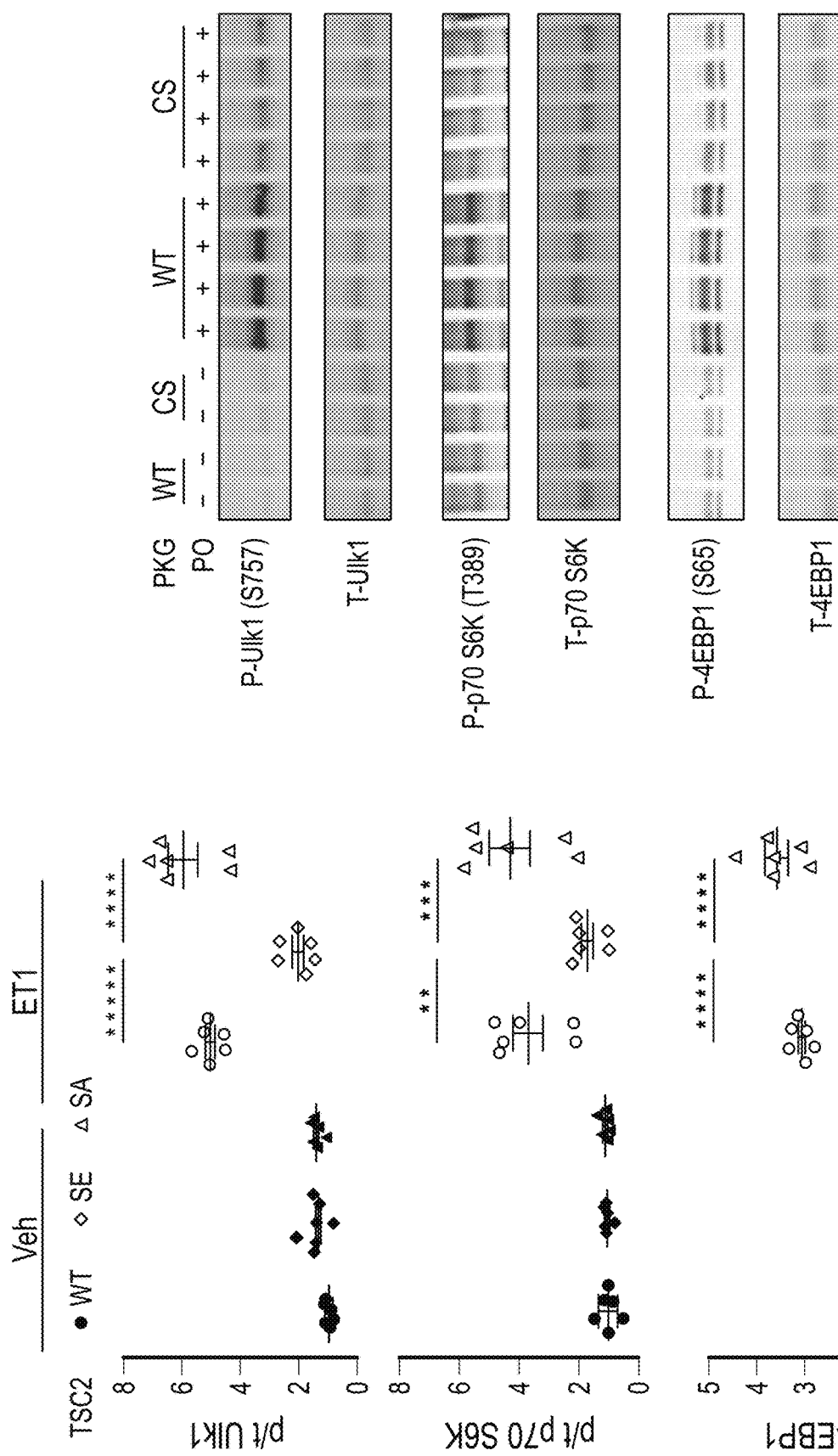
Figure 28:
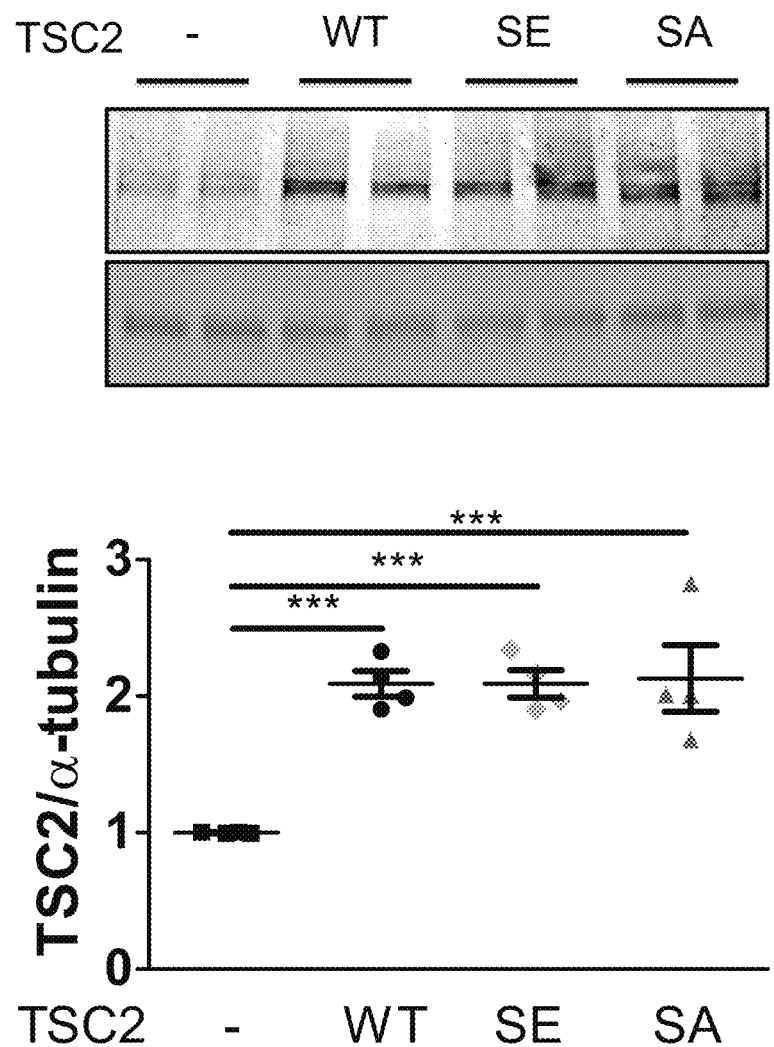
FIG. 28. Expression of phospho-mimetic (S1365E, "SE") and phospho-silenced (S1365A, "SA") TSC2 mutants in myocytes.

To identify the mTORC1-complex or regulatory proteins targeted by PKG1α, a phospho-proteomic assay of adult myocytes exposed to cGMP for 10 minutes to activate PKG1α was performed, and then phospho-peptide enriched lysates was assayed by mass spectrometry. Of all potential candidates, only TSC2 was differentially phosphorylated. This occurred at Ser1365, a highly conserved residue in an activation regulatory domain downstream of known GSK-3β and AMPK targeted sites (FIG. 2A). This site is found in phospho-protein databases including human breast cancer (15), but its functionality and targeting kinase were unknown. To resolve this, phospho-mimetic (S1365E, "SE") and phospho-silenced (S1365A, "SA") TSC2 mutants were generated, introduced into myocytes at similar expression levels (FIG. 28), and the cells were then stimulated with ET-1±SIL to co-activate PKG1α (FIG. 2B). Expression of either mutant or WT TSC2 did not impact resting Nppb expression. SE mimicked SIL in blocking Nppb rise induced by ET-1; whereas, SA increased the response. Both TSC2 mutants prevented further changes from PKG1α, unlike the response with WT-TSC2. These disparities were mirrored by differential activation of mTORC1 (FIG. 2C), confirming that pS1365 functionally regulates mTORC1 signaling and is targeted by PKG1α.

Figure 2E:
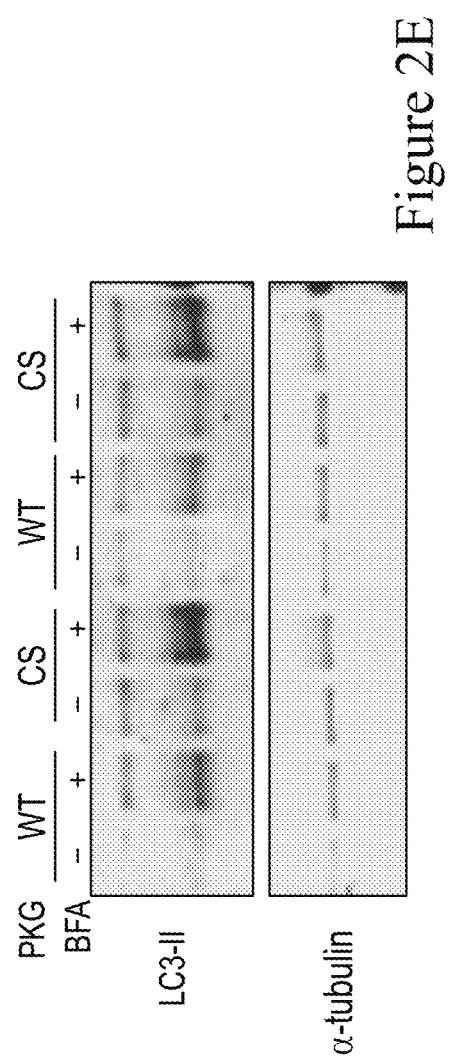
Figure 2F:
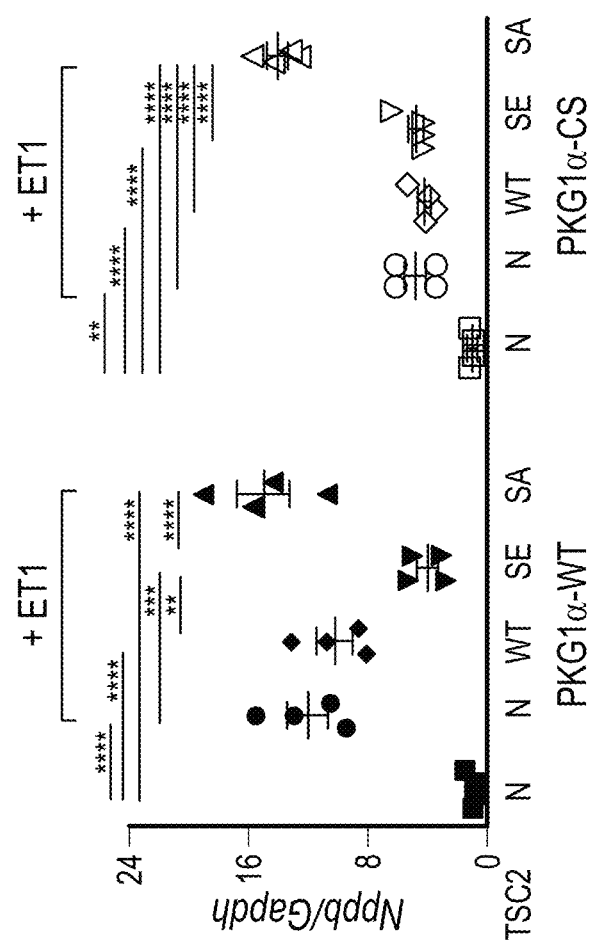
Figure 2G:
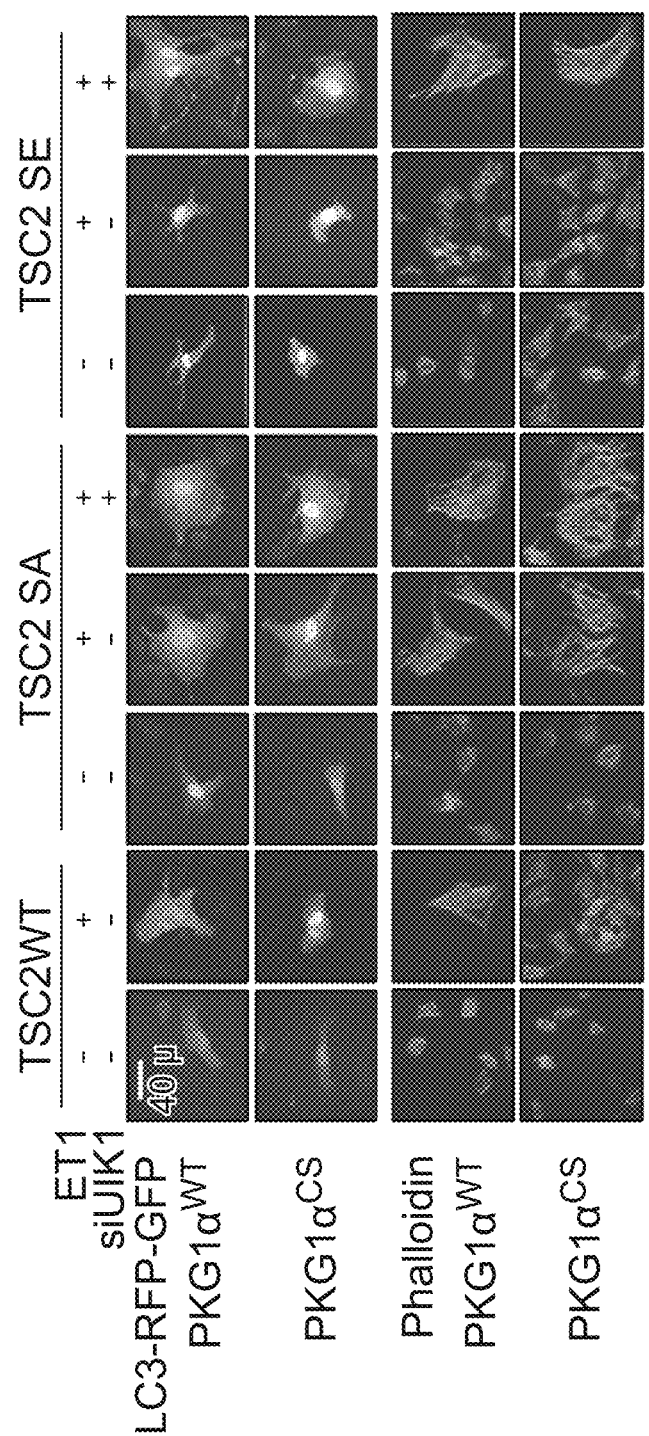
Figure 29:
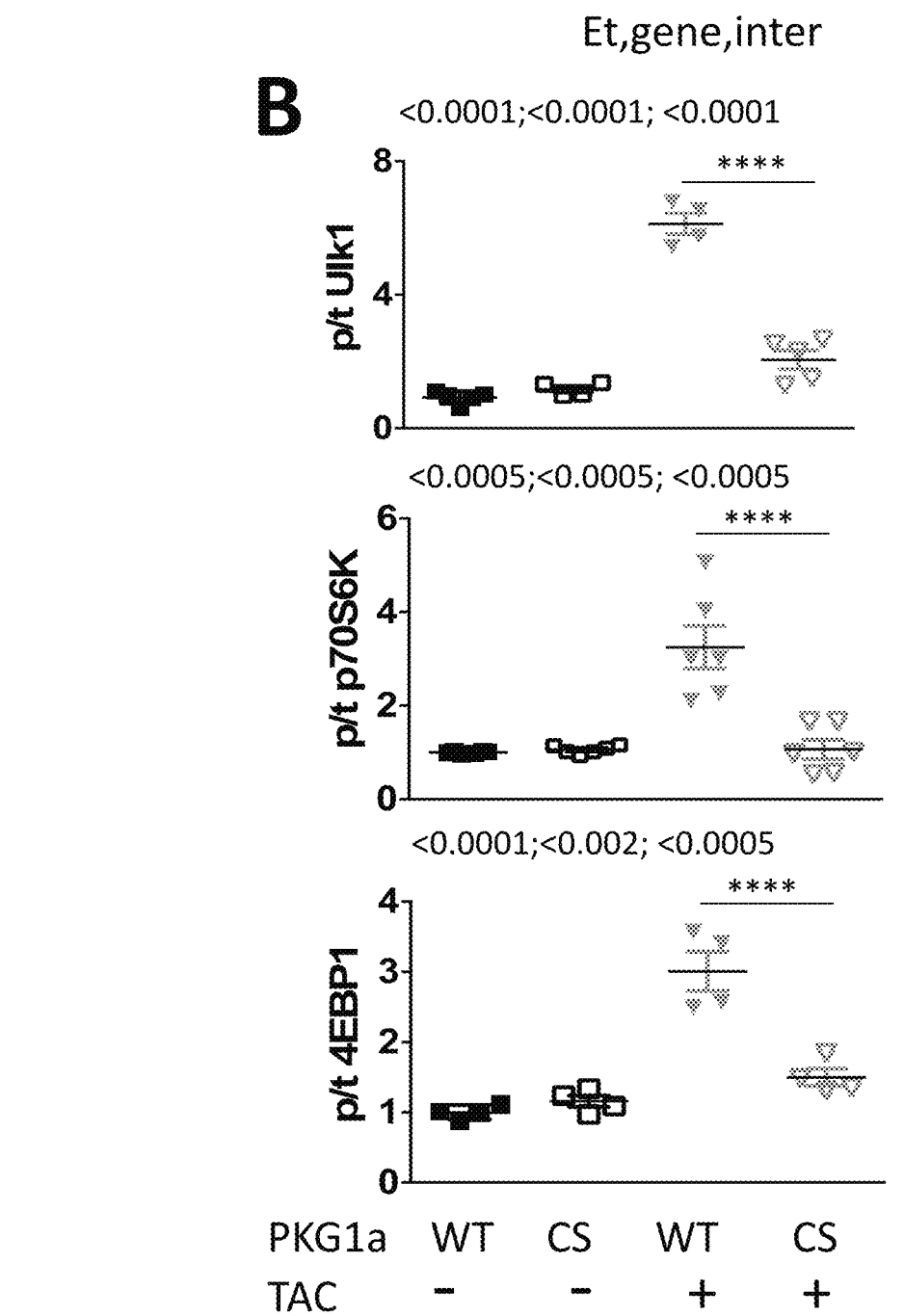
FIG. 29. C42S mutant strongly suppressed mTORC1 activation in PO-stress heart.
Figure 30:
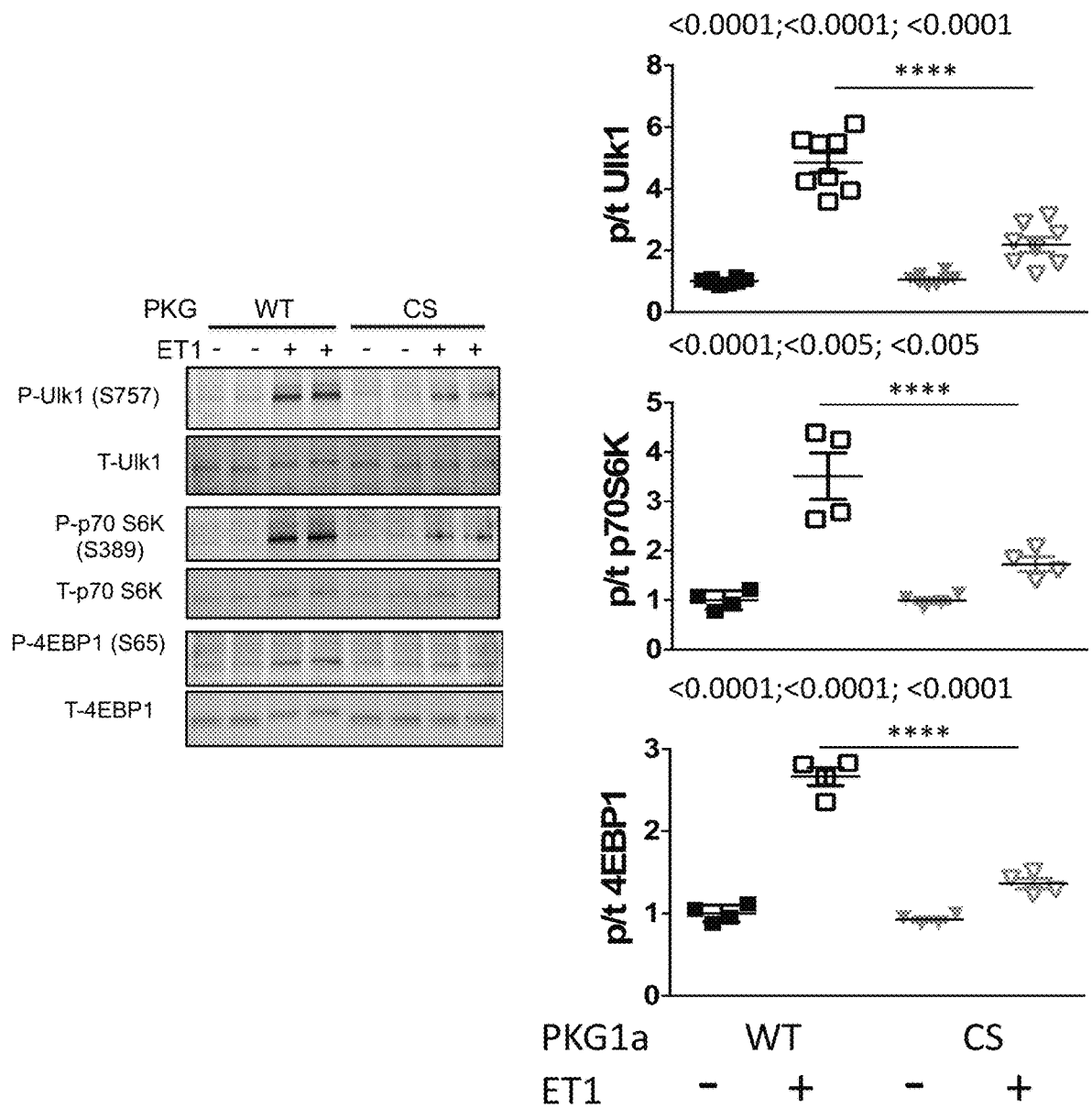
FIG. 30. C42S mutant strongly suppressed mTORC1 activation in ET-1 stimulated myocytes.
Figure 31:
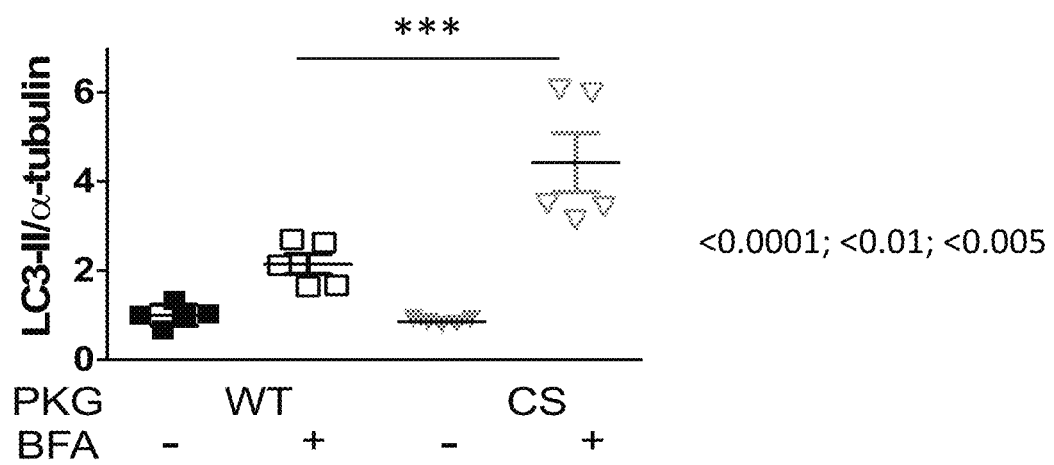
FIG. 31. C42S mutant enhanced autophagic flux (AuF).

PKG1α regulation is redox sensitive, as kinase oxidation results in a disulfide bond between homo-dimer C42-residues (16). This change, observed in human and experimental heart disease, limits the efficacy of PKG1α to counter pathological hypertrophy/fibrosis and dysfunction (17). It was therefore hypothesized that PKG1α-mTORC1 modulation is redox modulated. To test this, myocytes or hearts expressing WT or a redox-dead PKG1α (C42S) mutant were exposed to hormone or mechanical stress. This mutation only prevents PKG1α oxidation, leaving cellular and myocardial oxidative stress unaltered (17). When the C42S mutant was expressed, mTORC1 activation was strongly suppressed in the PO-stress heart (FIG. 2D, FIG. 29) and ET-1 stimulated myocytes (FIG. 30), and AuF was enhanced (FIG. 2E, FIG. 31).

PKG1α regulation is redox sensitive, as kinase oxidation results in a disulfide bond between homo-dimer C42-residues (16). This change, observed in human and experimental heart disease, limits the efficacy of PKG1α to counter pathological hypertrophy/fibrosis and dysfunction (17). It was therefore hypothesized that PKG1α-mTORC1 modulation is redox modulated. To test this, myocytes or hearts expressing WT or a redox-dead PKG1α (C42S) mutant were exposed to hormone or mechanical stress. This mutation only prevents PKG1α oxidation, leaving cellular and myocardial oxidative stress unaltered (17). When the C42S mutant was expressed, mTORC1 activation was strongly suppressed in the PO-stress heart (FIG. 2D, Supplemental FIG. 29) and ET-1 stimulated myocytes (Supplemental FIG. 30), and AuF was enhanced (FIG. 2E, Supplemental FIG. 31).

Example 3

The Role of TSC2 S1365 Modulation In Vivo

Figure 3A:
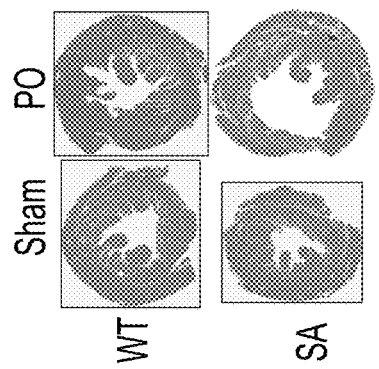
FIG. 3. A) Strategy and guide-RNA for CRISPR-Cas9 generation of S1365A (SA) knock-in mice. B) Survival curves of SA and littermate controls (WT) subjected to PO. Significance of Kaplan-Meier survival curve determined by log-rank (Mantel-Cox) test. C) Example post-mortem left ventricle of WT vs SA hearts subjected to sham or PO. D) Echocardiographic data for left ventricular end-diastolic dimension and fractional shortening. P-value for genotype time-course interaction in PO groups is shown. : between group difference at 2 weeks post-PO. E) mTORC1 growth/proliferation activation targets were increased after PO in SA versus WT mice, and unaltered in sham (baseline). F) LC3-II protein increased in WT-PO, but was absent in SA-PO (n=4/group). : $p<0.0001$; *: $p<0.001$; **: $p<0.01$; *: $p<0.05$ by Tukey multiple comparisons test following significance ($p<0.001$ or lower) deduced by 1-way ANOVA. 2W-ANOVA for PO, genotype, and interaction effects. and *- are as in FIG. 1.
Figure 3B:
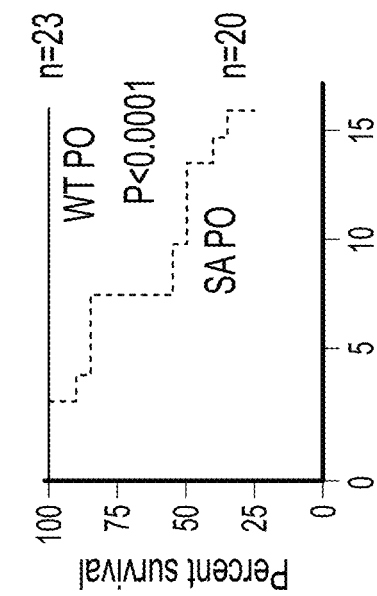
Figure 3C:
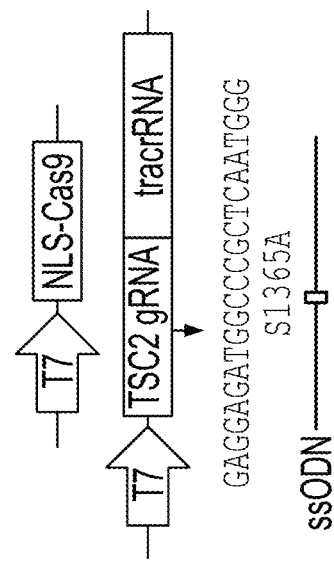
Figure 3D:
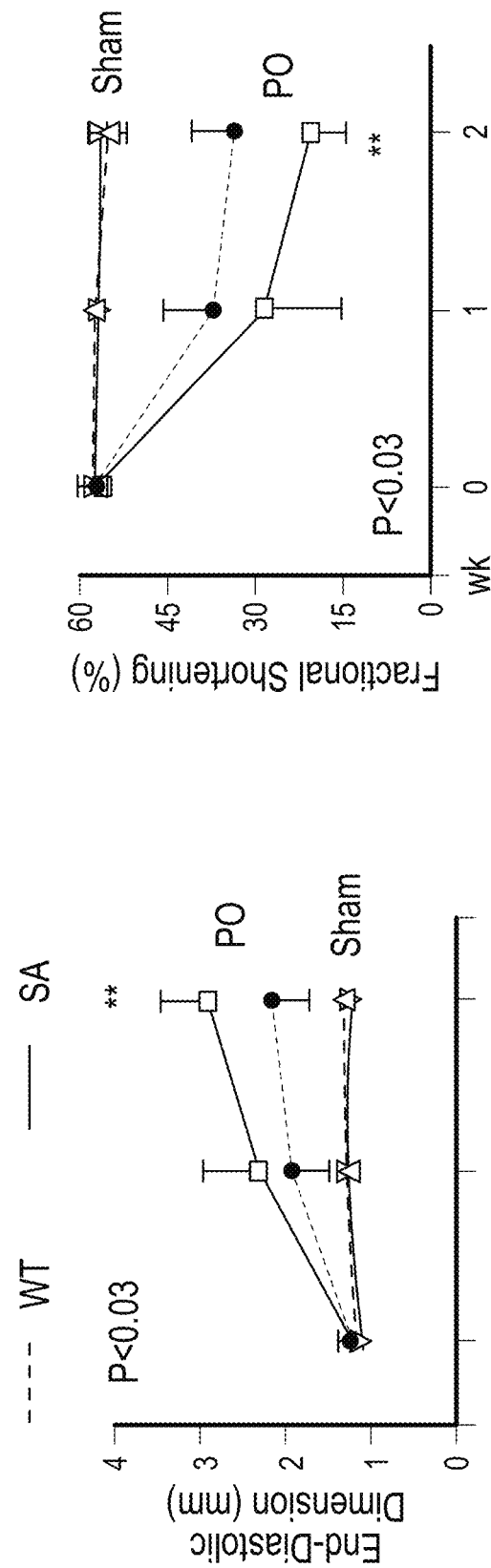
Figure 32A:
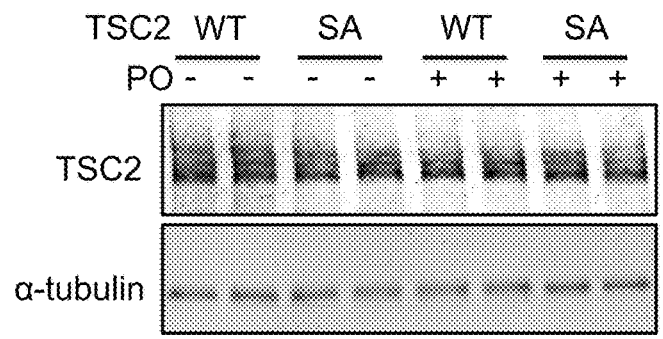
FIG. 32. A) Cardiac expression of TSC2 was similar in both SA and WT controls. B) Increased cardiac mortality was similarly observed following PO in both homozygote and heterozygote SA mice. C) Lung weight and A-type natriuretic peptide levels in SA and WT controls.
Figure 32B:
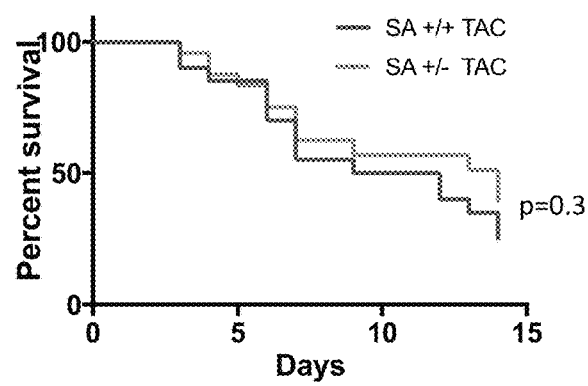
Figure 32C:
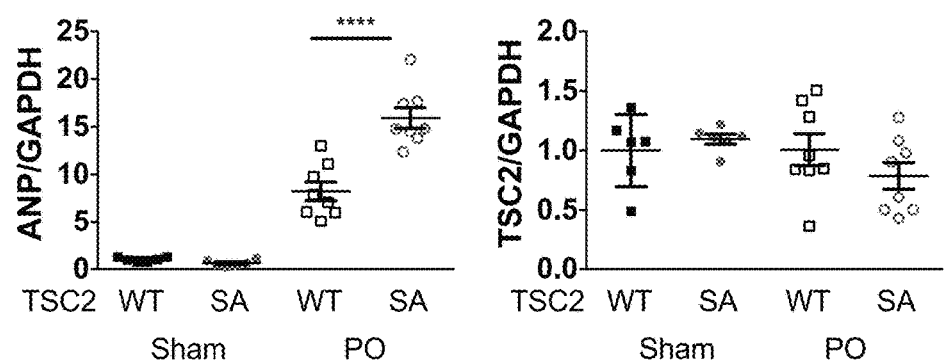
Figure 33:
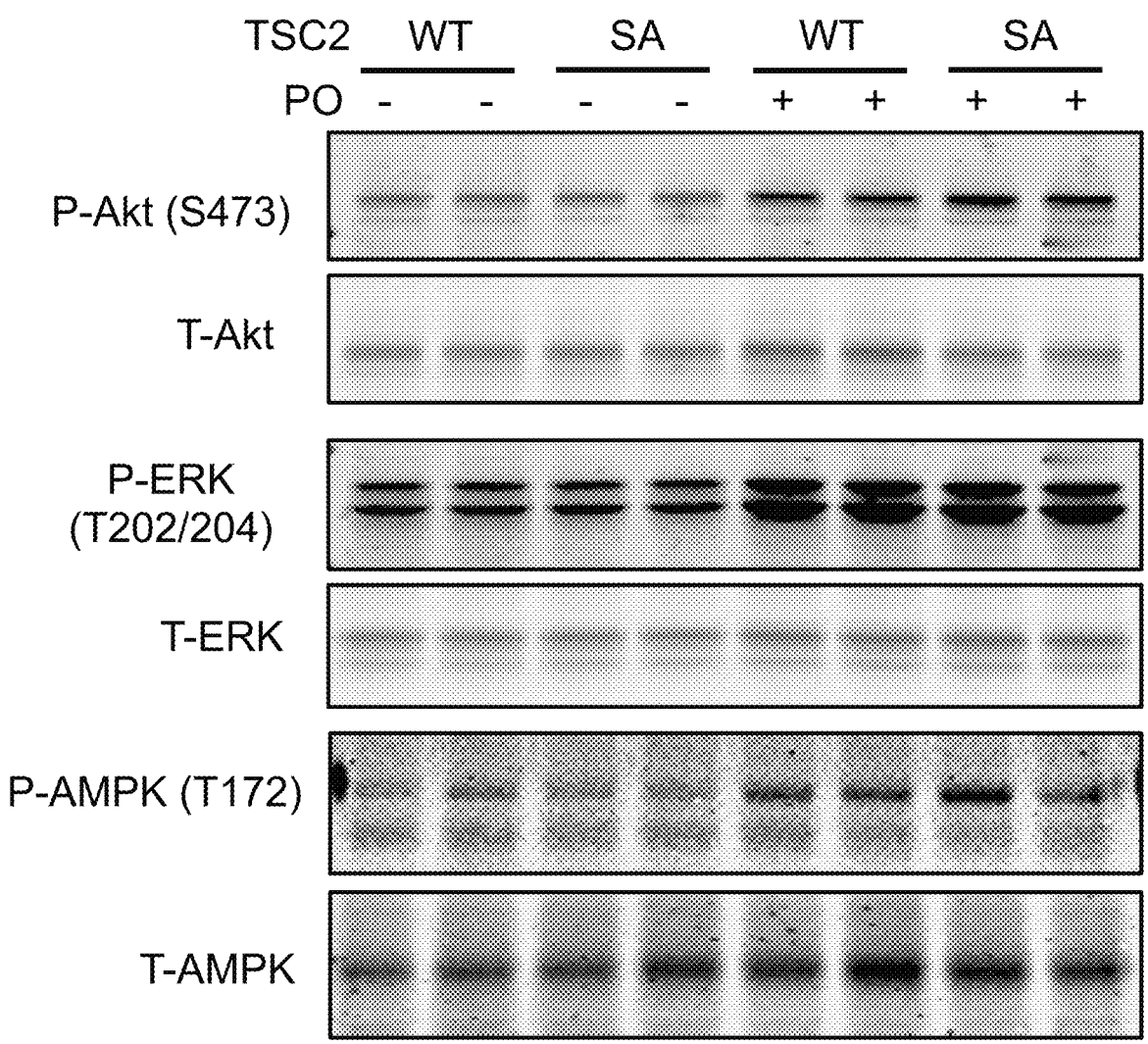
FIG. 33. Phosphorylation levels of other kinase modulators of TSC2, including Akt, ERK1/2, and AMPK.
Figure 34:
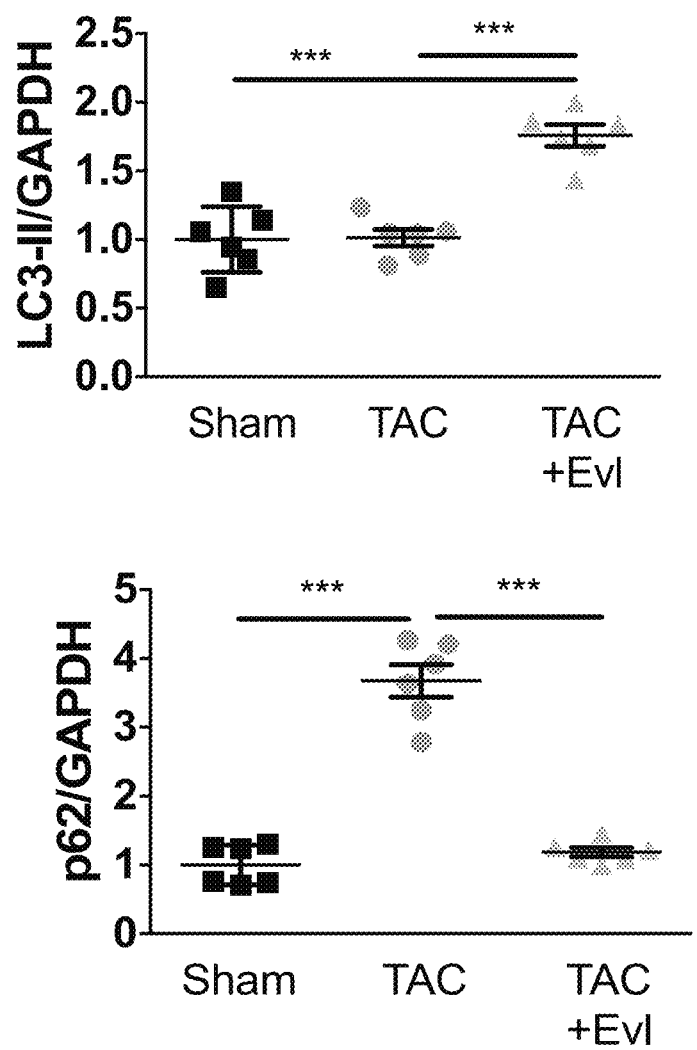
FIG. 34. mTORC1 inhibition by everolimus (Evl) increases autophagy reflected by LC3-II and p62.

To test the role of TSC2 S1365 modulation in vivo, S1365A mutant knock-in mice (SA) were generated using CRISPR (FIG. 3A). Homozygous knock-in mice were born healthy in normal Mendelian ratio, develop normally, and have normal cardiac morphology and function (Table 1, FIG. 26). Liver, lung, heart, and kidney histopathology appeared normal. Cardiac expression of TSC2 was similar in both SA and WT controls (FIG. 32A). When SA and WT mice (3 months old) were exposed to PO, SA mice displayed striking early mortality (75% by day 14) (FIG. 3B) attributable to dilated cardiac failure (FIG. 3C, 3D). Increased cardiac mortality was similarly observed following PO in both homozygote and heterozygote SA mice (FIG. 32B), indicating this is a potent effect. Lung weight and A-type natriuretic peptide were disproportionately greater, consistent with cardiac failure and dilation (FIG. 32C). As in isolated cells, SA expression in vivo did not alter resting mTORC1 activity; however, in response to PO, this activity exceeded controls (FIG. 3E). The impact on growth-stimulation pathways (p70S6K and 4EBP1) was quantitative, whereas autophagy effects were essentially binary. LC3-II increased in PO-stressed WT mice but there was no change from baseline in SA mice (FIG. 3F). Phosphorylation levels of other kinase modulators of TSC2, including Akt, ERK1/2, and AMPK were examined. All increased with PO, and these increases were similar in WT and SA PO mice (FIG. 34). Thus, the SA mutation overdrove other TSC2 regulatory inputs, markedly suppressing autophagy while amplifying mTORC1 anabolic signaling.

Example 4

Figures 4E, 4F, 4G:
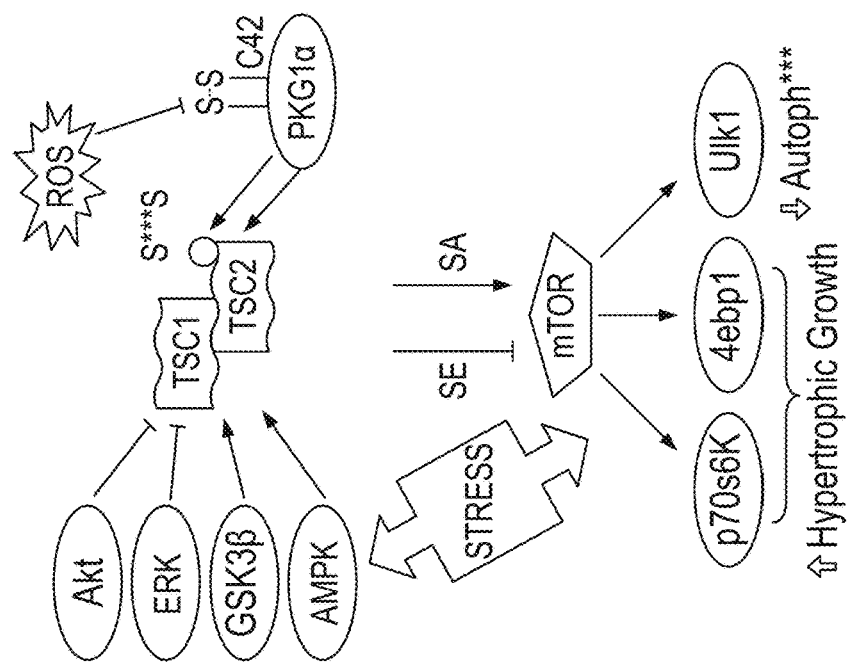
FIG. 4. A) Survival of SA-PO mice with or without everolimus (Evl) co-treatment. Significance of Kaplan-Meier survival curve determined by log-rank (Mantel-Cox) test. B) Heart and lung weights show near complete disease reversal with Evl-treatment in SA-PO mice. C) Example echocardiography shows normalized left ventricular function in Evl-treated mice. D) Autophagy is suppressed (low LC3-II, increased p62) in SA-PO mice, and augmented by Evl. E) Survival of C42S×SA mice versus C42S alone after PO. Significance of Kaplan-Meier survival curve determined by log-rank (Mantel-Cox) test. F) Chamber dilation is worse after PO in C42S×SA mice. G) Schematic summary of proposed signaling pathways. PKG1α is a new novel TSC2 regulating kinase targeting S1365, and this activity is suppressed by PKG1α oxidation. The state of S1365 bi-directionally impacts mTORC1 signaling, being particularly potent on Ulk1-dependent autophagy.
Figure 35A:
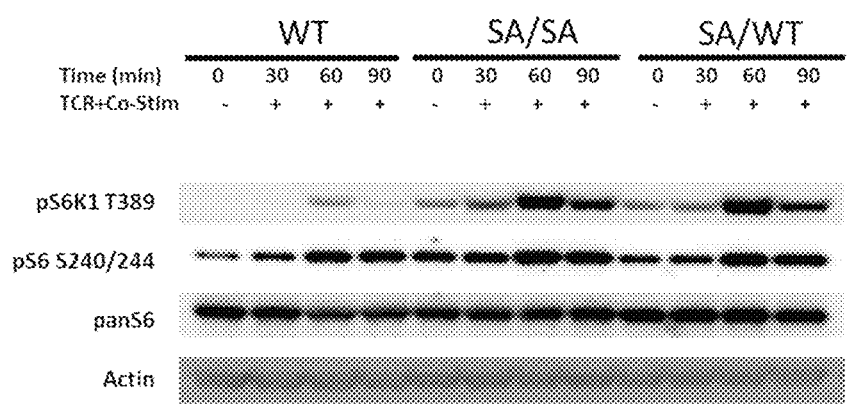
FIG. 35: Previously activated TSC2SA and TSC2SE mutant CD8+ effector T cells display differential mTOR activity compared to WT CD8+ T cells. A) Viable day-7 CD8+ T cells stimulated via TCR and co-stimulation were harvested, and cell lysate examined by immunoblotting. Western blot analysis assessed mTORC1 signaling targets such as pS6K1 and downstream S6. TSC2SA/SA mutant CD8+ T cells have more mTORC1 activity upon stimulation. This is similarly observed in cells from heterozygous mutant CD8+ T cells as well. Activation is also faster. B) TSC2 SE mutants show the opposite response to TCR/co-stimulation as observed in TSC2 SA mutants, with mTORC1 activation indexed by phosphorylation of S6K1 and S6 being reduced as compared with cells with either WT or the SA form.
Figure 35B:
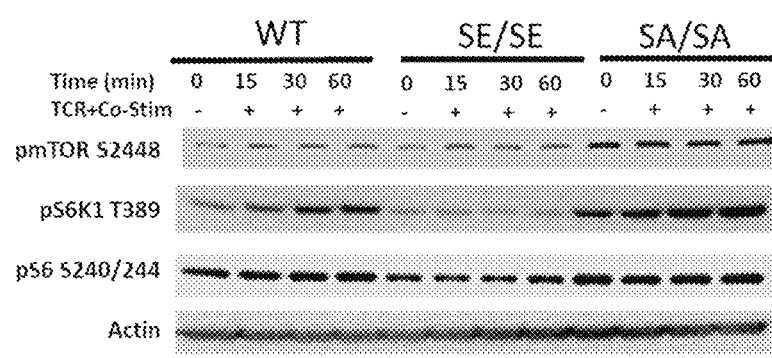

Hyper-activation of mTORC1 Caused the Adverse Outcomes and Early Mortality in SA-PO Mice To test if hyper-activation of mTORC1 caused the adverse outcomes and early mortality in SA-PO mice, a second cohort was co-treated with either Evl or vehicle, each started several days prior to PO. Evl fully prevented death (FIG. 4A) and restored cardiac structure and function to that of sham controls (FIG. 4B, 4C). Evl increased autophagy reflected by LC3-II and p62 (FIG. 4D; FIG. 35). Thus, solely by blocking S1365 phosphorylation in vivo in an integrated model of pathological stress, autophagy was abrogated and the pathological response was amplified by mTORC1 hyper-activation. Lastly, it was tested whether cardiac protection against PO previously reported in PKG1α C42S-KI mice (17) also requires S1365 phosphorylation. Double KI mice (C42S/SA) were bred and subjected to PO. Controls were C42S only. Mortality (FIG. 4E) and cardiac dilation (FIG. 4F) from PO were markedly worse in C42S/SA mice, supporting the link between redox sensitivity of PKG1α and S1365 targeting in vivo.

FIG. 4G summarizes the findings. PKG1α mediated TSC2 to regulate mTORC1 activity, acting as a single residue bi-directional rheostat capable of blunting or amplifying activity depending on the phosphorylation status of S1365. This impact was most potent on Ulk-1 dependent autophagy. Lastly, S1365 targeting by PKG1α was blunted by its oxidation at C42, linking oxidative stress to mTORC1 activity.

Example 5

The Role of the Mutant TSC2 Allele on CD8+ T Cell Activation and Differentiation To assess mTORC1 activation in naive T cells, WT and TSC2SA splenocytes were activated with (spleen and lymph node leukocytes) antibodies to the T cell receptor (TCR) and co-stimulatory molecules. TCR and co-stimulation represent Signal 1 and Signal 2 that activate a T cell and turn on mTORC1 signaling.

Spleen and lymph nodes were processed to obtain single suspension lymphocytes. T cells were stimulated with Signal 1 and 2 over time to measure T cell receptor induced mTORC1 activity. Cells at indicated time points were chemically fixed with 2% paraformaldehye to quickly preserve signaling status. Next, cells were permeabilized with 90% methanol. Cells were washed and then stained with flow antibodies for surface CD4 and CD8 and also unconjugated antibody to pS6 (S240.44) followed by with a secondary antibody for pS6 (S240.44). Cells were then run on a flow cytometer for analysis.

To measure mTORC1 activity in T cells upon TCR activation, phospho-flow cytometry was utilized by staining CD4 and CD8 T cells for phospho-S6 (S240.44) as a readout of downstream mTORC1 activity. Phospho-flow cytometry is a very sensitive method to measure signaling pathways on a per cell basis compared to traditional western blotting which is population based. Splenocytes stimulated with TCR+Co-Stim (anti-CD3/28) for 30, 60, 90, 120 minutes.

Figure 5:
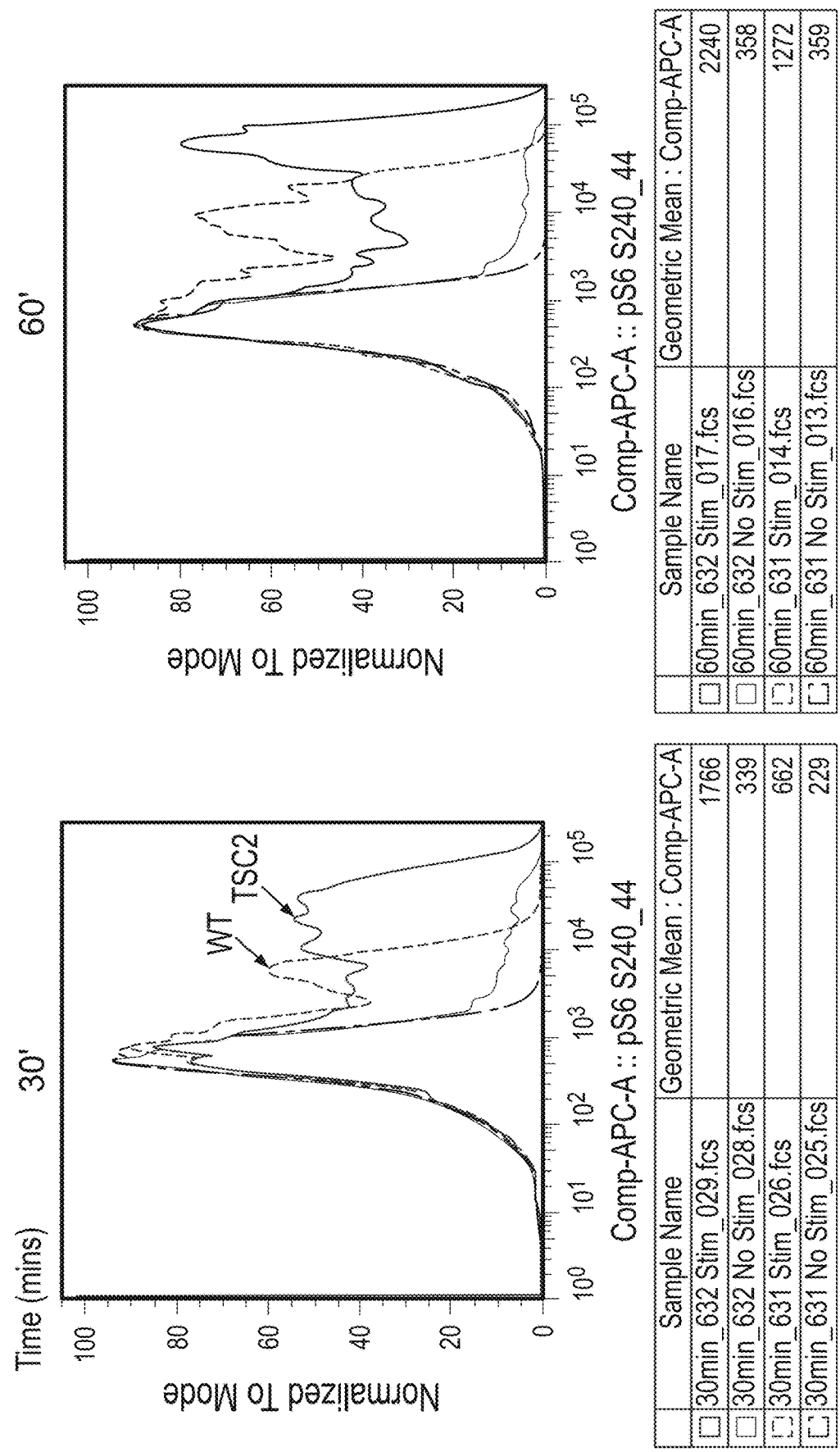
FIG. 5. TSC2 Mutant (TSC2*) CD4 T cells display higher mTORC1 activity (pS6 S240.44) upon T cell activation with Signal 1 plus Signal 2 over time. Geometric mean fluorescent intensity (MFI) indicates intensity of expression of mTORC1 activity in respective condition.
Figure 5:
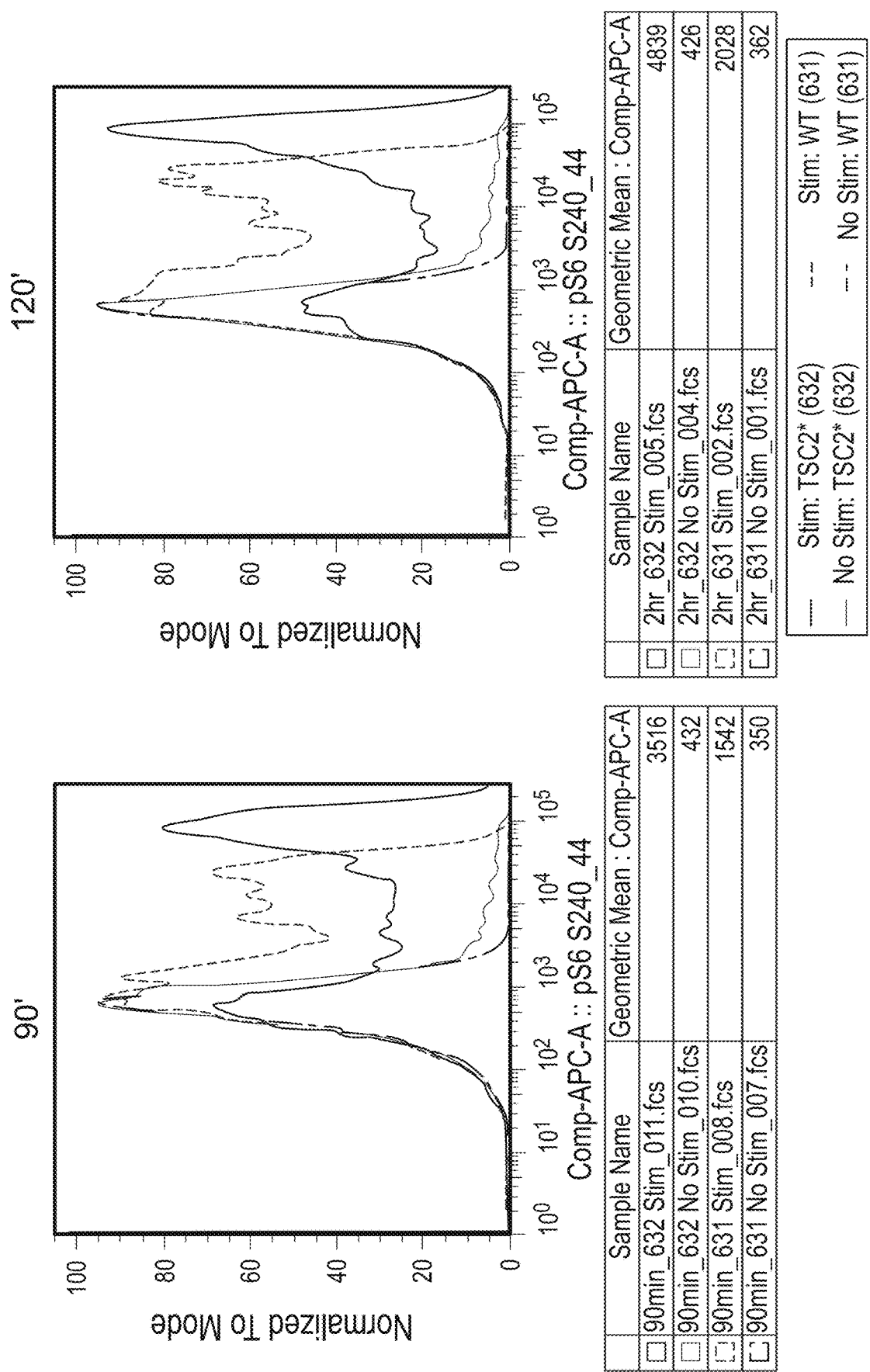
Figure 6:
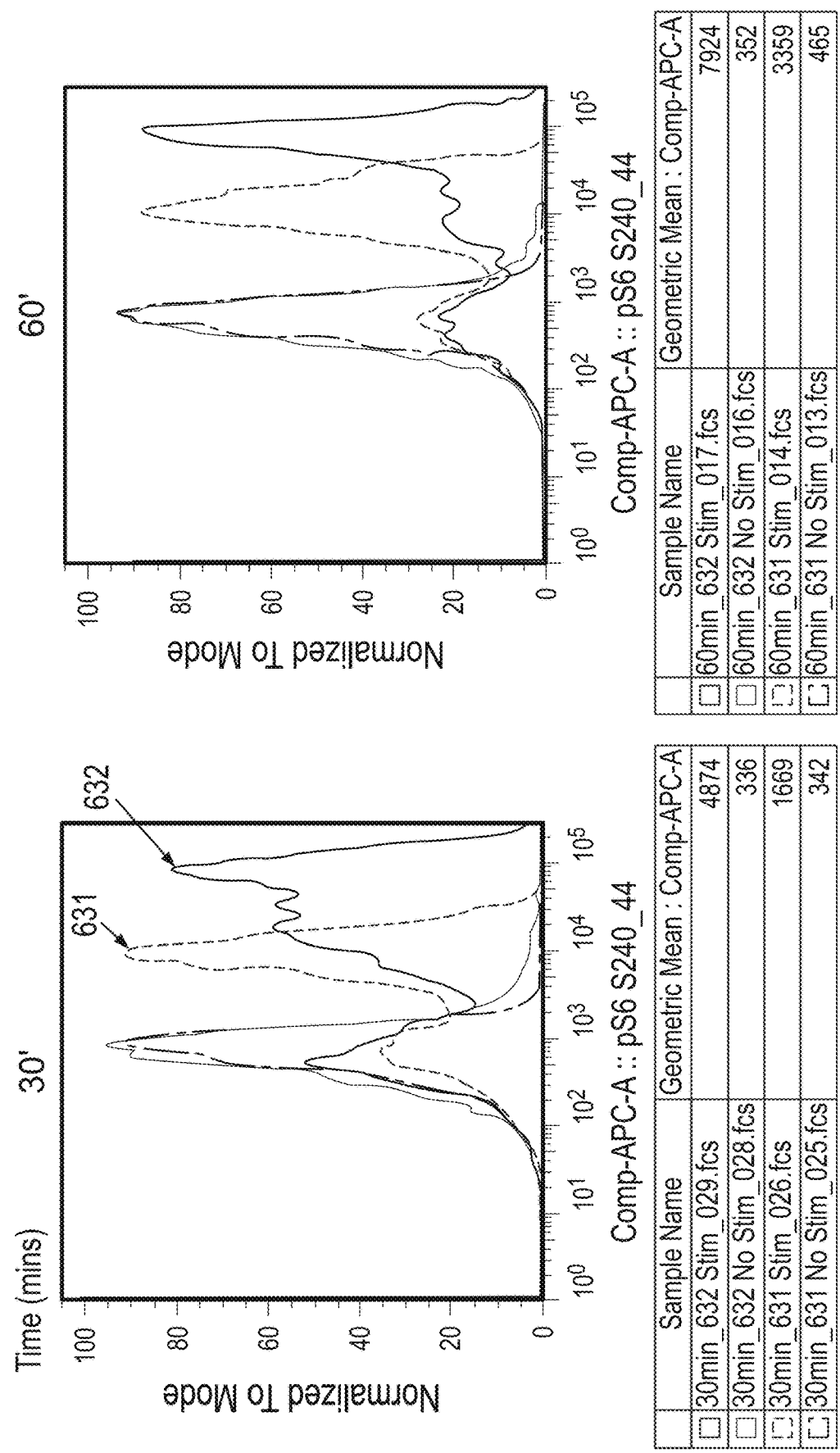
FIG. 6. TSC2 Mutant (TSC2*) CD8 T cells display higher mTORC1 activity (pS6 S240.44) upon T cell activation with Signal 1 plus Signal 2 over time. Geometric mean fluorescent intensity (MFI) indicates intensity of expression of mTORC1 activity in respective condition.
Figure 6:
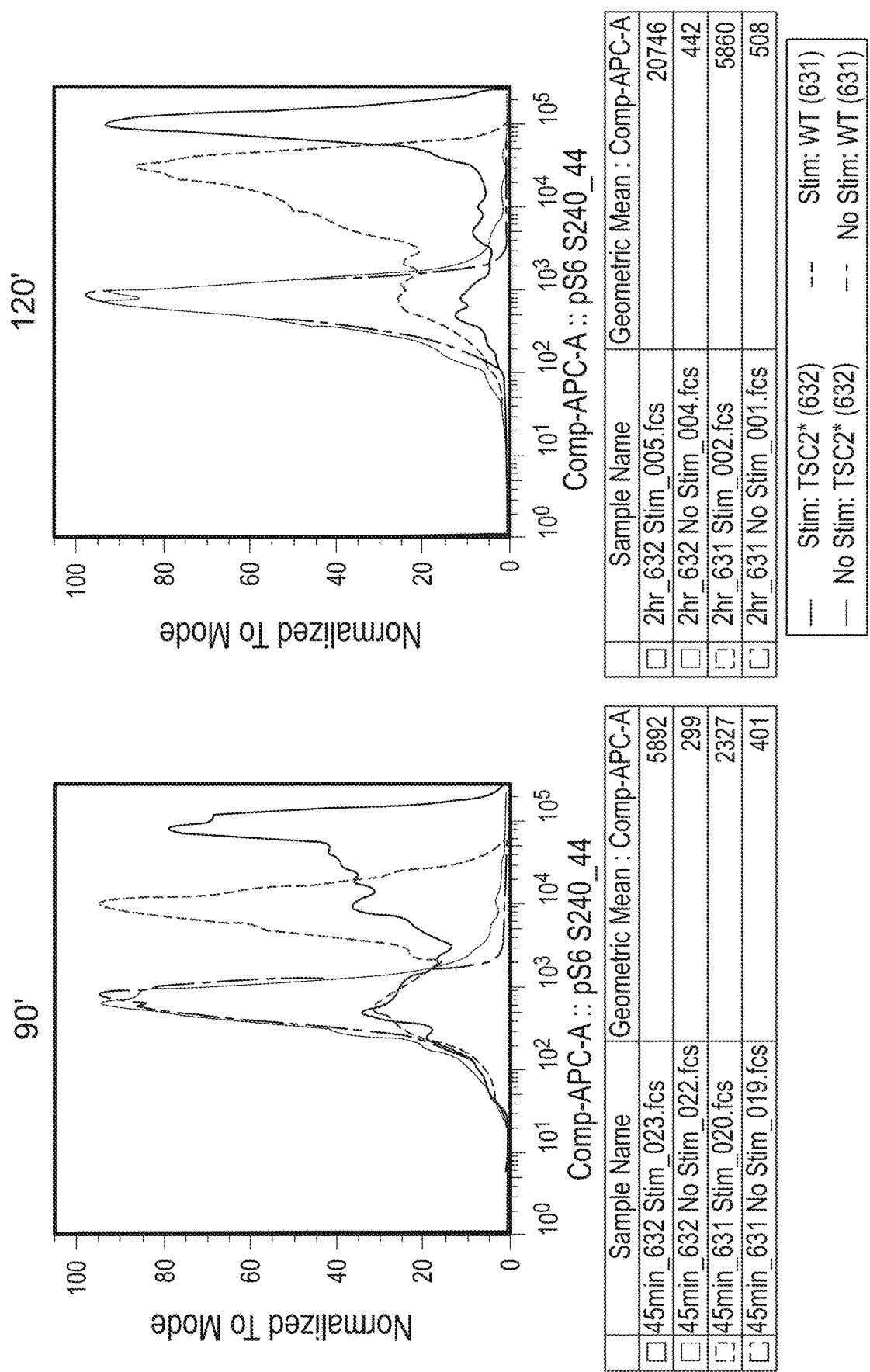
Figure 7A:
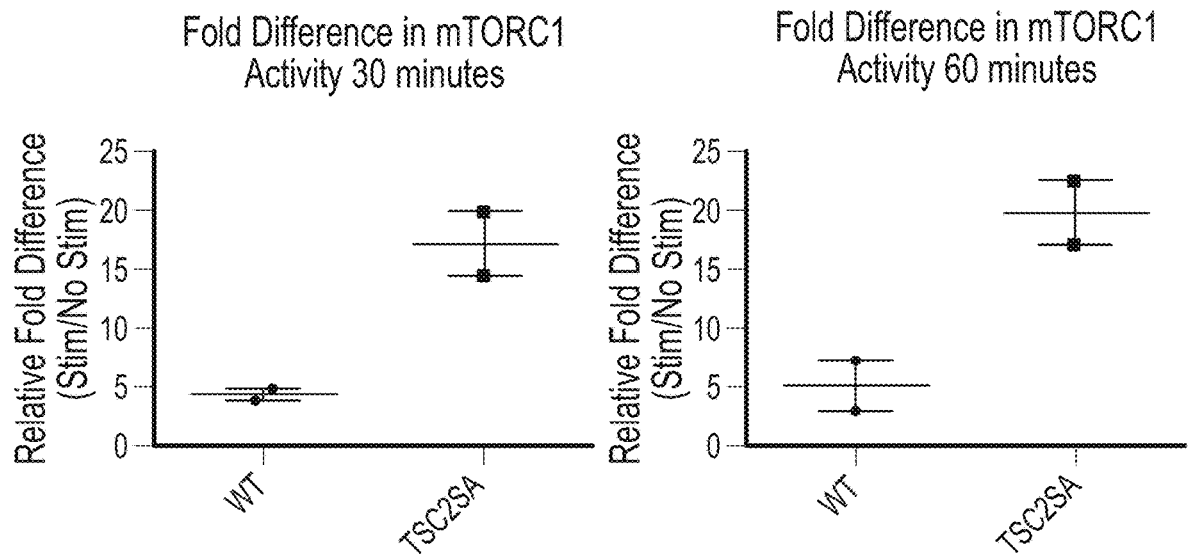
FIGS. 7A-7B. CD8 mTORC1 Activity. A. Fold difference in mTORC1 activity calculated based on MFI value of 30 and 60 minute stimulation time points versus MFI of no stimulation. B. TSC2 SE mutant CD8+ T cells display the opposite response to TSC2 SA cells, with markedly reduced mTORC1 activation following TCR stimulation. Data shown are at 90 minutes following stimulation. As with TSC2 SA mutant T cells, the TSC2 SE cells also show no differences in mTORC1 activity in the resting (non-stimulated) state.
Figure 7B:
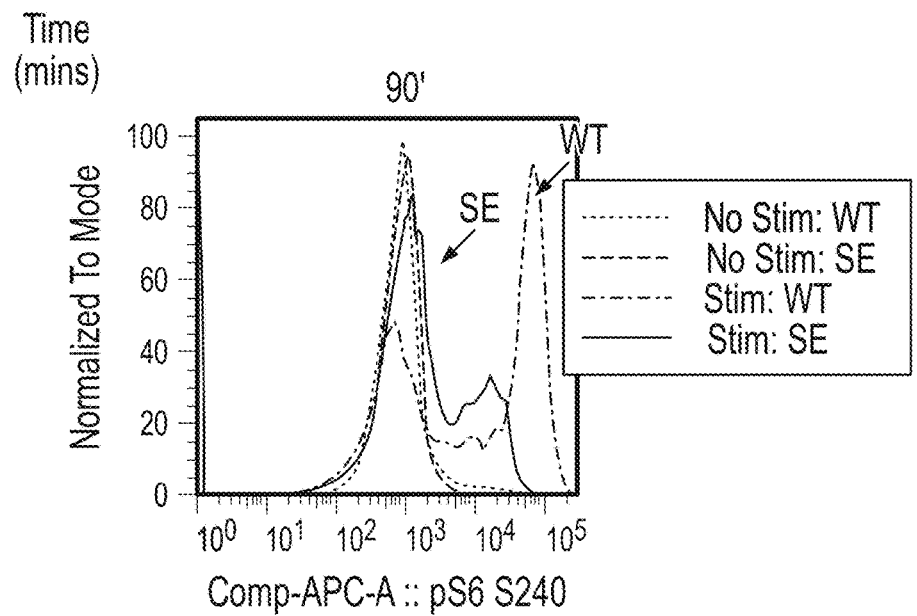

Minimal basal mTORC1 activity in both CD4 (FIG. 5) and CD8 (FIG. 6) T cells in unstimulated cells was observed. Upon TCR activation, there was an immediate increase in mTORC1 activity in WT T cells; however, TSC2SA mutant T cells displayed an even greater increase in mTORC1 activity throughout the time course experiment. FIG. 7A shows a graphical summary of two independent experiments displaying mTORC1 activity at 30 minutes and 60 minutes compared to basal levels in CD8+ T cells. Next, spleen and lymph nodes were processed to obtain single suspension lymphocytes. T cells were stimulated with Signal 1 and 2 over time to measure T cell receptor induced mTORC1 activity. Cells at indicated time points were chemically fixed with 2% paraformaldehye to quickly preserve signaling status, and were then permeabilized with 90% methanol. Cells were washed and then stained with flow antibodies for surface CD4 and CD8 and also unconjugated antibody to pS6 (S240.44) followed by with a secondary antibody for pS6 (S240.44). Cells were then run on a flow cytometer for analysis. TSC2SE Mutant CD8 T cells display reduced mTORC1 activity (pS6 S240.44) upon T cell activation with Signal 1 plus Signal 2 over time (FIG. 7B). Geometric mean fluorescent intensity (MFI) indicates intensity of expression of mTORC1 activity in respective condition.

Example 6

TSC2SA CD8+ T Cells Generate Potent Effector T Cells Compared to WT T Cells

To generate CD8+ effector T cells, the splenocytes were stimulated and expanded in effector promoting conditions with IL-2. Strong IL-2 signaling preferentially skewed CD8+ T cells to differentiate into effector T cells.

T cells were activated and then differentiated with IL-2 to promote proliferation, as well as effector T cell generation. Cells were expanded and then rested for 8 days total. On day 8, live cells were isolated based on density gradient using Ficoll. Live cells were re-stimulated with PMA, Ionomycin, and GolgiStop (to block cytokine secretion and to preserve cytokine within the cell) for 4 hours. Cells were stained with surface CD8 antibody and cell viability dye to exclude dead cells from analysis. Next, cells were fixed and permeabilized to detect intracellular cytokine expression using antibodies to respective cytokines. Finally, cells were analyzed using a flow cytometer. Day 8 resting live T cell cultures were re stimulated with PMA/Iono/GolgiStop for 4 hrs.

Figure 8A:
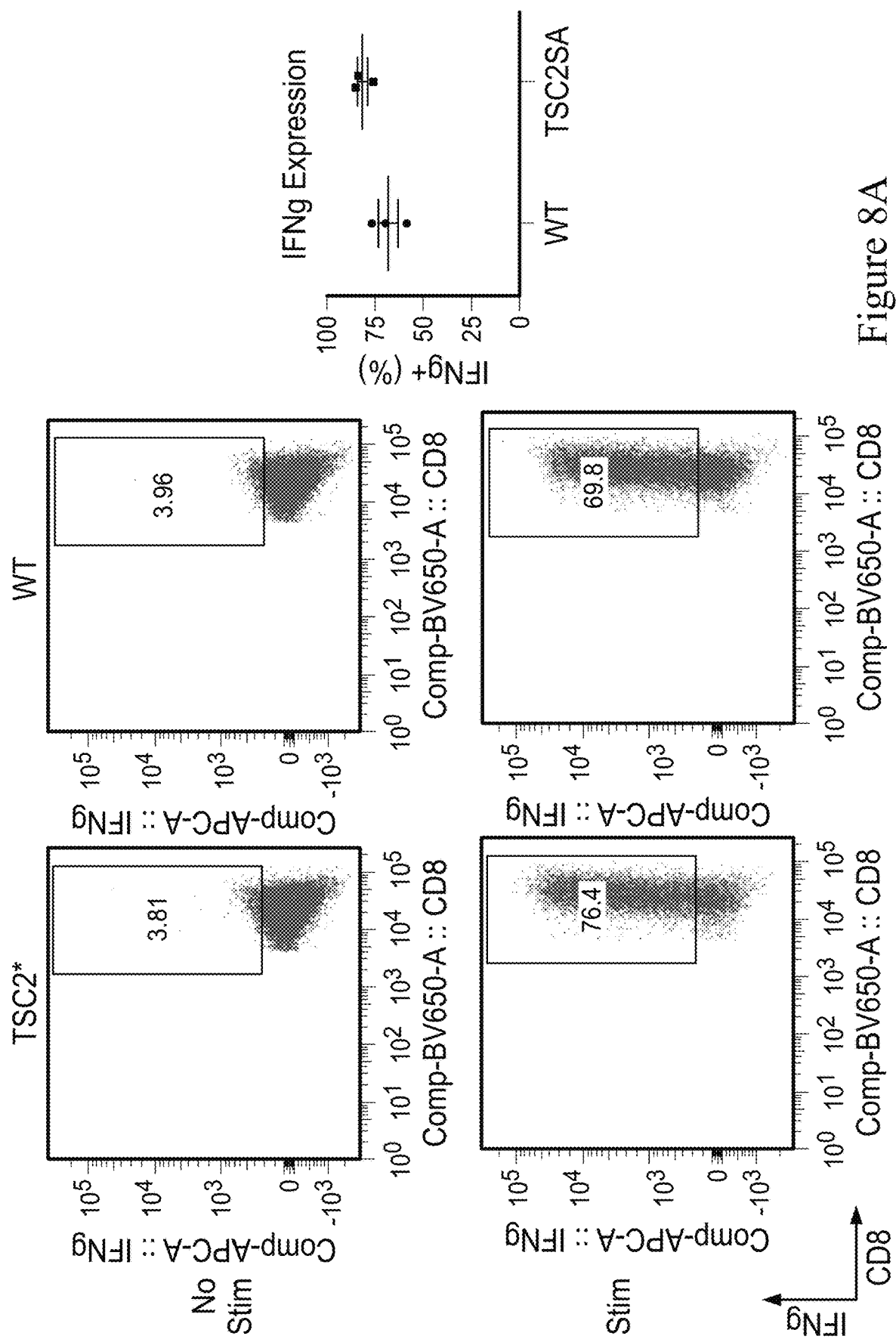
FIGS. 8A-8B. Interferon Gamma (IFNg) cytokine expression. A. TSC2 mutant CD8 T cells have enhanced effector function upon re-challenge assed by Interferon gamma (IFNg) expression. B. TSC2SE mutant CD8 T cells expressed less IFNg upon compared to WT CD8 T cells upon re-challenge.
Figure 8B:
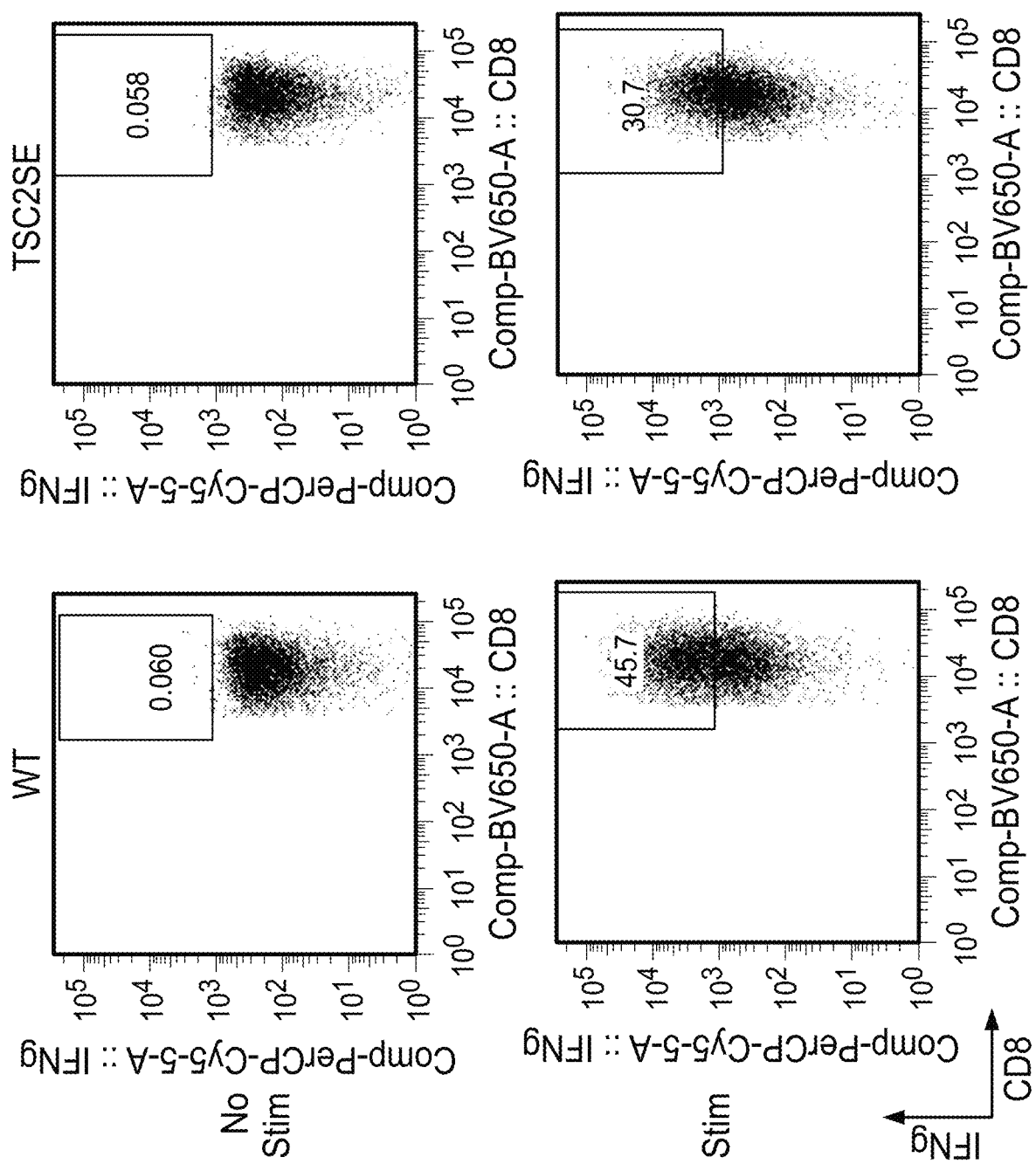
Figure 9:
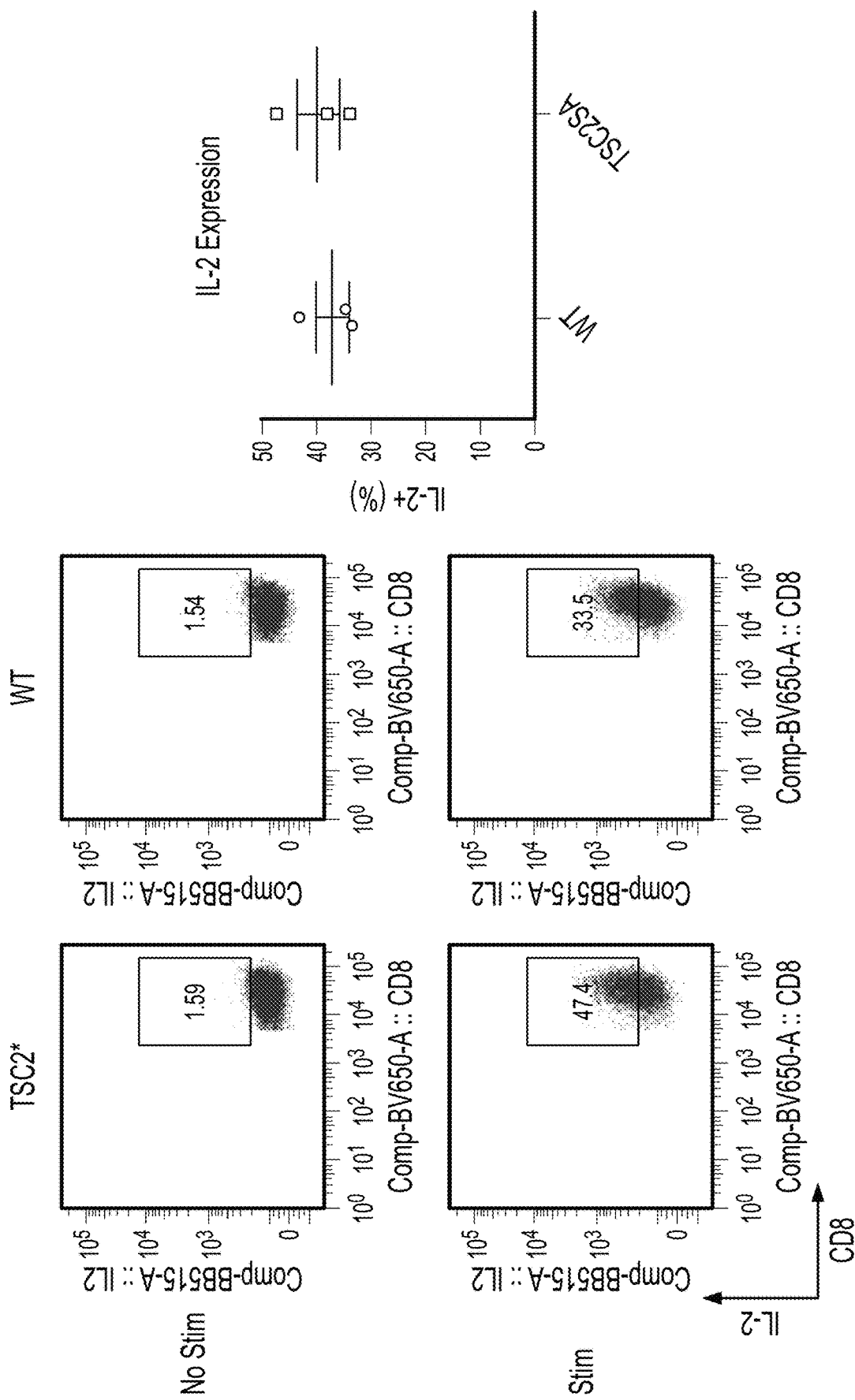
FIG. 9. TSC2 mutant CD8 T cells have enhanced effector function upon re-challenge assed by IL-2 expression.
Figure 10:
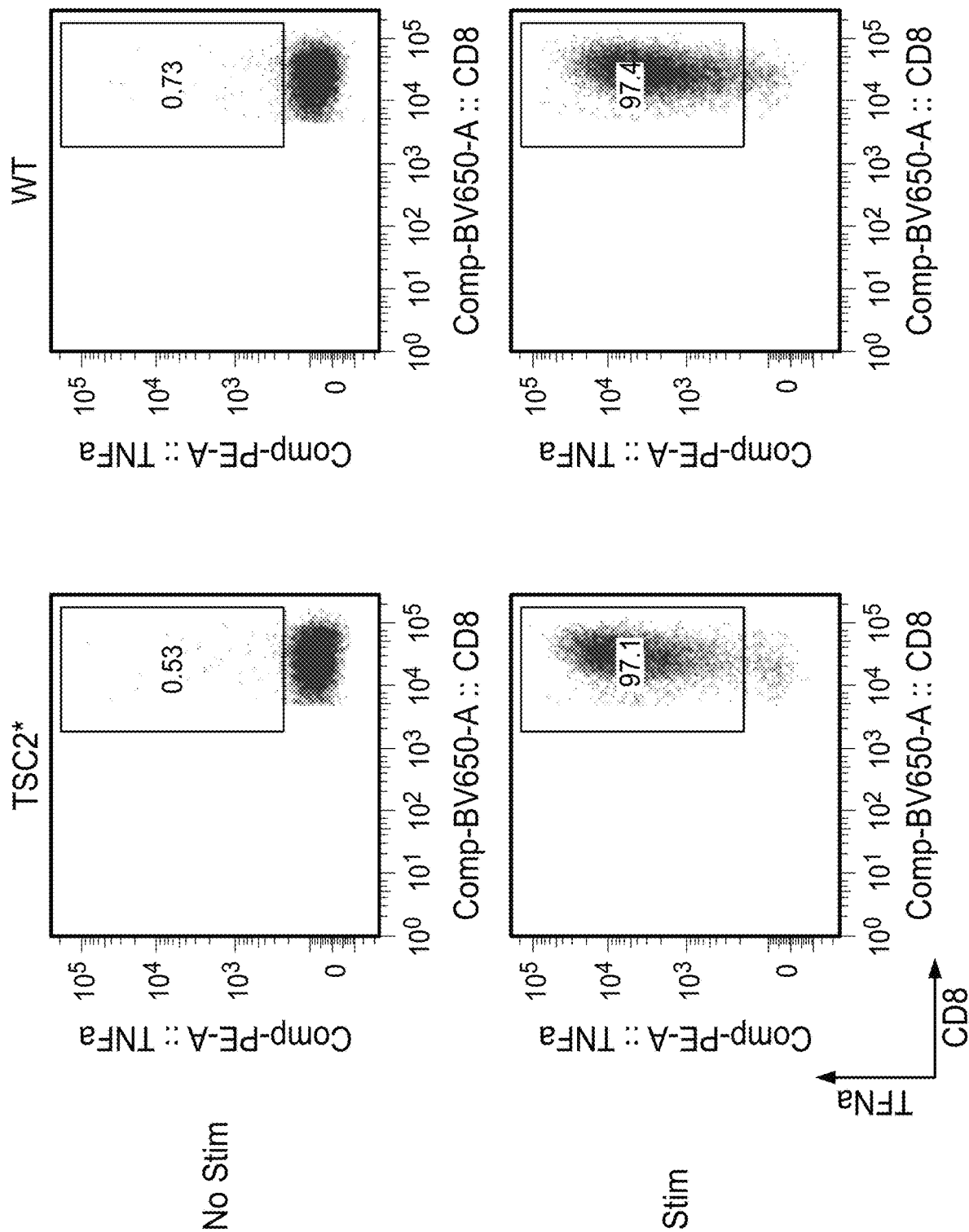
FIG. 10. TSC2 mutant CD8 T cells have enhanced effector function upon re-challenge assed by TNFa expression.
Figure 10:
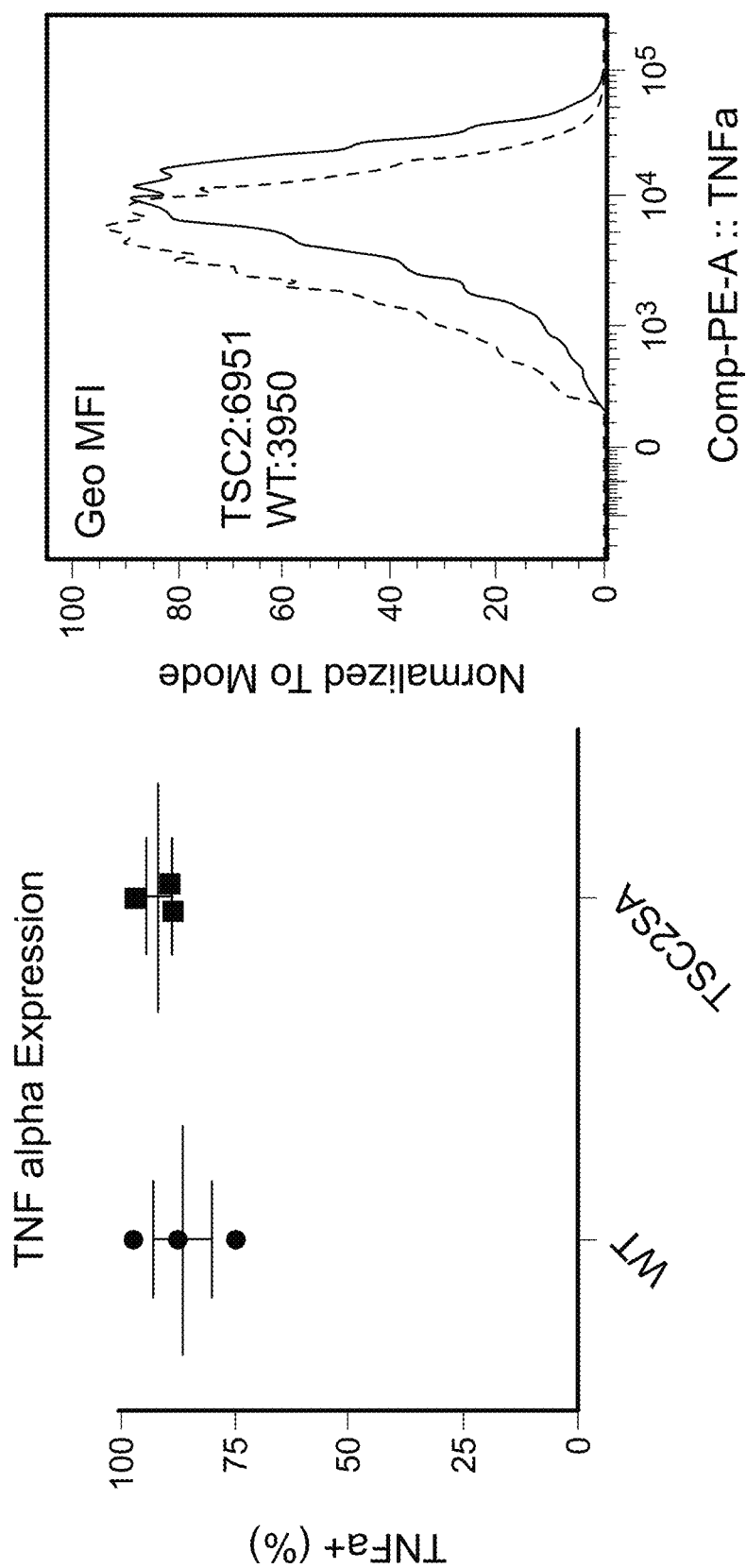

On Day 7, CD8+ cultures were processed to remove non-viable cells. To assess effector function, viable cells were re-stimulated with PMA and Ionomycin along with a golgi blocker to capture cytokines within the cells for later flow cytometry analysis. After 4 hours, cells were processed and stained to assess cytokine function. Interferon gamma (IFNg) (FIG. 8), tumor necrosis factor alpha (TNFa) (FIG. 10), and Interleukin-2 (IL-2) (FIG. 9) are hallmark cytokines of CD8+ effector T cells. TSC2SA mutant CD8+ T cells consistently showed elevated levels of these hallmark cytokines compared to WT CD8+ T cells.

Example 7

Previously Activated TSC2 Mutant T Cells Induce Faster and Higher mTORC1 Activity Compared to WT Control Cells T cells were activated and then differentiated with IL-2 to promote proliferation, as well as effector T cell generation. Cells were expanded and then rested for 8 days total. On day 8, live cells were isolated based on density gradient using Ficoll. Live cells were re-stimulated with Signal 1 and 2 over time. Cells were snap frozen at indicated times to preserve signaling. Cell pellets were lysed for immunoblotting to assess mTORC1 signaling at indicated time points. Dead cells were removed from day 8 resting T cell cultures by treatment with Ficoll. Live cells were stimulated with anti-CD3/28 for 15, 30, and 60 minutes for immunoblotting of mTORC1 activity.

Figure 11:
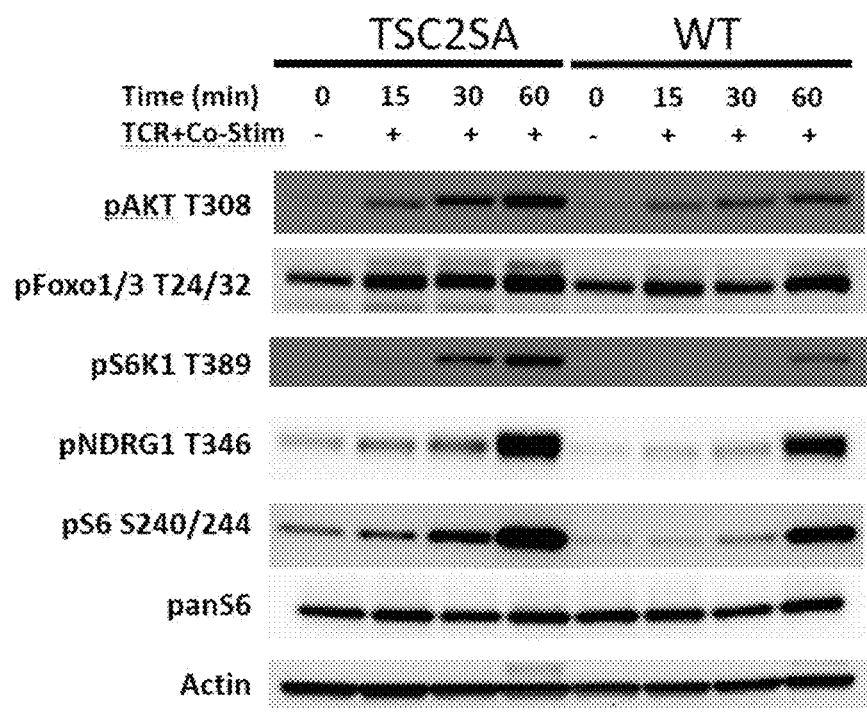
FIG. 11. Previously activated TSC2 mutant T cells induce faster and higher mTORC1 activity compared to WT control cells.

As shown in FIG. 11, TSC2SA mutant cells exhibited increased mTORC1 activity at earlier times than wild type cells, as assessed by Western blot analysis of mTORC1 signaling targets such as p70S6 Kinase (S6K1), S6 ribosomal protein (S6 S240/244), Akt (also Protein kinase B), and mTORC2 targets such as Forkhead Box Protein 1 (Foxo1) and N-myc Downstream Regulated Gene 1 Protein (NDRG1).

Example 8

Figure 12:
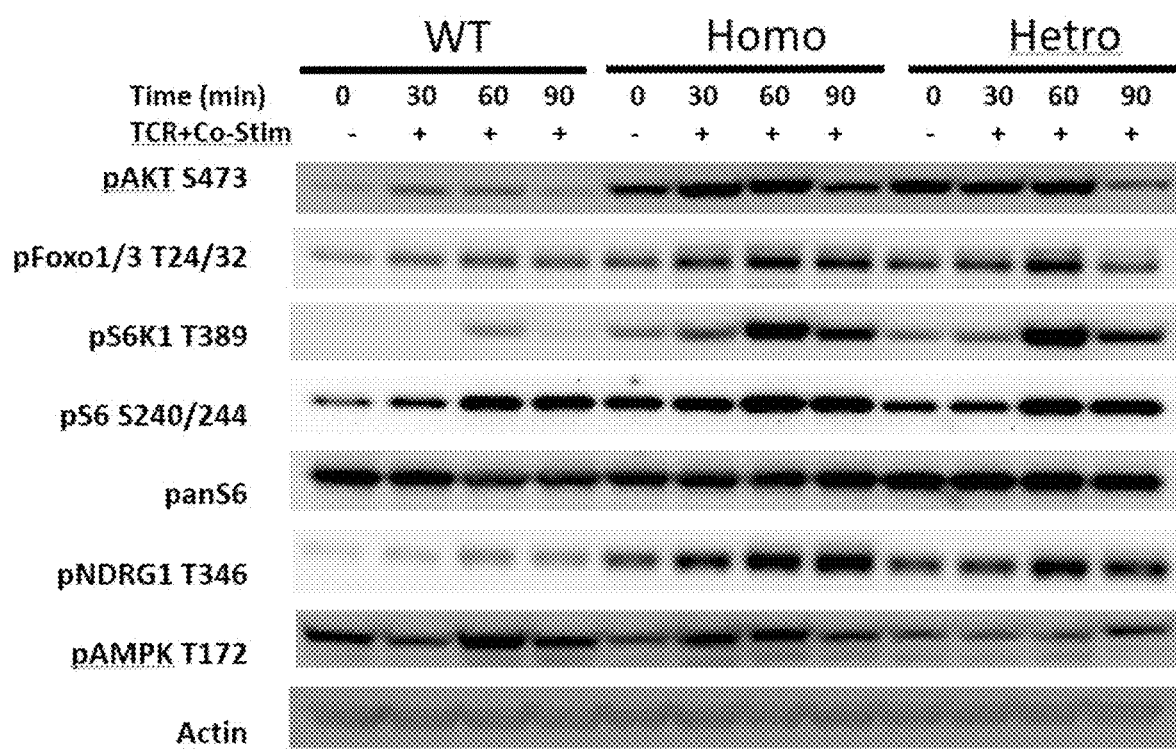
FIG. 12. TSC2SA mutant CD8+ effector T cells from homozygote or heterozygote SA-KI mice show hyperactivation of mTOR signaling pathways, with similar responses in cells expressing either one or two mutant alleles.

TSC2SA Mutant CD8+ Effector T Cells from Homozygote or Heteozygote SA-KI Mice Show Hyperactivation of mTOR Signaling Pathways, with Similar Responses in Cells Expressing Either One or Two Mutant Alleles Dead cells were removed from day 7 resting CD8 T cell cultures by treatment with Ficoll. Live cells were stimulated with anti-CD3/28 for 30, 60, and 90 minutes for immunoblotting of mTORC1 activity. TSC2SA mutant CD8+ effector T cells from homozygote or heteozygote SA-KI mice show hyperactivation of mTOR signaling pathways, with similar responses in cells expressing either one or two mutant alleles (FIG. 12).

Example 9

Treatment of SE and SA Cells with Insulin

Figure 13:
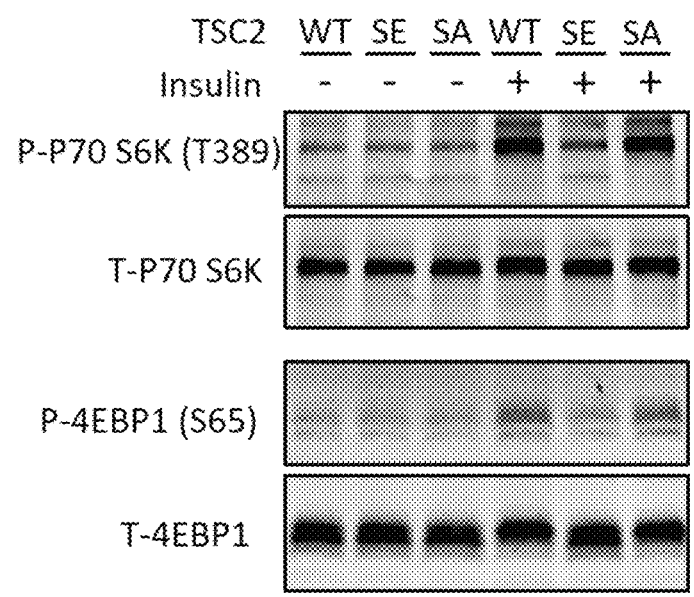
FIG. 13. Western blot analyses of phosphorylated/total Ulk1, p70 S6K and 4EBP1 from cultured neonatal rat cardiomyocytes (NRCMs) expressing a WT, S1365E, or S1365A TSC2 were treated with insulin (10 µg/ml) or vehicle for 15 minutes.

FIG. 13 shows western blot analyses of phosphorylated/total Ulk1, p70 S6K and 4EBP1 from cultured neonatal rat cardiomyocytes (NRCMs) expressing a WT, S1365E, or S1365A TSC2 were treated with insulin (10 μg/ml) or vehicle for 15 minutes.

Example 10

SA and SE Mutations in T Cells

T cells were activated and then differentiated with IL-2 to promote proliferation but also effector T cell generation. Cells were expanded and then rested for 8 days total. On day 8, live cells were isolated based on density gradient using Ficoll. Live cells were re-stimulated with Signal 1 and 2 over time. Live cells were stimulated with anti-CD3/28 for 30, 60, and 90 minutes for immunoblotting of mTOR activity. Cells were snap frozen at indicated times to preserve signaling. Cell pellets were lysed for immunoblotting to assess mTOR signaling at indicated time points. Previously activated TSC2SA and TSC2SE mutant CD8+ effector T cells display differential mTOR activity compared to WT CD8+ T cells (FIG. 35). SE/SE cells consistently observe less mTORC1 and mTORC2 activity.

Mice heterozygous for the TSC2 SA mutation were crossed with OT-I mutant mice to generate TSC2SA heterozygous (Het)/OTI (Ovalbumin (OVA) specific) CD8+

Figure 36B:
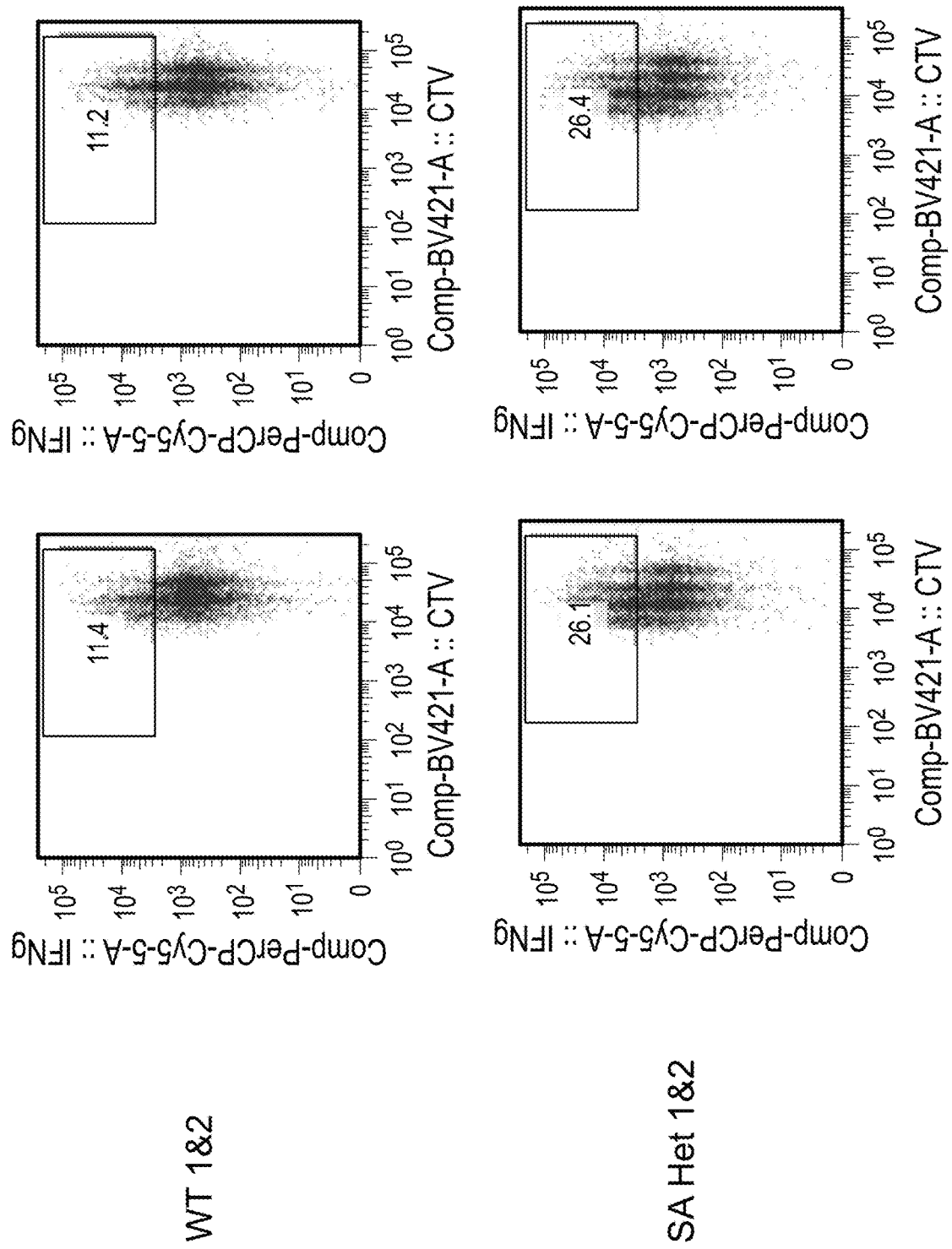
FIG. 36: TSC2SA heterozygous (Het) mutant transgenic (OT1) CD8+ T cells display a faster proliferative rate, higher mTOR activity, and effector function compared to WT CD8+ T cells. A) On Day 3, TSC2SA heterozygous/OTI mutant CD8+ T cells display greater proliferation reflected by more multiplications (leftward shift of periodic peaks indicates replications). B) These cells also display greater cytokine production (interferon gamma). C) These cells also display greater mTORC1 activation.
Figure 36C:
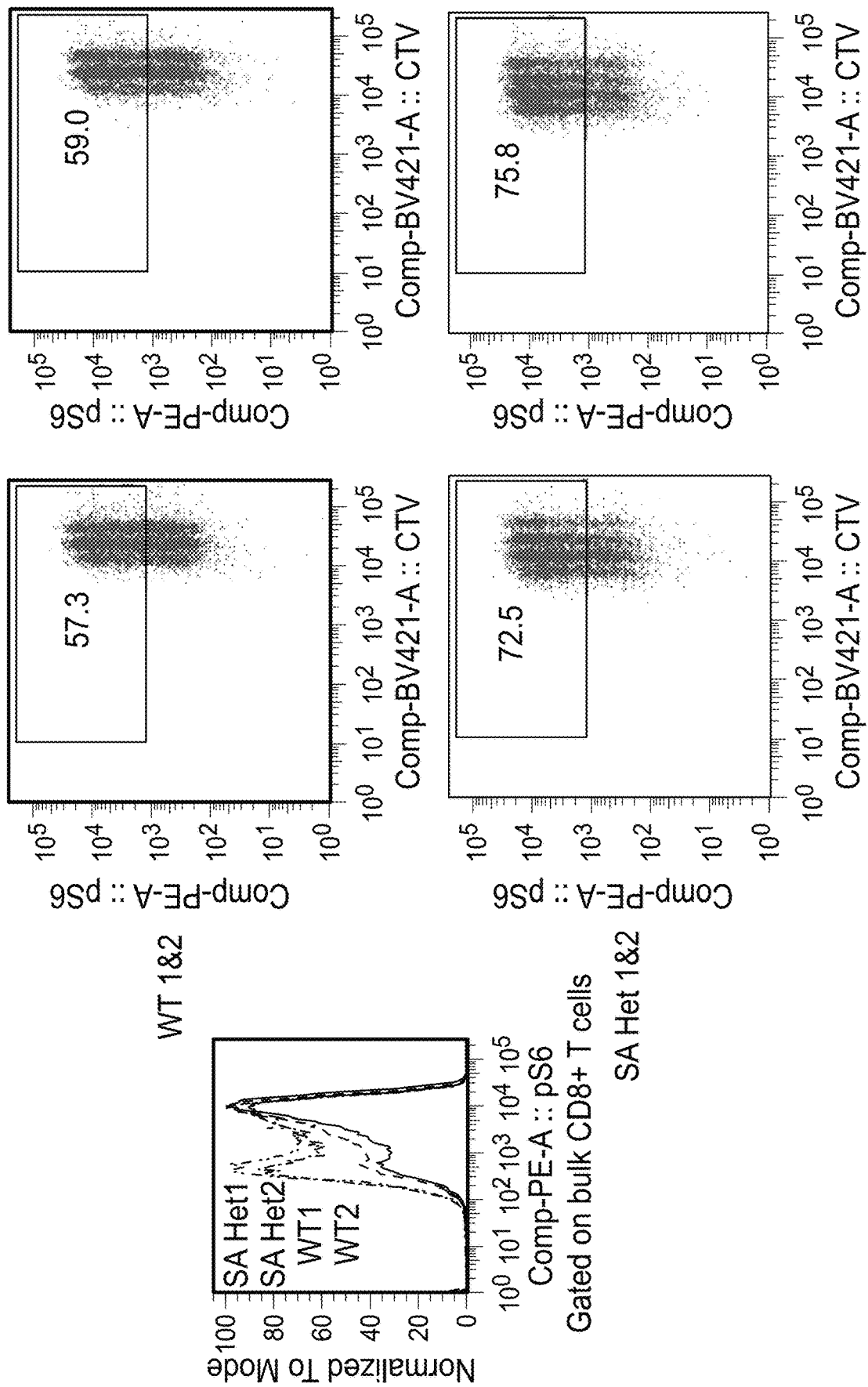

T-cells. Isolated T-Cells were labeled with a cell proliferation dye (cell trace violet (CTV)) to monitor division over time, and then stimulated with OVA I peptide (100 ng/mL) plus IL-2 (10 ng/mL) for three days before analysis. Cells were collected on day 3 to analyze proliferation along with IFNg effector function without any stimulation in only viable CD8 T cells via flow cytometry. During this 72 hour window, cells are actively producing cytokines; therefore, it is possible to measure without any further stimuli. Cells were stained with surface CD8 antibody and cell viability dye to exclude dead cells from analysis. Next, cells were fixed and permeabilized to assess proliferation between groups, to detect intracellular cytokine expression using antibodies to respective cytokines, and to detect mTORC1 activity via a directly conjugated antibody to pS6 (S240.44). Finally, cells were analyzed using a flow cytometer (n=2). TSC2SA heterozygous (Het) mutant transgenic (OT1) CD8$^{30}$ T cells display a faster proliferative rate, higher mTOR activity, and effector function compared to WT CD8$^{30}$ T cells (FIG. 36).

Figure 37:
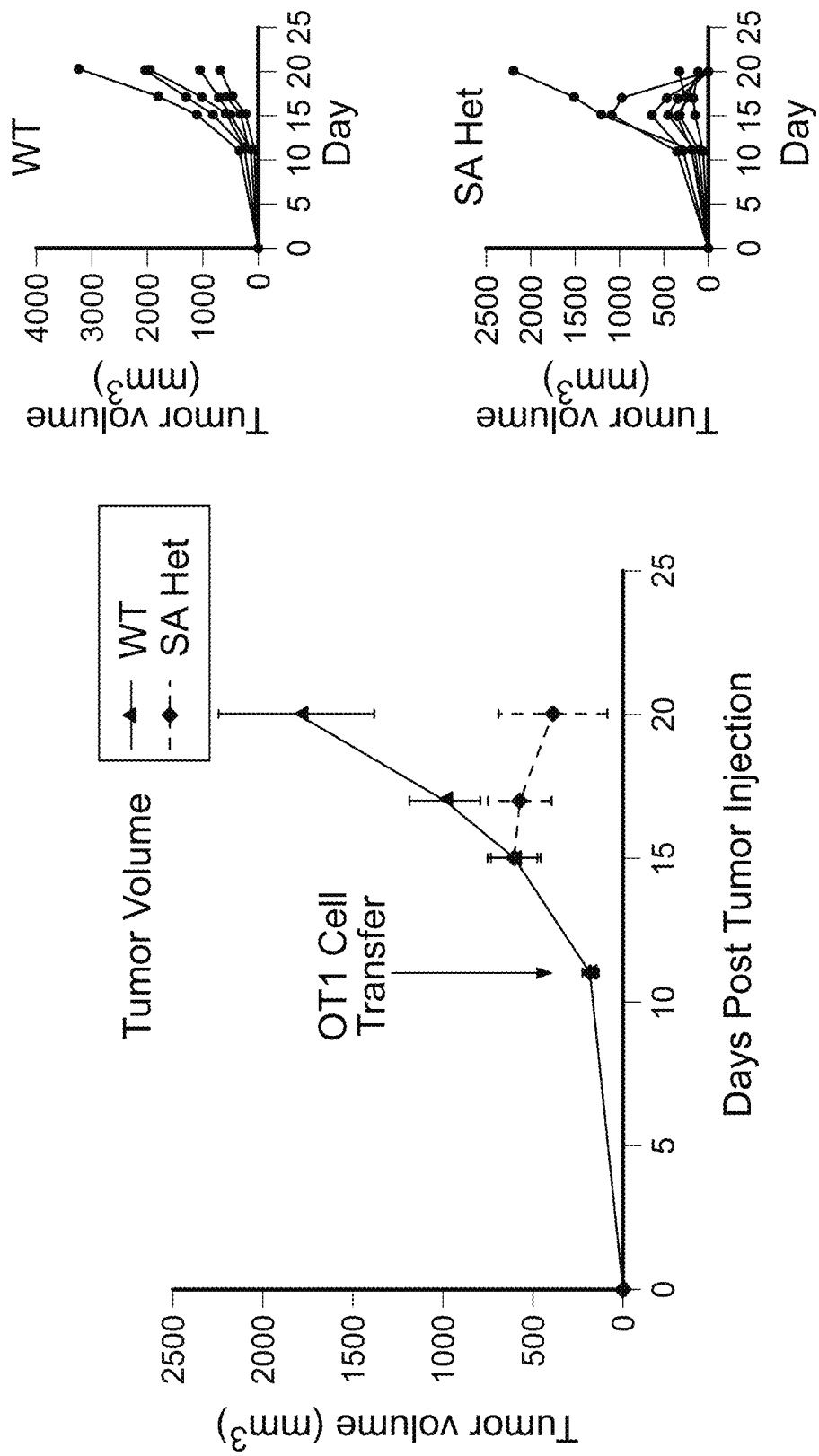
FIG. 37: TSC2SA heterozygous (Het) mutant transgenic (OVA I) CD8+ T cells compared to WT transgenic CD8 T cells perform better in adoptive cell therapy (ACT) to B16-OVA melanoma.

WT B6 recipients were implanted (by intradermal injection) with 250,000 B16 melanoma cells expressing OVA antigen (B16-OVA). On Day 11, tumor burden in mice was assessed to randomize mice for ACT therapy. On Day 11, tumor-bearing mice received (i.v.) 1E6 activated WT or SA-het mutant OTI T-cells as adoptive cell therapy. To activate WT (congenic Thy1.1/Thy1.2) and mutant (congenic Thy1.1/Thy1.1) CD8+ OTI T cells for ACT prior to injection, cells were stimulated with 100 ng/mL OVA I peptide. On Day 2, cells expanded by adding IL-2 (10 ng/mL) for 48 hours. On Day 4, cells were collected and ficolled to enrich for healthy viable cells. Cells were then counted and equal numbers of cells transferred into tumor bearing mice. Tumor burden (volume) was monitored over time with caliper measurements using the following formulate [(shortest$^2$)×(longest)]/2. TSC2SA heterozygous mutant CD8+ T cells used in ACT consistently showed better reduction of tumor burden associated with potent effector CD8 T cells (FIG. 37).

Tumors were chemically and mechanically processed to obtain tumor infiltrating lymphocytes (ITLs) for flow analysis. Cell analysis was conducted on viable CD45+, CD8+ T cells from the tumor. Based on the different congenic markers, WT and SA-mutant T cell populations could be separately identified in the tumor, compared with endogenous CD8 T cells, and readily analyzed for infiltration of the donor T cells compared to the endogenous CD8 T cells in the tumor. TSC2SA heterozygous mutant CD8+ T cells used in ACT compared to WT CD8 T cells were better able to infiltrate the tumor. Despite providing a 50:50 initial mix of WT and SA mutant T-cells for ACT, 90% of the T-cells in the tumor were SA mutants, 10% were WT. Adoptive cell therapy using TSC2SA/OT1 CD8+ T cells better infiltrates B16-OVA melanoma than TSC2WT/OV1 CD8+ T (FIG. 38). The use of the same host allows us to assess immune response within the same tumor microenvironment.

OTI CD8 T cells were obtained from WT, TSC2SA, and TSC2SE donors. All mice were marked with different congenic markers to readily identify the cells: WT (CD45.1, Thy1.1/Thy1.2), SA (Thy1.1/Thy1.2), SE (CD45.1, Thy1.2/Thy1.2). An approximately equal number (2500) of CD8 OT1 cells from all three genotypes were combined into a one sample for IV transfer into WT (Thy1.2/Thy1.2) hosts. Mice were subsequently infected (i.p.) with Vaccinia-OVA virus (1E6 pfu/mouse) to induce an acute viral infection. On Day 6, mice were sacrificed to analyze immune response of donor T cells within the same host. Donor T cells were identified based on different congenic markers. The percent of each donor cell genotype was determined. Percent of each genotype was based of all donor T cells. Cells with the SA TSC2 mutant expanded in vivo between 2-3 fold more as compared to WT and SE TSC2 expressing cells (FIG. 39). This in vivo analysis is similar to the replication data assessed in vitro. Using the same host allows us to assess immune response within the same microenvironment.

Figures 40A, 40B:
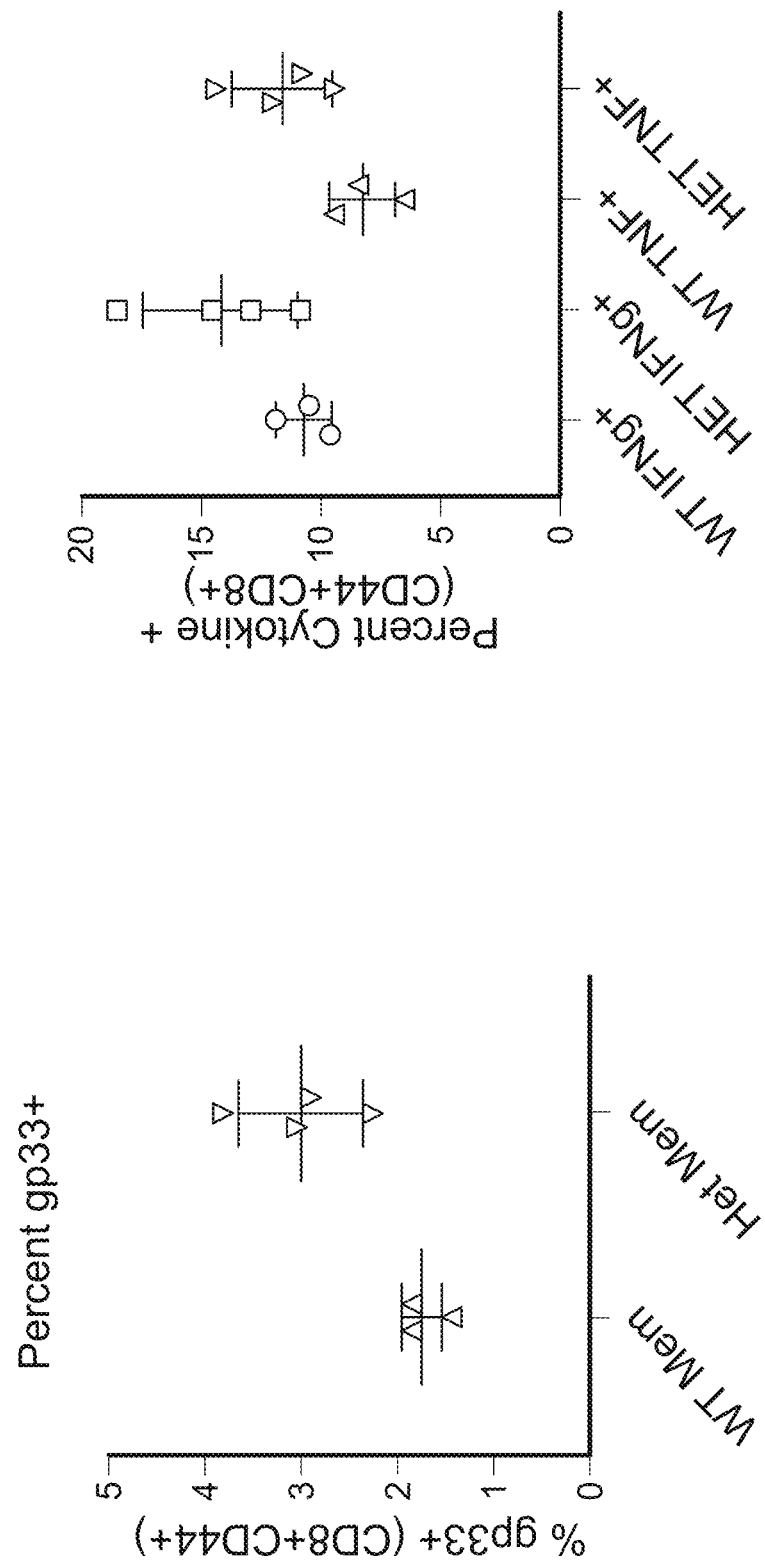
FIGS. 40A-40B: TSC2SA heterozygous mutant mice have more antigen specific memory CD8 T cells and display better effector function compared to WT mice in response to a viral infection. A) TSC2SA heterozygous mice infected with LCMV Armstrong have more antigen specific memory CD8+ T cells suggesting that the initial response resulted in more antigen specific T cells that transitioned into memory cells. B) Upon re-challenge with peptide, SA-mutant CD8 T cells secrete more effector cytokines compared to WT CD8 T cells (IFNg and TNFa).
Figure 41A:
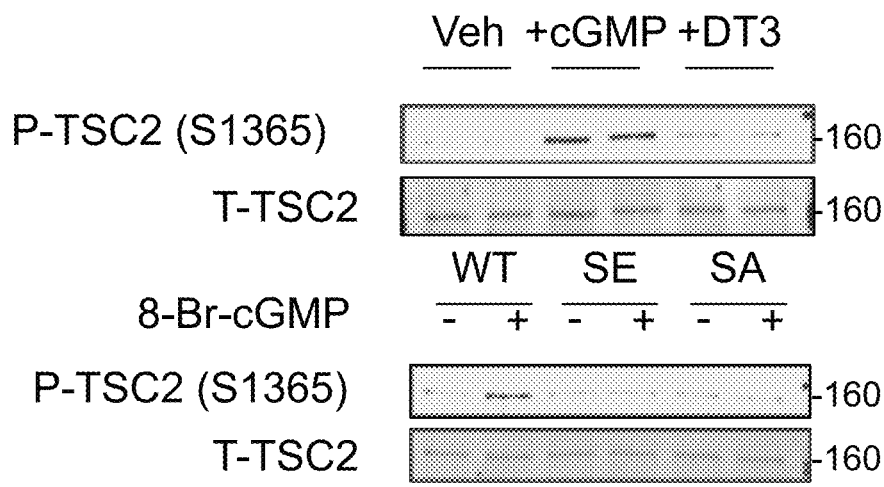
FIG. 41. S1365 phosphorylation of TSC2 is specifically detectable by phospho-antibody. A) Mouse embryonic fibroblasts (MEFs) treated for 15 minutes with 8-Br-cGMP +/− PKG inhibitor (DT3) or with vehicle alone. Data show increased phospho-TSC2 with cGMP stimulation that is prevented by blocking PKG activity. B) Phosphorylated/ Total TSC2 (pS1365) is detected in intact mouse left ventricle, increases with pressure overload (PO), and is further enhanced by co-treatment with PDE5 inhibitor sildenafil (SIL) but now by mTOR inhibitor everolimus (EVL). Summary data to the right, *<0.05 vs. Sham, #<0.001 vs. TAC. C) S1365 Phospho/total TSC2 directly correlates with in vivo myocardial PKG activity. D) pS1365 TSC2 is increased in human myocardium from patients with non-ischemic heart failure versus normal (non-failing donor control) hearts. *0.003 vs. Non-failing.
Figure 41B:
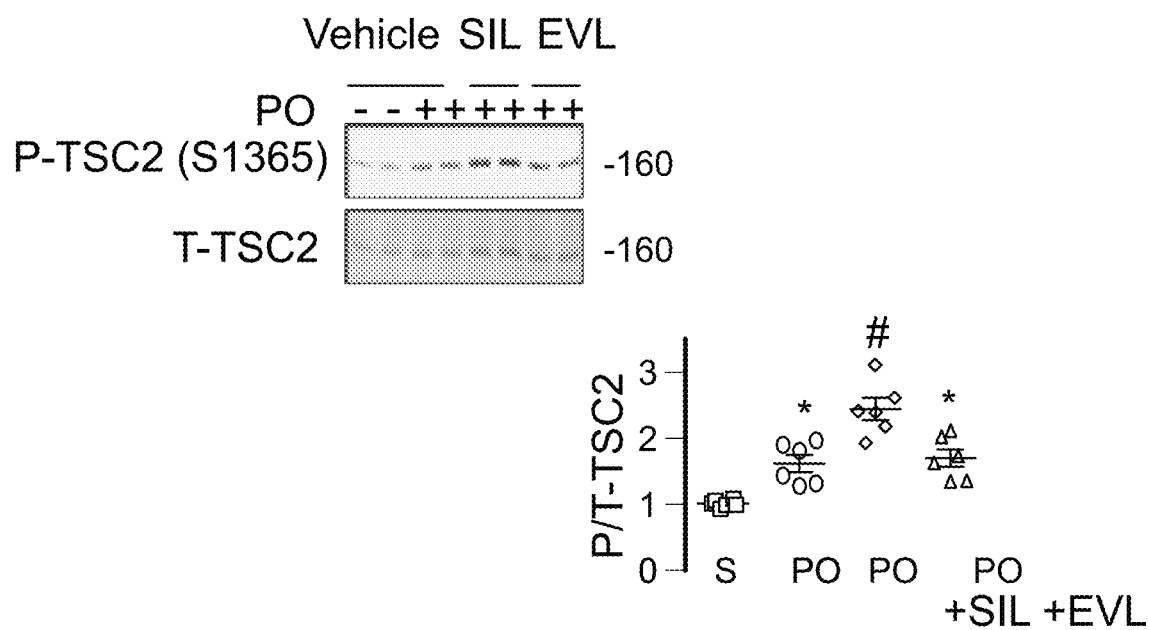
Figure 41D:
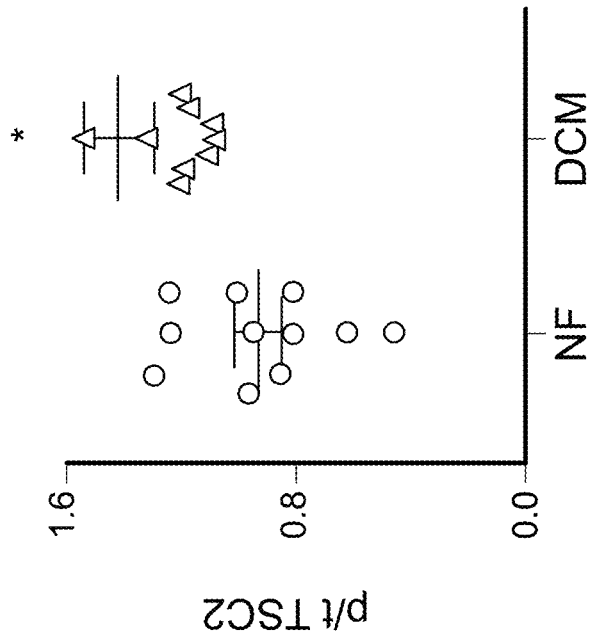
Figure 41C:
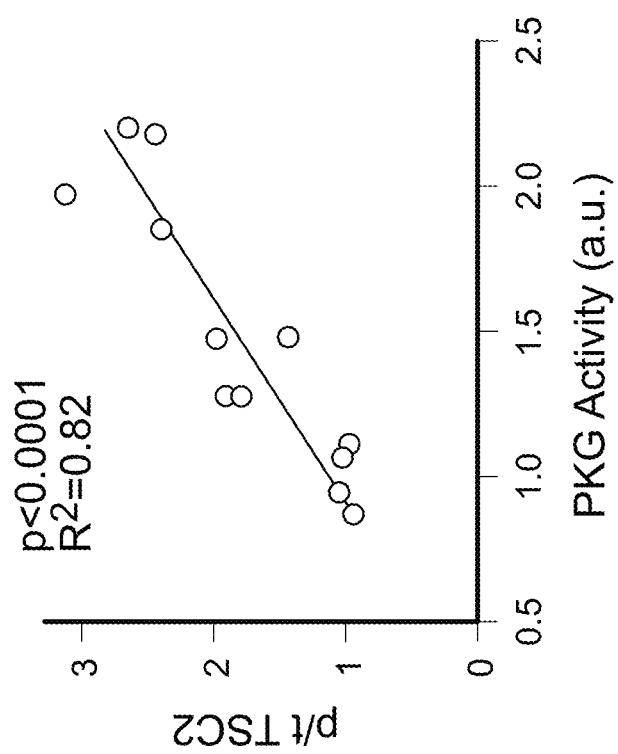

On Day 0, WT and TSC2SA mice were infected (i.p.) with 2E5 pfu of LCMV Armstrong to induce an acute viral infection. Mice were sacrificed 40 days later to analyze the number of antigen specific (gp33) CD8+ T cells to the original LCMV infection using gp33 specific tetramers. In addition, splenocytes were stimulated with 1 ug/mL gp33 peptide+GolgiStop to assess effector function using flow cytometry. Cells were stained with surface CD8 antibody and cell viability dye to exclude dead cells from analysis. Next, cells were fixed and permeabilized to detect intracellular cytokine expression using antibodies to respective cytokines. Finally, cells were analyzed using a flow cytometer. TSC2SA heterozygous mutant mice have more antigen specific memory CD8 T cells and display better effector function compared to WT mice in response to a viral infection (FIG. 40). Thus, the SA-mutant T cells exhibit simultaneously enhanced memory function following exposure to a viral infection, but also more effector function when re-exposed to the viral antigen.

Example 11

TSC2 S1365A (SA) Mice and S1365E (SE) Mice

Animal Models

Mice expressing a TSC2 knock-in mutation S1365A (SA) (FIG. 43A) or a TSC2 knock-in mutation S1365E (SE) (FIG. 57) were newly generated using CRISPR/Cas9 targeting/insertion methods. TSC2 guide RNA was designed using an algorithm described elsewhere (see, e.g., Inoki et al., 2003 *Cell* 115:577-590), and subsequently cloned into pSpCas9 (BB)-2A-Puro (PX459) V2.0 (Addgene plasmid #62988), as well as pUC57-sgRNA expression vector (Addgene plasmid #51132). DNA cleavage was tested in mouse N2a cells using the Surveyor Mutation Detection kit (Integrated DNA Technologies, Coralville, Iowa) described elsewhere (see, e.g., Schisler et al., 2013 *J Clin Invest* 123:3588-3599). In vitro transcription was performed for both Cas9 (from a modified pX330-U6-Chimeric_BB-CBh-hSpCas9 plasmid, Addgene plasmid #42230), and guide RNA using the Ambion mMES-SAGE mMACHINE kit and NEB HiScribe T7 High Yield RNA Synthesis kit respectively. ssODN for the S1365A point mutation was purchased from Integrated DNA Technologies. C57Bl/6 blastocyst injections were performed with a mix consisting of: 25 ng/μl Cas9; 12.5 ng/μl guide RNA, and 25 ng/82 l ssODN.

Pressure overload (PO) model. PO was induced by transaortic constriction (TAC), performed as described elsewhere (see, e.g., Lee et al., 2015 *Nature* 519:472-476). Sham controls underwent similar surgery without ligature placement. Age and weight-matched littermates were randomly divided into PO or sham groups with male and female mice equally represented in the presented data. Mice were followed for up to 6 weeks after PO, and were co-treated with everolimus (Evl, Sigma; oral gavage, 10 mg/kg/day), or sildenafil (Sil, Pfizer or Wako Pure Chemical Industries, 200 mg/kg/day in soft diet, Bioserv), or appropriate matched vehicle. Treatment started either 1-week following PO, or was initiated several days prior to PO. All protocols were approved by the Johns Hopkins Medical Institutions Animal Care and Use Committee.

Conscious mouse echocardiography. Intact heart morphology and function was determined in conscious mice by serial M-mode transthoracic echocardiography (VisualSonics Vevo 2100, 18-38 MHz linear array transducer; SanoSite Incorporated). Images were obtained and analyzed by an individual blinded to the animal condition.

Neonatal rat cardiomyocyte studies (NRCMs). NRCMs were isolated and cultured for 24 hours in DMEM with 10% FBS and antibiotics prior to study, as described elsewhere (see, e.g., Lee et al., 2015 Nature 519:472-476). Cells were then stimulated with endothelin 1 (ET1, 10 nM, Sigma) or vehicle for 15 minutes or for 48 hours, in serum-free DMEM supplemented with 0.1% Insulin-Transferrin-Selenium (Life Technologies). Additional interventions included Evl (1 µM) or vehicle starting 24-36 hours after isolation; transfection with plasmids expressing –TSC2-WT, TSC2-S1365A or –1365E mutations. Plasmid transfection was performed with Takara Clontech Xfect reagent per manufacturer protocol. FLAG-tagged TSC2 WT, SE, and SA vectors were packaged into adenoviruses by Welgen, Inc. (Worcester, Mass.).

MEFs

Human ventricle analysis. Human myocardium was obtained in accordance with institutional review board approvals at Johns Hopkins University and the University of Pennsylvania. Failing human hearts were obtained at time of explant surgery, and non-failing controls at time of other organ harvesting. LV free wall tissue was collected at the University of Pennsylvania under ice-cold cardioplegia and rapidly frozen in liquid nitrogen.

Protein analysis. Whole cell lysate was obtained (Cell Signaling Technology #9803) and protein concentration determined by BCA method (Pierce). Samples were prepared in SDS Tris-Glycine buffer (Life Technologies) and run on Novex 8-16% Tris-Glycine Gels (Life Technologies) and blotted onto a nitrocellulose membrane. The following primary antibodies were used to probe: Ser473-phosphorylated-Akt (S473) (#9271S), total Akt (#9272S), phosphorylated ERK (S202, 204) (#4370S), total ERK (#9102S), AMPK (T172) (#4188S), total AMPK (#2532S), phosphorylated p70 S6K (T389) (#9205S), total p70 S6K (#9202S), 4EBP1 (S65) (#9451S), total 4EBP1 (#9452S) Ulk-1 (S757) (#1420S), total Ulk-1 (8054S), GAPDH (#2118S), TSC2 (#3612S), and α-tubulin (#3873S) (Cell Signaling Technology), p-TSC2 (S1365) (#120718) (NovoPro Labs), LC3 (#M115-3) (MBL International Corp.), thiophosphate ester (#ab92570) and p62 (#ab109012) (Abcam), and ubiquitin (#SAB4503053) (Sigma). Antibody binding was visualized by infrared imaging (Odyssey, Licor) and quantified with Licor Image Studio Software 3.1.

Gene expression—qRT-PCR. Total RNA was isolated from left ventricular myocardium or cultured NRCMs using Trizol Reagent (Invitrogen), followed by reverse transcription to cDNA using a High Capacity RNA-to-cDNA Kit (Applied Biosystems, Life Technologies). cDNA underwent PCR amplification using TaqMan probes for atrial natriuretic peptide (ANP) (mouse #Mm01255747_g1, rat #Rn00664637_g1), brain or B-type natriuretic peptide (BNP) (mouse #Mm01255770_g1, rat #Rn00580641_m1), regulator of calcineurin-1 (Rcan-1) (mouse #Mm01213406_m1, rat #01458494_m1), tuberous sclerosis complex 2 (tuberin, TSC2) (mouse #Mm00442004_m1, rat #Rn00562086_m1), or glyceraldehyde-3-phosphate dehydrogenase (GAPDH) (mouse #99999915_g1, rat #Rn01775763_g1) (Applied Biosystems). The threshold cycle value was determined using the crossing point method. Samples were normalized to the GAPDH value for each run.

Bafilomycin autophagic flux assay. NRCMs were cultured as described above. Cells were stimulated with cGMP (50 µM, 15 minutes), and then with either vehicle control or bafilomycin A1 (BFA, 1 µM) (Sigma) for 3 hours. Mice received two injections of BFA (3 µM/kg, IP) 90 minutes apart. Tissue was collected 90 minutes after second injection (180 minutes from first). Protein extract was then analyzed by immunoblot for LC3-II, and relative increase±BFA used to index autophagic flux.

Protein Aggregation Assay. Protein aggregation was measured using with a protein aggregation assay Proteostat (Enzo #ENZ-51023). This assay was run according to manufacturer's instructions. Briefly, myocardium was lysed in proteostat lysis buffer, protein concentration assayed, equal amount of protein (10 µg) was loaded into a 96 well microplate, and combined with the proteostat substrate. Microplate was incubated and read in a spectrometer. Following background substraction, values were normalized to WT sham which was set to 1.

Tandem fluorescent LC3 probe analysis. NRCMs were infected with an adenovirus (10 MOI) expressing a tandem fluorescent (GFP-RFP) tagged LC316. This expresses LC3 with both green and red fluorescence as the autophagosomal membrane is forming; but upon merging with the acidic lysosome (autophagic flux), the GFP signal is quenched, leaving RFP. The ratio of green/yellow to red only puncta assesses autophagosome formation and autophagic flux, respectively.

In vitro protein kinase G activity. PKG activity was assessed by in vitro colorimetric assay (Cyclex, Cat #CY-1161, Nagano, Japan) following the manufacturer's instructions. The assay provides cGMP substrate, and a kinase-specific peptide-target to assess phosphorylation activity.

Proteomic analysis of PKG phosphokinome. Freshly isolated adult cardiac myocytes were obtained from male Wistar rats as described elsewhere (see, e.g., Shende et al., 2011 Circulation 123:1073-1082), and divided into two aliquots, each relaxed in Tyrode buffer (140 mM NaCl, 5 mM KCL, 10 mM HEPES, 1 mM glucose, 1 mM MgCl2, 1 mM Ca2+, pH 7.45). Cells were then exposed to 1 mM 8-Br-cGMP or Tyrode solution for 10 minutes to stimulate intracellular PKG1α activity. Cells were then centrifuged for 1 minute at 1000×g, the supernatant removed, and the pellet frozen in liquid nitrogen and stored at −80° C. Frozen samples (n=3/group) were then lysed in an 8M Urea, 0.5% SDS solution with brief sonication, and protein concentration determined by the BCA method. For each sample, 200 µg of total protein was digested with trypsin/Lys-C protease mixture (Promega), samples were desalted on 10 mg Oasis HLB cartridges (Waters) and eluted in 300 µL of 80% acetonitrile (ACN), 5% trifluoroacetic acid, 1 M glycolic acid and enriched by titanium dioxide (TiO2). Enriched peptides were desalted as above but eluted in 200 µL of 80% ACN, 0.1% formic acid (FA) and dried under vacuum. Dried peptides were re-suspended in 20 µL of 0.1% FA for LC-MS/MS analysis. Samples (4 µL) were injected in duplicate onto an EASY-nLC 1000 (mobile phase A was 0.1% FA in water and mobile phase B was 0.1% FA in ACN) connected to a Q-Exactive Plus (Thermo) equipped with a nano-electrospray ion source. Raw MS/MS data was searched using the Sorcerer 2TM-SEQUEST® algorithm (Sage-N Research) using default peak extraction parameters. Post-search analysis was performed using Scaffold 4 (Proteome Software, Inc.) with protein and peptide probability thresholds set to 95% and 90%, respectively, and one peptide required for identification, and spectra manually validated. Phospho-site localization was determined using Scaffold PTM version 2.1.3 and phospho-sites with probabilities less than 90% were ignored.

Results

PKG Activation Suppresses mTORC1 to Reduce Hypertrophy and Increase Autophagy

Figure 42A:
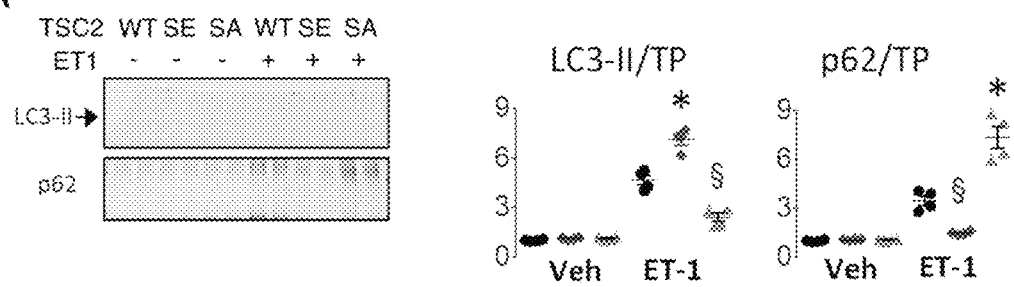
FIG. 42. S1365 phosphorylation regulates autophagy related signaling and impacts TSC2 regulation of mTORC1 by Rheb dependent signaling. A) Rat neonatal myocytes expressing wild-type TSC2, or the phospho-mimetic (SE) or phospho-silenced (SA) mutant are exposed to endothelin-1 (ET1) to stimulate growth. There is an increase in autophagosomes from ET1 (rise in LC3-II) but less effective autophagic flux to form auto-lysosomes (indicated by rise in p62). With SE expression, autophagy is enhanced reflected by a decline in p62 and further rise in LC3-II. By contrast, with SA expression, LC3-II declines and p62 markedly rises—so autophagy is inhibited. B) The ability of PKG activation to augment autophagy is in part dependent on its ability to access and phosphorylate TSC2 at S1365. TSC2 −/− MEFs are transfected with either WT or SA forms of TSC2, stimulated with endothelin-1 (ET1) +/− cGMP (to stimulate PKG). With WT TSC2, enhanced p62 (inadequate autophagy) stimulated by ET-1 is reversed by PKG activation. However, with SA TSC2, the increase in p62 with ET-1 is greater and it remains elevated despite PKG activation. LC3II does not increase with SA expression. C) mTOR signaling controlled by S1365 modification requires Rheb. MEFs expressing WT, SA, or SE forms of TSC2 were also exposed to siRNA to genetically delete the downstream TSC2 effector—Rheb. mTORC1 activation (P-p70 S6K) increases with ET1, but not in the absence of Rheb. The ET1 rise is prevented in SE but not SA expressing cells, and the latter is also prevented by silencing Rheb. Thus, the modulation of mTORC1 by the TSC2 mutants requires Rheb.
Figure 42B:
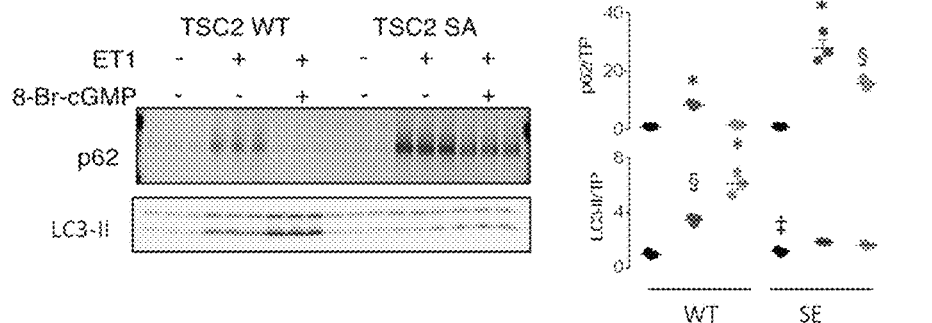
Figure 42C:
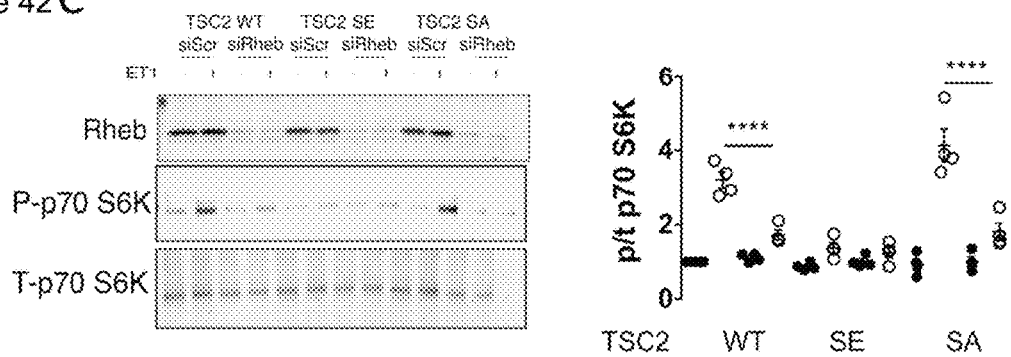
Figure 46:
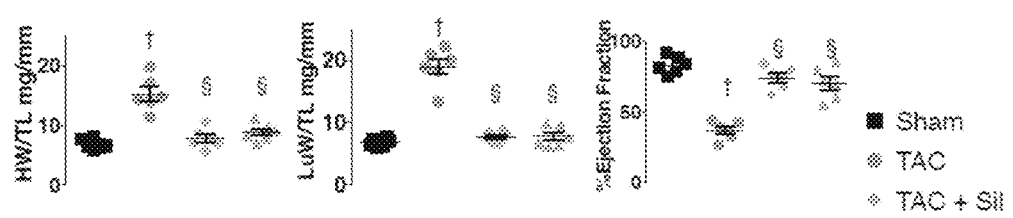
FIG. 46. Heart weight/tibia length (HW/TL), lung weight/tibia length (LuW/TL), cardiac ejection fraction (EF) from sham-operated mice and mice subjected to 6-wks of pressure-overload (PO) from trans-aortic constriction, and treated with either vehicle, sildenafil (Sil, 200 mg/kg/day) or everolimus (Evl, 10 mg/kg/day) starting 1 week post-PO (n=6/group). Lower panels: Myocardial gene expression of A-type natriuretic peptide (ANP, Nppa), B-type natriuretic peptide (BNP, Nppb), and the regulator of calcineurin 1 (Rcan1) normalized to Gapdh (n=6). †p<0.0001 vs. Sham, § p<0.0001 vs. PO by Tukey multiple comparisons test.
Figure 46:
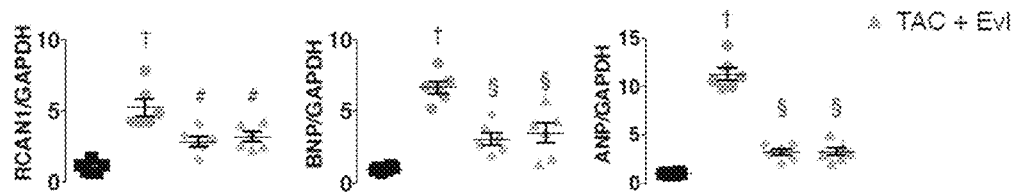
Figure 47:
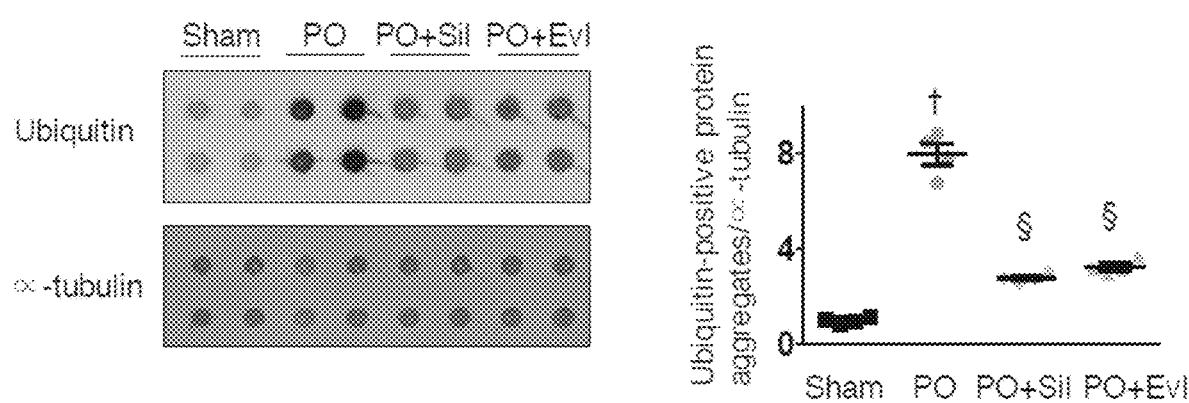
FIG. 47. Filter trap assay from sham-operated mice and mice subjected to 6-wks of pressure-overload (PO) from trans-aortic constriction, and treated with vehicle, sildenafil (Sil, 200 mg/kg/day) or everolimus (Evl, 10 mg/kg/day) starting 1 week post-PO (n=4/group). Membranes were probed for ubiquitin and ∝-tubulin. †p<0.0001 vs. Sham, § p<0.0001 vs. PO by Tukey multiple comparisons test.
Figure 48:
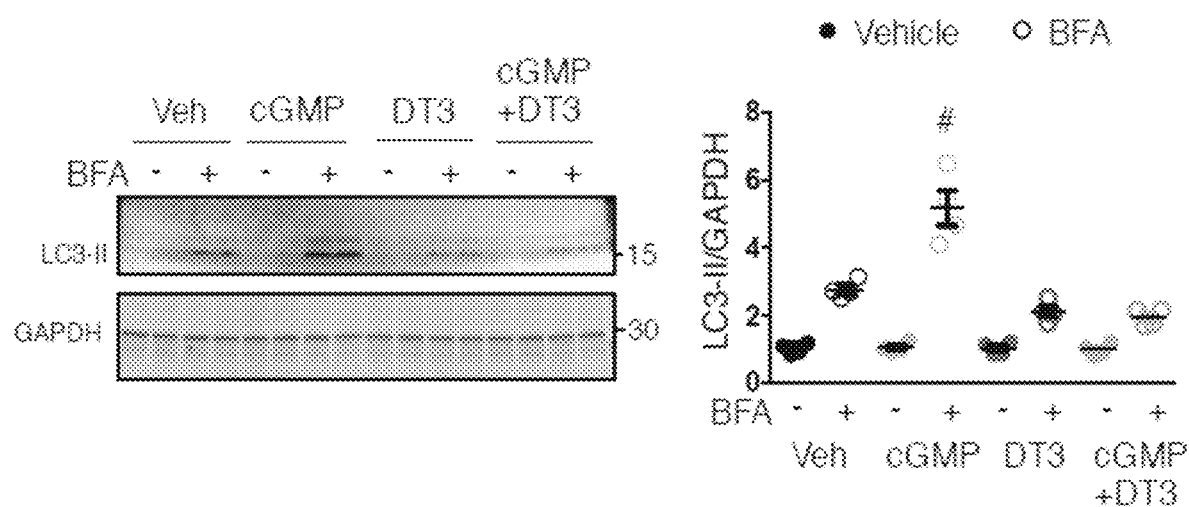
FIG. 48. Immunoblot of LC3-II in neonatal rat cardiomyocytes (NRCMs) with and without post-BFA treatment to block lysosomal proteolysis. Relative increase in LC3-II pre- and post-BFA treatment indexes AuF; example blot on the left, summary data on the right. N=4/group; #<0.0001 vs. Vehicle.

In control (vehicle-treated) mice (C57BL/6J) subjected to 4-weeks of pressure overload (PO) induced by transverse aortic constriction, increased phosphorylation was observed of the three major downstream effectors of mTORC1: Unc-51-like kinase-1 (Ulk-1) to inhibit autophagy, and p70S6K and 4EBP1 (eIF4E binding protein-1) that stimulate gene transcription and translation (FIG. 41). Co-treatment with the phosphodiesterase type-5 inhibitor, sildenafil (Sil), which blocks cGMP hydrolysis to stimulate PKG, inhibited each change, matching the effects from an mTORC1 inhibitor, everolimus (Evl). Both therapies were known to suppress pathological hypertrophy and cardiac dysfunction, and similar benefits were observed here as well (FIG. 46). Consistent with reduced Ulk1 phosphorylation, Sil and Evl similarly enhanced autophagy after PO, reflected by greater LC3-II (microtubule-associated protein light-chain 3-II) and reduced p62 protein expression (FIG. 42). Sil and Evl treatment also reduced myocardial protein aggregates that increased with PO (FIG. 47). Enhancement of autophagic flux by PKG was further assessed in isolated myocytes expressing a fluorescent reporter (TF-LC3), showing increased red-puncta indicative of auto-lysosome formation. Augmentation of LC3-II expression following exposure to bafilomycin A1 (BFA) (inhibiting lysosomal proteolysis) was also greater in cells with PKG co-stimulation (FIG. 48). Enhanced autophagy was important to anti-hypertrophic effects from PKG. Myocytes stimulated with endothelin-1 (ET1) exhibit hypertrophic signaling (reflected by increased Nppa gene expression). This was reduced by Sil, but not in cells pre-incubated with siRNA to ATG5 (autophagy related 5). Thus, PKG activation suppresses cardiac mTORC1 signaling, blunting growth stimulation while enhancing autophagy.

PKG Modulates mTORC1 by Phosphorylation of TSC2 at S1365

Figure 49:
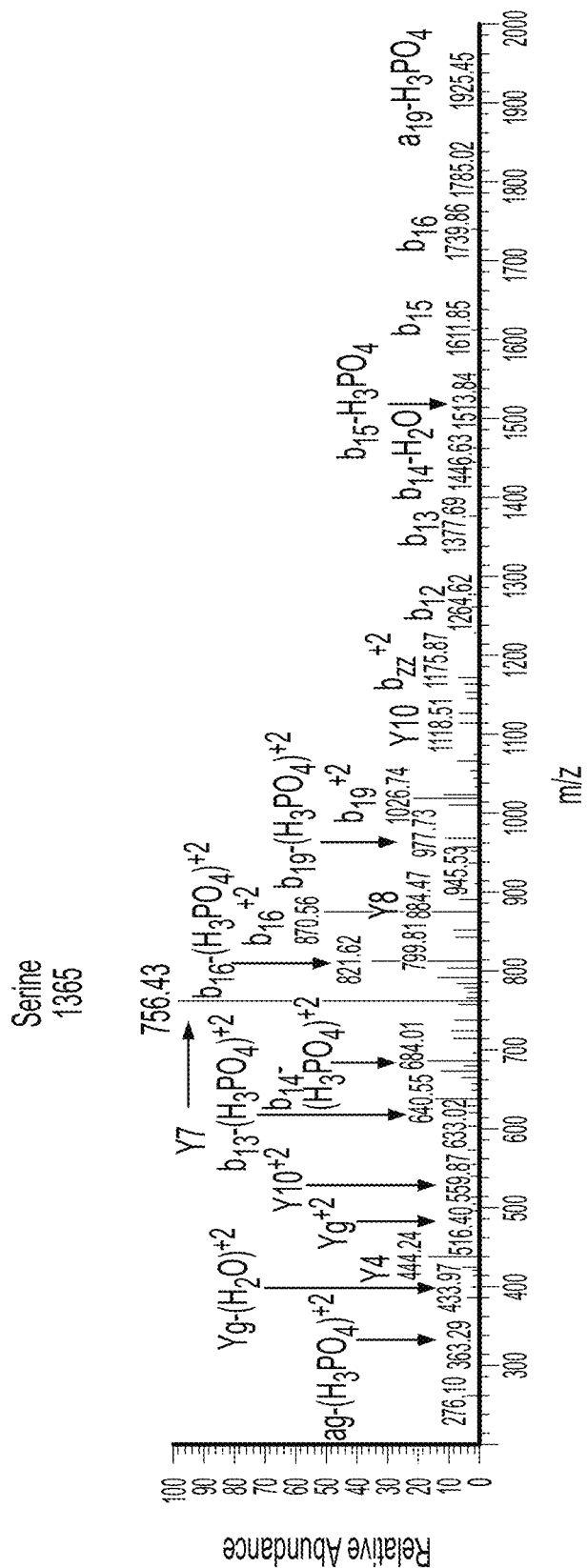
FIG. 49. Mass-spectrometry identification of TSC2 S1365 as a phosphorylation target of PKG. Adult rat ventricular myocytes were exposed to cGMP to stimulate PKG activity.

To determine the mechanism by which PKG suppresses mTORC1, adult myocytes were exposed to cGMP (to stimulate PKG) for 15 minutes, and performed phospho-proteomic analysis on cell lysates. Among mTORC1 complex and regulatory proteins, we identified a change in TSC2 at serine 1365 (S1364 in humans) (FIG. 49), a highly conserved residue in mammals that is located in an activation regulatory domain upstream of GSK-3β and AMPK targeting sites. PKG is among the highest predicted kinase to phosphorylate this residue in an open-source human bioinformatics knowledgebase (PhosphoNET, Kinexus).

Figure 50:
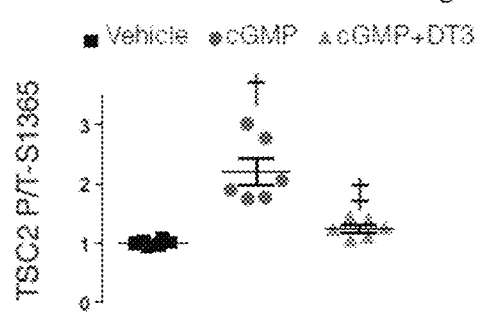
FIG. 50. Summary data for FIG. 2B. A) Mouse embryonic fibroblasts treated with 8-bromo-cGMP in the presence and absence of DT3 n=6/group. B) TSC2 knockout MEFs transfected with TSC2 WT, SE, or SA and stimulated with 8-bromo-cGMP for 15 minutes. (n=4/group). P<0.001 by 1-way ANOVA for each panel; †p<0.0001 vs. vehicle, ‡p<0.001 vs. cGMP.
Figure 50:
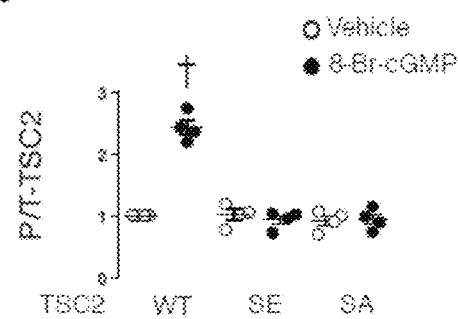

In mouse embryonic fibroblasts (MEFs), resting cells had minimal pS1365 antibody signal, but this increased after acute cGMP stimulation and the rise was blocked by co-incubation with a PKG kinase inhibitor—DT3 (FIG. 50). To test specificity, TSC2-KO MEFs were transfected with WT, phospho-silenced (S1365A, SA), or phospho-mimetic (S1365E, SE) TSC2, and then stimulated with cGMP. Only WT TSC2 showed a rise in pS1365 antibody signal with cGMP (FIG. 50). TSC2 pS1365 was detected in intact mouse myocardium, increased with PO and rose further with Sil (but not Evl) co-treatment (FIG. 41). The level of pS1365-TSC2 (normalized to total TSC2) directly correlated with PKG activity measured in the same tissue. pS1364 was detected in human myocardium from non-failing donor controls and this was significantly increased in dilated heart failure. Thus, S1365 is regulated by PKG activation, is detectable in mammalian heart including human, and increases with cardiac disease.

Figure 51A:
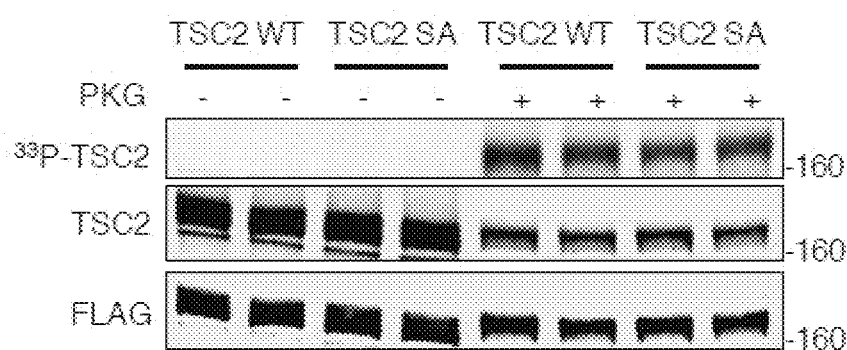
FIG. 51. PKG phosphorylation of WT and SA TSC2. A) Autoradiography with immunoprecipitated TSC2-FLAG WT or SA in the presence or absence of purified active PKG and [γ-33P]-ATP (upper lane) and immunoblots from the same samples for Flag and TSC2 (lower lanes). B) PKG phosphorylation identified in cell lysate from adenovirus infected TSC2-KO HEK cells incubated with mutated PKG (M438G) (+) that accepts a bulkier ATP (N6-Benzyl-ATPγS) or with WT PKG (−) that cannot. Following FLAG-immuneprecipitation, immuneblots for thiophosphate ester (recognizing phorphorylation by mutated PKG) and for FLAG are shown. FLAG superimposes the thiophosphate labeling only when mutated PKG is added. For both assays, the substitution of S1365 for alanine does not prevent direct phosphorylation of TSC2 by PKG.
Figure 51B:
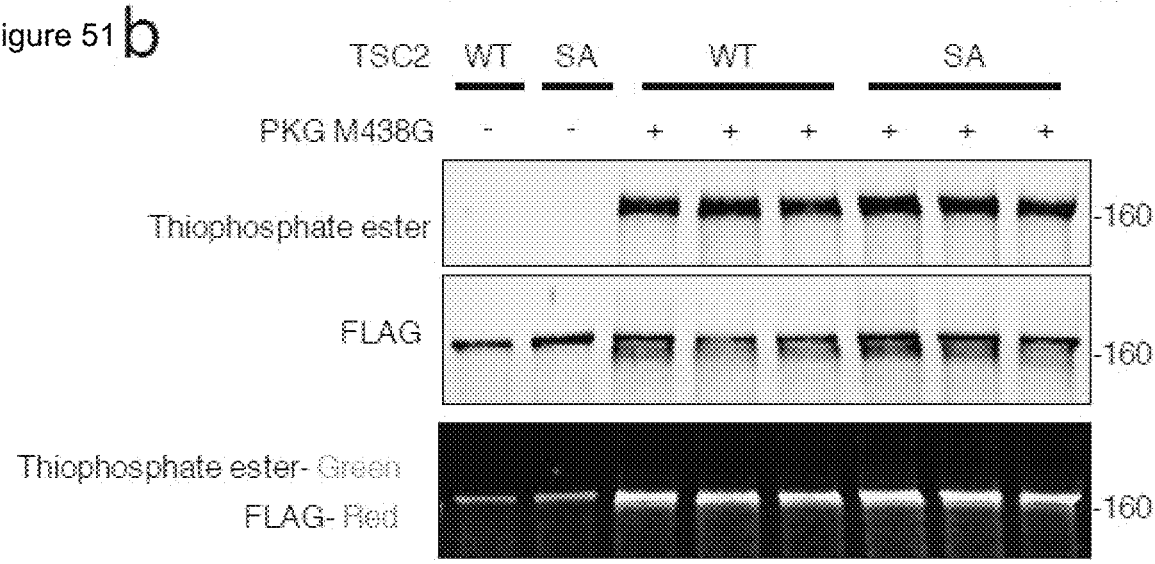

To test if PKG directly phosphorylates S1365, TSC2 KO HEK cells were generated and infected with adenovirus expressing WT-TSC2-FLAG or empty vector. FLAG-immune-precipitate was incubated with recombinant PKG and $[\gamma\text{-}^{33}P]$-ATP. ERK2-TSC2 phosphorylation served as a positive control, and similar TSC2 radiolabeling was observed upon PKG exposure in a dose dependent manner (FIG. 41). It was also tested if direct phosphorylation occurs in the presence of cytosolic proteins. HEK whole cell lysate containing TSC2-FLAG was incubated with a modified PKG (M438G) which can then bind an enlarged sulfonated-ATP (N6 benzyl ATPγS), and FLAG-immune precipitate then probed for thiophosphate ester modification of TSC2. This modification was only observed in lysate containing mutated PKG. Though MS analysis only identified pS1365 as being modified with PKG activation, both radioactive or thiophosphate ester labeling of TSC2 was also seen when SA TSC2 was used (FIG. 51). However, as shown in the subsequent studies, S1365 is the required site for PKG regulation of mTORC1.

Figure 52:
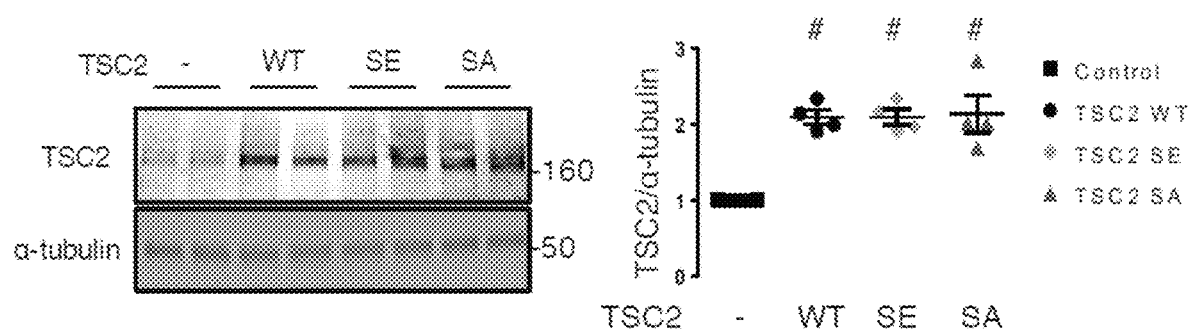
FIG. 52. Immunoblot for TSC2 (antibody recognizing C-terminus) for myocytes expressing native protein, or transduced with wild-type (WT), S1365A (SA), or S1365E (SE) TSC2 mutants. Expression of each TSC2 form was similar and increased compared to non-transduced cells. N=4/group. P<0.0001 1-way ANOVA; #<0.001 vs. Control by post hoc test.
Figure 53:
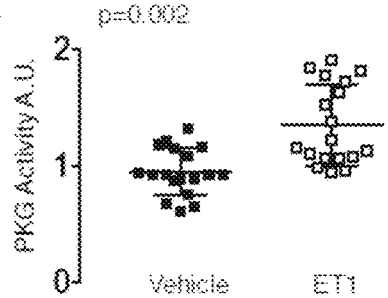
FIG. 53. Neonatal rat myocytes expressing a TSC2 SE, SA, or WT treated with endothelin 1 (ET1, 10 nM) or vehicle for 48 hours. A) PKG activity increases overall with ET1 treatment (all groups combined, n=18/group. B) Each group (n=6/group) shows similar increase in activity (box/whisker plot; p=0.0004 for ET-1 effect, p>0.8 for group effect by 2-way ANOVA). C) Quantification of FIG. 3b immunoblot for TSC2 S1365 phosphorylation in myocytes expressing different TSC2 forms and exposed to vehicle or endothelin-1, ET1. Data normalized to total TSC2. †p<0.0001 vs. WT vehicle. ET1 increased phosphorylation overall, most notably in WT (p=0.0004 for ET1 effect on p/t ratio).
Figure 53:
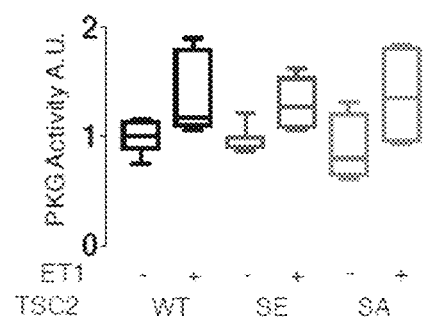
Figure 53:
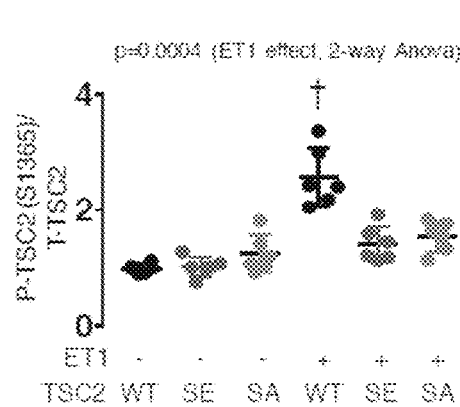
Figure 54:
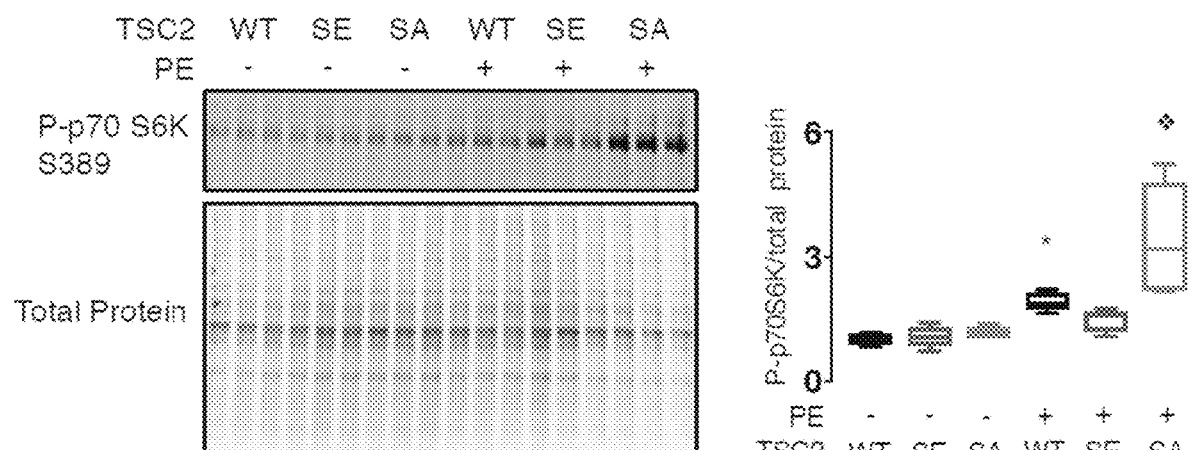
FIG. 54. Neonatal rat myocytes expressing WT, SA, or SE TSC2 protein, and exposed to either vehicle of phenylephrine (PE, 100 µM) for 48 hours. MTORC1 activation from PE is indexed by p70 S6K phosphorylation and increased more in SA expressing cells. Cells expressing SE had no significant increase over non-stimulated conditions, whereas both WT and SA groups displayed significant elevation over baseline. (n=6/group) *: p<0.05 vs WT vehicle; ❖ : p<0.001 vs WT ET1.

To test the functionality of S1365 phosphorylation, myocytes were transfected with WT, SA, or SE TSC2, each achieving similar protein levels (FIG. 52), and then stimulated with ET1 for 48 hours. Rest levels of Nppb (a hypertrophy gene marker) were similarly low regardless of the TSC2 form expressed. However, upon ET1 stimulation, Nppb increased more in SA and less in SE expressing cells compared to WT. Activating PKG (SIL) reduced Nppb in cells expressing WT-TSC2, but had no impact in cells expressing SA or SE mutants. It was also confirmed that ET1 exposure similarly increased PKG activity independent of the TSC2 form expressed (FIG. 53), and that this led to an increase in pS1365 in WT-expressing cells, but not SA or SE (FIG. 41). SA mutants amplified and SE attenuated mTORC1 signaling as compared to WT, but only in the presence of ET1 co-stimulation (FIG. 42). Similar differences were observed with an alternative stimulus (phenylephrine, FIG. 54). Autophagy and autophagic flux were also differentially impacted. Increased TF-LC3 labeled red punctae and LC3-II expression, and reduced p62 expression (FIG. 42) were consistent with enhanced autophagy with SE expression and suppression with SA.

Figure 55:
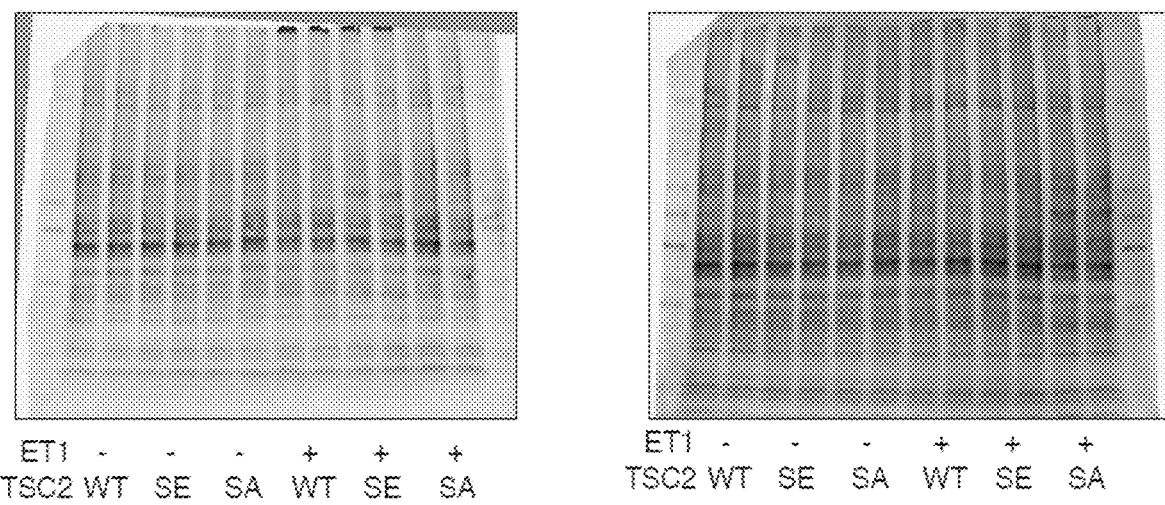
FIG. 55. Total protein stains corresponding to western blot images in FIG. 42 shows equal loading.

TSC2-S1365 is Required for PKG-modified Autophagy, Regulates mTORC1 Via Rheb, and Does Not Interfere with AMPK-TSC2-mTORC1 Regulation To test if TSC2 pS1365 is required for PKG to stimulate autophagy, TSC2 KO MEFs were transfected with either WT or SA TSC2, and then treated with ET1±cGMP for 48 hours. Cyclic GMP exposure reduced p62 and increased LC3-II expression in cells expressing WT TSC2, but these changes were substantially reduced when TSC2 SA was expressed (FIG. 42, FIG. 55).

Figure 56A:
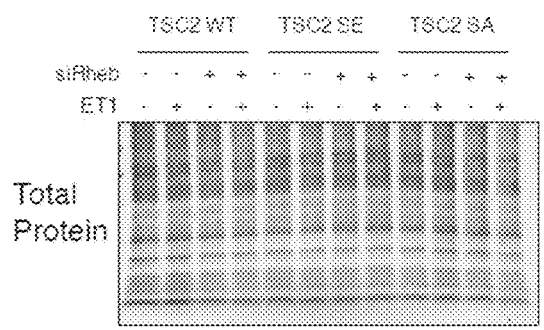
FIG. 56. A) Total protein stain corresponding to western blot images in FIG. 42 shows equal loading and quantification of Rheb to total protein. B) Summary data for upper lane, FIG. 42 for total Rheb protein expression in response to scrambled siRNA or siRNA to Rheb. (n=4/group) †p<0.0001 vs. vehicle, § p<0.0001 vs. ET1 by Tukey multiple comparisons test.
Figure 56B:
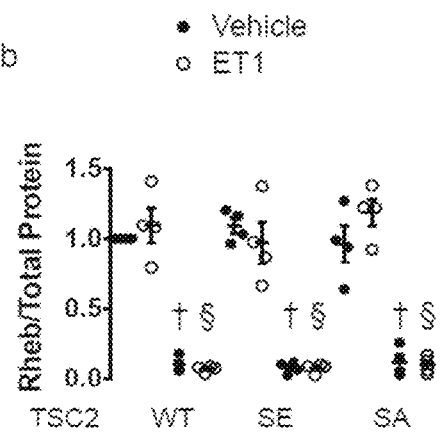

To determine if mTORC1 modulation by pS1365 requires Rheb, myocytes expressing WT, SA, or SE TSC2 were incubated with either an siRNA to Rheb or scrambled control (FIG. 42, FIG. 56). ET1 stimulation of mTORC1 (P-p70S6K) was observed with WT or SA expression but not in the absence of Rheb. With SE expression, mTORC1 stimulation was minimal and independent of Rheb.

S1365 resides in a region of TSC2 where multiple AMPK and GSK3β sites are located. This raised the question of whether S1365 acts independently of AMPK. To test this, TSC2 KO MEFs were infected with Adenovirus expressing WT or SA TSC2 or empty vector, exposed to ET1, and then to 2-deoxyglucose (2-DG) to physiologically stimulate AMPK. MEFs lacking TSC2 showed constitutive mTORC1 activation, and this fell similarly in cells expressing either WT or SA forms. Exposure to 2-DG resulted in further potent mTORC1 inhibition that was independent of whether S1365 could be phosphorylated or not. The decline in cells expressing either TSC2 form was significantly greater than in cells lacking TSC2. It was also confirmed that 2-DG exposure led to increased AMPK phosphorylation of TSC2 (pS1387) similarly in cells expressing either WT or SA TSC2. Thus, modulation of S1365 by PKG is needed for autophagy regulation, involves Rheb-dependent mTORC1 modulation, and does not impede AMPK activation of TSC2 to blunt mTORC1.

S1365A KI Mice Display Exacerbated mTORC1-dependent Stress Responses to PO

Figure 57:
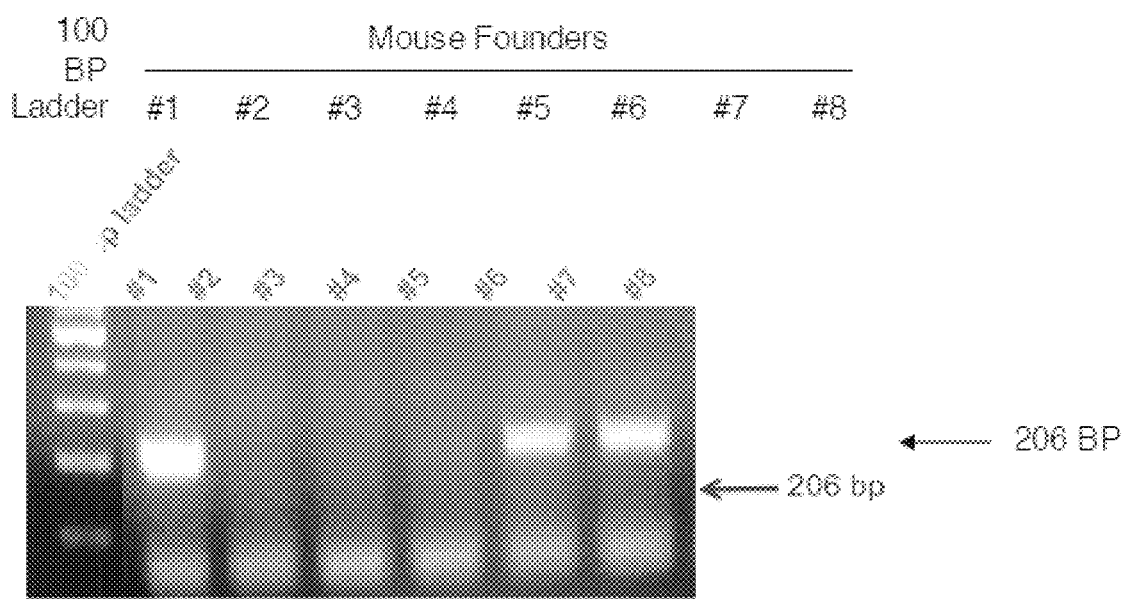
FIG. 57. TSC2 SA KI Genotyping by PCR detects a unique sequence based on the mutated residue as a 206 base pair (BP) fragment.

To test the impact of TSC2 S1365 modulation in vivo, S1365A (SA) TSC2 global knock-in mice were generated using CRISPR/Cas9 gene editing (FIG. 57). SA mice are born in normal Mendelian ratios and grow and develop normally, with no differences in cardiac structure or function compared to littermate controls (Supplementary Tables 1 and 2). TSC2 protein expression is similar to controls (FIG. 58).

Figure 59:
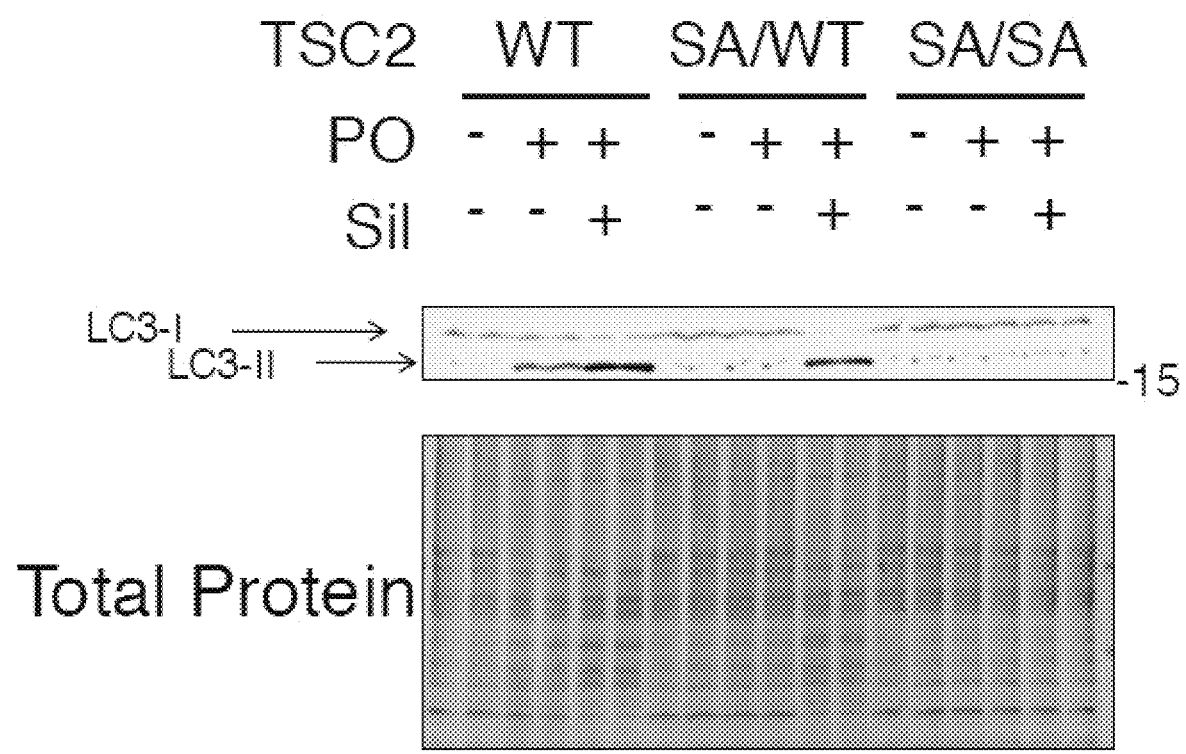
FIG. 59. Immunoblots of LC3 from TSC2 WT, Heterozygous (SA/WT), and homozygous (SA/SA) mice exposed to sham or PO with vehicle or Sildenafil (Sil) co-treatment. There was greater increase of LC3-II in TSC2 WT mice during PO, which was increased by sildenafil only in TSC2 WT and SA/WT but not SA/SA PO mice.
Figure 60:
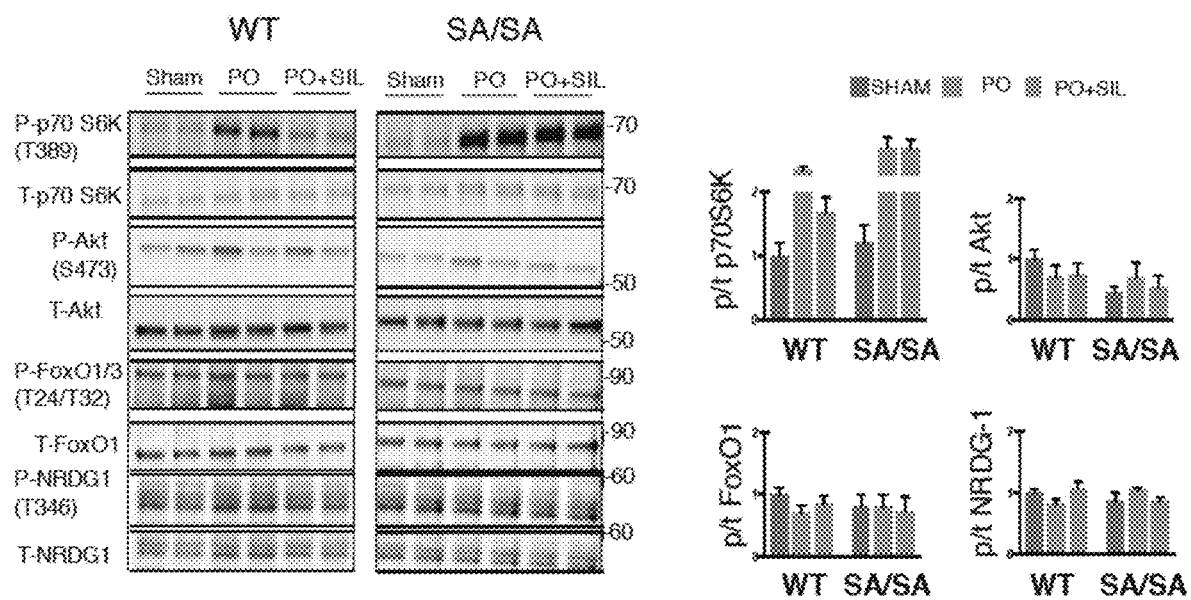
FIG. 60. Immunoblots and summary quantitation for mTORC2 targets from TSC2 WT and SA/SA mice subjected to sham or PO surgeries and treated with sildenafil or vehicle. No significant changes were detected between the genotypes at baseline or during PO. (n=4/group).

To test if partial or full prevention of S1365 phosphorylation modifies the cardiac stress response to PO as well as therapeutic efficacy of PKG activation, heterozygote (SA/WT), homozygote (SA/SA) and littermate control (WT) mice were subjected to PO, and then randomized to receive either vehicle or Sil. Survival data (FIG. 43) show similar marked early mortality after PO in both SA/WT and SA/SA vehicle-treated groups versus WT. Sil fully prevented SA/WT mortality after PO, but had had no effect in SA/SA mice (FIG. 43). With PO, hearts from SA/WT and SA/SA similarly developed marked hypertrophy as compared to WT, and only in WT and SA/WT was this reversed by Sil (FIG. 43). Similar disparities were found in lung weight, A-type natriuretic peptide expression (FIG. 58), (reflecting central volume increase), and in systolic dysfunction (FIG. 44). mTORC1 activity (P-p70S6K) was greater and autophagy (p62, LC3II) less after PO in SA/WT and SA/SA compared to WT. Both were also reversed by Sil in WT and SA/WT PO hearts, but not SA/SA (FIG. 44, FIG. 59). In vivo regulation by S1365A principally altered mTORC1, as MTOR-complex 2 effectors were not differentially activated (FIG. 60). All of these results were similar in males and females.

To test if mTORC1 hyper-activation was responsible for the adverse outcomes in SA mice after PO, SA/SA mice were randomized to receive Evl or vehicle starting 3 days before PO. Evl prevented death (FIG. 43) and cardiac structural and functional deterioration (FIG. 43 and FIG. 44), and enhanced autophagy, reflected by increased LC3-II and reduced p62 expression (FIG. 61). Taken together, these data show that the S1365A mutation is autosomal dominant and potently modulates stress-stimulated mTORC1 activity in vivo. S1365 phosphorylation is required for PKG activation to modulate mTORC1 and counter cardiac disease from PO, and its removal is sufficient to prevent such amelioration.

S1365E KI Mice have Reduced mTORC1 Activation with PO and are Protected

Figure 62:
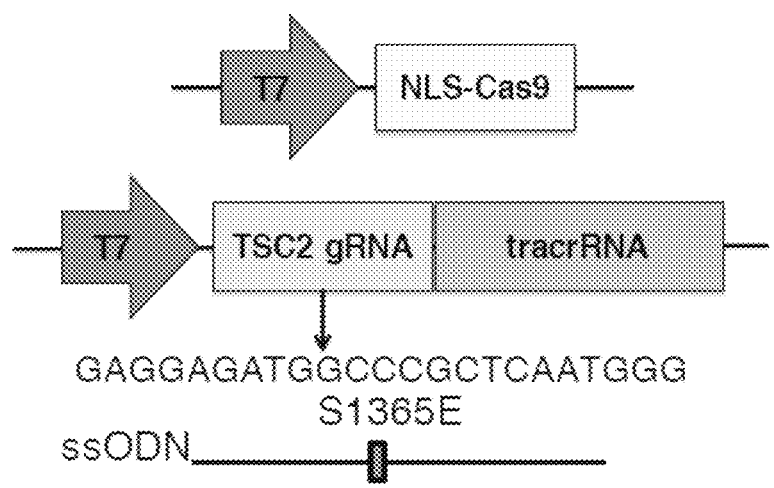
FIG. 62. Strategy and guide RNA (SEQ ID NO:12) for CRISPR-Cas9 protocol to generate S1365E (SE) knock-in mice.

In isolated myocytes, anti-hypertrophic effects and reduced mTORC1 activation were observed by expressing a phospho-mimetic S1365E mutation. To test this in vivo, we generated a second global KI mouse expressing this mutation (FIG. 62). SE mice are also born healthy in normal Mendelian ratios, and have normal resting cardiac morphology and function (Supplementary Tables 1 and 2). In contrast to SA mice, SE mice exposed to PO are protected, developing minimal cardiac hypertrophy and less ventricular dysfunction (FIG. 43 and FIG. 44) despite increased pressure-load. Heterozygote and homozygote SE mice displayed similar protection so this mutation is also autosomal dominant. Baseline mTORC1 activity was unchanged in SE mice compared to WT controls; however with PO stress, P-p70S6K increased in WT mice but remained at low levels in both SE/WT and SE/SE mice.

Figure 45:
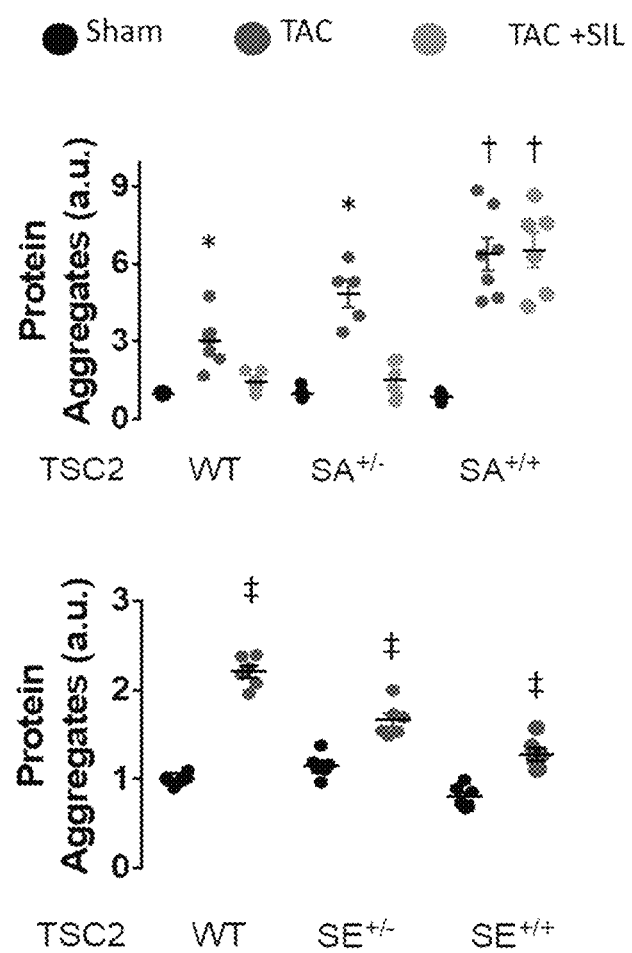
FIG. 45. Protein aggregates accumulate in TSC2-SA knock-in hearts subjected to pathological stress, and are reduced in TSC2-SE knock-in hearts—in a gene dose dependent manner. Protein aggregates assessed by Proteostat assay® were measured in hearts expressing WT, SA and SE forms of TSC2; both heterozygous and homozygous knock-ins. With SA expression, pressure overload stress results in a greater accumulation of protein aggregates (indicative of proteotoxicity, reduced autophagy) that is greater in homozygote than heterozygote KI mice. In SA+/− (heterozygote) mice, the increase in aggregation is reduced by activation of PKG, but this does not occur in homozygotes (SA+/+) knock-in. In SE expressing mice, the results are the opposite, with less protein aggregation in heterozygote KI and even less in homozygote KI. Panel A) *p<0.0005 vs other two groups; †p<0.0001 versus WT; ‡p<0.0005 vs Sham. There is a genetic dose response, with increasing SA correlating with greater aggregation after PO (p<0.0001, $r^2$=0.6) and increasing SE correlating with reduced aggregation after PO (p<0.0001, $r^2$=0.82).
Figure 63:
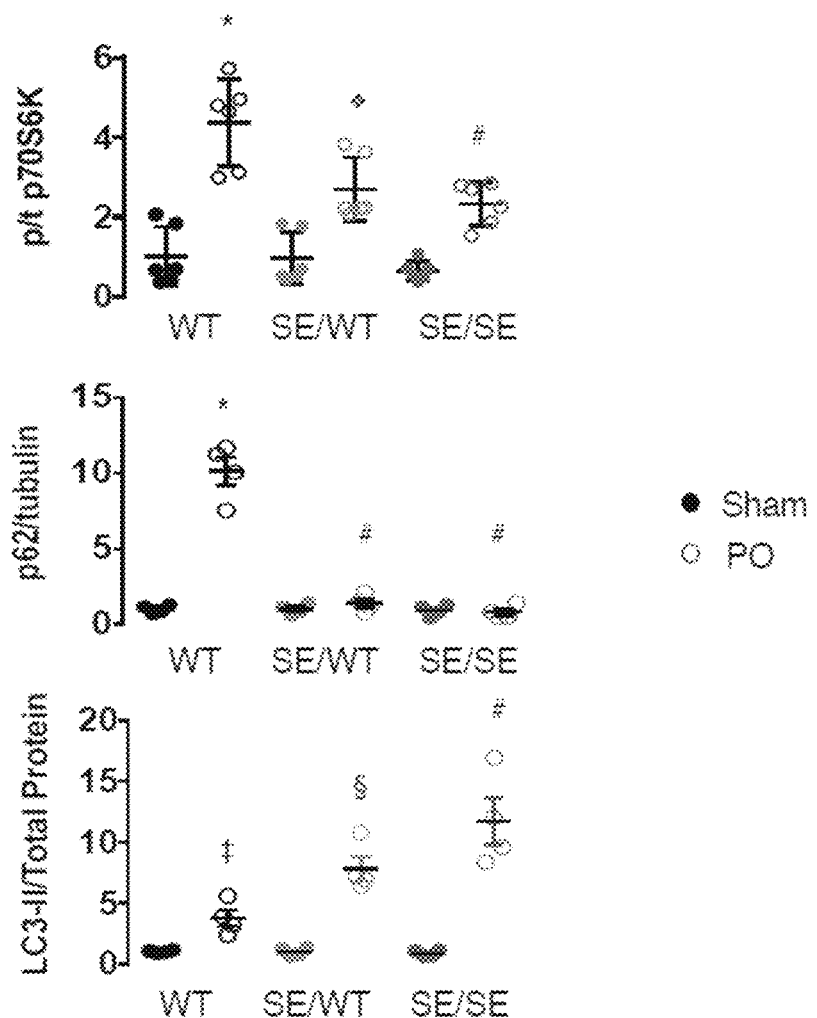
FIG. 63. Summary data for FIG. 6f. (n=4-6/group). P<0.0001 by 1 or 2-way ANOVA. Post hoc tests: *p<0.0001 vs. WT Sham, ‡p<0.05 vs. WT Sham, ❖ p<0.01 vs. WT PO, § p<0.001 vs. WT PO, #p<0.0001 vs. WT PO.
Figure 64:
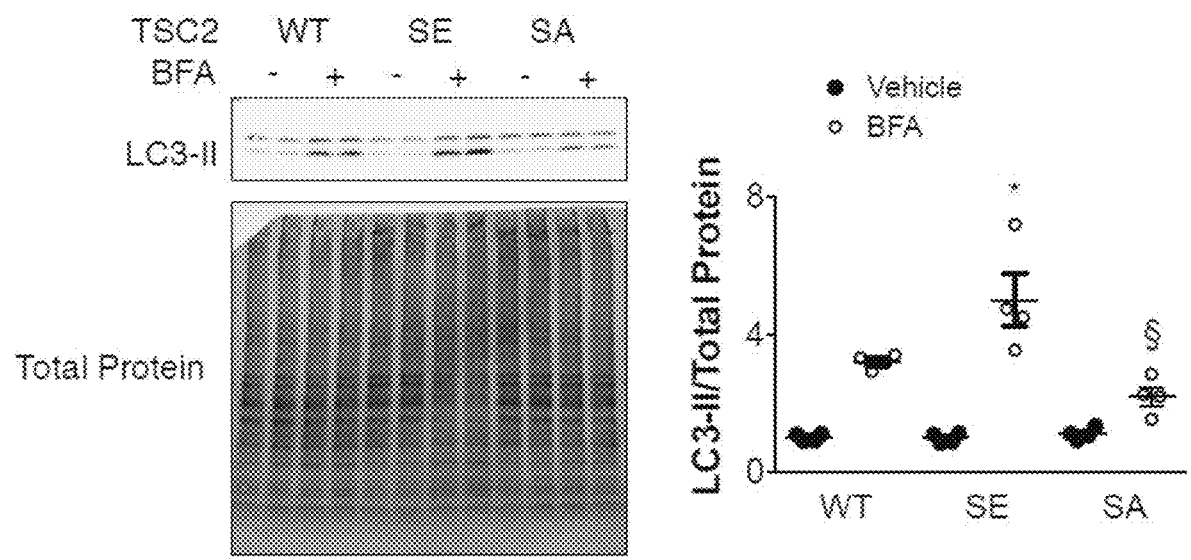
FIG. 64. Western blot analyses and summary data from TSC2 WT, SE, and SA mice treated with bafilomycin A1 (BFA) or vehicle. This autophagic flux assay revealed an increase of LC3-II that was greater in SE mice compared to WT mice which was greater than the increase seen in SA mice. (n=4/group); * Interaction vs WT (p<0.05); § interaction vs WT (p<0.005).

Opposite to SA mice, SE mice subjected to PO displayed reduced p62 and increased LC3-II expression, indicative of enhanced autophagy (FIG. 44 and FIG. 63). To compare baseline autophagic flux between SA and SE mice in vivo, mice were administered systemic BFA. BFA-induced increase in LC3-II was highest in SE and lowest in SA mice (FIG. 64). Lastly, we tested if differences in growth and autophagy in SA versus SE mice exposed to PO altered net myocardial protein aggregation. There was a gene dose-dependent increase in protein aggregates in SA and a reduction in aggregates with SE expression. Sil reversed aggregates in SA/WT and WT mice, but not in SA/SA (FIG. 45).

What is claimed is:

1. A method of treating a disease in a subject in need thereof, comprising:

administering to a subject an engineered immune cell comprising a nucleic acid encoding a polypeptide comprising SEQ ID NO: 1 operably linked to a nucleic acid that drives expression of the polypeptide in the engineered immune cell, such that said engineered immune cell comprises said polypeptide comprising SEQ ID NO: 1; and wherein upon recognizing an antigen associated with the disease, the immune cell exhibits increased activity as compared to a reference immune cell that lacks said polypeptide comprising SEQ ID NO: 1.

2. The method of claim 1, wherein the engineered immune cell is a cytotoxic T cell, a helper T cell, or a regulatory T cell.

3. The method of claim 1, wherein the increased activity comprises increased mTORC1 signaling.

4. The method of claim 1, wherein the increased activity comprises increased expression of one or more cytokines selected from the group consisting of: interferon gamma, tumor necrosis factor alpha, interleukin 2, and combinations thereof.

5. The method of claim 1, wherein the disease is cancer, a viral disease, a bacterial disease, fungal disease, or a parasitic disease.

6. The method of claim 1, wherein the disease is asthma, an autoimmune disease, or graft vs. host disease.

7. The method of claim 1, wherein the engineered immune cell is derived from an endogenous immune cell obtained from the subject.

8. The method of claim 1, wherein the engineered immune cell is a chimeric antigen receptor T (CAR-T) cell.

9. The method of claim 5, wherein said cancer is selected from the group consisting of lung cancer, papillary thyroid cancer, pheochromocytoma, breast cancer, colorectal cancer, ganglioneuromatosis of the gastroenteric mucosa, inflammatory myofibroblastic tumor, cervical cancer, adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain tumor, bronchial tumor, carcinoid tumor, cardiac tumors, chordoma, chronic myeloproliferative neoplasms, colon cancer, craniopharyngioma, endometrial cancer, ependymoma, esophageal cancer, Ewing sarcoma, eye cancer, fallopian tube cancer, gallbladder cancer, gastric cancer, gastrointestinal carcinoid tumor, gastrointestinal stromal tumors (GIST), germ cell tumor, gestational trophoblastic disease, glioma, hairy cell tumor, head and neck cancer, histiocytosis, islet cell tumors, Kaposi sarcoma, kidney cancer, laryngeal cancer, leukemia, lip and oral cavity cancer, liver cancer, lymphoma, macroglobulinemia, osteocarcinoma, melanoma, Merkel cell carcinoma, mesothelioma, midline tract carcinoma, multiple endocrine neoplasia syndromes, multiple myeloma, myelodysplastic neoplasms, myeloproliferative neoplasms, nasal cavity and paranasal sinus cancer, neuroblastoma, ovarian cancer, pancreatic cancer, papillomatosis, paraganglioma, parathyroid cancer, penile cancer, pharyngeal cancer, pituitary cancer, plasma cell neoplasm, pleuropulmonary blastoma, primary peritoneal cancer, prostate cancer, rectal cancer, retinoblastoma, rhabdomyosarcoma, salivary gland cancer, sarcoma, Sezary syndrome, skin cancer, small intestine cancer, soft tissue sarcoma, squamous cell carcinoma, testicular cancer, throat cancer, thymoma and thymic carcinoma, thyroid cancer, transitional cell cancer of the renal pelvis and ureter, unknown primary carcinoma, urethral cancer, uterine cancer, vaginal cancer, vulvar cancer, and Wilms' tumor.

10. The method of claim 1, wherein the subject is a human.

* * * * *

SEQUENCE LISTING

<160> NUMBER OF SEQ ID NOS: 11

<210> SEQ ID NO 1
<211> LENGTH: 1807
<212> TYPE: PRT
<213> ORGANISM: Artificial Sequence
<220> FEATURE:
<223> OTHER INFORMATION: human TSC2 polypeptide having a S1364A substitution

<400> SEQUENCE: 1

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

-continued

```
Gly Lys Gln Thr Glu Phe Ile Ile Thr Ala Glu Ile Leu Arg Glu Leu
             35                  40                  45

Ser Met Glu Cys Gly Leu Asn Asn Arg Ile Arg Met Ile Gly Gln Ile
 50                  55                  60

Cys Glu Val Ala Lys Thr Lys Phe Glu Glu His Ala Val Glu Ala
 65                  70                  75                  80

Leu Trp Lys Ala Val Ala Asp Leu Leu Gln Pro Glu Arg Pro Leu Glu
                 85                  90                  95

Ala Arg His Ala Val Leu Ala Leu Leu Lys Ala Ile Val Gln Gly Gln
                100                 105                 110

Gly Glu Arg Leu Gly Val Leu Arg Ala Leu Phe Phe Lys Val Ile Lys
             115                 120                 125

Asp Tyr Pro Ser Asn Glu Asp Leu His Glu Arg Leu Glu Val Phe Lys
         130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
```

```
            450                 455                 460
Val Leu Asp Val Leu Ser Phe Val Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
            515                 520                 525

Asp Ile Ile Glu Lys Val Met Ala Arg Ser Leu Ser Pro Pro Pro Glu
            530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Met Leu Val Ser
            580                 585                 590

His Ile Gln Leu His Tyr Lys His Ser Tyr Thr Leu Pro Ile Ala Ser
            595                 600                 605

Ser Ile Arg Leu Gln Ala Phe Asp Phe Leu Leu Leu Arg Ala Asp
610                 615                 620

Ser Leu His Arg Leu Gly Leu Pro Asn Lys Asp Gly Val Val Arg Phe
625                 630                 635                 640

Ser Pro Tyr Cys Val Cys Asp Tyr Met Glu Pro Glu Arg Gly Ser Glu
                645                 650                 655

Lys Lys Thr Ser Gly Pro Leu Ser Pro Thr Gly Pro Pro Gly Pro
            660                 665                 670

Ala Pro Ala Gly Pro Ala Val Arg Leu Gly Ser Val Pro Tyr Ser Leu
            675                 680                 685

Leu Phe Arg Val Leu Leu Gln Cys Leu Lys Gln Glu Ser Asp Trp Lys
            690                 695                 700

Val Leu Lys Leu Val Leu Gly Arg Leu Pro Glu Ser Leu Arg Tyr Lys
705                 710                 715                 720

Val Leu Ile Phe Thr Ser Pro Cys Ser Val Asp Gln Leu Cys Ser Ala
                725                 730                 735

Leu Cys Ser Met Leu Ser Gly Pro Lys Thr Leu Glu Arg Leu Arg Gly
                740                 745                 750

Ala Pro Glu Gly Phe Ser Arg Thr Asp Leu His Leu Ala Val Val Pro
            755                 760                 765

Val Leu Thr Ala Leu Ile Ser Tyr His Asn Tyr Leu Asp Lys Thr Lys
770                 775                 780

Gln Arg Glu Met Val Tyr Cys Leu Glu Gln Gly Leu Ile His Arg Cys
785                 790                 795                 800

Ala Ser Gln Cys Val Val Ala Leu Ser Ile Cys Ser Val Glu Met Pro
            805                 810                 815

Asp Ile Ile Lys Ala Leu Pro Val Leu Val Lys Leu Thr His
            820                 825                 830

Ile Ser Ala Thr Ala Ser Met Ala Val Pro Leu Leu Glu Phe Leu Ser
            835                 840                 845

Thr Leu Ala Arg Leu Pro His Leu Tyr Arg Asn Phe Ala Ala Glu Gln
            850                 855                 860

Tyr Ala Ser Val Phe Ala Ile Ser Leu Pro Tyr Thr Asn Pro Ser Lys
865                 870                 875                 880
```

```
Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
        915                 920                 925

Glu Lys Asp Ser Phe Arg Ala Arg Ser Thr Ser Leu Asn Glu Arg Pro
    930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ser Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu Gly Ser Ala Asp Glu Asn Ser Val
        995                 1000                1005

Ala Gln Ala Asp Asp Ser Leu Lys Asn Leu His Leu Glu Leu Thr
    1010            1015                1020

Glu Thr Cys Leu Asp Met Met Ala Arg Tyr Val Phe Ser Asn Phe
    1025            1030                1035

Thr Ala Val Pro Lys Arg Ser Pro Val Gly Glu Phe Leu Leu Ala
    1040            1045                1050

Gly Gly Arg Thr Lys Thr Trp Leu Val Gly Asn Lys Leu Val Thr
    1055            1060                1065

Val Thr Thr Ser Val Gly Thr Gly Thr Arg Ser Leu Leu Gly Leu
    1070            1075                1080

Asp Ser Gly Glu Leu Gln Ser Gly Pro Glu Ser Ser Ser Pro
    1085            1090                1095

Gly Val His Val Arg Gln Thr Lys Glu Ala Pro Ala Lys Leu Glu
    1100            1105                1110

Ser Gln Ala Gly Gln Gln Val Ser Arg Gly Ala Arg Asp Arg Val
    1115            1120                1125

Arg Ser Met Ser Gly Gly His Gly Leu Arg Val Gly Ala Leu Asp
    1130            1135                1140

Val Pro Ala Ser Gln Phe Leu Gly Ser Ala Thr Ser Pro Gly Pro
    1145            1150                1155

Arg Thr Ala Pro Ala Ala Lys Pro Glu Lys Ala Ser Ala Gly Thr
    1160            1165                1170

Arg Val Pro Val Gln Glu Lys Thr Asn Leu Ala Ala Tyr Val Pro
    1175            1180                1185

Leu Leu Thr Gln Gly Trp Ala Glu Ile Leu Val Arg Arg Pro Thr
    1190            1195                1200

Gly Asn Thr Ser Trp Leu Met Ser Leu Glu Asn Pro Leu Ser Pro
    1205            1210                1215

Phe Ser Ser Asp Ile Asn Asn Met Pro Leu Gln Glu Leu Ser Asn
    1220            1225                1230

Ala Leu Met Ala Ala Glu Arg Phe Lys Glu His Arg Asp Thr Ala
    1235            1240                1245

Leu Tyr Lys Ser Leu Ser Val Pro Ala Ala Ser Thr Ala Lys Pro
    1250            1255                1260

Pro Pro Leu Pro Arg Ser Asn Thr Val Ala Ser Phe Ser Ser Leu
    1265            1270                1275
```

```
Tyr Gln Ser Ser Cys Gln Gly Gln Leu His Arg Ser Val Ser Trp
    1280            1285             1290

Ala Asp Ser Ala Val Val Met Glu Glu Gly Ser Pro Gly Glu Val
    1295            1300             1305

Pro Val Leu Val Glu Pro Pro Gly Leu Glu Asp Val Glu Ala Ala
    1310            1315             1320

Leu Gly Met Asp Arg Arg Thr Asp Ala Tyr Ser Arg Ser Ser Ser
    1325            1330             1335

Val Ser Ser Gln Glu Glu Lys Ser Leu His Ala Glu Glu Leu Val
    1340            1345             1350

Gly Arg Gly Ile Pro Ile Glu Arg Val Val Ala Ser Glu Gly Gly
    1355            1360             1365

Arg Pro Ser Val Asp Leu Ser Phe Gln Pro Ser Gln Pro Leu Ser
    1370            1375             1380

Lys Ser Ser Ser Ser Pro Glu Leu Gln Thr Leu Gln Asp Ile Leu
    1385            1390             1395

Gly Asp Pro Gly Asp Lys Ala Asp Val Gly Arg Leu Ser Pro Glu
    1400            1405             1410

Val Lys Ala Arg Ser Gln Ser Gly Thr Leu Asp Gly Glu Ser Ala
    1415            1420             1425

Ala Trp Ser Ala Ser Gly Glu Asp Ser Arg Gly Gln Pro Glu Gly
    1430            1435             1440

Pro Leu Pro Ser Ser Ser Pro Arg Ser Pro Ser Gly Leu Arg Pro
    1445            1450             1455

Arg Gly Tyr Thr Ile Ser Asp Ser Ala Pro Ser Arg Arg Gly Lys
    1460            1465             1470

Arg Val Glu Arg Asp Ala Leu Lys Ser Arg Ala Thr Ala Ser Asn
    1475            1480             1485

Ala Glu Lys Val Pro Gly Ile Asn Pro Ser Phe Val Phe Leu Gln
    1490            1495             1500

Leu Tyr His Ser Pro Phe Phe Gly Asp Glu Ser Asn Lys Pro Ile
    1505            1510             1515

Leu Leu Pro Asn Glu Ser Gln Ser Phe Glu Arg Ser Val Gln Leu
    1520            1525             1530

Leu Asp Gln Ile Pro Ser Tyr Asp Thr His Lys Ile Ala Val Leu
    1535            1540             1545

Tyr Val Gly Glu Gly Gln Ser Asn Ser Glu Leu Ala Ile Leu Ser
    1550            1555             1560

Asn Glu His Gly Ser Tyr Arg Tyr Thr Glu Phe Leu Thr Gly Leu
    1565            1570             1575

Gly Arg Leu Ile Glu Leu Lys Asp Cys Gln Pro Asp Lys Val Tyr
    1580            1585             1590

Leu Gly Gly Leu Asp Val Cys Gly Glu Asp Gly Gln Phe Thr Tyr
    1595            1600             1605

Cys Trp His Asp Asp Ile Met Gln Ala Val Phe His Ile Ala Thr
    1610            1615             1620

Leu Met Pro Thr Lys Asp Val Asp Lys His Arg Cys Asp Lys Lys
    1625            1630             1635

Arg His Leu Gly Asn Asp Phe Val Ser Ile Val Tyr Asn Asp Ser
    1640            1645             1650

Gly Glu Asp Phe Lys Leu Gly Thr Ile Lys Gly Gln Phe Asn Phe
    1655            1660             1665

Val His Val Ile Val Thr Pro Leu Asp Tyr Glu Cys Asn Leu Val
```

```
                      1670                1675                1680

Ser Leu Gln Cys Arg Lys Asp Met Glu Gly Leu Val Asp Thr Ser
                1685                1690                1695

Val Ala Lys Ile Val Ser Asp Arg Asn Leu Pro Phe Val Ala Arg
                1700                1705                1710

Gln Met Ala Leu His Ala Asn Met Ala Ser Gln Val His His Ser
                1715                1720                1725

Arg Ser Asn Pro Thr Asp Ile Tyr Pro Ser Lys Trp Ile Ala Arg
                1730                1735                1740

Leu Arg His Ile Lys Arg Leu Arg Gln Arg Ile Cys Glu Glu Ala
                1745                1750                1755

Ala Tyr Ser Asn Pro Ser Leu Pro Leu Val His Pro Pro Ser His
                1760                1765                1770

Ser Lys Ala Pro Ala Gln Thr Pro Ala Glu Pro Thr Pro Gly Tyr
                1775                1780                1785

Glu Val Gly Gln Arg Lys Arg Leu Ile Ser Ser Val Glu Asp Phe
                1790                1795                1800

Thr Glu Phe Val
        1805

<210> SEQ ID NO 2
<211> LENGTH: 1807
<212> TYPE: PRT
<213> ORGANISM: Artificial Sequence
<220> FEATURE:
<223> OTHER INFORMATION: human TSC2 polypeptide having a S1364E
      substitution

<400> SEQUENCE: 2

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
                20                  25                  30

Gly Lys Gln Thr Glu Phe Ile Ile Thr Ala Glu Ile Leu Arg Glu Leu
            35                  40                  45

Ser Met Glu Cys Gly Leu Asn Asn Arg Ile Arg Met Ile Gly Gln Ile
        50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205
```

-continued

Thr Ala Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
    450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His Phe Asn Ser Leu Leu
        515                 520                 525

Asp Ile Ile Glu Lys Val Met Ala Arg Ser Leu Ser Pro Pro Glu
    530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Met Leu Val Ser
            580                 585                 590

His Ile Gln Leu His Tyr Lys His Ser Tyr Thr Leu Pro Ile Ala Ser
        595                 600                 605

Ser Ile Arg Leu Gln Ala Phe Asp Phe Leu Leu Leu Arg Ala Asp
    610                 615                 620

Ser Leu His Arg Leu Gly Leu Pro Asn Lys Asp Gly Val Val Arg Phe

-continued

```
            625                 630                 635                 640
Ser Pro Tyr Cys Val Cys Asp Tyr Met Glu Pro Glu Arg Gly Ser Glu
                    645                 650                 655
Lys Lys Thr Ser Gly Pro Leu Ser Pro Thr Gly Pro Gly Pro
                660                 665                 670
Ala Pro Ala Gly Pro Ala Val Arg Leu Gly Ser Val Pro Tyr Ser Leu
                675                 680                 685
Leu Phe Arg Val Leu Leu Gln Cys Leu Lys Gln Glu Ser Asp Trp Lys
            690                 695                 700
Val Leu Lys Leu Val Leu Gly Arg Leu Pro Glu Ser Leu Arg Tyr Lys
705                 710                 715                 720
Val Leu Ile Phe Thr Ser Pro Cys Ser Val Asp Gln Leu Cys Ser Ala
                    725                 730                 735
Leu Cys Ser Met Leu Ser Gly Pro Lys Thr Leu Glu Arg Leu Arg Gly
                740                 745                 750
Ala Pro Glu Gly Phe Ser Arg Thr Asp Leu His Leu Ala Val Val Pro
                755                 760                 765
Val Leu Thr Ala Leu Ile Ser Tyr His Asn Tyr Leu Asp Lys Thr Lys
            770                 775                 780
Gln Arg Glu Met Val Tyr Cys Leu Glu Gln Gly Leu Ile His Arg Cys
785                 790                 795                 800
Ala Ser Gln Cys Val Val Ala Leu Ser Ile Cys Ser Val Glu Met Pro
                    805                 810                 815
Asp Ile Ile Ile Lys Ala Leu Pro Val Leu Val Lys Leu Thr His
                820                 825                 830
Ile Ser Ala Thr Ala Ser Met Ala Val Pro Leu Leu Glu Phe Leu Ser
            835                 840                 845
Thr Leu Ala Arg Leu Pro His Leu Tyr Arg Asn Phe Ala Ala Glu Gln
            850                 855                 860
Tyr Ala Ser Val Phe Ala Ile Ser Leu Pro Tyr Thr Asn Pro Ser Lys
865                 870                 875                 880
Phe Asn Gln Tyr Ile Val Cys Leu Ala His His Val Ile Ala Met Trp
                    885                 890                 895
Phe Ile Arg Cys Arg Leu Pro Phe Arg Lys Asp Phe Val Pro Phe Ile
                900                 905                 910
Thr Lys Gly Leu Arg Ser Asn Val Leu Leu Ser Phe Asp Asp Thr Pro
                915                 920                 925
Glu Lys Asp Ser Phe Arg Ala Arg Ser Thr Ser Leu Asn Glu Arg Pro
            930                 935                 940
Lys Ser Leu Arg Ile Ala Arg Pro Pro Lys Gln Gly Leu Asn Asn Ser
945                 950                 955                 960
Pro Pro Val Lys Glu Phe Lys Glu Ser Ser Ala Ala Glu Ala Phe Arg
                    965                 970                 975
Cys Arg Ser Ile Ser Val Ser Glu His Val Val Arg Ser Arg Ile Gln
                980                 985                 990
Thr Ser Leu Thr Ser Ala Ser Leu  Gly Ser Ala Asp Glu  Asn Ser Val
            995                 1000                1005
Ala Gln  Ala Asp Asp Ser Leu  Lys Asn Leu His Leu  Glu Leu Thr
        1010                1015                1020
Glu Thr  Cys Leu Asp Met Met  Ala Arg Tyr Val Phe  Ser Asn Phe
        1025                1030                1035
Thr Ala  Val Pro Lys Arg Ser  Pro Val Gly Glu Phe  Leu Leu Ala
        1040                1045                1050
```

```
Gly Gly Arg Thr Lys Thr Trp Leu Val Gly Asn Lys  Leu Val Thr
    1055                1060                1065

Val Thr Thr Ser Val Gly Thr Gly Thr Arg Ser Leu  Leu Gly Leu
    1070                1075                1080

Asp Ser Gly Glu Leu Gln Ser Gly Pro Glu Ser Ser  Ser Ser Pro
    1085                1090                1095

Gly Val His Val Arg Gln Thr Lys Glu Ala Pro Ala  Lys Leu Glu
    1100                1105                1110

Ser Gln Ala Gly Gln Gln Val Ser Arg Gly Ala Arg  Asp Arg Val
    1115                1120                1125

Arg Ser Met Ser Gly Gly His Gly Leu Arg Val Gly  Ala Leu Asp
    1130                1135                1140

Val Pro Ala Ser Gln Phe Leu Gly Ser Ala Thr Ser  Pro Gly Pro
    1145                1150                1155

Arg Thr Ala Pro Ala Ala Lys Pro Glu Lys Ala Ser  Ala Gly Thr
    1160                1165                1170

Arg Val Pro Val Gln Glu Lys Thr Asn Leu Ala Ala  Tyr Val Pro
    1175                1180                1185

Leu Leu Thr Gln Gly Trp Ala Glu Ile Leu Val Arg  Arg Pro Thr
    1190                1195                1200

Gly Asn Thr Ser Trp Leu Met Ser Leu Glu Asn Pro  Leu Ser Pro
    1205                1210                1215

Phe Ser Ser Asp Ile Asn Asn Met Pro Leu Gln Glu  Leu Ser Asn
    1220                1225                1230

Ala Leu Met Ala Ala Glu Arg Phe Lys Glu His Arg  Asp Thr Ala
    1235                1240                1245

Leu Tyr Lys Ser Leu Ser Val Pro Ala Ala Ser Thr  Ala Lys Pro
    1250                1255                1260

Pro Pro Leu Pro Arg Ser Asn Thr Val Ala Ser Phe  Ser Ser Leu
    1265                1270                1275

Tyr Gln Ser Ser Cys Gln Gly Gln Leu His Arg Ser  Val Ser Trp
    1280                1285                1290

Ala Asp Ser Ala Val Val Met Glu Glu Gly Ser Pro  Gly Glu Val
    1295                1300                1305

Pro Val Leu Val Glu Pro Pro Gly Leu Glu Asp Val  Glu Ala Ala
    1310                1315                1320

Leu Gly Met Asp Arg Arg Thr Asp Ala Tyr Ser Arg  Ser Ser Ser
    1325                1330                1335

Val Ser Ser Gln Glu Glu Lys Ser Leu His Ala Glu  Glu Leu Val
    1340                1345                1350

Gly Arg Gly Ile Pro Ile Glu Arg Val Val Glu Ser  Glu Gly Gly
    1355                1360                1365

Arg Pro Ser Val Asp Leu Ser Phe Gln Pro Ser Gln  Pro Leu Ser
    1370                1375                1380

Lys Ser Ser Ser Ser Pro Glu Leu Gln Thr Leu Gln  Asp Ile Leu
    1385                1390                1395

Gly Asp Pro Gly Asp Lys Ala Asp Val Gly Arg Leu  Ser Pro Glu
    1400                1405                1410

Val Lys Ala Arg Ser Gln Ser Gly Thr Leu Asp Gly  Glu Ser Ala
    1415                1420                1425

Ala Trp Ser Ala Ser Gly Glu Asp Ser Arg Gly Gln  Pro Glu Gly
    1430                1435                1440
```

Pro Leu Pro Ser Ser Ser Pro Arg Ser Pro Ser Gly Leu Arg Pro
    1445                1450                1455

Arg Gly Tyr Thr Ile Ser Asp Ser Ala Pro Ser Arg Arg Gly Lys
    1460                1465                1470

Arg Val Glu Arg Asp Ala Leu Lys Ser Arg Ala Thr Ala Ser Asn
    1475                1480                1485

Ala Glu Lys Val Pro Gly Ile Asn Pro Ser Phe Val Phe Leu Gln
    1490                1495                1500

Leu Tyr His Ser Pro Phe Phe Gly Asp Glu Ser Asn Lys Pro Ile
    1505                1510                1515

Leu Leu Pro Asn Glu Ser Gln Ser Phe Glu Arg Ser Val Gln Leu
    1520                1525                1530

Leu Asp Gln Ile Pro Ser Tyr Asp Thr His Lys Ile Ala Val Leu
    1535                1540                1545

Tyr Val Gly Glu Gly Gln Ser Asn Ser Glu Leu Ala Ile Leu Ser
    1550                1555                1560

Asn Glu His Gly Ser Tyr Arg Tyr Thr Glu Phe Leu Thr Gly Leu
    1565                1570                1575

Gly Arg Leu Ile Glu Leu Lys Asp Cys Gln Pro Asp Lys Val Tyr
    1580                1585                1590

Leu Gly Gly Leu Asp Val Cys Gly Glu Asp Gly Gln Phe Thr Tyr
    1595                1600                1605

Cys Trp His Asp Asp Ile Met Gln Ala Val Phe His Ile Ala Thr
    1610                1615                1620

Leu Met Pro Thr Lys Asp Val Asp Lys His Arg Cys Asp Lys Lys
    1625                1630                1635

Arg His Leu Gly Asn Asp Phe Val Ser Ile Val Tyr Asn Asp Ser
    1640                1645                1650

Gly Glu Asp Phe Lys Leu Gly Thr Ile Lys Gly Gln Phe Asn Phe
    1655                1660                1665

Val His Val Ile Val Thr Pro Leu Asp Tyr Glu Cys Asn Leu Val
    1670                1675                1680

Ser Leu Gln Cys Arg Lys Asp Met Glu Gly Leu Val Asp Thr Ser
    1685                1690                1695

Val Ala Lys Ile Val Ser Asp Arg Asn Leu Pro Phe Val Ala Arg
    1700                1705                1710

Gln Met Ala Leu His Ala Asn Met Ala Ser Gln Val His His Ser
    1715                1720                1725

Arg Ser Asn Pro Thr Asp Ile Tyr Pro Ser Lys Trp Ile Ala Arg
    1730                1735                1740

Leu Arg His Ile Lys Arg Leu Arg Gln Arg Ile Cys Glu Glu Ala
    1745                1750                1755

Ala Tyr Ser Asn Pro Ser Leu Pro Leu Val His Pro Pro Ser His
    1760                1765                1770

Ser Lys Ala Pro Ala Gln Thr Pro Ala Glu Pro Thr Pro Gly Tyr
    1775                1780                1785

Glu Val Gly Gln Arg Lys Arg Leu Ile Ser Ser Val Glu Asp Phe
    1790                1795                1800

Thr Glu Phe Val
    1805

<210> SEQ ID NO 3
<211> LENGTH: 5424
<212> TYPE: DNA

<213> ORGANISM: Artificial Sequence
<220> FEATURE:
<223> OTHER INFORMATION: nucleic acid encoding a human TSC2 polypeptide having a S1364A substitution

<400> SEQUENCE: 3

```
atggccaaac caacaagcaa agattcaggc ttgaaggaga agtttaagat tctgttggga      60
ctgggaacac cgaggccaaa tcccaggtct gcagagggta acagacgga gtttatcatc     120
accgcggaaa tactgagaga actgagcatg gaatgtggcc tcaacaatcg catccggatg     180
ataggggaga tttgtgaagt cgcaaaaacc aagaaatttg aagagcacgc agtggaagca     240
ctctggaagg cggtcgcgga tctgttgcag ccggagcggc cgctggaggc ccggcacgcg     300
gtgctggctc tgctgaaggc catcgtgcag gggcagggcg agcgtttggg ggtcctcaga     360
gccctcttct ttaaggtcat caaggattac ccttccaacg aagaccttca cgaaaggctg     420
gaggttttca aggccctcac agacaatggg agacacatca cctacttgga ggaagagctg     480
gctgactttg tcctgcagtg gatggatgtt ggcttgtcct cggaattcct tctggtgctg     540
gtgaacttgg tcaaattcaa tagctgttac ctcgacgagt acatcgcaag gatggttcag     600
atgatctgtc tgctgtgcgt ccggaccgcg tcctctgtgg acatagaggt ctccctgcag     660
gtgctggacg ccgtggtctg ctacaactgc ctgccggctg agagcctccc gctgttcatc     720
gttaccctct gtcgcaccat caacgtcaag gagctctgcg agccttgctg aagctgatg     780
cggaacctcc ttggcaccca cctgggccac agcgccatct acaacatgtg ccacctcatg     840
gaggacagag cctacatgga ggacgcgccc ctgctgagag agccgtgtt ttttgtgggc     900
atggctctct ggggagccca ccggctctat tctctcagga actcgccgac atctgtgttg     960
ccatcatttt accaggccat ggcatgtccg aacgaggtgg tgtcctatga gatcgtcctg    1020
tccatcacca ggctcatcaa gaagtatagg aaggagctcc aggtggtggc gtgggacatt    1080
ctgctgaaca tcatcgaacg gctccttcag cagctccaga ccttggacag cccggagctc    1140
aggaccatcg tccatgacct gttgaccacg gtggaggagc tgtgtgacca aacgagttc    1200
cacgggtctc aggagagata ctttgaactg gtggagagat gtgcggacca gaggcctgag    1260
tcctccctcc tgaacctgat ctcctataga gcgcagtcca tccacccggc caaggacggc    1320
tggattcaga acctgcaggc gctgatggag agattcttca ggagcgagtc ccgaggcgcc    1380
gtgcgcatca aggtgctgga cgtgctgtcc tttgtgctgc tcatcaacag gcagttctat    1440
gaggaggagc tgattaactc agtggtcatc tcgcagctct cccacatccc gaggataaaa    1500
gaccaccagg tccgaaagct ggccacccag ttgctggtgg acctggcaga gggctgccac    1560
acacaccact caacagcct gctggacatc atcgagaagg tgatggcccg ctccctctcc    1620
ccaccccgg agctggaaga aagggatgtg gccgcatact cggcctcctt ggaggatgtg    1680
aagacagccg tcctggggct tctggtcatc cttcagacca agctgtacac cctgcctgca    1740
agccacgcca cgcgtgtgta tgagatgctg gtcagccaca ttcagctcca ctacaagcac    1800
agctacaccc tgccaatcgc gagcagcatc cggctgcagg cctttgactt cctgttgctg    1860
ctgcggggccg actcactgca ccgcctgggc ctgcccaaca aggatggagt cgtgcggttc    1920
agcccctact gcgtctgcga ctacatggag ccagagagag gctctgagaa gaagaccagc    1980
ggccccccttt ctcctcccac agggcctcct ggccggcgc ctgcaggccc cgccgtgcgg    2040
ctggggtccg tgccctactc cctgctcttc gcgtcctgc tgcagtgctt gaagcaggag    2100
tctgactgga aggtgctgaa gctggttctg ggcaggctgc ctgagtccct gcgctataaa    2160
```

```
gtgctcatct ttacttcccc ttgcagtgtg gaccagctgt gctctgctct ctgctccatg    2220
ctttcaggcc caaagacact ggagcggctc cgaggcgccc cagaaggctt ctccagaact    2280
gacttgcacc tggccgtggt tccagtgctg acagcattaa tctcttacca taactacctg    2340
gacaaaacca acagcgcga gatggtctac tgcctggagc agggcctcat ccaccgctgt    2400
gccagccagt gcgtcgtggc cttgtccatc tgcagcgtgg agatgcctga catcatcatc    2460
aaggcgctgc ctgttctggt ggtgaagctc acgcacatct cagccacagc cagcatggcc    2520
gtcccactgc tggagttcct gtccactctg gccaggctgc cgcacctcta caggaacttt    2580
gccgcggagc agtatgccag tgtgttcgcc atctccctgc cgtacaccaa ccctccaag    2640 tttaatcagt acatcgtgtg tctggcccat cacgtcatag ccatgtggtt catcaggtgc    2700
cgcctgccct tccggaagga ttttgtccct tcatcacta agggcctgcg gtccaatgtc    2760
ctcttgtctt ttgatgacac ccccgagaag gacagcttca gggcccggag tactagtctc    2820
aacgagagac caagagtct gaggatagcc agaccccca acaaggctt gaataactct    2880 ccacccgtga agaattcaa ggagagctct gcagccgagg ccttccggtg ccgcagcatc    2940
agtgtgtctg aacatgtggt ccgcagcagg atacagacgt ccctcaccag tgccagcttg    3000
gggtctgcag atgagaactc cgtggcccag gctgacgata gcctgaaaaa cctccacctg    3060
gagctcacgg aaacctgtct ggacatgatg gctcgatacg tcttctccaa cttcacggct    3120
gtcccgaaga ggtctcctgt gggcgagttc ctcctagcgg gtggcaggac caaaacctgg    3180
ctggttggga caagcttgt cactgtgacg acaagcgtgg aaccgggac ccggtcgtta    3240 ctaggcctgg actcggggga gctgcagtcc ggcccggagt cgagctccag ccccggggtg    3300
catgtgagac agaccaagga ggcgccggcc aagctggagt cccaggctgg gcagcaggtg    3360
tcccgtgggg cccgggatcg ggtccgttcc atgtcggggg gccatggtct tcgagttggc    3420
gccctggacg tgccggcctc ccagttcctg ggcagtgcca cttctccagg accacggact    3480
gcaccagccg cgaaacctga aaggcctca gctggcaccc gggttcctgt gcaggagaag    3540
acgaacctgg cggcctatgt gcccctgctg acccagggct gggcggagat cctggtccgg    3600
aggcccacag gaacaccag ctggctgatg agcctggaga cccgctcag cccttttctcc    3660 tcggacatca acaacatgcc cctgcaggag ctgtctaacg ccctcatggc ggctgagcgc    3720
ttcaaggagc accgggacac agccctgtac aagtcactgt cggtgccggc agccagcacg    3780
gccaaacccc ctcctctgcc tcgctccaac acagtggcct cttttcctc cctgtaccag    3840 tccagctgcc aaggacagct gcacaggagc gtttcctggg cagactccgc cgtggtcatg    3900
gaggagggaa gtccgggcga ggttcctgtg ctggtggagc cccagggtt ggaggacgtt    3960 gaggcagcgc taggcatgga caggcgcacg gatgcctaca gcaggtcgtc ctcagtctcc    4020
agccaggagg agaagtcgct ccacgcggag gagctggttg cagggcat ccccatcgag    4080 cgagtcgtcg cctcggaggg tggccggcc tctgtggacc tctccttcca gccctcgcag    4140
cccctgagca agtccagctc ctctcccgag ctgcagactc tgcaggacat cctcggggac    4200
cctggggaca aggccgacgt gggccggctg agccctgagg ttaaggcccg gtcacagtca    4260
gggaccctgg acggggaaag tgctgcctgg tcggcctcgg gcgaagacag tcggggccag    4320
cccgagggtc ccttgccttc cagctcccc cgctcgccca gtggcctccg gccccgaggt    4380
tacaccatct ccgactcggc cccatcacgc aggggcaaga gagtagagag ggacgcctta    4440
aagagcagag ccacagcctc caatgcagag aaagtgccag gcatcaaccc cagtttcgtg    4500
ttcctgcagc tctaccattc ccccttcttt ggcgacgagt caaacaagcc aatcctgctg    4560
```

```
cccaatgagt cacagtcctt tgagcggtcg gtgcagctcc tcgaccagat cccatcatac    4620
gacacccaca agatcgccgt cctgtatgtt ggagaaggcc agagcaacag cgagctcgcc    4680
atcctgtcca atgagcatgg ctcctacagg tacacggagt tcctgacggg cctgggccgg    4740
ctcatcgagc tgaaggactg ccagccggac aaggtgtacc tgggaggcct ggacgtgtgt    4800
ggtgaggacg gccagttcac ctactgctgg cacgatgaca tcatgcaagc cgtcttccac    4860
atcgccaccc tgatgcccac caaggacgtg acaagcacc gctgcgacaa gaagcgccac     4920
ctgggcaacg actttgtgtc cattgtctac aatgactccg gtgaggactt caagcttggc    4980
accatcaagg gccagttcaa ctttgtccac gtgatcgtca ccccgctgga ctacgagtgc    5040
aacctggtgt ccctgcagtg caggaaagac atggagggcc ttgtggacac cagcgtggcc    5100
aagatcgtgt ctgaccgcaa cctgcccttc gtggcccgcc agatggccct gcacgcaaat    5160
atggcctcac aggtgcatca tagccgctcc aaccccaccg atatctaccc ctccaagtgg    5220
attgcccggc tccgccacat caagcggctc cgccagcgga tctgcgagga agccgcctac    5280 tccaaccccca gcctacctct ggtgcaccct ccgtcccata gcaaagcccc tgcacagact    5340
ccagccgagc ccacacctgg ctatgaggtg ggccagcgga agcgcctcat ctcctcggtg    5400
gaggacttca ccgagtttgt gtga                                           5424

<210> SEQ ID NO 4
<211> LENGTH: 5424
<212> TYPE: DNA
<213> ORGANISM: Artificial Sequence
<220> FEATURE:
<223> OTHER INFORMATION: nucleic acid encoding a human TSC2 polypeptide
      having a S1364E substitution

<400> SEQUENCE: 4
atggccaaac caacaagcaa agattcaggc ttgaaggaga agtttaagat tctgttggga      60
ctgggaacac cgaggccaaa tcccaggtct gcagagggta acagacgga gtttatcatc      120 accgcggaaa tactgagaga actgagcatg gaatgtggcc tcaacaatcg catccggatg     180 ataggggcaga tttgtgaagt cgcaaaaaacc aagaaatttg aagagcacgc agtggaagca     240
ctctggaagg cggtcgcgga tctgttgcag ccggagcggc cgctggaggc ccggcacgcg     300
gtgctggctc tgctgaaggc catcgtgcag gggcagggcg agcgtttggg ggtcctcaga     360
gccctcttct ttaaggtcat caaggattac ccttccaacg aagaccttca cgaaaggctg     420
gaggttttca aggccctcac agacaatggg agacacatca cctacttgga ggaagagctg     480
gctgactttg tcctgcagtg gatggatgtt ggcttgtcct cggaattcct tctggtgctg     540
gtgaacttgg tcaaattcaa tagctgttac ctcgacgagt acatcgcaag gatggttcag     600
atgatctgtc tgctgtgcgt ccggaccgcg tcctctgtgg acatagaggt ctccctgcag     660
gtgctggacg ccgtggtctg ctacaactgc ctgccggctg agagcctccc gctgttcatc     720
gttaccctct gtcgcaccat caacgtcaag gagctctgcg agccttgctg gaagctgatg     780
cggaacctcc ttggcaccca cctgggccac agcgccatct acaacatgtg ccacctcatg    840
gaggacagag cctacatgga ggacgcgccc ctgctgagag gagccgtgtt ttttgtgggc     900
atggctctct ggggagccca ccggctctat tctctcagga actcgccgac atctgtgttg    960
ccatcatttt accaggccat ggcatgtccg aacgaggtgg tgtcctatga gatcgtcctg    1020
tccatcacca ggctcatcaa gaagtatagg aaggagctcc aggtggtggc gtgggacatt    1080
ctgctgaaca tcatcgaacg gctccttcag cagctccaga ccttggacag cccggagctc    1140
```

```
aggaccatcg tccatgacct gttgaccacg gtggaggagc tgtgtgacca gaacgagttc    1200
cacgggtctc aggagagata ctttgaactg gtggagagat gtgcggacca gaggcctgag    1260
tcctccctcc tgaacctgat ctcctataga gcgcagtcca tccacccggc caaggacggc    1320
tggattcaga acctgcaggc gctgatggag agattcttca ggagcgagtc ccgaggcgcc    1380
gtgcgcatca aggtgctgga cgtgctgtcc tttgtgctgc tcatcaacag gcagttctat    1440
gaggaggagc tgattaactc agtggtcatc tcgcagctct cccacatccc cgaggataaa    1500
gaccaccagg tccgaaagct ggccacccag ttgctggtgg acctggcaga gggctgccac    1560
acacaccact tcaacagcct gctggacatc atcgagaagg tgatggcccg ctccctctcc    1620
ccacccccgg agctggaaga aagggatgtg gccgcatact cggcctcctt ggaggatgtg    1680
aagacagccg tcctggggct tctggtcatc cttcagacca agctgtacac cctgcctgca    1740
agccacgcca cgcgtgtgta tgagatgctg gtcagccaca ttcagctcca ctacaagcac    1800
agctacaccc tgccaatcgc gagcagcatc cggctgcagg cctttgactt cctgttgctg    1860
ctgcgggccg actcactgca ccgcctgggc ctgcccaaca aggatggagt cgtgcggttc    1920 agccccctact gcgtctgcga ctacatggag ccagagagag gctctgagaa aagaccagc    1980 ggccccttt ctcctcccac agggcctcct ggcccggcgc ctgcaggccc cgccgtgcgg    2040
ctggggtccg tgccctactc cctgctcttc cgcgtcctgc tgcagtgctt gaagcaggag    2100
tctgactgga aggtgctgaa gctggttctg ggcaggctgc ctgagtccct cgcgctataa    2160
gtgctcatct ttacttcccc ttgcagtgtg gaccagctgt gctctgctct ctgctccatg    2220 cttttcaggcc caaagacact ggagcggctc cgaggcgccc cagaaggctt ctccagaact    2280
gacttgcacc tggccgtggt tccagtgctg acagcattaa tctcttacca taactacctg    2340
gacaaaacca acagcgcga tggtctac tgcctggagc agggcctcat ccaccgctgt    2400
gccagccagt gcgtcgtggc cttgtccatc tgcagcgtgg agatgcctga catcatcatc    2460
aaggcgctgc ctgttctggt ggtgaagctc acgcacatct cagccacagc cagcatggcc    2520
gtcccactgc tggagttcct gtccactctg gccaggctgc cgcacctcta caggaacttt    2580
gccgcggagc agtatgccag tgtgttcgcc atctccctgc cgtacaccaa cccctccaag    2640
tttaatcagt acatcgtgtg tctggcccat cacgtcatag ccatgtggtt catcaggtgc    2700
cgcctgccct tccggaagga ttttgtccct ttcatcacta agggcctgcg gtccaatgtc    2760
ctcttgtctt ttgatgacac ccccgagaag gacagcttca gggcccggag tactagtctc    2820
aacgagagac ccaagagtct gaggatagcc agaccccca aacaaggctt gaataactct    2880
ccacccgtga agaattcaa ggagagctct gcagccgagg ccttccggtg ccgcagcatc    2940
agtgtgtctg aacatgtggt ccgcagcagg atacagacgt ccctcaccag tgccagcttg    3000
gggtctgcag atgagaactc cgtggcccag gctgacgata gcctgaaaaa cctccacctg    3060
gagctcacgc aaacctgtct ggacatgatg gctcgatacg tcttctccaa cttcacggct    3120
gtcccgaaga ggtctcctgt gggcgagttc ctcctagcgg gtggcaggac caaaacctgg    3180
ctggttggga caagcttgt cactgtgacg acaagcgtgg aaccgggac ccggtcgtta    3240 ctaggcctgg actcggggga gctgcagtcc ggcccggagt cgagctccag ccccggggtg    3300
catgtgagac agaccaagga ggcgccggcc aagctggagt cccaggctgg gcagcaggtg    3360
tcccgtgggg cccgggatcg ggtccgttcc atgtcggggg gccatggtct tcgagttggc    3420
gccctggacg tgccggcctc ccagttcctg ggcagtgcca cttctccagg accacggact    3480
```

```
gcaccagccg cgaaacctga aaggcctca gctggcaccc gggttcctgt gcaggagaag      3540
acgaacctgg cggcctatgt gcccctgctg acccagggct gggcggagat cctggtccgg      3600
aggcccacag ggaacaccag ctggctgatg agcctggaga acccgctcag ccctttctcc      3660
tcggacatca acaacatgcc cctgcaggag ctgtctaacg ccctcatggc ggctgagcgc      3720
ttcaaggagc accgggacac agccctgtac aagtcactgt cggtgccggc agccagcacg      3780
gccaaacccc ctcctctgcc tcgctccaac acagtggccc ttttctcctc cctgtaccag      3840
tccagctgcc aaggacagct gcacaggagc gtttcctggg cagactccgc cgtggtcatg      3900
gaggagggaa gtccgggcga ggttcctgtg ctggtggagc ccccagggtt ggaggacgtt      3960
gaggcagcgc taggcatgga caggcgcacg gatgcctaca gcaggtcgtc ctcagtctcc      4020
agccaggagg agaagtcgct ccacgcggag gagctggttg caggggcat ccccatcgag      4080 cgagtcgtcg agtcggaggg tggccggccc tctgtggacc tctccttcca gccctcgcag      4140
cccctgagca gtccagctc ctctcccgag ctgcagactc tgcaggacat cctcggggac      4200
cctggggaca aggccgacgt gggccggctg agccctgagg ttaaggcccg gtcacagtca      4260
gggaccctgg acggggaaag tgctgcctgg tcggcctcgg gcgaagacag tcggggccag      4320
cccgagggtc ccttgccttc cagctccccc cgctcgccca gtggcctccg gccccgaggt      4380
tacaccatct ccgactcggc cccatcacgc aggggcaaga gagtagagag ggacgcctta      4440
aagagcagag ccacagcctc caatgcagag aaagtgccag gcatcaaccc cagtttcgtg      4500
ttcctgcagc tctaccattc ccccttcttt ggcgacgagt caaacaagcc aatcctgctg      4560
cccaatgagt cacagtcctt tgagcggtcg gtgcagctcc tcgaccagat ccatcatac      4620 gacacccaca agatcgccgt cctgtatgtt ggagaaggcc agagcaacag cgagctcgcc      4680
atcctgtcca tgagcatgg ctcctacagg tacacggagt tcctgacggg cctgggccgg      4740
ctcatcgagc tgaaggactg ccagccggac aaggtgtacc tgggaggcct ggacgtgtgt      4800
ggtgaggacg gccagttcac ctactgctgg cacgatgaca tcatgcaagc cgtcttccac      4860
atcgccaccc tgatgcccac caaggacgtg acaagcacc gctgcgacaa gaagcgccac      4920
ctgggcaacg actttgtgtc cattgtctac aatgactccg gtgaggactt caagcttggc      4980
accatcaagg gccagttcaa cttttgtccac gtgatcgtca cccgctgga ctacgagtgc      5040 aacctggtgt ccctgcagtg caggaaagac atggagggcc ttgtggacac cagcgtggcc      5100
aagatcgtgt ctgaccgcaa cctgccctcc gtggcccgcc agatggccct gcacgcaaat      5160
atggcctcac aggtgcatca tagccgctcc aaccccaccg atatctaccc ctccaagtgg      5220
attgcccggc tccgccacat caagcggctc cgccagcgga tctgcgagga agccgcctac      5280
tccaacccca gctacctct ggtgcaccct ccgtcccata gcaaagcccc tgcacagact      5340
ccagccgagc ccacacctgg ctatgaggtg ggccagcgga agcgcctcat ctcctcggtg      5400
gaggacttca ccgagtttgt gtga                                              5424
```

```
<210> SEQ ID NO 5
<211> LENGTH: 1807
<212> TYPE: PRT
<213> ORGANISM: Homo sapiens

<400> SEQUENCE: 5

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30
```

```
Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
        50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
                100                 105                 110

Gly Glu Arg Leu Gly Val Leu Arg Ala Leu Phe Phe Lys Val Ile Lys
                115                 120                 125

Asp Tyr Pro Ser Asn Glu Asp Leu His Glu Arg Leu Glu Val Phe Lys
        130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
                180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
        210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
                260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
        290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
                340                 345                 350

Leu Gln Val Val Ala Trp Asp Ile Leu Leu Asn Ile Ile Glu Arg Leu
                355                 360                 365

Leu Gln Gln Leu Gln Thr Leu Asp Ser Pro Glu Leu Arg Thr Ile Val
        370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
                420                 425                 430

Ser Ile His Pro Ala Lys Asp Gly Trp Ile Gln Asn Leu Gln Ala Leu
        435                 440                 445
```

-continued

```
Met Glu Arg Phe Phe Arg Ser Glu Ser Arg Gly Ala Val Arg Ile Lys
450                 455                 460

Val Leu Asp Val Leu Ser Phe Val Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
                500                 505                 510

Val Asp Leu Ala Glu Gly Cys His Thr His Phe Asn Ser Leu Leu
515                 520                 525

Asp Ile Ile Glu Lys Val Met Ala Arg Ser Leu Ser Pro Pro Pro Glu
530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Met Leu Val Ser
                580                 585                 590

His Ile Gln Leu His Tyr Lys His Ser Tyr Thr Leu Pro Ile Ala Ser
                595                 600                 605

Ser Ile Arg Leu Gln Ala Phe Asp Phe Leu Leu Leu Arg Ala Asp
610                 615                 620

Ser Leu His Arg Leu Gly Leu Pro Asn Lys Asp Gly Val Val Arg Phe
625                 630                 635                 640

Ser Pro Tyr Cys Val Cys Asp Tyr Met Glu Pro Glu Arg Gly Ser Glu
                645                 650                 655

Lys Lys Thr Ser Gly Pro Leu Ser Pro Pro Thr Gly Pro Pro Gly Pro
                660                 665                 670

Ala Pro Ala Gly Pro Ala Val Arg Leu Gly Ser Val Pro Tyr Ser Leu
                675                 680                 685

Leu Phe Arg Val Leu Leu Gln Cys Leu Lys Gln Glu Ser Asp Trp Lys
                690                 695                 700

Val Leu Lys Leu Val Leu Gly Arg Leu Pro Glu Ser Leu Arg Tyr Lys
705                 710                 715                 720

Val Leu Ile Phe Thr Ser Pro Cys Ser Val Asp Gln Leu Cys Ser Ala
                725                 730                 735

Leu Cys Ser Met Leu Ser Gly Pro Lys Thr Leu Glu Arg Leu Arg Gly
                740                 745                 750

Ala Pro Glu Gly Phe Ser Arg Thr Asp Leu His Leu Ala Val Val Pro
                755                 760                 765

Val Leu Thr Ala Leu Ile Ser Tyr His Asn Tyr Leu Asp Lys Thr Lys
770                 775                 780

Gln Arg Glu Met Val Tyr Cys Leu Glu Gln Gly Leu Ile His Arg Cys
785                 790                 795                 800

Ala Ser Gln Cys Val Val Ala Leu Ser Ile Cys Ser Val Glu Met Pro
                805                 810                 815

Asp Ile Ile Ile Lys Ala Leu Pro Val Leu Val Val Lys Leu Thr His
                820                 825                 830

Ile Ser Ala Thr Ala Ser Met Ala Val Pro Leu Leu Glu Phe Leu Ser
                835                 840                 845

Thr Leu Ala Arg Leu Pro His Leu Tyr Arg Asn Phe Ala Ala Glu Gln
850                 855                 860

Tyr Ala Ser Val Phe Ala Ile Ser Leu Pro Tyr Thr Asn Pro Ser Lys
```

```
              865                 870                 875                 880
        Phe Asn Gln Tyr Ile Val Cys Leu Ala His His Val Ile Ala Met Trp
                        885                 890                 895
        Phe Ile Arg Cys Arg Leu Pro Phe Arg Lys Asp Phe Val Pro Phe Ile
                        900                 905                 910
        Thr Lys Gly Leu Arg Ser Asn Val Leu Leu Ser Phe Asp Asp Thr Pro
                        915                 920                 925
        Glu Lys Asp Ser Phe Arg Ala Arg Ser Thr Ser Leu Asn Glu Arg Pro
                        930                 935                 940
        Lys Ser Leu Arg Ile Ala Arg Pro Pro Lys Gln Gly Leu Asn Asn Ser
        945                 950                 955                 960
        Pro Pro Val Lys Glu Phe Lys Glu Ser Ala Ala Glu Ala Phe Arg
                        965                 970                 975
        Cys Arg Ser Ile Ser Val Ser Glu His Val Val Arg Ser Arg Ile Gln
                        980                 985                 990
        Thr Ser Leu Thr Ser Ala Ser Leu Gly Ser Ala Asp Glu Asn Ser Val
                        995                 1000                1005
        Ala Gln Ala Asp Asp Ser Leu Lys Asn Leu His Leu Glu Leu Thr
                1010                1015                1020
        Glu Thr Cys Leu Asp Met Met Ala Arg Tyr Val Phe Ser Asn Phe
                1025                1030                1035
        Thr Ala Val Pro Lys Arg Ser Pro Val Gly Glu Phe Leu Leu Ala
                1040                1045                1050
        Gly Gly Arg Thr Lys Thr Trp Leu Val Gly Asn Lys Leu Val Thr
                1055                1060                1065
        Val Thr Thr Ser Val Gly Thr Gly Thr Arg Ser Leu Leu Gly Leu
                1070                1075                1080
        Asp Ser Gly Glu Leu Gln Ser Gly Pro Glu Ser Ser Ser Pro
                1085                1090                1095
        Gly Val His Val Arg Gln Thr Lys Glu Ala Pro Ala Lys Leu Glu
                1100                1105                1110
        Ser Gln Ala Gly Gln Gln Val Ser Arg Gly Ala Arg Asp Arg Val
                1115                1120                1125
        Arg Ser Met Ser Gly Gly His Gly Leu Arg Val Gly Ala Leu Asp
                1130                1135                1140
        Val Pro Ala Ser Gln Phe Leu Gly Ser Ala Thr Ser Pro Gly Pro
                1145                1150                1155
        Arg Thr Ala Pro Ala Ala Lys Pro Glu Lys Ala Ser Ala Gly Thr
                1160                1165                1170
        Arg Val Pro Val Gln Glu Lys Thr Asn Leu Ala Ala Tyr Val Pro
                1175                1180                1185
        Leu Leu Thr Gln Gly Trp Ala Glu Ile Leu Val Arg Arg Pro Thr
                1190                1195                1200
        Gly Asn Thr Ser Trp Leu Met Ser Leu Glu Asn Pro Leu Ser Pro
                1205                1210                1215
        Phe Ser Ser Asp Ile Asn Asn Met Pro Leu Gln Glu Leu Ser Asn
                1220                1225                1230
        Ala Leu Met Ala Ala Glu Arg Phe Lys Glu His Arg Asp Thr Ala
                1235                1240                1245
        Leu Tyr Lys Ser Leu Ser Val Pro Ala Ala Ser Thr Ala Lys Pro
                1250                1255                1260
        Pro Pro Leu Pro Arg Ser Asn Thr Val Ala Ser Phe Ser Ser Leu
                1265                1270                1275
```

```
Tyr Gln Ser Ser Cys Gln Gly Gln Leu His Arg Ser Val Ser Trp
    1280            1285                1290

Ala Asp Ser Ala Val Val Met Glu Glu Gly Ser Pro Gly Glu Val
    1295            1300                1305

Pro Val Leu Val Glu Pro Pro Gly Leu Glu Asp Val Glu Ala Ala
    1310            1315                1320

Leu Gly Met Asp Arg Arg Thr Asp Ala Tyr Ser Arg Ser Ser Ser
    1325            1330                1335

Val Ser Ser Gln Glu Glu Lys Ser Leu His Ala Glu Glu Leu Val
    1340            1345                1350

Gly Arg Gly Ile Pro Ile Glu Arg Val Val Ser Ser Glu Gly Gly
    1355            1360                1365

Arg Pro Ser Val Asp Leu Ser Phe Gln Pro Ser Gln Pro Leu Ser
    1370            1375                1380

Lys Ser Ser Ser Pro Glu Leu Gln Thr Leu Gln Asp Ile Leu
    1385            1390                1395

Gly Asp Pro Gly Asp Lys Ala Asp Val Gly Arg Leu Ser Pro Glu
    1400            1405                1410

Val Lys Ala Arg Ser Gln Ser Gly Thr Leu Asp Gly Glu Ser Ala
    1415            1420                1425

Ala Trp Ser Ala Ser Gly Glu Asp Ser Arg Gly Gln Pro Glu Gly
    1430            1435                1440

Pro Leu Pro Ser Ser Ser Pro Arg Ser Pro Ser Gly Leu Arg Pro
    1445            1450                1455

Arg Gly Tyr Thr Ile Ser Asp Ser Ala Pro Ser Arg Arg Gly Lys
    1460            1465                1470

Arg Val Glu Arg Asp Ala Leu Lys Ser Arg Ala Thr Ala Ser Asn
    1475            1480                1485

Ala Glu Lys Val Pro Gly Ile Asn Pro Ser Phe Val Phe Leu Gln
    1490            1495                1500

Leu Tyr His Ser Pro Phe Phe Gly Asp Glu Ser Asn Lys Pro Ile
    1505            1510                1515

Leu Leu Pro Asn Glu Ser Gln Ser Phe Glu Arg Ser Val Gln Leu
    1520            1525                1530

Leu Asp Gln Ile Pro Ser Tyr Asp Thr His Lys Ile Ala Val Leu
    1535            1540                1545

Tyr Val Gly Glu Gly Gln Ser Asn Ser Glu Leu Ala Ile Leu Ser
    1550            1555                1560

Asn Glu His Gly Ser Tyr Arg Tyr Thr Glu Phe Leu Thr Gly Leu
    1565            1570                1575

Gly Arg Leu Ile Glu Leu Lys Asp Cys Gln Pro Asp Lys Val Tyr
    1580            1585                1590

Leu Gly Gly Leu Asp Val Cys Gly Glu Asp Gly Gln Phe Thr Tyr
    1595            1600                1605

Cys Trp His Asp Asp Ile Met Gln Ala Val Phe His Ile Ala Thr
    1610            1615                1620

Leu Met Pro Thr Lys Asp Val Asp Lys His Arg Cys Asp Lys Lys
    1625            1630                1635

Arg His Leu Gly Asn Asp Phe Val Ser Ile Val Tyr Asn Asp Ser
    1640            1645                1650

Gly Glu Asp Phe Lys Leu Gly Thr Ile Lys Gly Gln Phe Asn Phe
    1655            1660                1665
```

```
Val His Val Ile Val Thr Pro Leu Asp Tyr Glu Cys Asn Leu Val
    1670                1675                1680

Ser Leu Gln Cys Arg Lys Asp Met Glu Gly Leu Val Asp Thr Ser
    1685                1690                1695

Val Ala Lys Ile Val Ser Asp Arg Asn Leu Pro Phe Val Ala Arg
    1700                1705                1710

Gln Met Ala Leu His Ala Asn Met Ala Ser Gln Val His His Ser
    1715                1720                1725

Arg Ser Asn Pro Thr Asp Ile Tyr Pro Ser Lys Trp Ile Ala Arg
    1730                1735                1740

Leu Arg His Ile Lys Arg Leu Arg Gln Arg Ile Cys Glu Glu Ala
    1745                1750                1755

Ala Tyr Ser Asn Pro Ser Leu Pro Leu Val His Pro Pro Ser His
    1760                1765                1770

Ser Lys Ala Pro Ala Gln Thr Pro Ala Glu Pro Thr Pro Gly Tyr
    1775                1780                1785

Glu Val Gly Gln Arg Lys Arg Leu Ile Ser Ser Val Glu Asp Phe
    1790                1795                1800

Thr Glu Phe Val
    1805

<210> SEQ ID NO 6
<211> LENGTH: 1814
<212> TYPE: PRT
<213> ORGANISM: Mus musculus

<400> SEQUENCE: 6

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
                20                  25                  30

Gly Lys Gln Thr Glu Phe Ile Ile Thr Ser Glu Ile Leu Arg Glu Leu
            35                  40                  45

Ser Gly Glu Cys Gly Leu Asn Asn Arg Ile Arg Met Ile Gly Gln Ile
        50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

Ala Arg His Ala Val Leu Thr Leu Leu Lys Ala Ile Val Gln Gly Gln
                100                 105                 110

Gly Asp Arg Leu Gly Val Leu Arg Ala Leu Phe Phe Lys Val Ile Lys
            115                 120                 125

Asp Tyr Pro Ser Asn Glu Asp Leu His Glu Arg Leu Glu Val Phe Lys
        130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
                180                 185                 190

Glu Tyr Ile Ala Ser Met Val His Met Ile Cys Leu Leu Cys Ile Arg
            195                 200                 205

Thr Val Ser Ser Val Asp Ile Glu Val Ser Leu Gln Val Leu Asp Ala
        210                 215                 220
```

```
Val Val Cys Tyr Asn Cys Leu Pro Ala Glu Ser Leu Pro Leu Phe Ile
225                 230                 235                 240

Ile Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys Arg Ile Met Glu Asp Arg Ser Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
                340                 345                 350

Leu Gln Ala Val Thr Trp Asp Ile Leu Asp Ile Ile Glu Arg Leu
            355                 360                 365

Leu Gln Gln Leu Gln Asn Leu Asp Ser Pro Glu Leu Lys Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415

Gln Arg Pro Glu Ser Ser Leu Leu Leu Ile Ser Tyr Arg Ala Gln
                420                 425                 430

Ser Ile His Pro Ala Lys Asp Gly Trp Ile Gln Asn Leu Gln Leu Leu
        435                 440                 445

Met Glu Arg Phe Phe Arg Asn Glu Cys Arg Ser Ala Val Ala Ile Lys
    450                 455                 460

Val Leu Asp Val Leu Ser Phe Val Leu Leu Ile Ile Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Glu
    530                 535                 540

Leu Glu Glu Arg Asp Leu Ala Val His Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Ser Leu Ile Ser
                580                 585                 590

His Ile Gln Leu His Tyr Lys His Gly Tyr Ser Leu Pro Ile Ala Ser
            595                 600                 605

Ser Ile Arg Leu Gln Ala Phe Asp Phe Leu Leu Leu Arg Ala Asp
        610                 615                 620

Ser Leu His Arg Leu Gly Leu Pro Asn Lys Asp Gly Val Val Arg Phe
625                 630                 635                 640
```

```
Ser Pro Tyr Cys Leu Cys Asp Cys Met Glu Leu Asp Arg Ala Ser Glu
                645                 650                 655

Lys Lys Ala Ser Gly Pro Leu Ser Pro Pro Thr Gly Pro Pro Ser Pro
            660                 665                 670

Val Pro Met Gly Pro Ala Val Arg Leu Gly Tyr Leu Pro Tyr Ser Leu
                675                 680                 685

Leu Phe Arg Val Leu Leu Gln Cys Leu Lys Gln Glu Ser Asp Trp Lys
        690                 695                 700

Val Leu Lys Leu Val Leu Ser Arg Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
                740                 745                 750

Thr Pro Glu Gly Phe Ser Arg Thr Asp Leu His Leu Ala Val Val Pro
            755                 760                 765

Val Leu Thr Ala Leu Ile Ser Tyr His Asn Tyr Leu Asp Lys Thr Arg
            770                 775                 780

Gln Arg Glu Met Val Tyr Cys Leu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Ile Lys Ala Leu Pro Val Leu Val Lys Leu Thr His
                820                 825                 830

Ile Ser Ala Thr Ala Ser Met Ala Ile Pro Leu Leu Glu Phe Leu Ser
            835                 840                 845

Thr Leu Ala Arg Leu Pro His Leu Tyr Arg Asn Phe Val Pro Glu Gln
    850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
                900                 905                 910

Thr Lys Gly Leu Arg Ser Asn Val Leu Leu Ser Phe Asp Asp Thr Pro
    915                 920                 925

Glu Lys Asp Ser Phe Arg Ala Arg Ser Thr Ser Leu Asn Glu Arg Pro
    930                 935                 940

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu  Gly Ser Ala Asp Glu  Asn Ser Met
            995                 1000                1005

Ala Gln Ala Asp Asp Asn Leu  Lys Asn Leu His Leu  Glu Leu Thr
    1010                1015                1020

Glu Thr Cys Leu Asp Met Met  Ala Arg Tyr Val Phe  Ser Asn Phe
    1025                1030                1035

Thr Ala Val Pro Lys Arg Ser  Pro Val Gly Glu Phe  Leu Leu Ala
    1040                1045                1050

Gly Gly Arg Thr Lys Thr Trp  Leu Val Gly Asn Lys  Leu Val Thr
```

```
                1055                1060                1065
Val Thr Thr Ser Val Gly Thr Gly Thr Arg Ser Leu Leu Gly Leu
                1070                1075                1080
Asp Ser Gly Asp Leu Gln Gly Gly Ser Asp Ser Ser Ser Asp Pro
                1085                1090                1095
Ser Thr His Val Arg Gln Thr Lys Glu Ala Pro Ala Lys Leu Glu
                1100                1105                1110
Ser Gln Ala Gly Gln Gln Val Ser Arg Gly Ala Arg Asp Arg Val
                1115                1120                1125
Arg Ser Met Ser Gly Gly His Gly Leu Arg Val Gly Val Leu Asp
                1130                1135                1140
Thr Ser Ala Pro Tyr Ser Pro Gly Gly Ser Ala Ser Leu Gly Pro
                1145                1150                1155
Gln Thr Ala Val Ala Ala Lys Pro Glu Lys Pro Pro Ala Gly Ala
                1160                1165                1170
Gln Leu Pro Thr Ala Glu Lys Thr Asn Leu Ala Ala Tyr Val Pro
                1175                1180                1185
Leu Leu Thr Gln Gly Trp Ala Glu Ile Leu Val Arg Arg Pro Thr
                1190                1195                1200
Gly Asn Thr Ser Trp Leu Met Ser Leu Glu Asn Pro Leu Ser Pro
                1205                1210                1215
Phe Ser Ser Asp Ile Asn Asn Met Pro Leu Gln Glu Leu Ser Asn
                1220                1225                1230
Ala Leu Met Ala Ala Glu Arg Phe Lys Glu His Gly His Ala Pro
                1235                1240                1245
Val Gln Val Ile Val Ser Ala Thr Gly Cys Thr Ala Lys Pro Pro
                1250                1255                1260
Thr Leu Pro Arg Ser Asn Thr Val Ala Ser Phe Ser Ser Leu Tyr
                1265                1270                1275
Gln Pro Ser Cys Gln Gly Gln Leu His Arg Ser Val Ser Trp Ala
                1280                1285                1290
Asp Ser Ala Met Val Leu Glu Glu Gly Ser Pro Gly Glu Thr Gln
                1295                1300                1305
Val Pro Val Glu Pro Pro Glu Leu Glu Asp Phe Glu Ala Ala Leu
                1310                1315                1320
Gly Thr Asp Arg His Cys Gln Arg Pro Asp Thr Tyr Ser Arg Ser
                1325                1330                1335
Ser Ser Ala Ser Ser Gln Glu Lys Ser His Leu Glu Glu Leu
                1340                1345                1350
Ala Ala Gly Gly Ile Pro Ile Glu Arg Ala Ile Ser Ser Glu Gly
                1355                1360                1365
Ala Arg Pro Ala Val Asp Leu Ser Phe Gln Pro Ser Gln Pro Leu
                1370                1375                1380
Ser Lys Ser Ser Ser Ser Pro Glu Leu Gln Thr Leu Gln Asp Ile
                1385                1390                1395
Leu Gly Asp Leu Gly Asp Lys Ile Asp Ile Gly Arg Leu Ser Pro
                1400                1405                1410
Glu Ala Lys Val Arg Ser Gln Ser Gly Ile Leu Asp Gly Glu Ala
                1415                1420                1425
Ala Thr Trp Ser Ala Thr Gly Glu Glu Ser Arg Ile Thr Val Pro
                1430                1435                1440
Pro Glu Gly Pro Leu Pro Ser Ser Ser Pro Arg Ser Pro Ser Gly
                1445                1450                1455
```

Leu Arg Pro Arg Gly Tyr Thr Ile Ser Asp Ser Ala Pro Ser Arg
1460                1465                1470

Arg Gly Lys Arg Val Glu Arg Asp Asn Phe Lys Ser Arg Ala Ala
1475                1480                1485

Ala Ser Ser Ala Glu Lys Val Pro Gly Ile Asn Pro Ser Phe Val
1490                1495                1500

Phe Leu Gln Leu Tyr His Ser Pro Phe Phe Gly Asp Glu Ser Asn
1505                1510                1515

Lys Pro Ile Leu Leu Pro Asn Glu Ser Phe Glu Arg Ser Val Gln
1520                1525                1530

Leu Leu Asp Gln Ile Pro Ser Tyr Asp Thr His Lys Ile Ala Val
1535                1540                1545

Leu Tyr Val Gly Glu Gly Gln Ser Ser Ser Glu Leu Ala Ile Leu
1550                1555                1560

Ser Asn Glu His Gly Ser Tyr Arg Tyr Thr Glu Phe Leu Thr Gly
1565                1570                1575

Leu Gly Arg Leu Ile Glu Leu Lys Asp Cys Gln Pro Asp Lys Val
1580                1585                1590

Tyr Leu Gly Gly Leu Asp Val Cys Gly Glu Asp Gly Gln Phe Thr
1595                1600                1605

Tyr Cys Trp His Asp Asp Ile Met Gln Ala Val Phe His Ile Ala
1610                1615                1620

Thr Leu Met Pro Thr Lys Asp Val Asp Lys His Arg Cys Asp Lys
1625                1630                1635

Lys Arg His Leu Gly Asn Asp Phe Val Ser Ile Ile Tyr Asn Asp
1640                1645                1650

Ser Gly Glu Asp Phe Lys Leu Gly Thr Ile Lys Gln Gly Gln Phe
1655                1660                1665

Asn Phe Val His Val Ile Ile Thr Pro Leu Asp Tyr Lys Cys Asn
1670                1675                1680

Leu Leu Thr Leu Gln Cys Arg Lys Asp Gly Pro Ala Cys Lys Cys
1685                1690                1695

Glu Trp Trp Arg Gln Pro Gly Glu Ile Val Val Trp Ala Leu Pro
1700                1705                1710

Val Val Met Glu Leu Thr Val Thr Ile Leu Leu Cys His Leu Gln
1715                1720                1725

Met Ala Ser Gln Val His His Ser Arg Ser Asn Pro Thr Asp Ile
1730                1735                1740

Tyr Pro Ser Lys Trp Ile Ala Arg Leu Arg His Ile Lys Arg Leu
1745                1750                1755

Arg Gln Arg Ile Arg Glu Glu Val His Tyr Ser Asn Pro Ser Leu
1760                1765                1770

Pro Leu Met His Pro Pro Ala His Thr Lys Ala Pro Ala Gln Ala
1775                1780                1785

Pro Glu Ala Thr Pro Thr Tyr Glu Thr Gly Gln Arg Lys Arg Leu
1790                1795                1800

Ile Ser Ser Val Asp Asp Phe Thr Glu Phe Val
1805                1810

<210> SEQ ID NO 7
<211> LENGTH: 1809
<212> TYPE: PRT
<213> ORGANISM: Rattus norvegicus -continued

```
<400> SEQUENCE: 7

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
            20                  25                  30

Gly Lys Gln Thr Glu Phe Ile Ile Thr Ala Glu Ile Leu Arg Glu Leu
        35                  40                  45

Ser Gly Glu Cys Gly Leu Asn Asn Arg Ile Arg Met Ile Gly Gln Ile
    50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

Ala Arg His Ala Val Leu Ala Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Pro Met Val His Met Ile Cys Leu Leu Cys Ile Arg
        195                 200                 205

Thr Val Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Ile Thr Leu Cys Arg Thr Val Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys Arg Ile Met Glu Asn Arg Ser Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Ala Val Thr Trp Asp Ile Leu Leu Asp Ile Ile Glu Arg Leu
        355                 360                 365

Leu Gln Gln Leu Gln Asn Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415
```

```
Gln Arg Pro Glu Ser Ser Leu Leu Asn Leu Ile Thr Tyr Arg Ala Gln
                420                 425                 430

Ser Ile His Pro Ala Lys Asp Gly Trp Ile Gln Asn Leu Gln Leu Leu
        435                 440                 445

Met Glu Arg Phe Phe Arg Asn Glu Cys Arg Ser Ala Val Arg Ile Lys
450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Leu Glu
530                 535                 540

Leu Glu Glu Arg Asp Leu Ala Val Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Thr Leu Ile Ser
            580                 585                 590

His Ile Gln Leu His Tyr Lys His Gly Tyr Ser Leu Pro Ile Ala Ser
        595                 600                 605

Ser Ile Arg Leu Gln Ala Phe Asp Phe Leu Leu Leu Leu Arg Ala Asp
610                 615                 620

Ser Leu His Arg Leu Gly Leu Pro Asn Lys Asp Gly Val Val Arg Phe
625                 630                 635                 640

Ser Pro Tyr Cys Leu Cys Asp Cys Ala Glu Leu Asp Arg Ala Ser Glu
                645                 650                 655

Lys Lys Ala Ser Gly Pro Leu Ser Pro Pro Thr Gly Pro Pro Ser Pro
            660                 665                 670

Val Pro Thr Gly Pro Ala Val Arg Leu Gly His Leu Pro Tyr Ser Leu
        675                 680                 685

Leu Phe Arg Val Leu Leu Gln Cys Leu Lys Gln Glu Thr Asp Trp Lys
690                 695                 700

Val Leu Lys Leu Val Leu Ser Lys Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
            740                 745                 750

Thr Pro Glu Gly Phe Ser Arg Thr Asp Leu His Leu Ala Val Val Pro
        755                 760                 765

Val Leu Thr Ala Leu Ile Ser Tyr His Asn Tyr Leu Asp Lys Thr Arg
        770                 775                 780

Gln Arg Glu Met Val Tyr Cys Leu Glu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Lys Ala Leu Pro Val Leu Val Val Lys Leu Thr His
            820                 825                 830
```

```
Ile Ser Ala Thr Ala Ser Met Ala Ile Pro Leu Leu Glu Phe Leu Ser
            835                 840                 845

Thr Leu Ala Arg Leu Pro His Leu Tyr Arg Asn Phe Ala Ala Glu Gln
        850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
            900                 905                 910

Thr Lys Gly Leu Arg Ser Asn Val Leu Leu Ser Phe Asp Asp Thr Pro
        915                 920                 925

Glu Lys Asp Lys Phe Arg Ala Arg Ser Thr Ser Leu Asn Glu Arg Pro
    930                 935                 940

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu  Gly Ser Ala Asp Glu  Asn Ser Met
        995                 1000                1005

Ala Gln  Ala Asp Asp Asn Leu  Lys Asn Leu His Leu  Glu Leu Thr
    1010                1015                1020

Glu Thr  Cys Leu Asp Met Met  Ala Arg Tyr Val Phe  Ser Asn Phe
    1025                1030                1035

Thr Ala  Val Pro Lys Arg Ser  Pro Val Gly Glu Phe  Leu Leu Ala
    1040                1045                1050

Gly Gly  Arg Thr Lys Thr Trp  Leu Val Gly Asn Lys  Leu Val Thr
    1055                1060                1065

Val Thr  Thr Ser Val Gly Thr  Gly Thr Arg Ser Leu  Leu Gly Leu
    1070                1075                1080

Asp Ser  Gly Asp Leu Gln Gly  Gly Ser Ala Ser Ser  Ser Asp Pro
    1085                1090                1095

Gly Thr  His Val Arg Gln Thr  Lys Glu Ala Pro Ala  Lys Leu Glu
    1100                1105                1110

Ser Gln  Ala Gly Gln Gln Val  Ser Arg Gly Ala Arg  Asp Arg Val
    1115                1120                1125

Arg Ser  Met Ser Gly Gly His  Gly Leu Arg Val Gly  Val Leu Asp
    1130                1135                1140

Thr Ser  Ala Pro Tyr Thr Pro  Gly Gly Pro Ala Ser  Leu Gly Ala
    1145                1150                1155

Gln Ala  Ala Pro Ala Ala Arg  Pro Glu Lys Pro Cys  Ala Gly Ala
    1160                1165                1170

Gln Leu  Pro Ala Ala Glu Lys  Ala Asn Leu Ala Ala  Tyr Val Pro
    1175                1180                1185

Leu Leu  Thr Gln Gly Trp Ala  Glu Ile Leu Val Arg  Arg Pro Thr
    1190                1195                1200

Gly Asn  Thr Ser Trp Leu Met  Ser Leu Glu Asn Pro  Leu Ser Pro
    1205                1210                1215

Phe Ser  Ser Asp Ile Asn Asn  Met Pro Leu Gln Glu  Leu Ser Asn
    1220                1225                1230

Ala Leu  Met Ala Ala Glu Arg  Phe Lys Glu His Arg  Asp Thr Ala
```

```
              1235               1240               1245

Leu Tyr Lys Ser Leu Ser Val Pro Ala Ala Gly Thr Ala Lys Pro
    1250                1255                1260

Pro Thr Leu Pro Arg Ser Asn Thr Val Ala Ser Phe Ser Ser Leu
    1265                1270                1275

Tyr Gln Pro Ser Cys Gln Gly Gln Leu His Arg Ser Val Ser Trp
    1280                1285                1290

Ala Asp Ser Ala Val Val Leu Glu Glu Gly Ser Pro Gly Glu Ala
    1295                1300                1305

His Val Pro Val Glu Pro Pro Glu Leu Glu Asp Phe Glu Ala Ala
    1310                1315                1320

Leu Gly Thr Asp Arg His Cys Gln Arg Pro Asp Ala Tyr Ser Arg
    1325                1330                1335

Ser Ser Ser Ala Ser Ser Gln Glu Glu Lys Ser His Leu Glu Glu
    1340                1345                1350

Leu Ala Ala Gly Gly Ile Pro Ile Glu Arg Ala Ile Ser Ser Glu
    1355                1360                1365

Gly Ala Arg Pro Thr Val Asp Leu Ser Phe Gln Pro Ser Gln Pro
    1370                1375                1380

Leu Ser Lys Ser Ser Ser Pro Glu Leu Gln Thr Leu Gln Asp
    1385                1390                1395

Ile Leu Gly Asp Leu Gly Asp Lys Thr Asp Ile Gly Arg Leu Ser
    1400                1405                1410

Pro Glu Ala Lys Val Arg Ser Gln Ser Gly Ile Leu Asp Gly Glu
    1415                1420                1425

Ala Ala Thr Trp Ser Ala Pro Gly Glu Glu Ser Arg Ile Thr Val
    1430                1435                1440

Pro Pro Glu Gly Pro Leu Pro Ser Ser Ser Pro Arg Ser Pro Ser
    1445                1450                1455

Gly Leu Arg Pro Arg Gly Tyr Thr Ile Ser Asp Ser Ala Pro Ser
    1460                1465                1470

Arg Arg Gly Lys Arg Val Glu Arg Asp Asn Phe Lys Ser Arg Thr
    1475                1480                1485

Ala Ala Ser Ser Ala Glu Lys Val Pro Gly Ile Asn Pro Ser Phe
    1490                1495                1500

Val Phe Leu Gln Leu Tyr His Ser Pro Phe Cys Gly Asp Glu Ser
    1505                1510                1515

Asn Lys Pro Ile Leu Leu Pro Asn Glu Ser Phe Glu Arg Ser Val
    1520                1525                1530

Gln Leu Leu Asp Gln Ile Pro Ser Tyr Asp Thr His Lys Ile Ala
    1535                1540                1545

Val Leu Tyr Val Gly Glu Gly Gln Ser Ser Ser Glu Leu Ala Ile
    1550                1555                1560

Leu Ser Asn Glu His Gly Ser Tyr Arg Tyr Thr Glu Phe Leu Thr
    1565                1570                1575

Gly Leu Gly Arg Leu Ile Glu Leu Lys Asp Cys Gln Pro Asp Lys
    1580                1585                1590

Val Tyr Leu Gly Gly Leu Asp Val Cys Gly Glu Asp Gly Gln Phe
    1595                1600                1605

Thr Tyr Cys Trp His Asp Asp Ile Met Gln Ala Val Phe His Ile
    1610                1615                1620

Ala Thr Leu Met Pro Thr Lys Asp Val Asp Lys His Arg Cys Asp
    1625                1630                1635
```

```
Lys Lys Arg His Leu Gly Asn Asp Phe Val Ser Ile Ile Tyr Asn
1640                1645                1650

Asp Ser Gly Glu Asp Phe Lys Leu Gly Thr Ile Lys Gly Gln Phe
        1655                1660                1665

Asn Phe Val His Val Ile Ile Thr Pro Leu Asp Tyr Lys Cys Asn
1670                1675                1680

Leu Leu Thr Leu Gln Cys Arg Lys Asp Met Glu Gly Leu Val Asp
        1685                1690                1695

Thr Ser Val Ala Lys Ile Val Ser Asp Arg Asn Leu Ser Phe Val
1700                1705                1710

Ala Arg Gln Met Ala Leu His Ala Asn Met Ala Ser Gln Val His
        1715                1720                1725

His Arg Arg Ser Asn Pro Thr Asp Ile Tyr Pro Ser Lys Trp Ile
1730                1735                1740

Ala Arg Leu Arg His Ile Lys Arg Leu Arg Gln Arg Ile Arg Glu
        1745                1750                1755

Glu Val His Tyr Ser Asn Pro Ser Leu Pro Leu Met His Pro Pro
1760                1765                1770

Ala His Thr Lys Val Pro Ala Gln Ala Pro Thr Glu Ala Thr Pro
        1775                1780                1785

Thr Tyr Glu Thr Gly Gln Arg Lys Arg Leu Ile Ser Ser Val Asp
1790                1795                1800

Asp Phe Thr Glu Phe Val
        1805

<210> SEQ ID NO 8
<211> LENGTH: 1814
<212> TYPE: PRT
<213> ORGANISM: Artificial Sequence
<220> FEATURE:
<223> OTHER INFORMATION: mouse TSC2 polypeptide having a S1365A
      substitution

<400> SEQUENCE: 8

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
                20                  25                  30

Gly Lys Gln Thr Glu Phe Ile Ile Thr Ser Glu Ile Leu Arg Glu Leu
            35                  40                  45

Ser Gly Glu Cys Gly Leu Asn Asn Arg Ile Arg Met Ile Gly Gln Ile
        50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

Ala Arg His Ala Val Leu Thr Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
```

-continued

```
                165                 170                 175
Leu Leu Val Leu Val Asn Leu Val Lys Phe Asn Ser Cys Tyr Leu Asp
            180                 185                 190

Glu Tyr Ile Ala Ser Met Val His Met Ile Cys Leu Leu Cys Ile Arg
            195                 200                 205

Thr Val Ser Ser Val Asp Ile Glu Val Ser Leu Gln Val Leu Asp Ala
            210                 215                 220

Val Val Cys Tyr Asn Cys Leu Pro Ala Glu Ser Leu Pro Leu Phe Ile
225                 230                 235                 240

Ile Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
                260                 265                 270

Ile Tyr Asn Met Cys Arg Ile Met Glu Asp Arg Ser Tyr Met Glu Asp
                275                 280                 285

Ala Pro Leu Leu Arg Gly Ala Val Phe Phe Val Gly Met Ala Leu Trp
            290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
                340                 345                 350

Leu Gln Ala Val Thr Trp Asp Ile Leu Leu Asp Ile Ile Glu Arg Leu
                355                 360                 365

Leu Gln Gln Leu Gln Asn Leu Asp Ser Pro Glu Leu Lys Thr Ile Val
            370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415

Gln Arg Pro Glu Ser Ser Leu Leu Asn Leu Ile Ser Tyr Arg Ala Gln
                420                 425                 430

Ser Ile His Pro Ala Lys Asp Gly Trp Ile Gln Asn Leu Gln Leu Leu
                435                 440                 445

Met Glu Arg Phe Phe Arg Asn Glu Cys Arg Ser Ala Val Ala Ile Lys
            450                 455                 460

Val Leu Asp Val Leu Ser Phe Val Leu Leu Ile Ile Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
                500                 505                 510

Val Asp Leu Ala Glu Gly Cys His Thr His Phe Asn Ser Leu Leu
            515                 520                 525

Asp Ile Ile Glu Lys Val Met Ala Arg Ser Leu Ser Pro Pro Glu
            530                 535                 540

Leu Glu Glu Arg Asp Leu Ala Val His Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Ser Leu Ile Ser
                580                 585                 590
```

His Ile Gln Leu His Tyr Lys His Gly Tyr Ser Leu Pro Ile Ala Ser
            595                 600                 605

Ser Ile Arg Leu Gln Ala Phe Asp Phe Leu Leu Leu Leu Arg Ala Asp
    610                 615                 620

Ser Leu His Arg Leu Gly Leu Pro Asn Lys Asp Gly Val Val Arg Phe
625                 630                 635                 640

Ser Pro Tyr Cys Leu Cys Asp Cys Met Glu Leu Asp Arg Ala Ser Glu
                645                 650                 655

Lys Lys Ala Ser Gly Pro Leu Ser Pro Pro Thr Gly Pro Pro Ser Pro
                660                 665                 670

Val Pro Met Gly Pro Ala Val Arg Leu Gly Tyr Leu Pro Tyr Ser Leu
            675                 680                 685

Leu Phe Arg Val Leu Leu Gln Cys Leu Lys Gln Glu Ser Asp Trp Lys
    690                 695                 700

Val Leu Lys Leu Val Leu Ser Arg Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
                740                 745                 750

Thr Pro Glu Gly Phe Ser Arg Thr Asp Leu His Leu Ala Val Val Pro
            755                 760                 765

Val Leu Thr Ala Leu Ile Ser Tyr His Asn Tyr Leu Asp Lys Thr Arg
    770                 775                 780

Gln Arg Glu Met Val Tyr Cys Leu Glu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Ile Lys Ala Leu Pro Val Leu Val Val Lys Leu Thr His
                820                 825                 830

Ile Ser Ala Thr Ala Ser Met Ala Ile Pro Leu Leu Glu Phe Leu Ser
    835                 840                 845

Thr Leu Ala Arg Leu Pro His Leu Tyr Arg Asn Phe Val Pro Glu Gln
    850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
                900                 905                 910

Thr Lys Gly Leu Arg Ser Asn Val Leu Leu Ser Phe Asp Asp Thr Pro
    915                 920                 925

Glu Lys Asp Ser Phe Arg Ala Arg Ser Thr Ser Leu Asn Glu Arg Pro
    930                 935                 940

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
                965                 970                 975

Cys Arg Ser Ile Ser Val Ser Glu His Val Val Arg Ser Arg Ile Gln
                980                 985                 990

Thr Ser Leu Thr Ser Ala Ser Leu  Gly Ser Ala Asp Glu  Asn Ser Met
            995                 1000                1005

```
Ala Gln Ala Asp Asp Asn Leu Lys Asn Leu His Leu Glu Leu Thr
    1010                1015                1020

Glu Thr Cys Leu Asp Met Met Ala Arg Tyr Val Phe Ser Asn Phe
    1025                1030                1035

Thr Ala Val Pro Lys Arg Ser Pro Val Gly Glu Phe Leu Leu Ala
    1040                1045                1050

Gly Gly Arg Thr Lys Thr Trp Leu Val Gly Asn Lys Leu Val Thr
    1055                1060                1065

Val Thr Thr Ser Val Gly Thr Gly Thr Arg Ser Leu Leu Gly Leu
    1070                1075                1080

Asp Ser Gly Asp Leu Gln Gly Gly Ser Asp Ser Ser Asp Pro
    1085                1090                1095

Ser Thr His Val Arg Gln Thr Lys Glu Ala Pro Ala Lys Leu Glu
    1100                1105                1110

Ser Gln Ala Gly Gln Gln Val Ser Arg Gly Ala Arg Asp Arg Val
    1115                1120                1125

Arg Ser Met Ser Gly Gly His Gly Leu Arg Val Gly Val Leu Asp
    1130                1135                1140

Thr Ser Ala Pro Tyr Ser Pro Gly Gly Ser Ala Ser Leu Gly Pro
    1145                1150                1155

Gln Thr Ala Val Ala Ala Lys Pro Glu Lys Pro Ala Gly Ala
    1160                1165                1170

Gln Leu Pro Thr Ala Glu Lys Thr Asn Leu Ala Ala Tyr Val Pro
    1175                1180                1185

Leu Leu Thr Gln Gly Trp Ala Glu Ile Leu Val Arg Arg Pro Thr
    1190                1195                1200

Gly Asn Thr Ser Trp Leu Met Ser Leu Glu Asn Pro Leu Ser Pro
    1205                1210                1215

Phe Ser Ser Asp Ile Asn Asn Met Pro Leu Gln Glu Leu Ser Asn
    1220                1225                1230

Ala Leu Met Ala Ala Glu Arg Phe Lys Glu His Gly His Ala Pro
    1235                1240                1245

Val Gln Val Ile Val Ser Ala Thr Gly Cys Thr Ala Lys Pro Pro
    1250                1255                1260

Thr Leu Pro Arg Ser Asn Thr Val Ala Ser Phe Ser Ser Leu Tyr
    1265                1270                1275

Gln Pro Ser Cys Gln Gly Gln Leu His Arg Ser Val Ser Trp Ala
    1280                1285                1290

Asp Ser Ala Met Val Leu Glu Glu Gly Ser Pro Gly Glu Thr Gln
    1295                1300                1305

Val Pro Val Glu Pro Pro Glu Leu Glu Asp Phe Glu Ala Ala Leu
    1310                1315                1320

Gly Thr Asp Arg His Cys Gln Arg Pro Asp Thr Tyr Ser Arg Ser
    1325                1330                1335

Ser Ser Ala Ser Ser Gln Glu Glu Lys Ser His Leu Glu Glu Leu
    1340                1345                1350

Ala Ala Gly Gly Ile Pro Ile Glu Arg Ala Ile Ala Ser Glu Gly
    1355                1360                1365

Ala Arg Pro Ala Val Asp Leu Ser Phe Gln Pro Ser Gln Pro Leu
    1370                1375                1380

Ser Lys Ser Ser Ser Ser Pro Glu Leu Gln Thr Leu Gln Asp Ile
    1385                1390                1395

Leu Gly Asp Leu Gly Asp Lys Ile Asp Ile Gly Arg Leu Ser Pro
```

-continued

```
            1400                1405                1410

Glu Ala Lys Val Arg Ser Gln Ser Gly Ile Leu Asp Gly Glu Ala
            1415                1420                1425

Ala Thr Trp Ser Ala Thr Gly Glu Glu Ser Arg Ile Thr Val Pro
            1430                1435                1440

Pro Glu Gly Pro Leu Pro Ser Ser Ser Pro Arg Ser Pro Ser Gly
            1445                1450                1455

Leu Arg Pro Arg Gly Tyr Thr Ile Ser Asp Ser Ala Pro Ser Arg
            1460                1465                1470

Arg Gly Lys Arg Val Glu Arg Asp Asn Phe Lys Ser Arg Ala Ala
            1475                1480                1485

Ala Ser Ser Ala Glu Lys Val Pro Gly Ile Asn Pro Ser Phe Val
            1490                1495                1500

Phe Leu Gln Leu Tyr His Ser Pro Phe Phe Gly Asp Glu Ser Asn
            1505                1510                1515

Lys Pro Ile Leu Leu Pro Asn Glu Ser Phe Glu Arg Ser Val Gln
            1520                1525                1530

Leu Leu Asp Gln Ile Pro Ser Tyr Asp Thr His Lys Ile Ala Val
            1535                1540                1545

Leu Tyr Val Gly Glu Gly Gln Ser Ser Ser Glu Leu Ala Ile Leu
            1550                1555                1560

Ser Asn Glu His Gly Ser Tyr Arg Tyr Thr Glu Phe Leu Thr Gly
            1565                1570                1575

Leu Gly Arg Leu Ile Glu Leu Lys Asp Cys Gln Pro Asp Lys Val
            1580                1585                1590

Tyr Leu Gly Gly Leu Asp Val Cys Gly Glu Asp Gly Gln Phe Thr
            1595                1600                1605

Tyr Cys Trp His Asp Asp Ile Met Gln Ala Val Phe His Ile Ala
            1610                1615                1620

Thr Leu Met Pro Thr Lys Asp Val Asp Lys His Arg Cys Asp Lys
            1625                1630                1635

Lys Arg His Leu Gly Asn Asp Phe Val Ser Ile Ile Tyr Asn Asp
            1640                1645                1650

Ser Gly Glu Asp Phe Lys Leu Gly Thr Ile Lys Gln Gly Gln Phe
            1655                1660                1665

Asn Phe Val His Val Ile Ile Thr Pro Leu Asp Tyr Lys Cys Asn
            1670                1675                1680

Leu Leu Thr Leu Gln Cys Arg Lys Asp Gly Pro Ala Cys Lys Cys
            1685                1690                1695

Glu Trp Trp Arg Gln Pro Gly Glu Ile Val Val Trp Ala Leu Pro
            1700                1705                1710

Val Val Met Glu Leu Thr Val Thr Ile Leu Leu Cys His Leu Gln
            1715                1720                1725

Met Ala Ser Gln Val His His Ser Arg Ser Asn Pro Thr Asp Ile
            1730                1735                1740

Tyr Pro Ser Lys Trp Ile Ala Arg Leu Arg His Ile Lys Arg Leu
            1745                1750                1755

Arg Gln Arg Ile Arg Glu Glu Val His Tyr Ser Asn Pro Ser Leu
            1760                1765                1770

Pro Leu Met His Pro Pro Ala His Thr Lys Ala Pro Ala Gln Ala
            1775                1780                1785

Pro Glu Ala Thr Pro Thr Tyr Glu Thr Gly Gln Arg Lys Arg Leu
            1790                1795                1800
```

<210> SEQ ID NO 9
<211> LENGTH: 1809
<212> TYPE: PRT
<213> ORGANISM: Artificial Sequence
<220> FEATURE:
<223> OTHER INFORMATION: rat TSC2 polypeptide having a S1366A substitution

<400> SEQUENCE: 9

```
Ile Ser Ser Val Asp Asp Phe Thr Glu Phe Val
    1805                1810

Met Ala Lys Pro Thr Ser Lys Asp Ser Gly Leu Lys Glu Lys Phe Lys
 1               5                  10                  15

Ile Leu Leu Gly Leu Gly Thr Ser Arg Pro Asn Pro Arg Cys Ala Glu
             20                  25                  30

Gly Lys Gln Thr Glu Phe Ile Ile Thr Ala Glu Ile Leu Arg Glu Leu
         35                  40                  45

Ser Gly Glu Cys Gly Leu Asn Asn Arg Ile Arg Met Ile Gly Gln Ile
     50                  55                  60

Cys Asp Val Ala Lys Thr Lys Lys Leu Glu Glu His Ala Val Glu Ala
 65                  70                  75                  80

Leu Trp Lys Ala Val Ser Asp Leu Leu Gln Pro Glu Arg Pro Pro Glu
                 85                  90                  95

Ala Arg His Ala Val Leu Ala Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Pro Met Val His Met Ile Cys Leu Leu Cys Ile Arg
        195                 200                 205

Thr Val Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Ile Thr Leu Cys Arg Thr Val Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys Arg Ile Met Glu Asn Arg Ser Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
```

-continued

```
                340                 345                 350
Leu Gln Ala Val Thr Trp Asp Ile Leu Leu Asp Ile Ile Glu Arg Leu
                355                 360                 365
Leu Gln Gln Leu Gln Asn Leu Asp Ser Pro Glu Leu Arg Thr Ile Val
                370                 375                 380
His Asp Leu Leu Thr Thr Val Glu Glu Leu Cys Asp Gln Asn Glu Phe
385                 390                 395                 400
His Gly Ser Gln Glu Arg Tyr Tyr Glu Leu Val Glu Ser Tyr Ala Asp
                405                 410                 415
Gln Arg Pro Glu Ser Ser Leu Leu Asn Leu Ile Thr Tyr Arg Ala Gln
                420                 425                 430
Ser Ile His Pro Ala Lys Asp Gly Trp Ile Gln Asn Leu Gln Leu Leu
                435                 440                 445
Met Glu Arg Phe Phe Arg Asn Glu Cys Arg Ser Ala Val Arg Ile Lys
                450                 455                 460
Val Leu Asp Val Leu Ser Phe Val Leu Leu Ile Asn Arg Gln Phe Tyr
465                 470                 475                 480
Glu Glu Glu Leu Ile Asn Ser Val Val Ile Ser Gln Leu Ser His Ile
                485                 490                 495
Pro Glu Asp Lys Asp His Gln Val Arg Lys Leu Ala Thr Gln Leu Leu
                500                 505                 510
Val Asp Leu Ala Glu Gly Cys His Thr His His Phe Asn Ser Leu Leu
                515                 520                 525
Asp Ile Ile Glu Lys Val Met Ala Arg Ser Leu Ser Pro Pro Leu Glu
                530                 535                 540
Leu Glu Glu Arg Asp Leu Ala Val Tyr Ser Ala Ser Leu Glu Asp Val
545                 550                 555                 560
Lys Thr Ala Val Leu Gly Leu Leu Val Ile Leu Gln Thr Lys Leu Tyr
                565                 570                 575
Thr Leu Pro Ala Ser His Ala Thr Arg Val Tyr Glu Thr Leu Ile Ser
                580                 585                 590
His Ile Gln Leu His Tyr Lys His Gly Tyr Ser Leu Pro Ile Ala Ser
                595                 600                 605
Ser Ile Arg Leu Gln Ala Phe Asp Phe Leu Leu Leu Arg Ala Asp
                610                 615                 620
Ser Leu His Arg Leu Gly Leu Pro Asn Lys Asp Gly Val Val Arg Phe
625                 630                 635                 640
Ser Pro Tyr Cys Leu Cys Asp Cys Ala Glu Leu Asp Arg Ala Ser Glu
                645                 650                 655
Lys Lys Ala Ser Gly Pro Leu Ser Pro Pro Thr Gly Pro Pro Ser Pro
                660                 665                 670
Val Pro Thr Gly Pro Ala Val Arg Leu Gly His Leu Pro Tyr Ser Leu
                675                 680                 685
Leu Phe Arg Val Leu Leu Gln Cys Leu Lys Gln Glu Thr Asp Trp Lys
                690                 695                 700
Val Leu Lys Leu Val Leu Ser Lys Leu Pro Glu Ser Leu Arg Tyr Lys
705                 710                 715                 720
Val Leu Ile Phe Thr Ser Pro Cys Ser Val Asp Gln Leu Ser Ser Ala
                725                 730                 735
Leu Cys Ser Met Leu Ser Ala Pro Lys Thr Leu Glu Arg Leu Arg Gly
                740                 745                 750
Thr Pro Glu Gly Phe Ser Arg Thr Asp Leu His Leu Ala Val Val Pro
                755                 760                 765
```

Val Leu Thr Ala Leu Ile Ser Tyr His Asn Tyr Leu Asp Lys Thr Arg
770                     775                     780

Gln Arg Glu Met Val Tyr Cys Leu Glu Gln Gly Leu Ile Tyr Arg Cys
785                     790                     795                     800

Ala Ser Gln Cys Val Val Ala Leu Ala Ile Cys Ser Val Glu Met Pro
                805                     810                     815

Asp Ile Ile Ile Lys Ala Leu Pro Val Leu Val Lys Leu Thr His
                820                     825                     830

Ile Ser Ala Thr Ala Ser Met Ala Ile Pro Leu Leu Glu Phe Leu Ser
                835                     840                     845

Thr Leu Ala Arg Leu Pro His Leu Tyr Arg Asn Phe Ala Ala Glu Gln
850                     855                     860

Tyr Ala Ser Val Phe Ala Ile Ser Leu Pro Tyr Thr Asn Pro Ser Lys
865                     870                     875                     880

Phe Asn Gln Tyr Ile Val Cys Leu Ala His His Val Ile Ala Met Trp
                885                     890                     895

Phe Ile Arg Cys Arg Leu Pro Phe Arg Lys Asp Phe Val Pro Tyr Ile
                900                     905                     910

Thr Lys Gly Leu Arg Ser Asn Val Leu Leu Ser Phe Asp Asp Thr Pro
                915                     920                     925

Glu Lys Asp Lys Phe Arg Ala Arg Ser Thr Ser Leu Asn Glu Arg Pro
930                     935                     940

Lys Ser Leu Arg Ile Ala Arg Ala Pro Lys Gln Gly Leu Asn Asn Ser
945                     950                     955                     960

Pro Pro Val Lys Glu Phe Lys Glu Ser Cys Ala Ala Glu Ala Phe Arg
                965                     970                     975

Cys Arg Ser Ile Ser Val Ser Glu His Val Val Arg Ser Arg Ile Gln
                980                     985                     990

Thr Ser Leu Thr Ser Ala Ser Leu  Gly Ser Ala Asp Glu  Asn Ser Met
                995                     1000                    1005

Ala Gln  Ala Asp Asp Asn Leu  Lys Asn Leu His Leu  Glu Leu Thr
    1010                    1015                    1020

Glu Thr  Cys Leu Asp Met Met  Ala Arg Tyr Val Phe  Ser Asn Phe
    1025                    1030                    1035

Thr Ala  Val Pro Lys Arg Ser  Pro Val Gly Glu Phe  Leu Leu Ala
    1040                    1045                    1050

Gly Gly  Arg Thr Lys Thr Trp  Leu Val Gly Asn Lys  Leu Val Thr
    1055                    1060                    1065

Val Thr  Thr Ser Val Gly Thr  Gly Thr Arg Ser Leu  Leu Gly Leu
    1070                    1075                    1080

Asp Ser  Gly Asp Leu Gln Gly  Gly Ser Ala Ser Ser  Ser Asp Pro
    1085                    1090                    1095

Gly Thr  His Val Arg Gln Thr  Lys Glu Ala Pro Ala  Lys Leu Glu
    1100                    1105                    1110

Ser Gln  Ala Gly Gln Gln Val  Ser Arg Gly Ala Arg  Asp Arg Val
    1115                    1120                    1125

Arg Ser  Met Ser Gly Gly His  Gly Leu Arg Val Gly  Val Leu Asp
    1130                    1135                    1140

Thr Ser  Ala Pro Tyr Thr Pro  Gly Gly Pro Ala Ser  Leu Gly Ala
    1145                    1150                    1155

Gln Ala  Ala Pro Ala Ala Arg  Pro Glu Lys Pro Cys  Ala Gly Ala
    1160                    1165                    1170

-continued

Gln Leu Pro Ala Ala Glu Lys Ala Asn Leu Ala Ala Tyr Val Pro
1175                1180                1185

Leu Leu Thr Gln Gly Trp Ala Glu Ile Leu Val Arg Arg Pro Thr
1190                1195                1200

Gly Asn Thr Ser Trp Leu Met Ser Leu Glu Asn Pro Leu Ser Pro
1205                1210                1215

Phe Ser Ser Asp Ile Asn Asn Met Pro Leu Gln Glu Leu Ser Asn
1220                1225                1230

Ala Leu Met Ala Ala Glu Arg Phe Lys Glu His Arg Asp Thr Ala
1235                1240                1245

Leu Tyr Lys Ser Leu Ser Val Pro Ala Ala Gly Thr Ala Lys Pro
1250                1255                1260

Pro Thr Leu Pro Arg Ser Asn Thr Val Ala Ser Phe Ser Ser Leu
1265                1270                1275

Tyr Gln Pro Ser Cys Gln Gly Gln Leu His Arg Ser Val Ser Trp
1280                1285                1290

Ala Asp Ser Ala Val Val Leu Glu Glu Gly Ser Pro Gly Glu Ala
1295                1300                1305

His Val Pro Val Glu Pro Pro Glu Leu Glu Asp Phe Glu Ala Ala
1310                1315                1320

Leu Gly Thr Asp Arg His Cys Gln Arg Pro Asp Ala Tyr Ser Arg
1325                1330                1335

Ser Ser Ser Ala Ser Ser Gln Glu Glu Lys Ser His Leu Glu Glu
1340                1345                1350

Leu Ala Ala Gly Gly Ile Pro Ile Glu Arg Ala Ile Ala Ser Glu
1355                1360                1365

Gly Ala Arg Pro Thr Val Asp Leu Ser Phe Gln Pro Ser Gln Pro
1370                1375                1380

Leu Ser Lys Ser Ser Ser Ser Pro Glu Leu Gln Thr Leu Gln Asp
1385                1390                1395

Ile Leu Gly Asp Leu Gly Asp Lys Thr Asp Ile Gly Arg Leu Ser
1400                1405                1410

Pro Glu Ala Lys Val Arg Ser Gln Ser Gly Ile Leu Asp Gly Glu
1415                1420                1425

Ala Ala Thr Trp Ser Ala Pro Gly Glu Glu Ser Arg Ile Thr Val
1430                1435                1440

Pro Pro Glu Gly Pro Leu Pro Ser Ser Ser Pro Arg Ser Pro Ser
1445                1450                1455

Gly Leu Arg Pro Arg Gly Tyr Thr Ile Ser Asp Ser Ala Pro Ser
1460                1465                1470

Arg Arg Gly Lys Arg Val Glu Arg Asp Asn Phe Lys Ser Arg Thr
1475                1480                1485

Ala Ala Ser Ser Ala Glu Lys Val Pro Gly Ile Asn Pro Ser Phe
1490                1495                1500

Val Phe Leu Gln Leu Tyr His Ser Pro Phe Cys Gly Asp Glu Ser
1505                1510                1515

Asn Lys Pro Ile Leu Leu Pro Asn Glu Ser Phe Glu Arg Ser Val
1520                1525                1530

Gln Leu Leu Asp Gln Ile Pro Ser Tyr Asp Thr His Lys Ile Ala
1535                1540                1545

Val Leu Tyr Val Gly Glu Gly Gln Ser Ser Ser Glu Leu Ala Ile
1550                1555                1560

Leu Ser Asn Glu His Gly Ser Tyr Arg Tyr Thr Glu Phe Leu Thr

Gly Leu Gly Arg Leu Ile Glu Leu Lys Asp Cys Gln Pro Asp Lys
         1580                1585                1590

Val Tyr Leu Gly Gly Leu Asp Val Cys Gly Glu Asp Gly Gln Phe
         1595                1600                1605

Thr Tyr Cys Trp His Asp Asp Ile Met Gln Ala Val Phe His Ile
         1610                1615                1620

Ala Thr Leu Met Pro Thr Lys Asp Val Asp Lys His Arg Cys Asp
         1625                1630                1635

Lys Lys Arg His Leu Gly Asn Asp Phe Val Ser Ile Ile Tyr Asn
         1640                1645                1650

Asp Ser Gly Glu Asp Phe Lys Leu Gly Thr Ile Lys Gly Gln Phe
         1655                1660                1665

Asn Phe Val His Val Ile Ile Thr Pro Leu Asp Tyr Lys Cys Asn
         1670                1675                1680

Leu Leu Thr Leu Gln Cys Arg Lys Asp Met Glu Gly Leu Val Asp
         1685                1690                1695

Thr Ser Val Ala Lys Ile Val Ser Asp Arg Asn Leu Ser Phe Val
         1700                1705                1710

Ala Arg Gln Met Ala Leu His Ala Asn Met Ala Ser Gln Val His
         1715                1720                1725

His Arg Arg Ser Asn Pro Thr Asp Ile Tyr Pro Ser Lys Trp Ile
         1730                1735                1740

Ala Arg Leu Arg His Ile Lys Arg Leu Arg Gln Arg Ile Arg Glu
         1745                1750                1755

Glu Val His Tyr Ser Asn Pro Ser Leu Pro Leu Met His Pro Pro
         1760                1765                1770

Ala His Thr Lys Val Pro Ala Gln Ala Pro Thr Glu Ala Thr Pro
         1775                1780                1785

Thr Tyr Glu Thr Gly Gln Arg Lys Arg Leu Ile Ser Ser Val Asp
         1790                1795                1800

Asp Phe Thr Glu Phe Val
         1805

<210> SEQ ID NO 10
<211> LENGTH: 1814
<212> TYPE: PRT
<213> ORGANISM: Artificial Sequence
<220> FEATURE:
<223> OTHER INFORMATION: mouse TSC2 polypeptide having a S1364E
      substitution

<400> SEQUENCE: 10

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
                20                  25                  30

Gly Lys Gln Thr Glu Phe Ile Ile Thr Ser Glu Ile Leu Arg Glu Leu
            35                  40                  45

Ser Gly Glu Cys Gly Leu Asn Asn Arg Ile Arg Met Ile Gly Gln Ile
        50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

```
Ala Arg His Ala Val Leu Thr Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
        130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Ser Met Val His Met Ile Cys Leu Leu Cys Ile Arg
        195                 200                 205

Thr Val Ser Ser Val Asp Ile Glu Val Ser Leu Gln Val Leu Asp Ala
        210                 215                 220

Val Val Cys Tyr Asn Cys Leu Pro Ala Glu Ser Leu Pro Leu Phe Ile
225                 230                 235                 240

Ile Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys Arg Ile Met Glu Asp Arg Ser Tyr Met Glu Asp
        275                 280                 285

Ala Pro Leu Leu Arg Gly Ala Val Phe Phe Val Gly Met Ala Leu Trp
290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Ala Val Thr Trp Asp Ile Leu Leu Asp Ile Ile Glu Arg Leu
        355                 360                 365

Leu Gln Gln Leu Gln Asn Leu Asp Ser Pro Glu Leu Lys Thr Ile Val
        370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Leu Leu
        435                 440                 445

Met Glu Arg Phe Phe Arg Asn Glu Cys Arg Ser Ala Val Ala Ile Lys
450                 455                 460

Val Leu Asp Val Leu Ser Phe Val Leu Leu Ile Ile Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
```

```
            515                 520                 525
Asp Ile Ile Glu Lys Val Met Ala Arg Ser Leu Ser Pro Pro Glu
    530                 535                 540

Leu Glu Glu Arg Asp Leu Ala Val His Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Ser Leu Ile Ser
            580                 585                 590

His Ile Gln Leu His Tyr Lys His Gly Tyr Ser Leu Pro Ile Ala Ser
                595                 600                 605

Ser Ile Arg Leu Gln Ala Phe Asp Phe Leu Leu Leu Arg Ala Asp
    610                 615                 620

Ser Leu His Arg Leu Gly Leu Pro Asn Lys Asp Gly Val Val Arg Phe
625                 630                 635                 640

Ser Pro Tyr Cys Leu Cys Asp Cys Met Glu Leu Asp Arg Ala Ser Glu
                645                 650                 655

Lys Lys Ala Ser Gly Pro Leu Ser Pro Pro Thr Gly Pro Pro Ser Pro
                660                 665                 670

Val Pro Met Gly Pro Ala Val Arg Leu Gly Tyr Leu Pro Tyr Ser Leu
                675                 680                 685

Leu Phe Arg Val Leu Leu Gln Cys Leu Lys Gln Glu Ser Asp Trp Lys
    690                 695                 700

Val Leu Lys Leu Val Leu Ser Arg Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
                740                 745                 750

Thr Pro Glu Gly Phe Ser Arg Thr Asp Leu His Leu Ala Val Val Pro
            755                 760                 765

Val Leu Thr Ala Leu Ile Ser Tyr His Asn Tyr Leu Asp Lys Thr Arg
    770                 775                 780

Gln Arg Glu Met Val Tyr Cys Leu Glu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Ile Lys Ala Leu Pro Val Leu Val Lys Leu Thr His
                820                 825                 830

Ile Ser Ala Thr Ala Ser Met Ala Ile Pro Leu Leu Glu Phe Leu Ser
            835                 840                 845

Thr Leu Ala Arg Leu Pro His Leu Tyr Arg Asn Phe Val Pro Glu Gln
    850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
                900                 905                 910

Thr Lys Gly Leu Arg Ser Asn Val Leu Leu Ser Phe Asp Asp Thr Pro
            915                 920                 925

Glu Lys Asp Ser Phe Arg Ala Arg Ser Thr Ser Leu Asn Glu Arg Pro
    930                 935                 940
```

-continued

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
            965                 970                 975

Cys Arg Ser Ile Ser Val Ser Glu His Val Val Arg Ser Arg Ile Gln
            980                 985                 990

Thr Ser Leu Thr Ser Ala Ser Leu Gly Ser Ala Asp Glu Asn Ser Met
        995                 1000                1005

Ala Gln Ala Asp Asp Asn Leu Lys Asn Leu His Leu Glu Leu Thr
    1010                1015                1020

Glu Thr Cys Leu Asp Met Met Ala Arg Tyr Val Phe Ser Asn Phe
    1025                1030                1035

Thr Ala Val Pro Lys Arg Ser Pro Val Gly Glu Phe Leu Leu Ala
    1040                1045                1050

Gly Gly Arg Thr Lys Thr Trp Leu Val Gly Asn Lys Leu Val Thr
    1055                1060                1065

Val Thr Thr Ser Val Gly Thr Gly Thr Arg Ser Leu Leu Gly Leu
    1070                1075                1080

Asp Ser Gly Asp Leu Gln Gly Gly Ser Asp Ser Ser Ser Asp Pro
    1085                1090                1095

Ser Thr His Val Arg Gln Thr Lys Glu Ala Pro Ala Lys Leu Glu
    1100                1105                1110

Ser Gln Ala Gly Gln Gln Val Ser Arg Gly Ala Arg Asp Arg Val
    1115                1120                1125

Arg Ser Met Ser Gly Gly His Gly Leu Arg Val Gly Val Leu Asp
    1130                1135                1140

Thr Ser Ala Pro Tyr Ser Pro Gly Gly Ser Ala Ser Leu Gly Pro
    1145                1150                1155

Gln Thr Ala Val Ala Ala Lys Pro Glu Lys Pro Ala Gly Ala
    1160                1165                1170

Gln Leu Pro Thr Ala Glu Lys Thr Asn Leu Ala Ala Tyr Val Pro
    1175                1180                1185

Leu Leu Thr Gln Gly Trp Ala Glu Ile Leu Val Arg Arg Pro Thr
    1190                1195                1200

Gly Asn Thr Ser Trp Leu Met Ser Leu Glu Asn Pro Leu Ser Pro
    1205                1210                1215

Phe Ser Ser Asp Ile Asn Asn Met Pro Leu Gln Glu Leu Ser Asn
    1220                1225                1230

Ala Leu Met Ala Ala Glu Arg Phe Lys Glu His Gly His Ala Pro
    1235                1240                1245

Val Gln Val Ile Val Ser Ala Thr Gly Cys Thr Ala Lys Pro Pro
    1250                1255                1260

Thr Leu Pro Arg Ser Asn Thr Val Ala Ser Phe Ser Ser Leu Tyr
    1265                1270                1275

Gln Pro Ser Cys Gln Gly Gln Leu His Arg Ser Val Ser Trp Ala
    1280                1285                1290

Asp Ser Ala Met Val Leu Glu Glu Gly Ser Pro Gly Glu Thr Gln
    1295                1300                1305

Val Pro Val Glu Pro Pro Glu Leu Glu Asp Phe Glu Ala Ala Leu
    1310                1315                1320

Gly Thr Asp Arg His Cys Gln Arg Pro Asp Thr Tyr Ser Arg Ser
    1325                1330                1335

```
Ser  Ser  Ala  Ser  Ser  Gln  Glu  Glu  Lys  Ser  His  Leu  Glu  Glu  Leu
     1340                    1345                    1350

Ala  Ala  Gly  Gly  Ile  Pro  Ile  Glu  Arg  Ala  Ile  Glu  Ser  Glu  Gly
     1355                    1360                    1365

Ala  Arg  Pro  Ala  Val  Asp  Leu  Ser  Phe  Gln  Pro  Ser  Gln  Pro  Leu
     1370                    1375                    1380

Ser  Lys  Ser  Ser  Ser  Pro  Glu  Leu  Gln  Thr  Leu  Gln  Asp  Ile
     1385                    1390                    1395

Leu  Gly  Asp  Leu  Gly  Asp  Lys  Ile  Asp  Ile  Gly  Arg  Leu  Ser  Pro
     1400                    1405                    1410

Glu  Ala  Lys  Val  Arg  Ser  Gln  Ser  Gly  Ile  Leu  Asp  Gly  Glu  Ala
     1415                    1420                    1425

Ala  Thr  Trp  Ser  Ala  Thr  Gly  Glu  Glu  Ser  Arg  Ile  Thr  Val  Pro
     1430                    1435                    1440

Pro  Glu  Gly  Pro  Leu  Pro  Ser  Ser  Ser  Pro  Arg  Ser  Pro  Ser  Gly
     1445                    1450                    1455

Leu  Arg  Pro  Arg  Gly  Tyr  Thr  Ile  Ser  Asp  Ser  Ala  Pro  Ser  Arg
     1460                    1465                    1470

Arg  Gly  Lys  Arg  Val  Glu  Arg  Asp  Asn  Phe  Lys  Ser  Arg  Ala  Ala
     1475                    1480                    1485

Ala  Ser  Ser  Ala  Glu  Lys  Val  Pro  Gly  Ile  Asn  Pro  Ser  Phe  Val
     1490                    1495                    1500

Phe  Leu  Gln  Leu  Tyr  His  Ser  Pro  Phe  Phe  Gly  Asp  Glu  Ser  Asn
     1505                    1510                    1515

Lys  Pro  Ile  Leu  Leu  Pro  Asn  Glu  Ser  Phe  Glu  Arg  Ser  Val  Gln
     1520                    1525                    1530

Leu  Leu  Asp  Gln  Ile  Pro  Ser  Tyr  Asp  Thr  His  Lys  Ile  Ala  Val
     1535                    1540                    1545

Leu  Tyr  Val  Gly  Glu  Gly  Gln  Ser  Ser  Ser  Glu  Leu  Ala  Ile  Leu
     1550                    1555                    1560

Ser  Asn  Glu  His  Gly  Ser  Tyr  Arg  Tyr  Thr  Glu  Phe  Leu  Thr  Gly
     1565                    1570                    1575

Leu  Gly  Arg  Leu  Ile  Glu  Leu  Lys  Asp  Cys  Gln  Pro  Asp  Lys  Val
     1580                    1585                    1590

Tyr  Leu  Gly  Gly  Leu  Asp  Val  Cys  Gly  Glu  Asp  Gly  Gln  Phe  Thr
     1595                    1600                    1605

Tyr  Cys  Trp  His  Asp  Asp  Ile  Met  Gln  Ala  Val  Phe  His  Ile  Ala
     1610                    1615                    1620

Thr  Leu  Met  Pro  Thr  Lys  Asp  Val  Asp  Lys  His  Arg  Cys  Asp  Lys
     1625                    1630                    1635

Lys  Arg  His  Leu  Gly  Asn  Asp  Phe  Val  Ser  Ile  Ile  Tyr  Asn  Asp
     1640                    1645                    1650

Ser  Gly  Glu  Asp  Phe  Lys  Leu  Gly  Thr  Ile  Lys  Gln  Gly  Gln  Phe
     1655                    1660                    1665

Asn  Phe  Val  His  Val  Ile  Ile  Thr  Pro  Leu  Asp  Tyr  Lys  Cys  Asn
     1670                    1675                    1680

Leu  Leu  Thr  Leu  Gln  Cys  Arg  Lys  Asp  Gly  Pro  Ala  Cys  Lys  Cys
     1685                    1690                    1695

Glu  Trp  Trp  Arg  Gln  Pro  Gly  Glu  Ile  Val  Val  Trp  Ala  Leu  Pro
     1700                    1705                    1710

Val  Val  Met  Glu  Leu  Thr  Val  Thr  Ile  Leu  Leu  Cys  His  Leu  Gln
     1715                    1720                    1725

Met  Ala  Ser  Gln  Val  His  His  Ser  Arg  Ser  Asn  Pro  Thr  Asp  Ile
```

```
                1730                1735                1740

Tyr Pro Ser Lys Trp Ile Ala Arg Leu Arg His Ile Lys Arg Leu
        1745                1750                1755

Arg Gln Arg Ile Arg Glu Glu Val His Tyr Ser Asn Pro Ser Leu
1760                1765                1770

Pro Leu Met His Pro Pro Ala His Thr Lys Ala Pro Ala Gln Ala
    1775                1780                1785

Pro Glu Ala Thr Pro Thr Tyr Glu Thr Gly Gln Arg Lys Arg Leu
1790                1795                1800

Ile Ser Ser Val Asp Asp Phe Thr Glu Phe Val
    1805                1810

<210> SEQ ID NO 11
<211> LENGTH: 1809
<212> TYPE: PRT
<213> ORGANISM: Artificial Sequence
<220> FEATURE:
<223> OTHER INFORMATION: rat TSC2 polypeptide having a S1364E
      substitution

<400> SEQUENCE: 11

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
            20                  25                  30

Gly Lys Gln Thr Glu Phe Ile Ile Thr Ala Glu Ile Leu Arg Glu Leu
        35                  40                  45

Ser Gly Glu Cys Gly Leu Asn Asn Arg Ile Arg Met Ile Gly Gln Ile
    50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

Ala Arg His Ala Val Leu Ala Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Pro Met Val His Met Ile Cys Leu Leu Cys Ile Arg
        195                 200                 205

Thr Val Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Ile Thr Leu Cys Arg Thr Val Asn Val Lys Glu Leu Cys Glu Pro Cys
                245                 250                 255

Trp Lys Leu Met Arg Asn Leu Leu Gly Thr His Leu Gly His Ser Ala
            260                 265                 270
```

```
Ile Tyr Asn Met Cys Arg Ile Met Glu Asn Arg Ser Tyr Met Glu Asp
            275                 280                 285

Ala Pro Leu Leu Arg Gly Ala Val Phe Phe Val Gly Met Ala Leu Trp
290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
            325                 330                 335

Glu Ile Val Leu Ser Ile Thr Arg Leu Ile Lys Lys Tyr Arg Lys Glu
            340                 345                 350

Leu Gln Ala Val Thr Trp Asp Ile Leu Leu Asp Ile Ile Glu Arg Leu
        355                 360                 365

Leu Gln Gln Leu Gln Asn Leu Asp Ser Pro Glu Leu Arg Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415

Gln Arg Pro Glu Ser Ser Leu Leu Asn Leu Ile Thr Tyr Arg Ala Gln
            420                 425                 430

Ser Ile His Pro Ala Lys Asp Gly Trp Ile Gln Asn Leu Gln Leu Leu
        435                 440                 445

Met Glu Arg Phe Phe Arg Asn Glu Cys Arg Ser Ala Val Arg Ile Lys
    450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Leu Glu
530                 535                 540

Leu Glu Glu Arg Asp Leu Ala Val Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Thr Leu Ile Ser
            580                 585                 590

His Ile Gln Leu His Tyr Lys His Gly Tyr Ser Leu Pro Ile Ala Ser
        595                 600                 605

Ser Ile Arg Leu Gln Ala Phe Asp Phe Leu Leu Leu Leu Arg Ala Asp
    610                 615                 620

Ser Leu His Arg Leu Gly Leu Pro Asn Lys Asp Gly Val Val Arg Phe
625                 630                 635                 640

Ser Pro Tyr Cys Leu Cys Asp Cys Ala Glu Leu Asp Arg Ala Ser Glu
                645                 650                 655

Lys Lys Ala Ser Gly Pro Leu Ser Pro Thr Gly Pro Pro Ser Pro
            660                 665                 670

Val Pro Thr Gly Pro Ala Val Arg Leu Gly His Leu Pro Tyr Ser Leu
        675                 680                 685

Leu Phe Arg Val Leu Leu Gln Cys Leu Lys Gln Glu Thr Asp Trp Lys
```

-continued

```
            690                 695                 700
Val Leu Lys Leu Val Leu Ser Lys Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
                740                 745                 750

Thr Pro Glu Gly Phe Ser Arg Thr Asp Leu His Leu Ala Val Val Pro
                755                 760                 765

Val Leu Thr Ala Leu Ile Ser Tyr His Asn Tyr Leu Asp Lys Thr Arg
770                 775                 780

Gln Arg Glu Met Val Tyr Cys Leu Glu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Ile Lys Ala Leu Pro Val Leu Val Lys Leu Thr His
                820                 825                 830

Ile Ser Ala Thr Ala Ser Met Ala Ile Pro Leu Leu Glu Phe Leu Ser
                835                 840                 845

Thr Leu Ala Arg Leu Pro His Leu Tyr Arg Asn Phe Ala Ala Glu Gln
                850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
                900                 905                 910

Thr Lys Gly Leu Arg Ser Asn Val Leu Leu Ser Phe Asp Asp Thr Pro
                915                 920                 925

Glu Lys Asp Lys Phe Arg Ala Arg Ser Thr Ser Leu Asn Glu Arg Pro
                930                 935                 940

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
                965                 970                 975

Cys Arg Ser Ile Ser Val Ser Glu His Val Val Arg Ser Arg Ile Gln
                980                 985                 990

Thr Ser Leu Thr Ser Ala Ser Leu  Gly Ser Ala Asp Glu  Asn Ser Met
                995                1000                1005

Ala Gln  Ala Asp Asp Asn Leu  Lys Asn Leu His Leu  Glu Leu Thr
    1010                1015                1020

Glu Thr  Cys Leu Asp Met Met  Ala Arg Tyr Val Phe  Ser Asn Phe
    1025                1030                1035

Thr Ala  Val Pro Lys Arg Ser  Pro Val Gly Glu Phe  Leu Leu Ala
    1040                1045                1050

Gly Gly  Arg Thr Lys Thr Trp  Leu Val Gly Asn Lys  Leu Val Thr
    1055                1060                1065

Val Thr  Thr Ser Val Gly Thr  Gly Thr Arg Ser Leu  Leu Gly Leu
    1070                1075                1080

Asp Ser  Gly Asp Leu Gln Gly  Gly Ser Ala Ser Ser  Ser Asp Pro
    1085                1090                1095

Gly Thr  His Val Arg Gln Thr  Lys Glu Ala Pro Ala  Lys Leu Glu
    1100                1105                1110
```

-continued

Ser Gln Ala Gly Gln Gln Val Ser Arg Gly Ala Arg Asp Arg Val
1115                1120                1125

Arg Ser Met Ser Gly Gly His Gly Leu Arg Val Gly Val Leu Asp
1130                1135                1140

Thr Ser Ala Pro Tyr Thr Pro Gly Gly Pro Ala Ser Leu Gly Ala
1145                1150                1155

Gln Ala Ala Pro Ala Ala Arg Pro Glu Lys Pro Cys Ala Gly Ala
1160                1165                1170

Gln Leu Pro Ala Ala Glu Lys Ala Asn Leu Ala Ala Tyr Val Pro
1175                1180                1185

Leu Leu Thr Gln Gly Trp Ala Glu Ile Leu Val Arg Arg Pro Thr
1190                1195                1200

Gly Asn Thr Ser Trp Leu Met Ser Leu Glu Asn Pro Leu Ser Pro
1205                1210                1215

Phe Ser Ser Asp Ile Asn Asn Met Pro Leu Gln Glu Leu Ser Asn
1220                1225                1230

Ala Leu Met Ala Ala Glu Arg Phe Lys Glu His Arg Asp Thr Ala
1235                1240                1245

Leu Tyr Lys Ser Leu Ser Val Pro Ala Ala Gly Thr Ala Lys Pro
1250                1255                1260

Pro Thr Leu Pro Arg Ser Asn Thr Val Ala Ser Phe Ser Ser Leu
1265                1270                1275

Tyr Gln Pro Ser Cys Gln Gly Gln Leu His Arg Ser Val Ser Trp
1280                1285                1290

Ala Asp Ser Ala Val Val Leu Glu Glu Gly Ser Pro Gly Glu Ala
1295                1300                1305

His Val Pro Val Glu Pro Pro Glu Leu Glu Asp Phe Glu Ala Ala
1310                1315                1320

Leu Gly Thr Asp Arg His Cys Gln Arg Pro Asp Ala Tyr Ser Arg
1325                1330                1335

Ser Ser Ser Ala Ser Ser Gln Glu Glu Lys Ser His Leu Glu Glu
1340                1345                1350

Leu Ala Ala Gly Gly Ile Pro Ile Glu Arg Ala Ile Glu Ser Glu
1355                1360                1365

Gly Ala Arg Pro Thr Val Asp Leu Ser Phe Gln Pro Ser Gln Pro
1370                1375                1380

Leu Ser Lys Ser Ser Ser Pro Glu Leu Gln Thr Leu Gln Asp
1385                1390                1395

Ile Leu Gly Asp Leu Gly Asp Lys Thr Asp Ile Gly Arg Leu Ser
1400                1405                1410

Pro Glu Ala Lys Val Arg Ser Gln Ser Gly Ile Leu Asp Gly Glu
1415                1420                1425

Ala Ala Thr Trp Ser Ala Pro Gly Glu Glu Ser Arg Ile Thr Val
1430                1435                1440

Pro Pro Glu Gly Pro Leu Pro Ser Ser Ser Pro Arg Ser Pro Ser
1445                1450                1455

Gly Leu Arg Pro Arg Gly Tyr Thr Ile Ser Asp Ser Ala Pro Ser
1460                1465                1470

Arg Arg Gly Lys Arg Val Glu Arg Asp Asn Phe Lys Ser Arg Thr
1475                1480                1485

Ala Ala Ser Ser Ala Glu Lys Val Pro Gly Ile Asn Pro Ser Phe
1490                1495                1500

-continued

| | | | | | | | | | | | |
|---|---|---|---|---|---|---|---|---|---|---|---|
| Val | Phe | Leu | Gln | Leu | Tyr | His | Ser | Pro | Phe | Cys | Gly | Asp | Glu | Ser |
| 1505 | | | | | 1510 | | | | | 1515 | |
| Asn | Lys | Pro | Ile | Leu | Leu | Pro | Asn | Glu | Ser | Phe | Glu | Arg | Ser | Val |
| 1520 | | | | | 1525 | | | | | 1530 | |
| Gln | Leu | Leu | Asp | Gln | Ile | Pro | Ser | Tyr | Asp | Thr | His | Lys | Ile | Ala |
| 1535 | | | | | 1540 | | | | | 1545 | |
| Val | Leu | Tyr | Val | Gly | Glu | Gly | Gln | Ser | Ser | Glu | Leu | Ala | Ile |
| 1550 | | | | | 1555 | | | | | 1560 | |
| Leu | Ser | Asn | Glu | His | Gly | Ser | Tyr | Arg | Tyr | Thr | Glu | Phe | Leu | Thr |
| 1565 | | | | | 1570 | | | | | 1575 | |
| Gly | Leu | Gly | Arg | Leu | Ile | Glu | Leu | Lys | Asp | Cys | Gln | Pro | Asp | Lys |
| 1580 | | | | | 1585 | | | | | 1590 | |
| Val | Tyr | Leu | Gly | Gly | Leu | Asp | Val | Cys | Gly | Glu | Asp | Gly | Gln | Phe |
| 1595 | | | | | 1600 | | | | | 1605 | |
| Thr | Tyr | Cys | Trp | His | Asp | Asp | Ile | Met | Gln | Ala | Val | Phe | His | Ile |
| 1610 | | | | | 1615 | | | | | 1620 | |
| Ala | Thr | Leu | Met | Pro | Thr | Lys | Asp | Val | Asp | Lys | His | Arg | Cys | Asp |
| 1625 | | | | | 1630 | | | | | 1635 | |
| Lys | Lys | Arg | His | Leu | Gly | Asn | Asp | Phe | Val | Ser | Ile | Ile | Tyr | Asn |
| 1640 | | | | | 1645 | | | | | 1650 | |
| Asp | Ser | Gly | Glu | Asp | Phe | Lys | Leu | Gly | Thr | Ile | Lys | Gly | Gln | Phe |
| 1655 | | | | | 1660 | | | | | 1665 | |
| Asn | Phe | Val | His | Val | Ile | Ile | Thr | Pro | Leu | Asp | Tyr | Lys | Cys | Asn |
| 1670 | | | | | 1675 | | | | | 1680 | |
| Leu | Leu | Thr | Leu | Gln | Cys | Arg | Lys | Asp | Met | Glu | Gly | Leu | Val | Asp |
| 1685 | | | | | 1690 | | | | | 1695 | |
| Thr | Ser | Val | Ala | Lys | Ile | Val | Ser | Asp | Arg | Asn | Leu | Ser | Phe | Val |
| 1700 | | | | | 1705 | | | | | 1710 | |
| Ala | Arg | Gln | Met | Ala | Leu | His | Ala | Asn | Met | Ala | Ser | Gln | Val | His |
| 1715 | | | | | 1720 | | | | | 1725 | |
| His | Arg | Arg | Ser | Asn | Pro | Thr | Asp | Ile | Tyr | Pro | Ser | Lys | Trp | Ile |
| 1730 | | | | | 1735 | | | | | 1740 | |
| Ala | Arg | Leu | Arg | His | Ile | Lys | Arg | Leu | Arg | Gln | Arg | Ile | Arg | Glu |
| 1745 | | | | | 1750 | | | | | 1755 | |
| Glu | Val | His | Tyr | Ser | Asn | Pro | Ser | Leu | Pro | Leu | Met | His | Pro | Pro |
| 1760 | | | | | 1765 | | | | | 1770 | |
| Ala | His | Thr | Lys | Val | Pro | Ala | Gln | Ala | Pro | Thr | Glu | Ala | Thr | Pro |
| 1775 | | | | | 1780 | | | | | 1785 | |
| Thr | Tyr | Glu | Thr | Gly | Gln | Arg | Lys | Arg | Leu | Ile | Ser | Ser | Val | Asp |
| 1790 | | | | | 1795 | | | | | 1800 | |
| Asp | Phe | Thr | Glu | Phe | Val |
| 1805 | | | | | |